US009738912B2

(12) United States Patent
Hattendorf et al.

(10) Patent No.: US 9,738,912 B2
(45) Date of Patent: *Aug. 22, 2017

(54) GENE DISRUPTANTS PRODUCING FATTY ACYL-COA DERIVATIVES

(71) Applicant: SHELL OIL COMPANY, Houston, TX (US)

(72) Inventors: Douglas A. Hattendorf, Oakland, CA (US); Jennifer L. Shock, San Francisco, CA (US); Louis Clark, San Francisco, CA (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/844,025

(22) Filed: Sep. 3, 2015

(65) Prior Publication Data

US 2016/0090612 A1 Mar. 31, 2016

Related U.S. Application Data

(62) Division of application No. 13/330,650, filed on Dec. 19, 2011, now Pat. No. 9,157,103.

(60) Provisional application No. 61/502,697, filed on Jun. 29, 2011, provisional application No. 61/427,032, filed on Dec. 23, 2010.

(51) Int. Cl.
| | |
|---|---|
| *C12P 7/64* | (2006.01) |
| *C12N 1/15* | (2006.01) |
| *C12N 1/19* | (2006.01) |
| *C12P 7/40* | (2006.01) |
| *C12P 7/62* | (2006.01) |
| *C12N 9/02* | (2006.01) |

(52) U.S. Cl.
CPC .............. *C12P 7/64* (2013.01); *C12N 9/0008* (2013.01); *C12P 7/40* (2013.01); *C12P 7/62* (2013.01); *C12Y 102/0105* (2013.01); *C12Y 102/01042* (2013.01); *C12Y 102/01084* (2015.07)

(58) Field of Classification Search
CPC .. C12N 9/0008; C12P 7/40; C12P 7/62; C12P 7/64; C12Y 102/01042; C12Y 102/0105; C12Y 102/01084; Y02P 20/52
See application file for complete search history.

(56) References Cited

U.S. PATENT DOCUMENTS

| | | |
|---|---|---|
| 5,411,879 A | 5/1995 | Pollard et al. |
| 2010/0205690 A1 | 8/2010 | Blasing et al. |
| 2011/0000125 A1 | 1/2011 | McDaniel et al. |
| 2012/0009640 A1 | 1/2012 | Behrouzian et al. |

FOREIGN PATENT DOCUMENTS

| | | |
|---|---|---|
| CN | 101698850 | 4/2010 |
| WO | 2007136762 | 11/2007 |
| WO | WO2008100251 | 8/2008 |
| WO | 2008106803 | 9/2008 |
| WO | 2008119082 | 10/2008 |
| WO | 2009111672 | 9/2009 |
| WO | 2010062480 | 6/2010 |
| WO | 2011008535 | 1/2011 |

OTHER PUBLICATIONS

Sadowski et al., Current Opinion in Structural Biology 19:357-362, 2009.*
Lida, T. et al., "The Cytochrome P450ALK Mutligene Family of an N-Alkane-Assimilating Yeast, Yarrowia lipolytica: Cloning and Characterization of Genes Coding for New CYP52 Family Members", Yeast, 2000, GB, vol. 16, pp. 1077-1087.
Madzak, C. et al., "Heterologous Protein Expression and Secretion in the Non-Conventional Yeast Yarrowia Lipolytica. A Review", Journal of Biotechnology, NL, vol. 109, No. 1-2, 2004, pp. 63-81.
Mekouar, M. et al, "Detection and Analysis of Alternative Splicing in Yarrowia Lipolytica Reveal Structural Constraints Facilitating Nonsense-Mediated Decay of Intron-Retaining Transcripts", Genome Biology, Biomed Central Ltd.,GB, vol. 11, No. 6, 2010, p. R65.
Supplementary European Search Report dated Apr. 4, 2015 for Application No. EP11850991.
Dujon, B. et al., "Genome Evolution in Yeast", Nature, vol. 430, 2004, pp. 35-45.
Akada, et al.; "PCR-mediated seamless gene deletion and marker recycling in *Saccharomyces cerevisiae*"; Yeast, vol. 23; pp. 399-405; 2006.
Boisrame et al.; "Interaction of Kar2p and Sis1p is required for efficient co-translational translocation of secreted proteins in the Yeast Yarrowia lipolytica"; J. Biol. Chem.; vol. 273; 30903; 1998.
Brat, et al.; "Functional expression of a bacterial xylose isomerase in *Saccharomyces cerevisiae*"; Applied and Environmental Microbiology; vol. 75; pp. 2304-2311; 2009.
Fickers et al.; "New disruption cassettes for rapid gene disruption and marker rescue in the years Yarrowia lipolytica"; Journal of Microbiological Methods; vol. 55; pp. 727-737; 2003.
GenBank Accession No. AB010392, Yarrowia lipolytica gene for ALK5 complete cds; Oct. 12, 2000; http://ncbi.nlm.nih.gov/nuccore/AB10392>; 2 pages.
GenBank Accession No. FP692155 FP692155 oleci acid medium in exponential phase Yarrowia lipolytica cDNA5-, mRNA sequence; Jun. 18, 2010. 2 pages.
GenBank Accession No. FP687460, FP687460 YPD medium in stationary phase Yarrowia lipolytica cDNA5-, mRNA sequence; Jun. 19, 2010. 2 pages.
GenBank Accession No. FP693979, FP693979 oleci acid medium in exponential phase Yarrowia lipolytica cDNA5-, mRNA sequence; Jun. 18, 2010. 2 pages.
Ho, et al.; "Genetically engineered *Saccharomyces* yeast capable of effective cofermentation of glucose and xylose"; Applied and Environmental Microbiology; vol. 64; pp. 1852-1859; 1998.

(Continued)

Primary Examiner — Delia Ramirez

(57) ABSTRACT

This invention provides microbial organisms, particularly yeasts such as *Yarrowia lipolytica*, that have one or more disrupted genes. The gene disruption(s) may yield improved production of fatty acyl-CoA derivatives.

20 Claims, 2 Drawing Sheets

(56) References Cited

OTHER PUBLICATIONS

Nicaud, et al; "Expression of invertase activity in Yarrowia lipolytica and its use as a selectable marker"; Current Genetics; vol. 16; pp. 253-260; 1989.
Swennen, et al; "Cloning the Yarrowia lipolytica homologue of the *Saccaromyces cerevisiae* SEC62 gene;" Curr Genet; vol. 31, No. 2; pp. 128-132; 1997.
Brandon, C.; "prediction, Engineering, and Design of Protein Structures"; Introduction to Protein Structure; 3 pages; 1991.
Seffernick, et al.; "Melamine Deaminase and Atrazine Chlorohydrolase: 98 Percent Identical but Functionally Different"; Journal of Bacteriology; pp. 2405-2410; Apr. 2001.
Witkowski et al.; "Conversion of a B-Ketoacyl Synthase to a Malonyl Decarboxylase by Replacement of the Active-Site Cysteine with Glutamine"; Biochemistry; vol. 38; pp. 11643-11650; 1999.
Branch, Andrea; "A good antisense molecule is hard to find"; TIBS; vol. 23; pp. 45-50; Feb. 1998.
Sousa et al.; "The AR04 gene of Candida albicans encodes a tyrosine-sensitive DAHP synthase: evolution, functional conversation and phenotype of Aro3p-, Aro4p-deficient mutants"; Microbiology; vol. 148; pp. 1291-1303; 2002.
Zhou et al.; "Global analysis of gene transcription regulation in prokaryotes"; Cell. Mol. Life Sci.; vol. 63; pp. 2260-2290; 2006.
Kozak, M., "Initiation of translation in Prokaryotes and Eukaryotes", Gene, vol. 234, 1999,pp. 187-208.

* cited by examiner

1. Glycolysis
2. Fatty acid synthase
3. β-oxidation pathway
4. Alkane monooxygenase
5. Fatty alcohol dehydrogenase/fatty alcohol oxidase
6. Fatty aldehyde dehydrogenase
7. Acyl-CoA synthase

SEQUENCE LISTING

<160> NUMBER OF SEQ ID NOS: 79

<210> SEQ ID NO 1
<211> LENGTH: 1536
<212> TYPE: DNA
<213> ORGANISM: Artificial sequence
<220> FEATURE:
<223> OTHER INFORMATION: Synthetic DNA codon optimized encoding FAR from Marinobacter algicola DG893

```
<400> SEQUENCE: 1
atggccaccc agcagcagca gaacggtgca tccgcttcgg gcgttctgga gcagcttaga      60
ggcaagcatg tcttgattac cggtactaca ggatttctgg gaaaggtggt tctggagaag     120
ctgatccgaa ccgtgcctga catcggtggt attcatctgc tgattagagg caacaagaga     180
catcctgctg ccagagaaag attcttgaac gaaatcgcct cttcctctgt gttcgagcgg     240
cttagacatg acgacaacga agcctttgag actttcctgg aggagcgtgt gcactgcatc     300
accggagaag tgaccgagtc gagatttggc cttactcctg agcggttccg agcccttgct     360
ggccaagtgg atgccttcat caattccgcc gcctctgtta acttcagaga ggagctggac     420
aaggcactca agatcaacac cctgtgtctg gagaacgtgg ctgctctggc cgaacttaac     480
tccgctatgg cagtgatcca gtttccacc tgttacgtga acggcaagaa ctctggacag     540
atcaccgagt ccgttatcaa gcccgctggc gaatccatcc ccagatccac agatggctac     600
tacgagatcg aggagctggt ccaccttctg caagacaaga tctccgacgt gaaggctcga     660
tactctggca aggtgttgga gaagaagctg gtggacctgg catccgaga ggcgaacaac      720
tacggctggt ctgacaccta ccttcacc aaatggctcg agagcagct tctgatgaaa        780
gctctgtccg gaagatccct gactatcgtg cggccttcca tcatcgagtc ggctcttgaa     840
gagccttctc caggttggat cgagggcgtg aaggttgctg acgccatcat ccttgcgtac     900
gccagagaga aggtttcgtt gttccccggc aagcgatctg catcatcga cgttatcccc      960
gtggatctgg tggccaactc tatcattctc tctcttgctg aagcccttc tggatctggc     1020
cagcgtagaa tctaccaatg ttgttctggc ggttctaacc cgatttctct gggcaagttc    1080
atcgactacc ttatggccga agccaagacc aactatgctg cctacgacca gctcttctac    1140
cgacgaccca ccaagccctt cgtcgctgtg aaccgaaagc tgttcgatgt tgtcgtggga    1200
ggaatgcgag tgcctctttc cattgctggc aaggccatga gattggcggg tcagaatcga    1260
gaattgaagg ttctcaagaa ccttgacact actcgatcgc tcgctactat ctttggattc    1320
tacactgctc ctgactacat cttccggaat gactctctga tggctcttgc ttcccgaatg    1380
ggagaactcg atcgtgtgct gttccctgtt gacgctcgac agatcgactg gcagctctac    1440
ttgtgtaaga tccacctggg cggcctgaac cgatatgctc tgaaagaacg aaagctgtac    1500
agccttagag ccgctgatac ccgaaagaag gctgct                              1536
```

<210> SEQ ID NO 2
<211> LENGTH: 512
<212> TYPE: PRT
<213> ORGANISM: Marinobacter algicola

<400> SEQUENCE: 2

```
Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95
```

```
Val His Cys Ile Thr Gly Glu Val Thr Glu Ser Arg Phe Gly Leu Thr
                100                 105                 110

Pro Glu Arg Phe Arg Ala Leu Ala Gly Gln Val Asp Ala Phe Ile Asn
            115                 120                 125

Ser Ala Ala Ser Val Asn Phe Arg Glu Glu Leu Asp Lys Ala Leu Lys
        130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Val Gly
385                 390                 395                 400

Gly Met Arg Val Pro Leu Ser Ile Ala Gly Lys Ala Met Arg Leu Ala
                405                 410                 415

Gly Gln Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
        435                 440                 445

Arg Asn Asp Ser Leu Met Ala Leu Ala Ser Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala Ala
            500                 505                 510
```

<210> SEQ ID NO 3
<211> LENGTH: 1542
<212> TYPE: DNA
<213> ORGANISM: Artificial sequence
<220> FEATURE:
<223> OTHER INFORMATION: Synthetic DNA codon optimized encoding FAR from Marinobacter aquaeolei

<400> SEQUENCE: 3

```
atggctatcc agcaggttca tcacgccgac acatcctcct ctaaagtcct gggtcaactt      60
cgtggtaaac gtgtcttgat taccggcact actggattct tgggtaaagt cgtcttggaa     120
cgtttgattc gtgccgttcc tgacatcggt gctatctacc tgctgattcg tggtaacaag     180
cgtcacccgg atgctcgttc tcgtttcttg gaggagattg ctacctcctc tgtctttgat     240
cgtttgcgtg aagctgattc cgaaggtttc gatgctttcc tggaagaacg tattcactgt     300
gttactggtg aagttactga agctggtttc ggtattggtc aagaggacta cgtaagttg      360
gccaccgaat tggacgcagt catcaattct gctgcctccg tcaacttccg tgaggagttg     420
gataaggctc tggccatcaa cactctgtgt ttgcgtaaca tcgctggtat ggtggatctt     480
aaccctaagc tggccgttct tcaagtctct acgtgttacg tcaacggtat gaactctggt     540
caagttactg aatccgtcat caaaccagct ggtgaagctg ttcctcgttc tcctgatgga     600
ttctacgaga tcgaggaatt ggttcgtctg ctgcaagaca agattgaaga cgttcaagca     660
cgttactctg gtaaggtgtt ggagcgtaag ttggttgatt gggtattcg tgaggctaat      720
cgttacggtt ggtctgatac atacaccttc acgaaatggt tgggtgaaca acttctgatg     780
aaagccttga atggtcgtac cttgactatt ctgcgtccta gcatcattga atctgctttg     840
gaagaaccag cacctggttg gattgaaggc gtgaaagttg cagatgcgat catcttggct     900
tatgctcgtg agaaggttac tttgtttccg ggtaaacgtt ctggtatcat tgatgtgatt     960
cctgttgact tggttgccaa ttccatcatc ttgtctttgg ctgaggctct gggcgaacct    1020
ggtcgtcgtc gtatctacca atgttgttct ggtggtggta tcctatctc cctgggcgag    1080
ttcattgatc acctgatggc tgaatccaaa gccaactatg ccgcatacga tcatctgttc    1140
taccgtcaac cctccaagcc tttccttgct gtcaaccgtg ctttgttcga cttggttatc    1200
tctggtgtcc gtctgccttt gtctttgacc gaccgtgtct tgaagctgct gggcaactcc    1260
cgtgacctga gatgctgcg taacctggat actacgcaat ccctggctac tatctttggc    1320
ttctacacag cccccgacta catcttccgt aatgacgagt tgatggccct ggctaaccgt    1380
atgggcgagg ttgataaggg tttgttcccc gttgatgctc gtctgattga ttgggaattg    1440
tacctgcgta agattcacct ggctggtttt aaccgttacg ccttgaagga gcgtaaggtt    1500
tactctttga agacagcccg tcagcgtaag aaggcagctt aa                       1542
```

<210> SEQ ID NO 4
<211> LENGTH: 513
<212> TYPE: PRT
<213> ORGANISM: Marinobacter aquaeolei

<400> SEQUENCE: 4

```
Met Ala Ile Gln Gln Val His His Ala Asp Thr Ser Ser Lys Val
1               5                   10                  15

Leu Gly Gln Leu Arg Gly Lys Arg Val Leu Ile Thr Gly Thr Thr Gly
            20                  25                  30

Phe Leu Gly Lys Val Val Leu Glu Arg Leu Ile Arg Ala Val Pro Asp
        35                  40                  45
```

```
Ile Gly Ala Ile Tyr Leu Leu Ile Arg Gly Asn Lys Arg His Pro Asp
 50                  55                  60

Ala Arg Ser Arg Phe Leu Glu Glu Ile Ala Thr Ser Ser Val Phe Asp
 65                  70                  75                  80

Arg Leu Arg Glu Ala Asp Ser Glu Gly Phe Asp Ala Phe Leu Glu Glu
                 85                  90                  95

Arg Ile His Cys Val Thr Gly Glu Val Thr Glu Ala Gly Phe Gly Ile
                100                 105                 110

Gly Gln Glu Asp Tyr Arg Lys Leu Ala Thr Glu Leu Asp Ala Val Ile
            115                 120                 125

Asn Ser Ala Ala Ser Val Asn Phe Arg Glu Glu Leu Asp Lys Ala Leu
130                 135                 140

Ala Ile Asn Thr Leu Cys Leu Arg Asn Ile Ala Gly Met Val Asp Leu
145                 150                 155                 160

Asn Pro Lys Leu Ala Val Leu Gln Val Ser Thr Cys Tyr Val Asn Gly
                165                 170                 175

Met Asn Ser Gly Gln Val Thr Glu Ser Val Ile Lys Pro Ala Gly Glu
                180                 185                 190

Ala Val Pro Arg Ser Pro Asp Gly Phe Tyr Glu Ile Glu Glu Leu Val
            195                 200                 205

Arg Leu Leu Gln Asp Lys Ile Glu Asp Val Gln Ala Arg Tyr Ser Gly
210                 215                 220

Lys Val Leu Glu Arg Lys Leu Val Asp Leu Gly Ile Arg Glu Ala Asn
225                 230                 235                 240

Arg Tyr Gly Trp Ser Asp Thr Tyr Thr Phe Thr Lys Trp Leu Gly Glu
                245                 250                 255

Gln Leu Leu Met Lys Ala Leu Asn Gly Arg Thr Leu Thr Ile Leu Arg
                260                 265                 270

Pro Ser Ile Ile Glu Ser Ala Leu Glu Glu Pro Ala Pro Gly Trp Ile
            275                 280                 285

Glu Gly Val Lys Val Ala Asp Ala Leu Ile Leu Ala Tyr Ala Arg Glu
290                 295                 300

Lys Val Thr Leu Phe Pro Gly Lys Arg Ser Gly Ile Ile Asp Val Ile
305                 310                 315                 320

Pro Val Asp Leu Val Ala Asn Ser Ile Ile Leu Ser Leu Ala Glu Ala
                325                 330                 335

Leu Gly Glu Pro Gly Arg Arg Ile Tyr Gln Cys Cys Ser Gly Gly
                340                 345                 350

Gly Asn Pro Ile Ser Leu Gly Glu Phe Ile Asp His Leu Met Ala Glu
            355                 360                 365

Ser Lys Ala Asn Tyr Ala Ala Tyr Asp His Leu Phe Tyr Arg Gln Pro
370                 375                 380

Ser Lys Pro Phe Leu Ala Val Asn Arg Ala Leu Phe Asp Leu Val Ile
385                 390                 395                 400

Ser Gly Val Arg Leu Pro Leu Ser Leu Thr Asp Arg Val Leu Lys Leu
                405                 410                 415

Leu Gly Asn Ser Arg Asp Leu Lys Met Leu Arg Asn Leu Asp Thr Thr
                420                 425                 430

Gln Ser Leu Ala Thr Ile Phe Gly Phe Tyr Thr Ala Pro Asp Tyr Ile
            435                 440                 445

Phe Arg Asn Asp Glu Leu Met Ala Leu Ala Asn Arg Met Gly Glu Val
450                 455                 460
```

```
Asp Lys Gly Leu Phe Pro Val Asp Ala Arg Leu Ile Asp Trp Glu Leu
465                 470                 475                 480

Tyr Leu Arg Lys Ile His Leu Ala Gly Leu Asn Arg Tyr Ala Leu Lys
            485                 490                 495

Glu Arg Lys Val Tyr Ser Leu Lys Thr Ala Arg Gln Arg Lys Lys Ala
            500                 505                 510

Ala

<210> SEQ ID NO 5
<211> LENGTH: 1542
<212> TYPE: DNA
<213> ORGANISM: Artificial sequence
<220> FEATURE:
<223> OTHER INFORMATION: Synthetic DNA codon optimized encoding FAR from
      Oceanobacter sp.RED65

<400> SEQUENCE: 5
atgtcccagt actcggcttt ctctgtttct caatctctga agggcaagca catctttctc      60
actggtgtca ctggctttct cggaaaggca attctggaga agctcttgta ctcggttccc     120
cagctggcac agatccatat ccttgtgaga ggcggcaaag tttctgccaa gaagcggttt     180
cagcacgaca tcctgggctc tagcatcttc gagagactta aggagcaaca cggagagcac     240
tttgaggaat gggttcagtc caagatcaac cttgtggagg agaactgac tcaaccaatg     300 tttgacctcc cttctgctga gttcgctgga cttgctaacc agctggacct gatcatcaac     360
tctgccgctt cggttaactt cgagagaaac ctggagaagg ctctgaacat caacaccctg     420
tgcctgaaca catcatcgc tctggctcag tacaatgtcg ctgcccagac tcctgtgatg     480
cagatttcca cctgctacgt gaacggcttc aacaagggcc agatcaacga gaagttgtg     540 ggacctgctt ctggactgat ccctcagctg tctcaagatt gctacgacat cgactccgtc     600
ttcaagagag tgcattccca gattgagcag gtgaagaaga aaagacaga cattgagcag     660 caggaacaag cccttatcaa gctcggtatc aagacttccc agcactttgg ctggaatgac     720
acttacacct tcaccaaatg gctcggcgaa cagctgttga ttcagaagct cggcaagcaa     780
tctctcacca ttcttcgacc ttcgatcatt gagtctgctg tgagagagcc tgcgcccgga     840
tgggtcgaag gagtgaaagt cgctgacgcc cttatctacg cttatgctaa gggaagagtc     900
tcgatctttc tggaagaga cgagggcatc cttgatgtga ttcccgttga ccttgttgcc     960
aatgctgctg ctctttctgc tgcacaactc atggagtcca accacagac tggctaccga    1020 atctaccaat gctgctctgg atctcgaaac cccatcaagc tgaaggagtt catccgacac    1080
atccagaacg tggctcaggc ccgataccag gaatggccta agctgtttgc cgataagcct    1140
caagaggcct tcaagactgt ctctcccaag agattcaagc tgtacatgtc cggcttcact    1200
gccatcacct gggctaagac catcattggc cgagtgttcg gctctaacgc agcctcccag    1260
cacatgctga aggcaaagac cacagcttcc ctggccaaca tcttcggctt ctacactgca    1320
cccaactacc ggttctcttc ccagaagttg gaacagctgg tgaagcagtt cgacactacc    1380
gagcagcgac tgtacgacat tcgagctgac cacttcgact ggaagtacta cctgcaagag    1440
gttcacatgg atggccttca caagtacgct ttggccgatc gtcaggagct gaaacccaag    1500
cacgtgaaga agagaaagcg ggagactatc cgacaagctg cg                       1542

<210> SEQ ID NO 6
<211> LENGTH: 514
<212> TYPE: PRT
<213> ORGANISM: Artificial Sequence
```

<220> FEATURE:
<223> OTHER INFORMATION: Synthetic polypeptide encoded by codon optimized DNA for FAR from Oceanobacter sp. RED65

<400> SEQUENCE: 6

```
Met Ser Gln Tyr Ser Ala Phe Ser Val Ser Gln Ser Leu Lys Gly Lys
1               5                   10                  15
His Ile Phe Leu Thr Gly Val Thr Gly Phe Leu Gly Lys Ala Ile Leu
            20                  25                  30
Glu Lys Leu Leu Tyr Ser Val Pro Gln Leu Ala Gln Ile His Ile Leu
        35                  40                  45
Val Arg Gly Gly Lys Val Ser Ala Lys Lys Arg Phe Gln His Asp Ile
50                  55                  60
Leu Gly Ser Ser Ile Phe Glu Arg Leu Lys Glu Gln His Gly Glu His
65                  70                  75                  80
Phe Glu Glu Trp Val Gln Ser Lys Ile Asn Leu Val Glu Gly Glu Leu
                85                  90                  95
Thr Gln Pro Met Phe Asp Leu Pro Ser Ala Glu Phe Ala Gly Leu Ala
            100                 105                 110
Asn Gln Leu Asp Leu Ile Ile Asn Ser Ala Ala Ser Val Asn Phe Arg
        115                 120                 125
Glu Asn Leu Glu Lys Ala Leu Asn Ile Asn Thr Leu Cys Leu Asn Asn
130                 135                 140
Ile Ile Ala Leu Ala Gln Tyr Asn Val Ala Ala Gln Thr Pro Val Met
145                 150                 155                 160
Gln Ile Ser Thr Cys Tyr Val Asn Gly Phe Asn Lys Gly Gln Ile Asn
                165                 170                 175
Glu Glu Val Val Gly Pro Ala Ser Gly Leu Ile Pro Gln Leu Ser Gln
            180                 185                 190
Asp Cys Tyr Asp Ile Asp Ser Val Phe Lys Arg Val His Ser Gln Ile
        195                 200                 205
Glu Gln Val Lys Lys Arg Lys Thr Asp Ile Glu Gln Gln Glu Gln Ala
210                 215                 220
Leu Ile Lys Leu Gly Ile Lys Thr Ser Gln His Phe Gly Trp Asn Asp
225                 230                 235                 240
Thr Tyr Thr Phe Thr Lys Trp Leu Gly Glu Gln Leu Leu Ile Gln Lys
                245                 250                 255
Leu Gly Lys Gln Ser Leu Thr Ile Leu Arg Pro Ser Ile Glu Ser
        260                 265                 270
Ala Val Arg Glu Pro Ala Pro Gly Trp Val Glu Gly Val Lys Val Ala
275                 280                 285
Asp Ala Leu Ile Tyr Ala Tyr Ala Lys Gly Arg Val Ser Ile Phe Pro
290                 295                 300
Gly Arg Asp Glu Gly Ile Leu Asp Val Ile Pro Val Asp Leu Val Ala
305                 310                 315                 320
Asn Ala Ala Ala Leu Ser Ala Ala Gln Leu Met Glu Ser Asn Gln Gln
                325                 330                 335
Thr Gly Tyr Arg Ile Tyr Gln Cys Cys Ser Gly Ser Arg Asn Pro Ile
            340                 345                 350
Lys Leu Lys Glu Phe Ile Arg His Ile Gln Asn Val Ala Gln Ala Arg
        355                 360                 365
Tyr Gln Glu Trp Pro Lys Leu Phe Ala Asp Lys Pro Gln Glu Ala Phe
370                 375                 380
```

```
Lys Thr Val Ser Pro Lys Arg Phe Lys Leu Tyr Met Ser Gly Phe Thr
385                 390                 395                 400

Ala Ile Thr Trp Ala Lys Thr Ile Ile Gly Arg Val Phe Gly Ser Asn
            405                 410                 415

Ala Ala Ser Gln His Met Leu Lys Ala Lys Thr Thr Ala Ser Leu Ala
        420                 425                 430

Asn Ile Phe Gly Phe Tyr Thr Ala Pro Asn Tyr Arg Phe Ser Ser Gln
    435                 440                 445

Lys Leu Glu Gln Leu Val Lys Gln Phe Asp Thr Thr Glu Gln Arg Leu
450                 455                 460

Tyr Asp Ile Arg Ala Asp His Phe Asp Trp Lys Tyr Tyr Leu Gln Glu
465                 470                 475                 480

Val His Met Asp Gly Leu His Lys Tyr Ala Leu Ala Asp Arg Gln Glu
            485                 490                 495

Leu Lys Pro Lys His Val Lys Lys Arg Lys Arg Glu Thr Ile Arg Gln
            500                 505                 510

Ala Ala

<210> SEQ ID NO 7
<211> LENGTH: 3207
<212> TYPE: DNA
<213> ORGANISM: Yarrowia lipolytica

<400> SEQUENCE: 7
```

| | | | | | |
|---|---|---|---|---|---|
| atggatacccc | aggttcacgc | caaccactac | gagcaagccc | gaaaacgaaa | gtcctcctcc | 60 |
| accaccttg | tgcccaccgt | cttgcttctg | tcgccgccag | acctcccca | agcaacagcc | 120 |
| cacgcaccca | cacaaaacac | aggtggcctc | cggggctcga | tccgaggatc | catccggtct | 180 |
| ctgagggat | ctctgcgtag | acacaaacac | gacacgacgc | tacccaccat | acagacggtg | 240 |
| cctcttcagc | gagcaggaac | tcctatacag | gctcctccta | tccagaaacc | cttccaggca | 300 |
| attctttccg | gagctacaac | agtctttgac | gaccccaaaa | gtggagccct | caccgtcgcc | 360 |
| tccacccaag | catcaacccg | ccatttccac | actgctggca | ccggaggaag | cgctctttc | 420 |
| acaaacaact | ccgcccatac | actcgccgtc | gtcggcaaca | gcacctactc | aggagaaact | 480 |
| accaagagcg | cagtcggccc | caaagacaac | tcggttacaa | acagcagcag | aacgcagtcg | 540 |
| ccggcttttt | cgggaaacca | agaaagcatg | tactctccct | actcgtctgc | agtgttgtca | 600 |
| ggcctggaga | acccggtgat | cttccaggac | ccggagaagg | cagttgtcaa | gaccatcacc | 660 |
| aatactattg | acccccaggt | tcttgtagct | gcacagcaaa | agactctcac | gccccagcag | 720 |
| ccgacaacgt | ccccacgacc | cactactctc | caggacttgc | agcagccgcc | ccaagagctc | 780 |
| gtagcatctc | cactgtcctc | tgttgtcctc | aagccggcag | ccctgcagcc | cgattactgc | 840 |
| gtgtacacgg | agaacacgga | tccagaaacg | acagagattc | tcctcgacag | tggatccgtc | 900 |
| gagcccgcta | tcaactcccc | accaccccca | tctggagaag | aagaggattt | tggaattgcc | 960 |
| aacctgctgt | ttctggacgg | ctcggacgag | ttcgactaca | cgctcaacac | gtttcccaag | 1020 |
| atctccacca | tgaccaagga | ggaaatgcag | aacaatatga | cgccaattat | cgaggtggac | 1080 |
| tccactgctg | cagtttctgc | actggaaaaa | gacagaacaa | ttgctcttcc | cactcctggt | 1140 |
| gacatgccac | ctcacccct | gcccgtacac | cggtccctca | gccacatgtc | caacgtggac | 1200 |
| cttgtgcaca | acattaacat | ggagtctgcc | agcggtgctg | cgtccatctc | gacgatggga | 1260 |
| atacctccca | tcgctcccaa | ggatcgggct | ctcatggagg | agcgccggag | ccactgtctc | 1320 |
| caggagctca | ttctttccga | ggagagctac | ttgagctctc | tgcgaatgct | ggcgaacatg | 1380 |

```
tatttttgcca ccattgagtc gtgcaatgcc cttggcaagg aggctgttgc tcttttggag    1440
aacgatacac ggtcgctcat tgagtttcac caggagctac tggatgatat tcagtccgag    1500
tatcccaaca tcaccatctc caacaagcct gctgccccca cgctgcaggt caaaattacc    1560
cctggtgtca acgacttcac acgagcagtg tggacttctt tgaaggatgt ccctcctagc    1620
aatttggaaa atctggggta tcgagatgga aagtgggtca agcctgctct caccactctt    1680
tctccccagt ttgctgcccg catcagtcag cttgttgcag acaaggccat cagtctctat    1740
ctttacgaac aatactgcat caattacgac gccactattg agcttctgcg ctcctaccgt    1800
ggtacgggca aggagcggtt ctggatcaag ggctgcgaga acctgctcaa cgcagctcaa    1860
catgatggtc gccgaaagga cctctccctg cagagcctga tgattgtccc cgctgcacgg    1920
atcagtaagt acaggctact tctggagcag ctggccaaaa acacttgtcc ggttgaggag    1980
actgaatctc accttgtgat tctcgattcg ctggagaagg tggaggacaa gctgcggcag    2040
cttgaccaca atcatcttgt agagcggttc cgtcgccagt cgcacatttt gtggaacagt    2100
ctttacttca agaacgagct gcccttcagt gtgcagtatt ttggccttgc aattctctgt    2160
ggcgctctca acgtcacctg gctgggcccc gatggctcca tcaagtttca ctacatggga    2220
tgctttctct tcaagtccta cttgattctt gccaacgttg ccaaccctga gggtcgcttc    2280
tacgtcaagt tcattattcc gctgcactgt tgccgtctcg agaacccat caactcagtt    2340 gttggtctgc aaacctccag ttctttgact aagaagctga ttttcgagca aactttggt    2400 ctgtacgaga ttctgttgac tgcaaccact gttgaggagc tcaagtcgtg gcaggagaag    2460
ctagaggtgc agattctctc cgtcaatgga atctacatgt gggacttcaa ggcttcggac    2520
atgagtctgc aggggtacaa cagtgcatcg tggattcctc ccatgaagcc tcttccgtt    2580 gcttttcaga gcggtctcg atggcgaaac ttctttggaa gctacaggag cgggttcagc    2640
gatcctctgg ctctccagct caagatccaa cacttttatg tcgacggaga cctggagtcc    2700
aactatgggg cacacacggc agccacgcgt gacgagaacg atggcatcaa gtgcgagacc    2760
atccacattc gacgatacgc ccggctggag gccgagaagg ctctgggggt catttggagc    2820
atggatgacc tgcctctgat cccctcttgc aacgccgatg ataccatca gcccatcaac    2880 aatgtgcgcc acatggttcg gcgggtggcc tcgatgaaat cgactttcaa ccggggaggt    2940
cagcgacagg ggtcagcacg aggtgtcttt ggaggtaacg cagcaagag ccttccgcat    3000 gacaatgtca gtgccaagga gtgttatagc aagtacgact tgagcagcgg gacggatgag    3060
ttttttgacg ctctatcgca agctcgaagt gtatgggtca cactccttta tgacgagctc    3120
ggtcgaagtt ctcggttccc cacttttaag ctggcaggcg agcgtcttcg tcggttcaag    3180
accaaggtat ggaagcatca tcattag                                       3207

<210> SEQ ID NO 8
<211> LENGTH: 1047
<212> TYPE: DNA
<213> ORGANISM: Yarrowia lipolytica

<400> SEQUENCE: 8
atgacaatcc ccaagaccca gaaagccatt gtgttcgaaa cctctggagg tcccctggag     60
tacaaggacg tgcctgtgcc cgtgcccggc gaccatcaga ttctcgtcaa cgtcaagtac    120
tcgggagttt gccactctga cctccacgcc tggatgggag actggcctct acccaccaag    180
ctccctctta tcggcggcca cgaaggagcc ggcgtcgtgg tggccaaggg aaaaaacgtg    240
```

```
accacgttcg aaattggaga ctacgccgga atcaagtgga tcaaccaggc gtgctacacg    300
tgcgagttct gccaggaggc ctacgagccc aactgtccca aggcccagat ctcgggatac    360
acaatggacg gaaccttcca gcagtatgca cttgcagatg ctgtgcaggc agcccacatt    420
ccccagggca cagacctttc tcaggtggct cctattctgt gtgccggagt gactgtttac    480
aaggccatca agacctctgg acgaaaggca ggagaatggt tggccgtgac aggtgcagga    540
ggaggactcg gatcgctggc ggtgcagtac gccaaggcca tgggtttccg agtgctggcc    600
atcgacacca ccgaggagaa ggagaagatg tgtctggaac tgggagcaga ggtctttgtg    660
gactttgcca agactgacaa tctggtggca cgagttcagg agattactgg aggtggccct    720
catggagtca tcaacgtttc tgtgtccgag tttgccatca accagtctct cgagtacgtt    780
cggtccgttg aactgttgt tctggtgggt ctgcctgctg agctgtgtg caagtcgccc    840 atcttctcgc aggtggcccg ggctattacc atcaagggct ctcctgtggg taaccgagcc    900
gacacccagg aggctctgtc attctttacc cgaggattgg ttcactcgcc tattcatgtg    960
gtcggactgt ctgagctgca gaaggtgttt accttgatgg aggagggaaa gattgcgggt   1020
cggtatgttg tcgataccag caagtaa                                        1047
```

<210> SEQ ID NO 9
<211> LENGTH: 1050
<212> TYPE: DNA
<213> ORGANISM: Yarrowia lipolytica

<400> SEQUENCE: 9

```
atgaccacca tccccaagac ccagaaagcc gtcatcttcg agacctccgg cggccccctc     60
atgtacaagg acgtgcctgt gcccgtgcct gccgacgacg agattctggt caacgtcaag    120
tactccggcg tgtgccacac ggacctgcac gcctggaagg gcgactggcc cctggacacc    180
aagctccccc tgattggcgg ccacgagggc gccggcgtgg ttgttgccaa gggcaagaac    240
gtgaccacct tgagattgg cgactacgcc ggtatcaagt ggatcaacaa ggcctgctac    300
acctgcgagt ctgccaggt ggcggccgag cccaactgcc caaggccac catgtccgga    360 tacacccacg acggctcttt ccagcagtac gccaccgcca acgctgtcca ggccgcccac    420
atccccaaga actgtgacct cgcccaggtt gcccccattc tctgcgccgg tatcaccgtc    480
tacaaggctc tcaagaccgc tggcctcaag gctggtgagt gggccgccgt gaccggagct    540
ggaggaggcc tcggctctct ggccgtccag tacgccaagg ccatgggcta ccgagtgctg    600
gccattgaca ctggcgctga caaggagaag atgtgcaagg agctcggcgc cgaggtcttc    660
atcgactttg ccaagtccaa ggatctggtc aaggacgtcc aggaggccac caagggcgga    720
ccccacgccg tcatcaacgt gtctgtctcc gagtttgccg tcaaccagtc tgttgagtac    780
gtgcgaaccc tgggaaccgt tgttctggtc ggtctgcccg ccggtgccgt ctgcaagtcg    840
cccatcttcc agcaggttgc tcgatctatt cagatcaagg gctcttacgt cggaaaccga    900
gccgactccc aggaggccat tgagttcttt gcccgaggac tggtcaagtc ccccatcatt    960
attgttggtc tctccgagct cgaatccgtc tacaagctca tggaggaggg caagattgcc   1020
ggtcgatacg ttctggactg ctccaagtaa                                    1050
```

<210> SEQ ID NO 10
<211> LENGTH: 1053
<212> TYPE: DNA
<213> ORGANISM: Yarrowia lipolytica

<400> SEQUENCE: 10

```
atgtctgaat tcgctcacga agaaaagttt ctcaaggcca agtcctctct gaacattgac      60
aacattgtca agctcgcaga caagatcctg ctcaaccctc tgtttgcagg cgccgccctg     120
gccctgtctt accagaatgg tgacctttac gagaacctgc cccgattcgc tggcattgct     180
ggcgctggca tcctcaccac catcctctac ttcttccgag tcatctctcg acgatacctg     240
aagatcaagg gctggaagct gacttcccga gatgttgcgg tcatcaccgg aggctccaac     300
ggtctcggac attacattgc ctatgagctg tccaagcgag gcgtgcgatg tgccattctc     360
gaccgagaga agcccgcccg aaccctgccc ggttccacct actactactg tgacctcact     420
gacaagaccg tcattgacaa ggccttcgcc gaggtgcagc gagacatggg tcccatctcc     480
attctggtca acaacgccgg tatgatgtgc gagcagcgag tccaggacct caacgagaag     540
ctcattcgaa acctgttcga ggtcaacatt gtctcgcact ctggaccct gcaggccgtc      600 atccccgact cctcaagta caagcgagga tgggtcgtgt ctgtcgcctc caccgtcggt      660
ctcattggac ccggccacat gtctgcctac acctcttcca acatgccgt ggtcggtctg      720 catgactcca tcacccacga gcgaggtctt gctggcaagg tcggaactac ccttgtgtgc     780
cccggtcaga tgaacacccg tctgtttgcc gatctgtcca ctcccaccaa gttctttgct     840
cccgtcgttg agtcccaggc tctggccaag atcattgtcg acaacattgc caacggccag     900
cgaggcgagg tcattgagcc tctgtacgcc agactcaccc ctctggctcg aatcgtgccc     960
cactggctgg ccgacttctg ccgatgggcc accaacctcg atggctgcat ggaggaggtt    1020
gagcacaaga aggtgggccg aggagagctg taa                                 1053

<210> SEQ ID NO 11
<211> LENGTH: 900
<212> TYPE: DNA
<213> ORGANISM: Yarrowia lipolytica

<400> SEQUENCE: 11
atggccgaaa acgataacgt cgctcacgcc cttgccggcg ccggaggagg agccctctca      60
atggtcgtca cctaccctct catcactctg tccacccgag cccagaccga gtccatgcga     120
accaagaagg actccaaagc tgagacgctg tctgccctgg ctgccgcccg gaagatcgtc     180
aagcgagagg gtatcgctgg tctgtactcc ggtctggact cggctctgtt cggtatctcc     240
gtcaccaact tcgtctacta ctacttctac gagtcgtcac gaaccatctt ccagctctcc     300
aaggccgctg ctggagctgc cagcatgaac ctgaccactg gtgagtccat gctcgccggt     360
gccgttgctg gatccgccac cgtcgttctg accaacccca tctgggtcgt caacacccga     420
atgactgtgt ccgagaagaa gcagggcact ctcgccacca tcaaggagat tgcctccaag     480
gacggcctca gacctttctt ctccggcatt gctcccgccc tggtgcttgt catcaacccc     540
attctccagt acaccatttt cgagcagctg aagaaccgag tggagaagcg acgaaagttc     600
acctccatcg acgccttcct ctacgcgccc ctgggcaagc ttgtgccac caccgtcact      660 tatccttaca tcaccctcaa gtctcgaatg caggtcaagc agaaggacgg ccagcagctc     720
aacttcctgt ccggaattaa aaagatcatc aacgacgagg gcattgccgg tctgtacaag     780
ggtctggaca ccaaggtggt gcagtccgtg ctcacctccg ccttcctttt cttcttcaag     840
gagcagcttt tccactttgc catcatcttc ctggccattc tgcgaagctt ccgaaagtaa     900

<210> SEQ ID NO 12
<211> LENGTH: 1797
<212> TYPE: DNA
```

<213> ORGANISM: Yarrowia lipolytica

<400> SEQUENCE: 12

```
atgtcaatca ttcacaaatc gccggtgccg gacgtgcaac tgttctacgg ctcgtggccg      60
gatctgatgc gaacgtcgcc acacgcccac aacgactcca aaccggtggt gttcgacttt    120
gacaccaagc agcagctgac gtggaaacag gtgtggcagc tgagtgcgcg gctccgggcc    180
cagctgtacc acaagtacgg catcggtaag cccggcgctc tggccccgtt ccacaacgac    240
ccctctctcg gcgacgtggt catcttctac acgcccaaca cttacagctc gttgccctac    300
cacctggctc ttcacgatct gggcgccacc atttcgcccg ccagcacctc gtacgacgtg    360
aaggacatat gccaccagat tgtcaccacc gacgcggtcg tggtggtggc tgcggccgaa    420
aaaagcgaaa ttgcccgcga gcggtccag ctatcgggca gagacgtgag ggtcgtggtc     480
atggaagacc tcatcaacaa tgcgcccacc gttgcgcaaa acgacattga ctcagccccg    540
cacgtgtccc tgtcccggga ccaggcgcgg gccaaaatcg cctacctggg aatgtcttca    600
ggcacgtccg gcggactgcc caaggcggtc cgtctgaccc acttcaacgt cacctccaac    660
tgtctccagg tctccgccgc cgcccccaac ctcgcccaga acgtggtcgc cagcgccgtc    720
atccccacca cccacatcta cggcctcacc atgtttctgt cggtgcttcc ctacaacggc    780
tcggtggtga tccatcacaa gcaattcaac ttgagagatc tgctggaggc gcaaaaaaca    840
tacaaggtga gcctgtggat tctggtgccg cccgtcatcg tccagctcgc caaaaaccccc   900
atggttgacg agtacctgga ctctattaga gcccatgtgc ggtgcattgt gtctggagcc    960
gctcctctgg gtggaaatgt cgtggatcag gtctctgttc gtcttacagg caacaaggaa   1020
ggcattctgc caacggaga caagctggtc attcaccagg cctatggctt gaccgagtcg   1080
tcccccgatcg tcggcatgct cgaccccctg tctgaccaca ttgatgtcat gaccgtgggc   1140
tgtctcatgc ccaacactga ggcccgaatc gtggacgaag aaggaaatga tcagcccgcg   1200
gtccacgtga ccgacacccg aggtattggc gccgctgtga gcggggcga aaagattccc    1260
tccggagaac tatggattcg aggtccccag atcatggacg ataccacaa gaaccccgag    1320
tcgtcacgtg agtcgctgga gcccagcacc gagacgtacg tctgcagca cttccaggac    1380
cggtggctgc ggactggaga cgtggctgtc attgacacct tggccgtgt catggttgtg    1440
gatcgaacca aggagctcat caagtccatg tctcgacagg tggctccggc tgagctcgag   1500
gctcttcttc tgaaccatcc ttcggtgaac gatgtggctg tggttggcgt tcacaacgac   1560
gataatggca cagagtctgc gcgggcgttt gtagtgcttc aaccgggcga cgcatgtgat   1620
cccaccacca taaagcactg gatggaccag caggtgccga gttacaagcg gctgtatggc   1680
ggcattgtgg tcattgatac tgtgcccaag aatgccagtg caagattttt gcgaagattg   1740
ttgagacagc ggagagatga tagggtgtgg gggttggcca aggtggcgaa gctgtaa      1797
```

<210> SEQ ID NO 13
<211> LENGTH: 1026
<212> TYPE: DNA
<213> ORGANISM: Yarrowia lipolytica

<400> SEQUENCE: 13

```
atgaaagcag ctttcacaac aggatacggt ggtcctgaga agatcgagta cgctgaggat       60
ctgccaaaaac cccagcttgc cgacgaagac cacgtcatga tcaaagtagc agctgcctcg    120
ctgaatccca ttgacggtgt tcgaaacagg ggctatctgc ggttcttagt gtccgacaag    180
caccctcata tcttcgggta cgacgtggca ggcgttgttg aggatgcggg ccctaaggca    240
```

```
gacgggttca gcgtgggtga cagagtctac agtcggatcc cacttggccc tcaaggtact      300
gtggcggaat atgtgagtgt caagggagag tttgtatcac ttgcaccttc aaacgtgtct      360
ctttccgacg ccagcagttt ccctctggtg ggtttggctg tggtacaggc ttttcgagct      420
ggcaacctga agaatggcca gaccatcttc atctcaaaag gtgctggtgg agtcggcact      480
tttgcgatcc agctggccaa acatgtgtat ggctgccacg tcatcacaac agccaccgag      540
gacaaggcgc agctactgcg ggacctgggc gcagacgttg tgattgacta cacaaaggtg      600
aattttcgcc aggtggtcaa gaacgtggac ttcagcttcg acgtgtccaa cgagccttat      660
gcccacgccg ccatcacgaa gcgaggcggc tacgtggttc tctgagagg tattccgtct      720 cctgaagcta ttcacgacac gttcaactat gaggttccgt tgtgctcgc caaggcgctc      780 aaggtagtga atgttactgc atacgccatt cgacggctat atggagtgca atatcatgct      840
ttctcgggtc gaccttccgg agccgatctg gctgaaatca aggagtacat cgagaaaggc      900
cagatcaagc ccgttattga taccatgttt gatattcgca atgcccgaca ggccatggag      960
aaggtggagg gtggtcattc caccggcaaa gtcgttgtga gggttgatac tagtgttgac      1020
atgtag                                                                 1026

<210> SEQ ID NO 14
<211> LENGTH: 1041
<212> TYPE: DNA
<213> ORGANISM: Yarrowia lipolytica

<400> SEQUENCE: 14
atgcgaagcc tatatataaa cgttccgggt cttttttcctt ccacctctct agcacgagaa      60
acagtccacc acagaacaga aatgctccga accatccgat cttcctctcg acttggcgtc     120
cgagccatgt ctaccgctgc cacccgacga gctgcccaga ttggcttcca cacccgagtc     180
cccactgtcg tcaccaaggc ccccaccctc cgaatgcaga ccaccccttt ctcttcctct     240
gctcccgccc agacctttgg tgacaagaag tacgagcaca tcctgacctc cacccccgtc     300
cccaaggtcg ctctcgtcac cctcaaccgg cccaaggccc tcaacgccct gtgcactcct     360
ctcattaagg agctgaacga ggctctccag gctgctgatg ccgaccccac cattggcgcc     420
atcgttctca ccggatccga gaagtccttt gctgccggcg ccgacatcaa ggagatgaag     480
gacaagaccg tcacttccgt gctcaacgag aacttcatcg aggagtgggg caacatggcc     540
aacatcaaga aacccatcat tgctgccgtc aacggctttg ccctcggtgg tggatgcgag     600
cttgccatga tggccgacat catctacgcc ggcgccaagg ccaagtttgg ccagcccgag     660
atcaagcttg gtgtcattcc cggagctgga ggaacccagc gactcacccg agccattggc     720
ctctaccgag ctaaccacta cattcttacc ggagagatgt tcactgctca gcaggctgct     780
gactggggtc tggccgccaa ggtctacgag cccgcccagc tcgttgacga gtccgtcaag     840
gctgctgctc agatcgcctc ttacggccag ttggctgtcc aggccgccaa ggcttctgtc     900
caccagtccg ctgaggtcgg tctccgagcc ggtctcgagt ttgagcgagt ccgattccac     960
ggtctctttg gcacccacga ccagaaggag ggcatggctg cttttgccga gaagcgagag    1020
cccaacttca agaacgagta a                                               1041

<210> SEQ ID NO 15
<211> LENGTH: 1596
<212> TYPE: DNA
<213> ORGANISM: Yarrowia lipolytica
```

<400> SEQUENCE: 15

```
atgctacaac tctttggcgt ccttgtgttg gcgctgacaa ccgctctgct cgcccagctg      60
gcctacaaca agtatgaata caaccgcaag gtgaagcagt ttggctgtgg tgaactaacc     120
gtcgcgaaga acggctttt gggctggaag ggaatccgag cagtgctcca tgtgctcaaa     180
accaagaagg gaccagctgc tcttaaggag cgaatcgatg cgtatggacg aacctatgtc     240
tttcacattg gccctgcccc tgtgatttcc accatggagc tgagaacat caaggcaatg     300
ttggcgactc aatttaagga cttttctctg ggaactcgat acagatccct ggctcctact     360
cttggagacg gaattttac tcttgacggt catggatgga cccactctcg agctcttctc     420
cgacctcagt ttgcccgaga gcaggtttct cgactcgact cactcgaagc tcattccag     480
atcctgaaaa tgtgcgttga taaggagatg cgagagaagg gaaacgatcc cagaggattt     540
gacatccaga acctcttctt cctctttact ctggactctg ctaccgagtt tttgtttggt     600
tcttcggtgg actcgcttgt ggacttcctc gacgacccct cagtgcgcac gggagaccac     660
ggaggagtcg acgaggctgc tcgaaagggt ttcaacaact ccttcaatca cgctcaggaa     720
ttgtgtgccc tgcgatcccg actacatact cttactgga ttgtaggatc cgttgtcaag     780
aaggagcctt ttgagcggta caacaaggag atcaagactt ttgtggattt tttcgctgcg     840
aaggctctga aggcccgaaa ggagaaggac atgtctctca tggacaatga tcagtacatt     900
tttatgtacg agttggtcaa ggaaaccacc aaccccgtca cctcagaga ccagatgctt     960
aacattctcc ttgctggacg agataccacc gcctccatgt tgtcgtggat ctactttcga    1020
ctggctcgag accccaagct gtacgctaag ctccgaagtg ctattcttga agactttgga    1080
accactcccg aagccatcac tttcgagtct ctgaagcaat gtgactatct ccgatacgtt    1140
cttaatgagg cccttcgact ctaccccgtt gttcccatca acggaagaac cgccactcgg    1200
gacactactc ttcctagagg aggtggaccc gaccagtccc agcccatttt cattcccaaa    1260
ggccagaccg tgtcttactc tgtttactgg actcaccgag accctcgatt ctggggcgag    1320
gatgctgagg agttcattcc tgagcgatgg gatcctcgaa cggcaacat ggccgaggg    1380
tgggagtacc tgccgttcaa cggtggtcct cgaatctgcc ttggtcagca gtttgctctt    1440
accgaggttg gatacgttct gagtagactg gttcagacat atgagacact tgagacttgt    1500
gaccacaagc ctctgccccc tctgtacaac catgctctta cgatgtgcca tgaggagggt    1560
gtttgggtca agatgtataa gggtgagaag gcgtag                              1596
```

<210> SEQ ID NO 16
<211> LENGTH: 1830
<212> TYPE: DNA
<213> ORGANISM: Yarrowia lipolytica

<400> SEQUENCE: 16

```
atgtctgacg acaagcacac tttcgacttt atcattgtcg gtggaggaac cgccggcccc      60
actctcgccc ggcgactggc cgatgcctgg atctccggta agaagctcaa ggtgctcctg     120
ctcgagtccg gcccctcttc cgagggtgtt gatgatattc gatgccccgg taactgggtc     180
aacaccatcc actccgagta cgactggtcc tacgaggtcg acgagcctta cctgtctact     240
gatggcgagg agcgacgact ctgtggtatc ccccgaggcc attgtctggg tggatcctct     300
tgtctgaaca cctctttcgt catccgagga acccgaggtg atttcgaccg aatcgaagag     360
gagaccggcg ctaagggctg gggttgggat gatctgttcc cctacttccg aaagcacgag     420
tgttacgtgc cccagggatc tgcccacgag cccaagctca ttgacttcga cacctacgac     480
```

```
tacaagaagt tccacggtga ctctggtcct atcaaggtcc agccttacga ctacgcgccc      540
atctccaaga agttctctga gtctctggct tctttcggct acccttataa ccccgagatc      600
ttcgtcaacg gaggagcccc ccaggggttgg ggtcacgttg ttcgttccac ctccaacggt     660
gttcgatcca ccggctacga cgctcttgtc cacgccccca agaacctcga cattgtgact      720
ggccacgctg tcaccaagat tctctttgag aagatcggtg gcaagcagac cgccgttggt     780
gtcgagacct acaaccgagc tgccgaggag ctggccccta cctacaaggc ccgatacgag      840
gtggttgtgt gctgcggctc ttatgcctct ccccagcttc tgatggtttc cggtgttgga      900
cccaagaagg agctcgagga ggttggtgtc aaggacatca ttttggactc tccttacgtt      960
ggaaagaacc tgcaggacca tcttatctgc ggtatctttg tcgaaattaa ggagcccgga     1020
tacacccgag accaccagtt cttcgacgac gagggactcg acaagtccac cgaggagtgg     1080
aagaccaagc gaaccggttt cttctccaat cctccccagg gcattttctc ttacggccga     1140
atcgacaacc tgctcaagga tgatcccgtc tggaaggagg cctgcgagaa gcagaaggct     1200
ctcaaccctc gacgagaccc catgggtaac gatccctctc agccccattt cgagatctgg     1260
aatgctgagc tctacatcga gctagagatg acccaggctc ccgacgaggg ccagtccgtc     1320
atgaccgtca tcggtgagat tcttcctcct cgatccaagg gttacgtcaa gctgctgtcc     1380
cccgacccta tggagaaccc cgagattgtc cacaactacc tgcaggaccc tgttgacgct     1440
cgagtcttcg ctgccatcat gaagcacgcc gccgacgttg ccaccaacgg tgctggcacc     1500
aaggacctcg tcaaggctcg atggccccg gagtccaagc ccttcgagga aatgtccatc     1560
gaggaatggg agacttacgt ccgagacaag tctcacacct gtttccaccc ctgtggtact     1620
gtcaagcttg tggtgctaa tgataaggag gccgttgttg acgagcgact ccgagtcaag     1680
ggtgtcgacg gcctgcgagt tgccgacgtc tctgtccttc cccgagtccc caacggacac     1740
acccaggctt ttgcctacgc tgttggtgag aaggctgccg acctcatcct tgccgacatt     1800
gctggaaagg atctccgacc tcgaatctaa                                       1830

<210> SEQ ID NO 17
<211> LENGTH: 414
<212> TYPE: DNA
<213> ORGANISM: Yarrowia lipolytica

<400> SEQUENCE: 17
atggattccc gatcagcctc caactcggcc acgccgccca ccgccgggtc gcccgagagc       60
gccaaaaagt ctgcgcgccg aaagtcgacg gtgcagccca tgccgcgggc ccagaagccc     120
aagggcgagc tgctgacggt ggaggagaag aaggccaacc acattgccag cgagcagaag     180
cgccgtcagg cgatccgcga ggggtttgag cgcatcacca agattgtgcc caacctggac     240
aagagccagg gccggtccga ggcgattgtg ctcaataaga cggtggcctt tttgaagaac     300
ctcattgcgg agggcaagga gctcgagctg cggtgcaacg agctgcaaat tgtcactcct     360
ccgccggcgg gcatgtccaa ggagaaggtc aagaaagagg agtctccggt ctag           414

<210> SEQ ID NO 18
<211> LENGTH: 1431
<212> TYPE: DNA
<213> ORGANISM: Yarrowia lipolytica

<400> SEQUENCE: 18
atgtcttctt ctccaacctc gtaccacacc atgacttcac attcgaccgc gcccacggag       60
```

```
ccgctgagcc cgagcgcag tgtgtccacg acatggaca acagcctgca aagccaggaa    120
cacgagattc cgtcgttcca gaaaaacgtc aacaaccacg gcagactgcc gttgaccatc    180
cagcccacca aaggcagatt cgacactctc acggccaagc agatggaacg actcaagcag    240
ctgtgggccg tcctgctcaa ggccatgaac gtgacccaga aggtcatcga ggtgggcaca    300
caaacgtcgc tgcctcccac acgagtcaga tcaagtgggg gcacaggcgc agacagcatt    360
tcatccacgt cgacacgcga gtcggaaatg agctcggcgt ccagaaagaa gaaacacgca    420
cccgaacatc ttgccaacct gtttctagaa cgcctcgagc cggaggaggt caagcaggcg    480
ctgtggcaca tggctcgaac cctcactccc gacaacctct tgtgtcggtt cctgcgcgcg    540
cggcgatggt cggtgccccg cacatgtgtg ctgctcgaaa aagcaatgta ctggcgcatg    600
aaggagtctg tctcgacga gctgcagttc cggggcgaga ttggggcctt cagaagcaac    660
gatattgact acatcaacca gtaccggtca aaaaagtcgt acattcgggg cagagacaag    720
gcgggccgtc ccgtcattca gatttacaca cggcgacatt tcaaaacaga ccagtcagtc    780
aagtgtatta aggacttcac tctggccgtg tttgaggcgt ctctgctcat gttggacgat    840
tacaacgaca atgtcacctt cctctttgac atgaccgact ttaccctctt caacatggac    900
tatccttaca tgaggcatct gttgaagatg ttccagatct tctatcccga atctctgggt    960
ctactgctgg tccacaatgc accttgggtc tacgagggtg tctacaacat catcaagcat   1020
tggatggagc cctgtgtcac ctccaagttc aagttcacca gaaccctcaa agagctgtca   1080
cagtacattg atatggacca gatccccgaa ggtatgggag aacggatca gtggaactac   1140 gagtacattg agcctcgaga gcatgaggct gacaagctgc aggaccattt tggccgagaa   1200
gctgctcttc aggagcgatc catgctcacc caaaaggtgg aaaagaacac tgtcgagtgg   1260
ctccaggcgg tgcctggcag cgaggccgag ggagagacgc ttgatgagcg acgagtcatg   1320
atcgacgagc tgagagacca gtattggacg gttgatcggt acatccgagc tgtgactgtg   1380
agtgatcggt taggtcaaat tcctgccacc agagggcaag tgcatgctta a            1431
```

<210> SEQ ID NO 19
<211> LENGTH: 1233
<212> TYPE: DNA
<213> ORGANISM: Yarrowia lipolytica

<400> SEQUENCE: 19

```
atgacagtag ccacacaagc aggacgatac ggcaacctga ccccgaaca gaccctcaag     60 ctcaaggaca tgtgggccca tcttctgggc gccatggag ttctggacga gaccaccgcc    120
aagcagctgt ctgcttctgt gcacaccgga ggcgcggccg cctctgaggc tccggccccc    180
aagaagtctg gaggaggcct gtttggccga agaaggcag ccccgagcc ggaggaggat     240 ctgtctaacc aggcctcgtt caaggacgtg ctgggcacaa tctccattga gcagctgcga    300 ctggcttttct ggaacatggt gcgatgcgac aaccccgaca acctgctgct gcgattcctg    360
cgagcccgaa agtgggacgt gcccaaggcc ctgtccatga tggccgccac cttcaagtgg    420
cgtctccagg agggcgacgt tgaggagatt gagtttaagg gcgagctggg agccctaaag    480
gagaacgacg aggagttcct gcttcaattg cgatctaaga aggcctacat ccacggccga    540
gacctcgagg gccgacccat tgtctacgtg cgacctcgat tccacaaccc caaggcccag    600
aaggagaagt gcattgagaa cttcaccgtc cacatcatcg agaccgctcg actgaccctc    660
aacgaccctg ttgacaccgc cgccgtgctc ttcgatcttt ccggctttgc tctctccaac    720
atggactacg ccgccgtcaa gttcatcatc aagtgcttcg aggcccacta ccccgagtgt    780
```

```
ctgggagttc tgctcatcca caaggctcct tggatcttct ctggaatctg gaacatcatc    840
aaaaactggc tggaccccgt ggtggcttcc aagatccact tcaccaagaa cacctcggac    900
ctcgagaagt acatccccaa gaaatacatc cccaaggagc tcggtggaga cgatccgttt    960
gtctacgagt acattgagcc caaggagggc gagggcgacc gacttcagga cgaggccact   1020
cgaaacaaga tgctgcagga ccgaatccag atctactcgg gcctggagaa gaacaccatt   1080
gactggatca agtccaccaa gcagaccgag ggtcctcttc tgcaggagcg atctgagctc   1140
accaagaagc tgcgatctca gtactggcag attgatcctt atctccgagc tccttccatt   1200
ctcgaccgtc tcggagaaat tacttacgct tag                                1233
```

<210> SEQ ID NO 20
<211> LENGTH: 1017
<212> TYPE: DNA
<213> ORGANISM: Yarrowia lipolytica

<400> SEQUENCE: 20

```
atgcccccgaa caggaatcgc ccaggtcgtg gagaaccaca aactgactct caaagagccc     60
acggtcaaaa ttgacactcc taaagacgtg gtggtcaagg tcgaatttgc tgcccagaac    120
cccattgatg tgcgaaccta tgatctgaaa cagatccccg acggagagat cgccggccga    180
gatctcgttg gaattgtgga cgtgattgct ccgaagttgt ggacaagga gctcaaggga     240 actcgaattg ctgcttttgc caatggaagc actccctcca agtctggagc gtttgctcaa    300
tgggccattg ccaaggacga gatctacgtg gtcattccg ataacattgc tcctgaggca     360
gctgccactc ttcccgtggg cttttttcacg gccgttcacg gcctttactt gcctcacaag    420
ctgggtcttg agagaggagg cagtaagtcg gagctcgtgc tcatctgggg tggaaactcg    480
tccgttggcc gatacgccat tcaattggcc aagctgggag gccaccgagt catcaccgtg    540
gcgtctcctg cctctgctga cgaactcaag gctctgggag ccgaaaaggt gtttctcttac    600 aaggacgctg atgttgtgga gcagattcga aaggagtatg gcgacattcc caatgtccta    660
gacgccattg gaaccctga ttcagccaca acgtcctcta agactactgg aagctctccc     720
gcaaagtaca ccaccgtgcg tcgaaacgca gagcacacgg aaaacttccc caaacacatt    780
actgtgtcgc ccatccaggc ctaccgagtc tttgatcagg agcatcttcc cgaggtgact    840
attgccaagg agtatgctaa gctgctgact ggttggctca aggagggcaa gattgttcct    900
aacaaaccaa aggtgcttgg aggcctggag aaggtcgaag agggttacca gctccatcgg    960
gacggtaaga ttcatggaga gaagctcgtt tatgacattg ctaagacaaa gctctaa     1017
```

<210> SEQ ID NO 21
<211> LENGTH: 1041
<212> TYPE: DNA
<213> ORGANISM: Yarrowia lipolytica

<400> SEQUENCE: 21

```
atgagagccg ctttcaccac cgcgtacggc ggtcccgaca agatcgagta ctccgattct     60
ctgcccaagg tgaagcttgg aggtgacgac cacgtgctca tccgagttgc cgacgcctcc    120
atcaacccca ttgatgggct gcgaaaccga ggaatgctgc gtattctcat gtgtgacgac    180
catccccacg tcttttggata cgacgtcgga ggcttcgtcg aagaggtcgg ctccaagtgc    240
accaacctca aggttggcga ccgagtctac ggccgaattg cgagtctca gagcggcacc    300 ctcgccggct acgtttctgc ccaggagagc gtcattgccg tggctcctac taacctgcct    360
```

```
ctgagcgaga ctgctggtgt gcctttggtt ggtctcactg cctaccaggc tctgagagcg    420
ggcgatgtgc agcctggaca gcgagtcttc atctccaagg gcgctggagg agttggaacc    480
atcgctatcc agctcgccaa gcacgtcttt ggagcttatg tcattactac tggttcggac    540
cacaaggcca gcttctcaa agagcttgga gctgacgagg tcatcaacta ccgaaaggaa    600
aagttccagg acgtgatcaa ggagccagtc gactttgcct ttgacgtttc cgacgagcct    660
gccgcacatg caaagatcac caagaagaac ggattcgtgg cggctctgcg aggagctcct    720
tctcccgcta ctgccaagaa gattctggcc caccctcctg gattcctcat gaacaacgtt    780
ctgcgagccg ctaactttgc aacctcccga actgcctggt ggtacggagt ccgatacgag    840
gccatctact gcgttccttc tgctaaggat ctggacactc tgcgaggcta ccttgaaaag    900
ggtactatca gcccatcgt tgactgcact tatgacctca aggatgccaa gctagcaatg    960
gagaagcttg agagtggacg agctaccggc aagatcatcc ttagtgtgga tgatactctt   1020
gataaggagt tcaagcagta a                                             1041

<210> SEQ ID NO 22
<211> LENGTH: 2211
<212> TYPE: DNA
<213> ORGANISM: Yarrowia lipolytica

<400> SEQUENCE: 22
atggaccgtc tcaaaacgtc ggctgtgggc caaaaggtgg tgtcgtacgt gagcgcgcgg     60
tcgcccgtat ggggcgcgac ctatctgcgc cacagatcga aaatcctctg gtctatctac    120
atggtgcttt ttctgtccaa ttttgctgga gtgggctcca agcgcagcaa gaaaaaggcc    180
aggaaggagg agaaggagga ggagcgcaag gccgagcgcg aggtgctggg ctcggccaac    240
gccattccgg aaaagaaggt caagagcgaa atcaacagag agttctttct caagttcaaa    300
cgggtcatca aggtcatgtt tccgaacggc ctgcgatcca aggagttctg gctgctgtgt    360
ctgcacacca tgtttctcat catgcggtcc gtcatctctc tgtacgtggc caatctggat    420
ggtaaactgg tttccgatct ggtcagaggt aaaggccggg cctttctgtg gggaattgtc    480
tggtggatgg ttgtgtctgt gcccgccacc ttcaccaact ccattctctc ctacctccag    540
tgcattttgg cgctgagata cagaaacaac ctgacccagc acattgtggg cgagtatctg    600
cccgaaagcg gtaaccccgt ctactactcg atccataatc tcgacgaccg aatcaaaaac    660
gctgaccagc tcatcgccgt tgatgttcaa cggctctcac actccgtttc ccatctctac    720
tcgaacctcg caaagcccac gctcgacatg ttcctctact cgtggtcgct gtctcgaaac    780
cttggaggag aaggcatgct tttggtaggt ttcctgatcc agggctccgc cgtcgtcatg    840
cgagcgctca cacctccctt tggccgatac gccgccaccg aggcagccct ggaaggagag    900
ttccgattcg aacacactcg tctgattgag tacgctgaag aggttgcact ttacaacggc    960
caggagcacg agaagacaat tctcgacaag ggatactttg cgctgattaa acacaagaac   1020
cgaattctcg tccgacgact gtaccattcg ttcatggagg attttatcat caagtacttc   1080
tggggagctc tgggtctggc tctctgttcc atccccatct tcttcaaggt acctggcgtg   1140
gacgttgctt ctgccgcagc ctctggctcc gaacgaaaa agtttgtcac caacagacga   1200
atgcttctgt cgtgttccga cgcctttggc cgaatcatgt tttcgtataa ggagattgcg   1260
cagctgtccg gctacactgc ccgagtggtg gcgttaatgg acgtaatgga ggatatcaag   1320
catggcaact ttgacaagaa ccagatttcc ggcaagcagg tggacgcccg gcacgaaaag   1380
acactggctt ctgtcactga gtcgtcgctc gtcaagaccc gatactccga cccctctgag   1440
```

```
gcttctggaa agaccatcat tggctcggac atcatctttg accgtgtccc tgtggtttct    1500
ccctctggcg acgtgcttgt tccggagttg tcgtttgagg tcaaatatgg gcgccatcta    1560
ctcatcgtgg gacccaacgg atgcggaaag tcgtctctgt tccgaattct cggaggactg    1620
tggcccgtct acgctggtac gctcactaaa cctccctcat cagatatctt ttacattccc    1680
caaagacctt atctctctcg aggtactctt cgacagcagg tcatctaccc ctctaccgag    1740
gccgagaaca agacttccga caaagagctg aagaaattc tcaagattgt caagattgat    1800
cacattgtgg aggctgttgg aggctgggat gccgagcgag agtggcgaga agacctgtcc    1860
atgggcgtac agcagcgaat cgctatgcgc cgtctcttct accacaagcc gaagtttgcc    1920
attctcgacg agtgtacttc ttcggtgacc gccgatatgg agtatgtcat gtacacgcat    1980
tctcaggagc tgggcatttc tctgctgtct gtgtcgcatc gaacttcgtt gtggaagtat    2040
cacgatctta ttctccagtt tgatggccag ggtggttatc tctttggcga cctggacccc    2100
gaagagcgac tcaaggttga ggaggagagc cgacagctga tgcttacat tcgaagcgtt    2160 cctgatatgg aagaacgtct agcaatgctc aaggcgtctg ttgctcagta g            2211

<210> SEQ ID NO 23
<211> LENGTH: 939
<212> TYPE: DNA
<213> ORGANISM: Yarrowia lipolytica

<400> SEQUENCE: 23
atggaaatca ccccggaaaa gctggagttt cacgctccct tcactaagca cacatccaac     60
aatctggagc tgcgaaaccc tactaacgag tactttgcct tcaaggtcaa gaccacagcc    120
cccaagttgt tctgcgtccg accaaacgcc tccattgtcg cccccaatga gagcctgacc    180
gtgtccatta cccaccaggc cctcccccag gagcccggtc ccgactacac ctccaaggac    240
aagttcctga ttctgtcggc acctctcaac gaggctgccg tccaggccgg tgagaacctc    300
gccaactttg ttgagaagac taaggagaac attgccgagt tctggaccca ggccgaacac    360
accaagtccg tgcccatcac cagcaaaaag atgaaggtgc aggtgcgacc ctttgacgcc    420
aacggtcagc actctcacga gctcggagcc ggaggcgccc cccttggagc tggggccgtg    480
gctggaggtg cccttggcca cagcgcctct cgaggcgacc agactctcgg cgacgagtcc    540
tttgccaact acgaggctgc cgcccagtct cctgctcccc actcccctgc caaccagcag    600
tttaacaact ccagcagca gcagcagcaa cactaccagc agcaggttcc ctcctctgcc    660
tccggtattg cttctcatcc gaccgaggcc gtcaaccgag gcgctgaggc cgttggtgct    720
ccctctgcct cctctcaggt ccactcccag gactctgctg cccttggaca ggcacaggac    780
aacatttctt ctctcaagaa ggacatcgga agcacctctg agaagcatac tgttccctct    840
acccaaacct tcaggctgt cggctcccag ggtgtgcctg ttggagttgt tgctattgtt    900
gctctcctgg ctcttcttgt tggatggttc ttcttatag                           939

<210> SEQ ID NO 24
<211> LENGTH: 1581
<212> TYPE: DNA
<213> ORGANISM: Yarrowia lipolytica

<400> SEQUENCE: 24
atggaagtcc gacgacgaaa aatcgacgtg ctcaaggccc agaaaaacgg ctacgaatcg     60
ggcccaccat ctcgacaatc gtcgcagccc tcctcaagag catcgtccag aacccgcaac    120
```

| | |
|---|---|
| aaacactcct cgtccaccct gtcgctcagc ggactgacca tgaaagtcca aagaaacct | 180 |
| gcgggacccc cggcgaactc caaaacgcca ttcctacaca tcaagcccgt gcacacgtgc | 240 |
| tgctccacat caatgctttc gcgcgattat gacggctcca accccagctt caagggcttc | 300 |
| aaaaacatcg gcatgatcat tctcattgtg gaaatctac ggctcgcatt cgaaaactac | 360 |
| ctcaaatacg gcatttccaa cccgttcttc gaccccaaaa ttactccttc cgagtggcag | 420 |
| ctctcaggct tgctcatagt cgtggcctac gcacatatcc tcatggccta cgctattgag | 480 |
| agcgctgcca agctgctgtt cctctctagc aaacaccact acatggccgt ggggcttctg | 540 |
| cataccatga acactttgtc gtccatctcg ttgctgtcct acgtcgtcta ctactacctg | 600 |
| cccaaccccg tggcaggcac aatagtcgag tttgtggccg ttattctgtc tctcaaactc | 660 |
| gcctcatacg ccctcactaa ctcggatctc cgaaaagccg caattcatgc ccagaagctc | 720 |
| gacaagacgc aagacgataa cgaaaaggaa tccacctcgt cttcctcttc ttcagatgac | 780 |
| gcagagactt tggcagacat tgacgtcatt cctgcatact acgcacagct gccctacccc | 840 |
| cagaatgtga cgctgtcgaa cctgctgtac ttctggtttg ctcccacact ggtctaccag | 900 |
| cccgtgtacc ccaagacgga gcgtattcga cccaagcacg tgatccgaaa cctgtttgag | 960 |
| ctcgtctctc tgtgcatgct tattcagttt ctcatcttcc agtacgccta ccccatcatg | 1020 |
| cagtcgtgtc tggctctgtt cttccagccc aagctcgatt atgccaacat ctccgagcgc | 1080 |
| ctcatgaagt tggcctccgt gtctatgatg gtctggctca ttgattcta cgctttcttc | 1140 |
| cagaacggtc tcaatcttat tgccgagctc acctgttttg gaaacagaac cttctaccag | 1200 |
| cagtggtgga ttcccgctc cattggccag tactggactc tatggaacaa gccagtcaac | 1260 |
| cagtacttta gacaccacgt ctacgtgcct cttctcgctc ggggcatgtc gcggttcaat | 1320 |
| gcgtcggtgg tggtttttctt tttctccgcc gtcatccatg aactgcttgt cggcatcccc | 1380 |
| actcacaaca tcatcggagc cgccttcttc ggcatgatgt cgcaggtgcc tctgatcatg | 1440 |
| gctactgaga accttcagca tattaactcc tctctgggcc ccttccttgg caactgtgca | 1500 |
| ttctggttca cctttttcct gggacaaccc acttgtgcat tcctttatta tctggcttac | 1560 |
| aactacaagc agaaccagta g | 1581 |

<210> SEQ ID NO 25
<211> LENGTH: 846
<212> TYPE: DNA
<213> ORGANISM: Yarrowia lipolytica

<400> SEQUENCE: 25

| | |
|---|---|
| atgggcacca ttctgcagcc accacgcccc ctcgtcctgg acgacactct ccaggacctg | 60 |
| cgagtccagg tccagaagct cgacctcaaa atcaaacgag actcatcgcc accatcagac | 120 |
| aagccgcgga ctctcccctc tttgcatctc caggcgtctg agcgaccgtc tcgatcggaa | 180 |
| atgtccgccg tggactctgc agccgacaaa atcaccagta gcctgggcaa aaacggattc | 240 |
| aactcgacgt cgccctacga cgacgtgcgg gtcgtactgg cgcgatacga ggataccatc | 300 |
| gacagcatca tgagcgagga cgacgacgca gacgccatcg acccgatcgg actcgtggca | 360 |
| tgcattctag agccccatat catcagcaag atgcaccgac ggctgcaacg gggctccttc | 420 |
| tcagccgacc cgtcggacct ggacagcccc atcgagtggg agaaggtcaa ggcgtggctg | 480 |
| gtgggcaagt attcgcggtt cgagtccgat gcggcctgca tcgacgccat gaaggagcac | 540 |
| ttctacgagg tcatgcccgg ctccattgca ttcagcagca cctggtgct ccaagagaag | 600 |
| ctgggccgta tcgacgtgct ggccaagacc accaaggacg agtcgtttga ccccaaggag | 660 |

| | |
|---|---|
| ttttcgcagt tatgaagag ccagttccca ctcgagtcgc aggagtgcga cgtagaggag | 720 |
| gtcaacaaca ttgacaaggc cagcgaggct cttcagcagc tgtttgctgt gggcaagcga | 780 |
| atgctggccg tcatgctggg tcaggagtac gattacaacg atgacgactg tgactatgat | 840 |
| ttttaa | 846 |

<210> SEQ ID NO 26
<211> LENGTH: 1101
<212> TYPE: DNA
<213> ORGANISM: Yarrowia lipolytica

<400> SEQUENCE: 26

| | |
|---|---|
| atggctcttc cgtccgaaat ctgggtccta gtgttttgtc actgtgatgt tcagggtctt | 60 |
| gtcagtctag acaagtgaa tcggctgtta tttgagattt tgagatcgcc gagcatggag | 120 |
| agagtgctgg agacggcagt taccggcgcg tgtccgttca tgagccattc tgagctgttt | 180 |
| gactgcgacc tgggtggttc agagcctcgg ttgaacggat ggttagggtc tgctcttgtt | 240 |
| ctcaacaaga ggatgcaaaa acacaatgtt ttgttggcag attttgttga aaagaccccc | 300 |
| gcatcgaatg agtactccta tctgaccggt ttacacggtc tcagcaccac gcagtattct | 360 |
| ccaggcatgc aaaggctcct ttctgccgac gaatcgagtt tcgaacgaca aatggccctg | 420 |
| agaaagacca aggggccct cgaagacatg ttgggtgtgg agggagagga agagaccaag | 480 |
| ttttcgaca atggagtgga actggcggct cacaagggta ccaagatggt gctagctagg | 540 |
| tggaaagatg gccaactaga cttggacaat gctcaccttc tgtctattgg ggagggtgga | 600 |
| gaagctggat cgagaacttg tctttctcaa ctgacaagcc acacattgat tatcaaatcg | 660 |
| aaagactgct accattccta ctacctcctc aaggaacacc accatctcca acttgtacat | 720 |
| ctcttcactc tccaggcact cgttcctccc cccgtattcg attacaacgg atacttgtgg | 780 |
| acaatactca atcaccagct ggtttcaatc ttcaccagct tcaacgacaa ctcgtgcaac | 840 |
| tcctatacca ccaatatgga gccggttcat ctgcccaaca aaccactctc acgcaccttc | 900 |
| tgcacgctgg cagagactcc cttcgacac agaaacggaa tgaaacggtt cctgctgctc | 960 |
| tcagaaaacc cgtactccac atgcgatctc tttgtggact tgaaaacagg ccaaaagtac | 1020 |
| gccagtagac cactcgaggc cacgacaag gtgtatcctg taatggatcg acagagattg | 1080 |
| tgtttcgtca agagaagcta g | 1101 |

<210> SEQ ID NO 27
<211> LENGTH: 1050
<212> TYPE: DNA
<213> ORGANISM: Yarrowia lipolytica

<400> SEQUENCE: 27

| | |
|---|---|
| atgaccacca tccccaagac ccagaaggct gtcattttcg agacctccgg cggtcctctc | 60 |
| atgtacaagg acgtgcctgt gcctgttcct gccgacgacg agattctcgt caacgtcaag | 120 |
| ttttccggag tgtgccacac tgacctccat gcctggaagg gcgactggcc tcttgacacc | 180 |
| aaacttcctc tcattggcgg ccacgagggc gccggagttg tcgtggccaa gggcaagaac | 240 |
| gtgaccacct tcgaaatcgg cgactacgcc ggtatcaagt ggattaacaa ggcctgttac | 300 |
| acctgtgagt tctgccaggt gtctgccgag cccaactgtc ctaaagctac catgtcggga | 360 |
| tacacccacg acggctcgtt ccagcagtac gccactgcca acgctgtcca ggcagcccat | 420 |
| atccccaaga actgcgacct cgcccagatt gctcccattc tctgcgccgg catcaccgtc | 480 |

| | | | | | |
|---|---|---|---|---|---|
| tacaaggctc | ttaagaccgc | tggcctcaag | gctggtgagt | gggccgccgt | taccggagct | 540 |
| ggaggaggcc | tcggttctct | ggccgtccag | tacgctaagg | ccatgggcta | ccgagtgctg | 600 |
| gccattgaca | ccggcgccga | caaggagaag | atgtgcaagg | agctcggcgc | cgaggtcttc | 660 |
| atcgactttg | ctaagtccaa | ggatctggtc | aaggacgtcc | aggatgccac | caagggcgga | 720 |
| ccccacgccg | ttatcaacgt | gtctgtctcc | gagtttgccg | tcaaccagtc | cgtcgagtac | 780 |
| gtgcgaactc | tgggcaccgt | ggttctggtc | ggcctgcccg | ctggagctgt | ctgcaagtcg | 840 |
| cccatcttcc | agcaagtggc | tcgatccatt | cagatcaagg | gttcctatgt | tggcaaccga | 900 |
| gccgactcgc | aggaggccat | tgaattcttc | gcccggggcc | ttgtcaagtc | tcccattatt | 960 |
| attgtgggtc | tttcccagct | ggagtccgtc | tacaagctga | tggaggaggg | caagattgcc | 1020 |
| ggcagatacg | ttctggacac | ttacaagtaa | | | | 1050 |

<210> SEQ ID NO 28
<211> LENGTH: 1737
<212> TYPE: DNA
<213> ORGANISM: Yarrowia lipolytica

<400> SEQUENCE: 28

| | | | | | |
|---|---|---|---|---|---|
| atgaacagaa | tctcacgagc | cgcccagagc | gtctctcgaa | ttgcctccag | gcaattggct | 60 |
| cgaagtaact | tctccacaca | ggcaagatca | tcccagccat | ctatcagctg | gggtgctgtt | 120 |
| gcaggagccg | ctggtgtcgc | tgcgggagtg | acctacttca | ttaccaagtc | cgacaagaac | 180 |
| gctgtggccc | ttaagaagga | agatgaggat | gttggccgag | gaatccagaa | ggtcctcgat | 240 |
| ggtgcctctc | tcgacacgga | cttctctcac | aagcccaagt | acggaggtga | ggaggagttc | 300 |
| aagaaggccc | tgccggaatt | tatcaaggct | atcggtgagg | aatacgtttc | taccgacgag | 360 |
| gaggatatcc | aattccatgg | ctggtccaac | gtttcttctt | ccaacctcga | cactctgccc | 420 |
| tttggtgttc | tgtaccccaa | gtctactgag | gaggttctg | ccattgccaa | gatctgccac | 480 |
| aagcacaagc | ttcccatggt | cggctactcc | ggaggtactt | ctctggaggg | ccacctttct | 540 |
| gccgcctacg | gaggtgtctg | catcgacttc | tccaacatga | acaaaattat | tgctattaga | 600 |
| cccgatgata | tggatgccac | tgtccagccc | tctgttggct | gggttgatct | gaacaacgag | 660 |
| attctcaagg | agggccatcg | cctgtttctg | gctgttgatc | ccggcccaac | agcacaggtg | 720 |
| ggaggcatgg | ttgccaactc | ttgttctgga | accaactgtg | ttaagtacgg | acccatgcga | 780 |
| gatcacgttg | ttaatctcac | tgttgtcctg | gcggacggta | ccattctcaa | gacccggcag | 840 |
| cgacctcgaa | agacctctgc | tggatacaac | ctcaaccatc | tattcgctgg | aaccgaggga | 900 |
| acacttggtc | tgatcaccga | aatcaccgtt | aagctccagc | ccatccccaa | tgtcacctct | 960 |
| gtcgccgtcc | aacagtttcc | gaccgtccac | gccgcttgca | agactgctat | ggatatcctc | 1020 |
| aaggagggta | tccccatggc | tgctcttgaa | cttatggatg | atcagcacat | gatctgggtc | 1080 |
| aacaactccg | gttacgccaa | gagaaagtgg | aagagaagcc | ccgccctgtt | catgaagttc | 1140 |
| gccggtgcct | ccgaggaaac | tgtcgccgag | caggtgaagg | ttgctaagga | gaaggctgcc | 1200 |
| aagtacacag | actctcccct | tgcatttcgga | agagatcagg | aggaacagga | tgagctgtgg | 1260 |
| tctgcccgaa | aaaacgcgct | ttacctcgct | cttgctgccg | agaaggacgg | tatgaaggca | 1320 |
| tggaccactg | atgttgctgt | tccccttcct | cagcttcctg | atattgtcat | gaaggcaaag | 1380 |
| cagagcatca | ctgatgctgg | tcttcttgga | ggagttctgg | ccacattgg | tgacggaaac | 1440 |
| taccatgcca | tcatgcttta | cactcccgag | caggccgata | ttgtcaccga | cgtcgtccat | 1500 |
| aagatggtcg | accagggtct | ggctgccgag | ggaacctgca | ctggtgagca | cggtgttgga | 1560 |

```
ttcggaaaga tcgaggggct tcttcacgag gttggtcctg tctctctcaa cctgatgcga    1620
accatcaagc tgtctcttga tccccttgag ctacttaacc ccggcaagat cttcactgac    1680
gatgccattc agcagggtct caagactctg ataacaaca aggctggtaa gacttaa       1737

<210> SEQ ID NO 29
<211> LENGTH: 1041
<212> TYPE: DNA
<213> ORGANISM: Yarrowia lipolytica

<400> SEQUENCE: 29
atgcaggccg ctttcaccac cgcctacggc ggtcccgaca agattgagta ctcggagaac     60
ttctccttgg cccagctcaa atccaacgac catgttctga ttcaggtggc caactccgca    120
ctcaacccca tcgacggtct gcgtaaccgg ggctacctgc gtcttctcca gcccgactcg    180
cacccccata tctttgctta tgacgttgct ggcttcgtgg cagaggtagg cacagctgtc    240
accgccttca gaagggcga tcgggtgtac gctcgaatcg gcgagtctga gcaaggcacc    300
acggctggct ttgtgtccgt tcgagacgcc catgtagcca ttgcgcccaa gaacaagcct    360
cttcttgaga ccgctggtat tcccctggtt ggacttaccg tgctgcagag ctttgaagcc    420
ggtaatctga gcggggtca gcgaatcttc atctccaagg gcgccggagg agttggtact    480
tttgccatcc agctcgctaa gcacgtctac ggcgcctacg tcattaccac tgcttccgag    540
aagaagattc ctcttctgaa ggagctcgga gccgacgagg tgattgacta ccacaagacc    600
aacttctggg acgtggtcaa ggacgtggat ttcgcctacg acgtttccga ccagccctgg    660
gcccatgcca tgatcaccaa gaagggtggt gtcgtggttg ctctcagagg tgtgcctact    720
gctcagagtg ccaagaatat tctcagcacc gagcctggcc tcattctctc gtatgtgctt    780
gctgcaggca actttctgac ctcccggttt gcctggtggt acggcaccag gtacgatgct    840 gtttttttgcg ctgccagcgg caaggatctg gcccagattg caaagtacat tgaggagggc    900
aagatcaagc ccattgtgga ctcagtgtac gatctgcgaa acgccaagga tgccgtggag    960
aagctggaga gtggacgagc caccggaaag gtcatcatca gtgtcgatga cacccttgat   1020
aagggcttca agctgcccttа a                                             1041

<210> SEQ ID NO 30
<211> LENGTH: 1194
<212> TYPE: DNA
<213> ORGANISM: Yarrowia lipolytica

<400> SEQUENCE: 30
atgcgactca ctctgccccg acttaacgcc gcctacattg taggagccgc ccgaactcct     60
gtcggcaagt tcaacggagc cctcaagtcc gtgtctgcca ttgacctcgg tatcaccgct    120
gccaaggccg ctgtccagcg atccaaggtc cccgccgacc agattgacga gtttctgttt    180
ggccaggtgc tgaccgccaa ctccggcag gcccccgccc acaggtggt tatcaagggt    240 ggtttccccg agtccgtcga ggccaccacc atcaacaagg tgtgctcttc cggcctcaag    300
accgtggctc tggctgccca ggccatcaag gccggcgacc gaaacgttat cgtggccggt    360
ggaatggagt ccatgtccaa caccccctac tactccggtc gaggtcttgt tttcggcaac    420
cagaagctcg aggactccat cgtcaaggac ggtctctggg acccctacaa caacatccac    480
atgggcaact gctgcgagaa caccaacaag cgagacggca tcacccgaga gcagcaggac    540
gagtacgcca tcgagtccta ccgacgggcc aacgagtcca tcaagaacgg cgccttcaag    600
```

-continued

```
gatgagattg tccccgttga gatcaagacc cgaaagggca ccgtgactgt ctccgaggac      660
gaggagccca agggagccaa cgccgagaag ctcaagggcc tcaagcctgt ctttgacaag      720
cagggctccg tcactgccgg taacgcctcc cccatcaacg atggtgcttc tgccgttgtc      780
gttgcctctg caccaaggc caaggagctc ggtaccccg tgctcgccaa gattgtctct       840
tacgcagacg ccgccaccgc ccccattgac tttaccattg ctccctctct ggccattccc      900
gccgccctca gaaggctgg ccttaccaag gacgacattg ccctctggga gatcaacgag       960
gccttctccg tgtcgctct cgccaacctc atgcgactcg gaattgacaa gtccaaggtc      1020
aacgtcaagg tggagctgt tgctctcggc caccccattg tgcctccgg taaccgaatc       1080 tttgtgactt tggtcaacgc cctcaaggag ggcgagtacg gagttgccgc catctgcaac    1140
ggtggaggag cttccaccgc catcgtcatc aagaaggtct cttctgtcga gtag          1194
```

<210> SEQ ID NO 31
<211> LENGTH: 1074
<212> TYPE: DNA
<213> ORGANISM: Yarrowia lipolytica

<400> SEQUENCE: 31

```
atgtcttcta acccgtcatt tgttcttcga aagccattgg atctcgtctt tgaggatcgg       60
cccgacccca agatccagga cccccactcc gtcaaggtgg cagtcaaaaa gaccggagtt      120
tgcggctcgg atgtccacta ctatctgcat ggaggaatcg gcgacttcat tgtcaaggct      180
cccatggttc taggccatga agtgccgga gaggtggttg aggttggtcc tgaagtcaag      240
gacctcaagg tgggagatcg agtggctctc gagcccggag tgccgtctcg attgtcacag      300
gagtacaagg agggacgata caacctgtgt ccttgcatgg tgtttgctgc caccctctcc      360
tacgacggta ctctgtgtcg tcactacatc attcccgagg acttttgtgt caagctgcct      420
gatcatgtgt ctctcgagga gggagctctt gtggagcctc tgtccgtggc tgtccactgc      480
aacaagctgg ccaagaccac tgcccaggac gtggttattg tgtttggagc tggcccagtc     540
ggactgctag ccgtgggagt ggccaatgcc tttggatcat ctaccattgt gtgtgttgat      600
cttgttcccg agaagctgga gctcgccaag aagttcggtg ccactcatac gtttgtaccc     660
actaagggag acagtcccaa cgagtctgct gacaagatcc gagctctgat caagggcgct     720
ggtctctctg actcgcccaa tgtggctttg gagtgcaccg gagctgagcc ttctattcag     780
actgctgttt ctgtgctggc cacttccggt cgacttgtgc aggtcggcat gggcaaggat     840
gacgtcaact tccctatcac caaatgcatt gtaaaggaga ttaccgtgct cggatcgttc     900
cgatactgcc atggtgacta tcccctggct gttcagctgg ttgcttctgg caagattgac     960
gtcaagaagc tggtgaccaa ccggttcacc ttcaaggagg ctgagcaggc gtacaagacg    1020
gcggccgagg gcaaggccat caagatcatc attgacggtc ccgaggagga gtag          1074
```

<210> SEQ ID NO 32
<211> LENGTH: 1752
<212> TYPE: DNA
<213> ORGANISM: Yarrowia lipolytica

<400> SEQUENCE: 32

```
atgcaccgtc ggccgaattg ccctgttcta ttctacacat ccagtgcgtc atatgatatc       60
gcactgcttg tgctgaatac tcttgctctc cctcttttcc ttcctggccg gactccgttg      120
agatgcatcg tatttaggtt accccggaat cggagtgcat ttattactca cctatatata     180
acgccgctga gtactccttc atctcacgac acgacaagta tccacaccat ggcgactctt     240
```

```
cagaaaacga tttccaagac cggagccggg atcttcatcc ccggcgccca ggagctgacc    300
tacagccagt tcttcgatct cattggcgac ttccagaaac agcttgccca ggtcggtctt    360
cctccccaga gtgctgtttc cattgccatc cccaactctc tcgagtttgc cgtgaccttc    420
ctggcagtca ccttctctcg atacattgct gctcctctca actcggcgta caaaaagtcc    480
gagtttgagt tctacatcga cgatctcaag tccaagctgg tgctggtacc caagggagcc    540
gtggcccaga acctggcctc cgttcaggct gcccgaactt ttaatgctgc catcgctgag    600
gtctactggg acgaccagaa gaagcgaatt gtcatggaca tcaaggaggg ccctacaaac    660
cctcccgttg ccgtccccac ccccgacgag gtctcccccg aagacgtggc tctcgtgctg    720
cacaccagtg gaaccaccgg ccgacctaag gccgttcccc tgacccagcg aaacctgtgc    780
cgaaccatgc acaacattgt cgacacatac aagctcacca gtaaggacac cacttatctg    840
gtcatgcctc tgttccacgt ccacggtctt ctgtgtgcct tcctggcccc tctggcctct    900
ggtggaggaa tcgtaatccc tagcaagttc tctgcctcgc agttctggga cgactttgtc    960
aagtacaagt gcaactggta cactgccgtg cccaccatcc accagattct gctgaacaca    1020
aagattcccc agcctctgcc cgagatccgg ttcattcgat cgtgctcttc ggccctggca    1080
cccgccacct tccaccagat tgaaaaggca ttcaaggccc ccgtcctgga ggcttacgcc    1140
atgactgagg ctgcccatca gatgacttct aacaatcttc ctcccggaca gcgaaagcct    1200
ggaaccgtcg gagttggcca gggtgtcgaa gtcgccattc tggacgacaa cggagacgaa    1260
gtccctcagg gaaagattgc cgagatctgt atccgaggag aaaacgtcac caagggttac    1320
atcaacaacc ccgaggccaa taagtcgtcg ttcaccaaga gcggtttctt ccgaaccgga    1380
gatcagggct tcctggacaa ggacggcttt gtcaacatca ccggccgaat caaggagctc    1440
atcaaccgag gaggagagaa gatctcaccc attgagcttg acggagtcat gctggagcac    1500
cctgccgtgg ccgaggctgt gtgtttcggt gcacccgatg agatgtacgg acagcaggtg    1560
aatgccgcta tcgttctcaa gaaggacgcc aaggccactg agcaagatat caaggacttc    1620
atggctgata aggtcgcaaa gttcaagatt cctgctcgag ttttcttcac cgacattatg    1680
cccaagactg ccactggtaa gattcagcga agatttgtcg cccagaagtt ccttgacaag    1740
gctaagctct aa                                                        1752
```

<210> SEQ ID NO 33
<211> LENGTH: 867
<212> TYPE: DNA
<213> ORGANISM: Yarrowia lipolytica

<400> SEQUENCE: 33

```
atgcccaaca ctcttactcc cgaatggctc aagacctgcg tctacaaccc cggcctgttt    60
gatggcaagg ttgtgtttgt gaccggagga gcaggcacca tttgtcgagt gcaaaccgaa    120
gctctcattc tgctgggtgc caacgctgcc gtgatcggac gacgaccaga agtgacacaa    180
aaggccgcgg aggagatgca gcagctgcgt cctggtgcca aggtaattgg aattggcaac    240
tgtgacgtgc gagaagtcaa gtcgctggtg gcggcggccg agaaggctgt gcaggagctg    300
ggtcgaattg actacgtaat tgcaggagcc gcaggcaact tcctggctga cttcaatcac    360
ctgtctgcca acgccttcaa gtccgtcatc tcaatcgatc tgttgggctc ctacaatacc    420
gtcaaggcat gtttccccga gctgagaaag aacaagggta aggtgctatt cgtgtctgct    480
acgctgcact acagaggagt ctcgctgcag tcacacgtgt cagcagcaaa ggcaggtatc    540
```

-continued

```
gacgcacttt cgcaggctct agccgtggag ctagggcctc tcggcatcgc tgtcaattgt    600
ctggctcctg gtcctattga cggcaccgaa ggtctcggac gtctgcttcc ttcggatgct    660
cggaagcgat ctctgcagct tgtgcccgtg cagagatttg aaccacaga ggacattgcc    720 aacggaaccg tgtttctctt ctctgatgcg gcctcataca tctcaggtac cactcttgtc    780
attgacggag cagcatggca cacttctgcc cgaactactt acccggagac tgtcattgtg    840
cagggcaaca agcccccgaa gctatag                                        867

<210> SEQ ID NO 34
<211> LENGTH: 2706
<212> TYPE: DNA
<213> ORGANISM: Yarrowia lipolytica

<400> SEQUENCE: 34
atgtctggag aactaagata cgacggaaag gtcgtcattg ttaccggtgc cggtggcggt     60
ctcggtaagg catacgccct tttctacggc tctcgaggag cctctgttgt tgtcaacgat    120
cttggtggcg acttcaaggg cgacggtgcc caggctggca gtggcaagcg agttgccgat    180
gttgtcgtcg acgagattgt ttccaaggga ggcaaggctg ttgctaacta cgactctgtc    240
gagaacggtg acaagattgt cgagactgcc gtcaaggctt ttggctccgt ccacattgtc    300
atcaacaacg ccggtattct ccgagatatt tccttcaaga agatgaccga caaggactgg    360
gatcttgtct acaaggtcca cgtttttcggt gcctacaagg ttacccgagc tgcctggcct    420
tacttccgaa agcagaagta cggtcgagtt atctctacct cttccgctgc tggtctttac    480
ggaaacttcg gccagaccaa ctactccgct gccaagctcg ccctggttgg tttcggtgag    540
actctcgcca aggagggtgc caagtacaac attacttcca acgtcatcgc tcctcttgct    600
gcttcccgaa tgaccgagac agtcatgccc gaggatatcc tcaagctcct caagcctgag    660
tacgttgttc ctctggtcgg ctacctcacc cacgactctg tcaccgagtc ttatggtatt    720
tacgaggtcg gtgctggtta catggctaaa atccgatggg agcgaggcaa cggtgctgtt    780
ttcaagggcg acgacacttt caccccgtct gctattctga gcgatgggga tgaggtcacc    840
tcttttgaga gccccaccta ccctaacggc cctgctgact tcttcaaata cgctgaggag    900
tctgttaagc gacccgagaa cccccaggga cccaccgtct ccttcaagga ccaggttgtc    960
attgtcactg gagccggtgc tggcattggc cgagcttact ctcacctcct tgctaagctt   1020
ggtgccaagg tcgttgttaa cgatttcggt aaccctcaga aggttgtcga tgaaattaag   1080
gccctcggtg gtatcgccgt cgctgacaag aacaacgtca tccacggtga aggttgtt     1140 cagaccgcta tcgacgcctt cggtgctgtc cacgccgttg tcaacaacgc tggtattctc   1200
cgagacaagt ctttcgccaa catggatgat gagatgtggc agctgatctt tgatgtccac   1260
ctcaacggta cttactccgt taccaaggcc gcgtggcccc acttccttaa gcagaagtac   1320
ggccgtgtca tcaacaccac ctcaacttct ggtatctacg taacttcgg ccaggccaac   1380 tactctgccg ccaaggctgg tatcctcggt ttctcccgag ctcttgctcg agagggtgag   1440
aagtacaaca tccttgtcaa caccattgcc cctaacgctg gtactgccat gactgcttct   1500
gtcttcactg aggagatgct cgagctcttc aagcccgatt tcatcgcacc catcaccgtc   1560
ctgcttgctt ccgatcaggc tcccgtcacc ggtgatctgt ttgagactgg ttctgcttgg   1620
atcggacaga ctcgatggca gcgagctggt ggtaaggcct tcaacaccaa gaagggtgtc   1680 accccgaaa tggttcgaga cagctgggct aagatcgtcg acttcgatga tggtaactcc   1740
acccatccca ccactccctc cgagtctact actcagattc ttgagaacat cttcaacgtg   1800
```

```
cctgatgagg aggttgagga gactgctctc gttgctggtc ccggtggtcc cggtatcctc    1860
aacaaggagg gcgaacctttt cgactacact tacacttacc gagacctcat tctttacaac    1920
cttggtctcg gtgccaaggc taatgagctc aagtatgtct tcgagggtga tgatgacttc    1980
cagaccgtgc ccactttcgg tgttatccct tacatggggt gcctcatcac taccaactat    2040
ggcgacttcg ttcctaactt caaccctatg atgcttctcc acggtgagca gtaccttgaa    2100
atccgacagt ggcctattcc taccaatgct acattggaga caaggctaa ggtcatcgat    2160 gtcgttgaca agggcaaggc tgccctcctt gtcactgcta ccaccaccac gaacaaggag    2220
actggtgagg aggttttcta caacgagtct tctctcttca tccgaggctc tggtggtttc    2280
ggtggtaagt ctaccggtac tgaccgtggc gctgccactg ctgccaacaa gcccctgct     2340 cgagctcctg acttcgttaa ggagatcaag atccaggagg accaggctgc catttaccga    2400
ctttctggtg attacaaccc tcttcacatc gaccctgctt ttgctgctgt tggtaacttt    2460
gaccgaccta ttctccacgg tctctgctct tttggtgtct ccggtaaggc tctttacgat    2520
cagtttggtc ctttcaagaa cgctaaggtc cgatttgctg gtcacgtctt ccctggtgag    2580
accctgaagg ttgagggctg gaaggagggc aacaaggtca ttttccagac caaggttgtt    2640
gagcgaggta ctaccgccat cagcaatgcc gccattgagc tcttccccaa ggatgctaag    2700
ctctaa                                                                 2706

<210> SEQ ID NO 35
<211> LENGTH: 1566
<212> TYPE: DNA
<213> ORGANISM: Yarrowia lipolytica

<400> SEQUENCE: 35
atgtcagagt tcgattggga gtcaattttg ccggcaacac cactaggtga gatcgagaag      60
gatattcaaa ccctacgaca gggcttcagg tccggaaaga cgctggattt gaacttcagg     120
cttgaccaga ttcgtaagct tttctatgct ctctatgata atgtcgatgc gatcaaagaa     180
gcaattcata aggatctcgg acgtccggtc ttcgagactg aactttgcga gatctccttt     240
cagtggggtg aattcaataa tgtcgtttct aacttgaaga aatgggcagc tgatgagacg     300
gtgaagggaa ccaccattca atacactctc acccggccaa agattagaaa gcgtccactt     360
ggtaccgtcc ttatcatatc tccttggaac tacccatttg ttctgaccat ctctcccctg     420
cttgctgctc tagcggcagg aaatacggtg gccctaaagt tctccgaaat gtgcccacat     480 acatcgctt tgctgggaaa gttgtgcaca gaggcacttg ataaagaaat tttcaaggca     540
tttcagggag gcgttccggt agtgtcggag attctcaagt acaagttcga caaaatcatg     600
tacactggaa atcatcgagt tggcaagatc atcttggacg cagctaacaa ataccctcacc    660 cccgttatttt tggagcttgg aggcaaatca ccagtcttcg tgactaagaa ttgccaaaac    720
gtatctcttg ctgccaagcg tgctctgtgg ggtaaactgt tcaacgctgg acaaacatgc    780 gttgccccg attacatcat cgtcgagcct gaggtcgaac aggagtttat caaagcttgc    840
cagtactggg ttgagaagtt ctaccgaggt ggagttgact ctgatcataa ggacttcact    900
catattgcaa cacctggaca ttggagacga ttgcatcca tgcttgccca gacagaggga    960
aatatcatca caggcggaaa ttcggacgag aaatcacggt tcttgctcc cacagttgtt    1020 gcgaaagttc ctgatggtga ttctttgatg aatgatgaga tcttggccc tatcctgccc    1080 atcctgacag ccagatccgt tgacgaaggt attcgctatg ttcatgagaa tcacgacact    1140
```

```
cccctggcca tgtatgtctt tactgataat gcatcagaag gagagtatat ccaatctcaa    1200
atcaactcag gtggcctgat attcaatgat agtcttgttc acgttggctg cgtgcaggcg    1260
ccttttggtg gtgtcggcca atccggctat gggtcttatc acggcgaaga ttccttcttg    1320 gcttttcac acaggcagac tttcatgaag cagccccatt tcatcgaacg accaatggcc    1380
atcagatatg ccccctacac tagtcgaaaa caaaaggctg tccagggtag tctagctgct    1440 ccatctttc ctcgaacagg aaaggttgac cgctccctgt tggagcggat atttggtaag    1500
ctatggttct gggtgatcgt tttagggcta ggagcagcca gtttgaagtc aggaattttc    1560
ttatga                                                              1566
```

<210> SEQ ID NO 36
<211> LENGTH: 1056
<212> TYPE: DNA
<213> ORGANISM: Yarrowia lipolytica

<400> SEQUENCE: 36

```
atgtctgctc ccgtcatccc caagacccag aagggtgtca tcttcgagac ctccggcggt      60
cctctcatgt acaaggacat ccccgtgcct gtgcctgccg acgacgagat tctggtcaac     120
gtcaagttct ccggagtctg ccacacggat ctgcacgcct ggaagggcga ctggcctctg     180
gacaccaagc ttcctctggt cggaggccac gagggtgccg agtggttgt tgccaagggt      240 aagaacgttg acacgtttga gattggcgac tatgccggca tcaagtggat caacaaggcc     300
tgctacacct gcgagttctg ccaggtggcc gccgagccca actgtcccaa cgctaccatg     360
tctggataca cccacgacgg ctctttccag cagtacgcca ccgccaacgc cgtgcaggcc     420
gcgcacattc caagaactg cgatctcgcc gagattgccc ccattctgtg cgccggaatc      480
accgtctaca aggctctcaa gactgccgcc atcctcgctg ccagtgggt tgccgttact      540 ggtgctggag gaggactcgg aacacttgct gtccagtacg ccaaggccat gggctaccga     600
gtgctggcca ttgacactgg cgccgacaag gagaagatgt gcaaggacct tggtgccgag     660
gttttcatcg actttgccaa gaccaaggac ctcgtcaagg acgtccagga ggccaccaag     720
ggcggacccc acgccgtcat caatgtgtct gtctccgagt ttgcagtcaa ccagtccatt     780
gagtacgtgc gaaccctggg aaccgttgtt ttggtcggtc tgcccgccgg cgccgtctgc     840
aagtctccca tcttccagca ggtggctcga tctatccaga tcaagggctc ttacgttgga     900
aaccgagccg actcccagga ggccattgag ttcttctccc gaggtctcgt caagtcgccc     960
atcatcatca tcggtctgtc cgagctggaa aaggtctaca agcttatgga ggagggcaag    1020
attgccggcc gatacgttct ggacacctcc aagtaa                             1056
```

<210> SEQ ID NO 37
<211> LENGTH: 948
<212> TYPE: DNA
<213> ORGANISM: Yarrowia lipolytica

<400> SEQUENCE: 37

```
atgagcaggc taatgtctcg actgactata cgaccaggcc accgaatcgt ttatcgccac      60
caaatcgttt atcgccacca aatcgtttct cgactctttt ccacactttc cgcttccatg     120
tcacgacacc ctagcctcaa ggagctcgag aaggagcgac cggcattcgt agatcgaccg     180
ggattcacct tcacaaacac gcccaacacg gagtggcagt tggagatgg agccaactcg      240 caggatgacg ggtggaagaa acacaaaaag gtgagcttca gtcccacggc cgagggccgg     300
ccgcccatgt tcaattacaa gctgctgatt ggcgccgtga cccccggcc cattgcgttt     360
```

```
ctgtccacag tgagcaagga cggagtgcgg aacctagcgc ccttctcctt cttcaacatg      420
gtgtcgtcag acccgcccgt gttcgccatt ggcatgaccc gaacccccaa cggccacaaa      480
gacagctgcc aaaacctgct cgacaccaag gaggccacca tcaacatcat cagtgagtgg      540
ttcgttgaag cggccaactc gtgtgccatt gccgcgccct ccgacgtgga tgagtggctg      600
gtgagcggtc tcaccccgt ggagtctgaa attgtcaagc ctgctcacgt ggccgagtcg       660
tgtttctccg tggaggtgaa gcttctgcat cattacgatc tgtactcggt cgctgatccc      720
aacaagcata ccaacaccac ggttctggtg caggcggtcc agttccacgc ccgcgaggac      780
gtgatcaacg aggatctcaa ctttctcgac gtgaccaaga tcaaggccgt gtctcgactc      840
ggaggcattt cttacggccg aaccaccgag ggctacgaac tgcctcgaat ggtccacgcc      900
gacgagaagg acaaggacga atacaagaag gccgtccacc gggagtaa                   948

<210> SEQ ID NO 38
<211> LENGTH: 1245
<212> TYPE: DNA
<213> ORGANISM: Yarrowia lipolytica

<400> SEQUENCE: 38
atggaccgac ttaacaacct cgccacccag ctcgagcaga accccgccaa gggcctcgac       60
gctatcacct ccaagaaccc cgatgacgtt gtcatcaccg ccgcctaccg aactgcccac      120
accaagggag gcaagggtct gttcaaggac acctcttctt ccgagctgct cgcctctctg      180
ctggagggcc tcgtcaagga gtccaagatc gaccccaagc tcatcggtga tgtcgtctgc      240
gggaacgttc tcgctgccgg tgccggtgcc actgagcacc gagctgcctg ccttgttgcc      300
ggcatccccg agaccgttcc cttcgtcgct ctcaaccgac agtgctcctc tggtctgatg      360
gccgtcaacg acgttgccaa caagatccga gccggccaga ttgacattgg tatcggctgt      420
ggtgtcgagt ccatgtccaa ccagtacggt cccaactccg tcaccccctt ctccaacaag      480
ttccagaaca cgaggaggc taagaagtgc ctgatcccca tgggtatcac ttccgagaac       540
gttgccgcca agtacaacgt gtcccgaaag gccaggacg cctttgctgc caagtcctac       600
gagaaggccg ccgctgccca ggccgccggc aagttcgacc aggagatcct ccccatcaag      660
accactgttc tcgatgatga tgacaacgag aaggaggtta ccgtcaacaa ggacgacggt      720
atccgacctg gtgtcaccgc cgagaagctc ggcaagctca agcctgcttt ctccgccgag      780
ggaaccaccc acgctggtaa cgcctctcag atctccgacg gtgccggagc cgttctcctc      840
atgcgacgat ctgttgccga gaagcttggc cagcccatcc ttgccaagtt tgtccactgc      900
aagaccgtcg gtgttccccc cgagctcatg gaattggcc ccgcttacgc cattcctgct       960
gtccttgagg accttggtct gaccgtcaac gacgttgacg ttttcgagat caacgaggct     1020
ttcgcttccc aggctctgtt ctccatccag cattgtggaa tcgacgagtc caaggtcaac     1080
ccccgaggtg gtgccattgc tattggccac cctctgggag ccaccggtgc tcgacagttt     1140
gccactctgc tctccgagct taaggagtct ggcaagaagg tcggtgtcac ctccatgtgc     1200
attggtaccg gtatgggtgc cgcttctctg gttgttgccg agtaa                    1245

<210> SEQ ID NO 39
<211> LENGTH: 2391
<212> TYPE: DNA
<213> ORGANISM: Yarrowia lipolytica

<400> SEQUENCE: 39
```

| | |
|---|---|
| atggaaacca tcgaagtggc ctcgcggtcg tttgtcatca agtgggtcac tgcccccgag | 60 |
| ggctccgcca tcaccttcaa agttcacccc ctgaaaaagt ccatcaacgt gggcatcttc | 120 |
| gagaaggagc ggagcaacaa cttgcaggtc gaaatcgagg ctgaaggaca caatgccggc | 180 |
| cgacgagcct ccatctcggc tccccactcg ggaaccatcg aaaaacgact tgaatcaagc | 240 |
| ggattgtccc ctgttctgcc gctcaaaaag tgcaacgcca acgaacagtc cgagggagtc | 300 |
| tacaaggtcc ccaagggaaa gggaggcatc tacgcccttg tgttcgacaa caccttctcc | 360 |
| aaaaccacac ccaaaaccgt ccatttcact gtccaggcca tggaagaggg acatgcggct | 420 |
| aacaatgctc cccataccct tgtctccgag accgccgtat ccggtatcct gctcaaaaag | 480 |
| cgacgaaaga agctccaggg atacacccga cggtactttg ttctggatct caagctggcc | 540 |
| attctcaatt actacacaga ccccaagtcc aactcgttgc gaggctctct gcccctgacc | 600 |
| ttgtgtgcca tctctgcctc caaggcccag agactcatct ttgtggactc gggtatggag | 660 |
| gtgtggaacc tcaaggccct caacgacgcc gactggcaga tctgggtcga cacctttgag | 720 |
| cggatcagaa agggcaagag cggaggagct gctgacgaac ctgttcccgc agtcgctgct | 780 |
| gtgaccgcac ctgaccagga gaagtttgct cagcttgtgg ccaagctacg agagaccaag | 840 |
| gatatttccg atgtggctgc tcaggagccc ggcgcttcca acgtgaccaa ggacctcaat | 900 |
| gcgcgcctag cagcgctgta tctcgagttc accgacgtgg tgtcccatgt tgctcatgag | 960 |
| agcgccatgt actcacagcc catggccaag cgagcgtcct taacggctc catcatgtcc | 1020 |
| gagcatgaca ctttctacga cgctgaggag aaccccgaca aggacggagt tgtgttcctg | 1080 |
| gacgacgacg ctgttgacga cgatgacgac ggagctgagc acgactccac agacgaggag | 1140 |
| gacgagggac accatgttgc tcctgttgtc catgatgctg atgacgctga tgatctgtac | 1200 |
| ccactgcatg aggttcagcc ggtcaagcac cgagtcactc ttcctgatgc tgcttccacc | 1260 |
| ccccttcca tgttgggtat cctcaagaag agtgtcggca aggatatggg ctccatggcc | 1320 |
| gtccccatca ccaccaacga gcctatttct gctctacaga gattcgccga gatgttcgag | 1380 |
| taccccagc tgctggacga ggctgaaaac gtgcctgcca atgacggaga gcgaatcatc | 1440 |
| tacgtggcca cctgggctgt ctcctacctc gcctccatgc gagctaagga gcgagctctc | 1500 |
| cgaaagcctt tcaaccctct tcttggagag acctatgagc tggttcgacc cgatctcggt | 1560 |
| tacagactca tctctgaaaa agtgtgtcat caccctcccg ttatggctct gcatgtagac | 1620 |
| tccgagcatg gctggtctgt ggcccactcg tctgagcccg tgcagaagtt ctggggtaag | 1680 |
| tcgatggaaa ttaactacct gggccctatc gtcgttaagt ccgacagtc cggcgaggtt | 1740 |
| ttccactgga gcaaccccac cacgtacctg cgaaacatca tggctggtga aagtacacc | 1800 |
| gagcctgttg gcgacttcac catcttctct tccaccggag agaaggccat tgtcgagttc | 1860 |
| aaggccggag gaatgttctc cggtcgaagc gaagagctca acatcaaggc tgtttcagct | 1920 |
| aatggttcta acctgccctg cttcgcctcc ggtaagtgga ccgagcagat caccctcaac | 1980 |
| aacgccaagg gtcagaagaa gaccatctgg aaggtcggca acctcgtcaa caaccacacc | 2040 |
| aagaagtggg gtttcaccga gttcaccgcc ggtctcaacg aggtcacccc catcgaaaaa | 2100 |
| ggacacgctt cccttacga ctcgcggttc cgacccgacc agaaggagta cgaggctggc | 2160 |
| cagaccgaca aggccgaggc cggcaaacag gagctggagg agaagcagcg ggagcgacga | 2220 |
| aaggtgctac aggactcggg taagacgtac aagcccacct ttttcgaaaa gtcgtctggt | 2280 |
| ttggacgagt tcaacgagca gggcgatctg tacctgctta ccaagggtcc caacaactac | 2340 |
| tggaaccgac gaaagcaggg caactgggag ggtcttactc ctttgtggta g | 2391 |

<210> SEQ ID NO 40
<211> LENGTH: 1572
<212> TYPE: DNA
<213> ORGANISM: Yarrowia lipolytica

<400> SEQUENCE: 40

| | | | | | |
|---|---|---|---|---|---|
| atgtccaacg | ccctcaacct | gtcgctggcg | ctcggcgtct | ttctgctagc | ctactatggc | 60 |
| ttctccgtga | tccagtacca | catcaaaacc | cgcaagctcg | aaaagaagtg | aagtgtggt | 120 |
| aagcccaagg | atatttcacg | attccccttt | tcagcctcct | tcttcatccc | cttcctggtt | 180 |
| gagtccaaga | agaaccgact | gctcgagttt | gttcagtgga | tgtttgagtc | ccaggtctac | 240 |
| cccggttaca | cctgcaagac | caccgtgttc | ggcgttgaca | tgtaccacac | tgtcgaccct | 300 |
| gagaacctca | aggctgttct | agccacccag | ttcaaggact | tttgtctcgg | tgagcgacac | 360 |
| gctcagttcc | tccccgttct | tggcaacggt | atctttactc | ttgacggcca | gggatggcag | 420 |
| cattctcgag | ccatgctgcg | accccagttt | gctcgagatc | aggtttccga | cgttgagatg | 480 |
| atcgaggagc | acatccagta | catgacctct | cgaatcccca | aggatggctc | tgcctttgat | 540 |
| gcccaagagc | tcttcttcaa | cctgactctt | gacactgcca | ccgagttcct | gtttggccag | 600 |
| tctgtcggtt | cccagaccgt | cgaaaccaac | cccactgccg | tccccaccga | tatgcccgtc | 660 |
| catctccgaa | agtctttcca | ggaggacttc | aacaccgctc | aggagcacct | tggccagcga | 720 |
| gctcgtcttc | agatgttcta | ctgggcctgg | agaccccgag | agctgtactc | ttctggagag | 780 |
| cgagtccatg | cctttgtcga | ccactacgtt | aagaaggctc | ttgaggagtc | cgagaagcac | 840 |
| gttgacgacg | gtaagtacgt | tttcctccga | gagcttgcca | aggagaccaa | ggaccccatt | 900 |
| gttctgcgag | accaggctct | caacattctt | cttgctggcc | gagataccac | tgcttctctt | 960 |
| ctgtcttggt | gcctgtatct | gatggctcga | cgacccgagg | tttatgccaa | gctgcagag | 1020 |
| gaggtcattg | agaaccttgg | agacggtgag | gatctgtcca | ccatcacctt | tgagtctctc | 1080 |
| aagcgatgcg | actacctgcg | atacgttctt | aacgaagtcc | tgcgactcta | ccctctgtc | 1140 |
| cctgccaaca | tgcgatacgc | tacccgagac | accactcttc | cccgaggagg | aggacctgac | 1200 |
| ggaatgcagc | ccattgtcgt | ccgaaagggc | aacctcgttt | cataccacgt | tttcaccact | 1260 |
| caccgactca | aggagttctg | gggtgaggac | gctgaggagt | ccgacccga | gcgatggtac | 1320 |
| gaggatggtg | cctcccaggc | taagggatgg | gagtacctgc | ccttcaatgg | aggaccccga | 1380 |
| atctgtctgg | gccagcagta | cgctcttacc | gaggctggct | atgctcttgc | acgaatcgcg | 1440 |
| cagctctacg | acaccatcga | gaacgctgac | gacaagcctg | agcctcccgt | caagttccat | 1500 |
| gctctgacca | tgtgccacca | cactggtgtc | ctggtcaagc | tctacaactc | caagaccacc | 1560 |
| aaggctcagt | aa | | | | | 1572 |

<210> SEQ ID NO 41
<211> LENGTH: 1437
<212> TYPE: DNA
<213> ORGANISM: Yarrowia lipolytica

<400> SEQUENCE: 41

| | | | | | |
|---|---|---|---|---|---|
| atggatagcg | actacggaat | ccagtcaatt | ttgtcggacg | acgagcaaga | cgcctgggac | 60 |
| gaaattgacg | ctccttttct | cgagcggccc | agctcctccg | gtctggtgat | gcctgcgatt | 120 |
| tcctccgacg | gctccgtagt | gtctagtcga | gagataatga | gcaagggaga | cggctttctg | 180 |
| aacggtgatt | tcccaatgcc | aaaatttgcg | cagttatgga | acaaatccgg | gtgtttgtgt | 240 |

-continued

| | | | | |
|---|---|---|---|---|
| atagagccgc | tctgtggttg | tgacaaggtg | agggaaaagg | tggaggctca tcttggcaat | 300 |
| atgactgaga | agcagagggg | atacgtggtt | gtcttcgagg | tcgagcctga agctgcccag | 360 |
| ctggccaaga | tggcagtgtt | aaggaactgg | aaaggagacg | agaaagtctt catgttttg | 420 |
| gataccaaat | tcgagctttc | caagaagatg | cgagatggta | ttaatgaggt ggaaagagtg | 480 |
| gaactggttg | ttttgggtgg | tgaagagaag | aaggcagatg | gtgatattac cattgatgcg | 540 |
| aaaccggcac | atggtacaaa | agaatgagc | gccgacgcag | tatcctcctt cctcaaaatt | 600 |
| ctcttttcta | ttgggattgt | gttcgttctg | ttcaaccctc | agaagcaaac cagtccctct | 660 |
| ttctcagcct | ccaataccac | cttctatggt | cctccgcagc | ctgtgacccc gtttaagtat | 720 |
| gagattccag | actccatgat | atttccatct | tgctattact | tggacaagcc agaggtccac | 780 |
| gtcaccgctc | cttcccatca | gaacagttta | agcatagaaa | cagtcttcaa ctttctttct | 840 |
| gagggctttc | agcgactatg | gaacggtatc | ctgagcatac | cgtctttgct gagtcgactt | 900 |
| ttgggacttg | ataaagatgt | gtttgagacc | aacagtgaac | gaacgttgag gaagattggg | 960 |
| ctcgacatgg | atctattggt | tgaactaatg | gacgaaattc | ttgaggagca gactgagcaa | 1020 |
| tctcttcacg | atgccctcta | tgtctggaac | aagatgggct | ccgacatagc tgagcccctc | 1080 |
| aagcgcctga | agtacgacga | aagacaact | tctgccaact | ttctgtcaat cataaagctt | 1140 |
| gagaggagat | tgaaggtagt | aggggagaag | ctggctacaa | ctaagagaga ggttagtgca | 1200 |
| atgagagatc | gtgagaaggg | aggggcacga | gagaaagcaa | gaggaggtga gattgctcgt | 1260 |
| ccacgtgaga | agatcaattc | tcatccgatt | gttggcgcac | gtgaaaatcc tgatgttcta | 1320 |
| aatatgtctc | cattacccac | tgactacatg | aaccgaatgg | aataccgcga ccgacagggc | 1380 |
| catgggcgac | gaggaaggaa | gagagagaga | gagaggggag | gaccgaggcg ctcatag | 1437 |

<210> SEQ ID NO 42
<211> LENGTH: 960
<212> TYPE: DNA
<213> ORGANISM: Yarrowia lipolytica

<400> SEQUENCE: 42

| | | | | |
|---|---|---|---|---|
| atgaaacatt | cgaccttcac | cctagctgcg | ctgctgacgc | tcgtgcacgc ccagaacaac | 60 |
| cctctggtcg | cctccatcgc | ccaaaatgtc | gtggctggta | ttgtctcagc caaaacagac | 120 |
| aacgacgtgt | ctgaccagca | ggccacctcc | gagatccaaa | gtgtggtcga cattgtcagc | 180 |
| gccaacactg | acgtgcagaa | cctgattggc | agtttcggat | ccctggccgc gaacggtgtc | 240 |
| gactcgtcga | atttccccga | gctgctatct | atggccactg | ccactctaag tgcctttgag | 300 |
| ggctcgcctg | acttctcgaa | ggcctccgag | ggctttaaga | acgtgctgac tcactacaac | 360 |
| gtgcccgagg | ccaagtctaa | tgtggcaaac | aatctcgctc | tcatcatcaa cgcagtcaca | 420 |
| gtcgctctac | ccaccctcac | ccctgaacac | agcagtgaat | gggcggcagc aacttcgcag | 480 |
| gtgatgcagc | tggcctcttc | cttgggtctc | gatgcgaccg | ccgcctcaag tgctgcgccg | 540 |
| agcactagtg | ctgccagtgc | agctcctagt | tctagttcca | actctggggg aaactctggg | 600 |
| ggcaatgcgg | gtggagcagc | tggaggcagc | tctggaggca | gctctggagg cagctctgga | 660 |
| ggcagctctg | gaggcagctc | tggaggatcc | agcaactctg | gaaccaactc cggctccaat | 720 |
| ggtaactcgg | gaggaaactc | gggcgaagtt | accactgttg | tcgttggacc accgggccag | 780 |
| tctacttcca | tcagcgctcg | aagcacagtt | acagtctatg | ccactggagg tggtaacgga | 840 |
| cagcccacta | ccatcgagaa | acccaagccc | tcgcaacaaa | acgcagcgg atccagactg | 900 |
| tacaacgtgc | gactgactgg | cttggtcgca | attgcaggcg | ttgtggttgc tctgatctag | 960 |

<210> SEQ ID NO 43
<211> LENGTH: 849
<212> TYPE: DNA
<213> ORGANISM: Yarrowia lipolytica

<400> SEQUENCE: 43

| | | | | | |
|---|---|---|---|---|---|
| atgacccacc | aatacaacga | caaacacggc | tgcgaactgc | tgggcaagta | cattctgcga | 60 |
| ggccaggtca | gagccatgcc | ctaccttccc | acagacggcc | ccgtgcatcc | tcaggccgaa | 120 |
| caacaactga | tgatggtcac | ctcttcatgg | gtgaacgtgc | ccgagatccg | agaccagcga | 180 |
| tcttttgttc | tgtggctgcg | atggatgaac | cgtgccgaaa | tcgagctcga | caagtgggct | 240 |
| gctgcctgct | cccccttcc | tcctgtggac | ctcgtgtgga | aggagctcac | ccgaaagggc | 300 |
| gttcgaggcg | cgacggagt | caactggtac | cagcgattcc | gaaacgccgc | cttccacgat | 360 |
| ctcggagaca | tggcaggcca | ccagcttgct | ctggagaccc | tcgtcaacct | ccatcctgcc | 420 |
| gcctttccg | agcctctcga | gtacatgaag | atttactgtg | ttctgtgtga | gctcactggc | 480 |
| aaccccttca | acattgagca | cgcgctcaag | agaatctgca | actgggctga | gaattacgac | 540 |
| cctcaaatct | ccttcgacac | ggtcattcag | acagcccgac | ccgacctggc | cggctggagt | 600 |
| tacatcaact | cgcgatcttg | gtcggaggct | cgagcccgaa | ccctggctat | ccagcgagaa | 660 |
| ctcaaggaga | gcctgcccaa | ggcaactgcc | gtcatgagca | gttcgcagag | cacgcgatcg | 720 |
| gtggcttccc | agaaaagtaa | caaagcgcg | ggaagcagta | agtccagcaa | gagcatattc | 780 |
| gatcgagtga | gactgggtac | ctttagcggg | gcttcgtcgg | tgtacgagac | cacccagacc | 840 |
| tcgaggtaa | | | | | 849 |

<210> SEQ ID NO 44
<211> LENGTH: 1710
<212> TYPE: DNA
<213> ORGANISM: Yarrowia lipolytica

<400> SEQUENCE: 44

| | | | | | |
|---|---|---|---|---|---|
| atgttcgatc | tggcgacgct | ggatacacgg | ctggggccct | cagacgatgt | caaaagacgc | 60 |
| gacggtgtta | tcgccaaagc | tggaccgtcg | cgatggagat | ctcccgagtt | catcgcatac | 120 |
| tacatcattc | acctgattgc | gctgcccatc | atgttcaagg | gtgcttacga | cgcgtccaac | 180 |
| ccacccaatc | ccaactacga | gctcatcaag | aaggacctgg | aacccggctg | gattttcgga | 240 |
| cgaaaggtgg | acaacacaga | ccaccagtat | tctggtttca | gaaacaacct | gccgtacctg | 300 |
| gctgctgtga | ttgtggccca | gcagctgctc | aagaagctgt | tcaagctatt | cagcaacgac | 360 |
| agccggtttt | tcgatgtcgg | ctttgcattt | gtgtttctga | ttgtggctca | cgggatctcc | 420 |
| acagtgaaga | ttcttgccat | catcattgca | aactacttga | tcggaagcaa | gatctcaaac | 480 |
| tccaacgcag | gaacaattgc | cacctggatt | tttggaatcg | caatcttgtt | cgccaacgaa | 540 |
| aaggcgctgg | gataccccatt | caccaaatac | tgtccccctc | tggcattcct | ggatgactat | 600 |
| gctggtctca | tgcccagatg | ggatgtcaca | ttcaacttca | gcatgcttcg | aatggtgtcg | 660 |
| ttcaatgtgg | accgataccg | cgcagttgat | ggaacgaccg | aacaatggcc | attggacaca | 720 |
| aagggagaaa | ttgatctgtc | gaagtccaag | accggagaag | gagagaagag | tacctcccctt | 780 |
| actgcttccg | atatcagcga | gcgatcacga | attgatatca | gtcactcacc | atcaacctac | 840 |
| tccatgtaca | attccttct | ctatatgctg | tatagtcctc | tgtttatggc | gggtcctatc | 900 |
| atgacattca | atgacttcat | cttccagcac | aagaagggcc | ctctggcttc | gctatctttt | 960 |

| | | | | |
|---|---|---|---|---|
| aagcgagtct | ccgtttacgc | cttgcgactg | gtgttttgca | tctttgtcat ggaaaccctg | 1020 |
| ttacattact | gctacgtagt | tgccgtgagt | caggagaagg | cctgggatgg agattcggct | 1080 |
| ttccagatct | ccatgatcgg | tttcttcaac | ctgaacatca | tctggctcaa gctactgatt | 1140 |
| ccttggagac | tgttccgact | atggtccatg | gttgacggaa | ttgatcctcc agaaaacatg | 1200 |
| gttcgatgca | tggacaacaa | tttctccgca | ctatcattct | ggagagcttg gcatcggtct | 1260 |
| ttcaatcgat | ggatcattcg | gtacgtgtac | ggccccattg | gaggttcttc gcgacctgtg | 1320 |
| ctcaactctc | ttatcgtctt | ctctttcgtg | gccatctggc | acgacattca gcttagactg | 1380 |
| cttgtatggg | gttggatggt | ggtattcttc | atcatccccg | agttgaccgc taccttcatc | 1440 |
| ttcaagcgtc | ctcagtttac | gagcaagtgg | tggttccgac | acctctgtgc tgttggagca | 1500 |
| gctctcaaca | tatggatgat | gatgattgca | aacctggtgg | gcttctgtgt gggtctcgac | 1560 |
| ggcatgggag | acatgctcag | gcaaatgttt | ggaacccgag | acggcatcat atattgcatt | 1620 |
| agtgcctcat | gcgcactatt | cgttggctct | caggtcatgt | ttgaggtacg ggagagcgag | 1680 |
| aagcggcgtg | ggatcaacat | cagatgctga | | | 1710 |

<210> SEQ ID NO 45
<211> LENGTH: 2103
<212> TYPE: DNA
<213> ORGANISM: Yarrowia lipolytica

<400> SEQUENCE: 45

| | | | | |
|---|---|---|---|---|
| atgcaccttt | cccacccaca | ggagaaacaa | gtcttcatca | ccactccgtc cccgtcgtcc | 60 |
| tctgtttcaa | cccagtccac | cgcctcgtcg | tcactgtcgc | tattccacac ggcagactcc | 120 |
| gatctctccg | cctccgaaga | agacgacttt | ccgtaccacg | caacaaccca cacaaatata | 180 |
| aagcctggtg | tgtctttctc | cgccacctca | ggcacaatga | tgagtgcgtt atccctgtc | 240 |
| tcggtgcagt | ctccgtcgac | cgttttcatg | atgaaggaac | ccgcacaggc acaggcccag | 300 |
| atgtcccacg | acaacaacaa | caacaacaac | agtagcagca | atgtcaccac ccctaaacac | 360 |
| aacgccgccc | ctgtaaccaa | atcagacgac | cccttcgatg | tcgacaacta ccccaccgac | 420 |
| tttgactccg | ccttcctcaa | cctgtcgccc | accatgggga | tgggcccccgg cgacggcatg | 480 |
| gatggtattc | cgctgttcaa | cgcagaggag | gagtccgctt | tctcgtcctt cctcgacaac | 540 |
| gtggctctgg | atcctaactt | catcttcgag | cccaatctct | ctgatgccct gcccaagtgg | 600 |
| cccgaatcga | aaccctgggg | ccccaacgac | tcgcataagc | cacgaaccga caagttcacc | 660 |
| aagtttggca | actctcccgg | tctcgatttg | ctcgctgcca | attcccccga cgcagttaac | 720 |
| atccacgaac | gcctactgaa | acacgagtcg | aaggagtatc | tcagccccaa ccacaacgac | 780 |
| tatgctcaga | gcgactcgcg | ggcccaggcg | ctcgccatgc | tgaaacaca gggctacgga | 840 |
| cagctaaaac | acaaagaaag | ccgctcatcg | ttatcacagc | cctcgtcgct acacaacaac | 900 |
| agcgtgacgg | ggtcgtcagt | cacaaccaca | cgtcccctcgc | cacaaacgtc gggaccctcc | 960 |
| cccgtgtcgt | cgggcacgtc | agcggcgtcg | tccgcaccca | tgggccttca tttcggctca | 1020 |
| gaccctgcat | ttggaggctc | cagcttccag | cccaacagcg | gcaccccagc cctcaaaaag | 1080 |
| gtgcggggct | tcgacgagct | gcccctgcc | gtccacgagg | acacgggca catgcacatg | 1140 |
| cagccacaac | gcatggtgac | cggtctggag | ggtgtagtca | accccaagct ggtggttgca | 1200 |
| gctgcacaga | tgagccaggg | cgtgacggac | cagaacatct | tcatgctcaa gcgacgaaag | 1260 |
| tcggacaaca | tggctgcaag | catgaactcg | aacgtgccac | acgatatcta tgctcccgtc | 1320 |
| ccacatgctg | agcagatgta | tcatatgcaa | caacaacagc | aacagcagca tctccaccag | 1380 |

```
caacagcagc aacaacatca ccaacaatca caaaatcagc atatccaaca acagcagcaa    1440
cagcagcagc atcagatgca ccaccctcac catacacagc agcacttcca ggcacgaatg    1500
cactttggcg acggcatgga tggcgaggtg tccatgagta ccgtctctca ggcgggtttg    1560
cacatgaact ccaaccctag catgttgttc cccgacaagg atgctctagc agactcgtac    1620
cagcagcagc agcagcaaat gcatagtcaa cacaaccctc cttcgcatca tcctcagcac    1680
aaccagcagc agcagcagca accgcaggtc aagactgagc agaatatgtc tgcatcgcct    1740
actccgggat ctcccaacct cacggaggac cagaaacgta tgaaccacat ctcttccgaa    1800
aagcgacggc gggatctcat caagcaggag tttgaggaaa tgtgcggcct ggtgcctcgt    1860
ctggctgcaa acagcgatga aagggcaagc gacgccatg gtcatcgagg acgtatgccc     1920
aaggactcgg acaaggacaa ggatactgga accaagtcca agtcgattct actatcgatt    1980
gtgtacgaat acatgtgcga gctggtggag cgaaacaagg ccatgcgggg catgatcacc    2040
gaaaagggcg atatcacag cgatatcgcc aatgctcttc atcctcccaa gattgatgag     2100
taa                                                                   2103

<210> SEQ ID NO 46
<211> LENGTH: 1545
<212> TYPE: DNA
<213> ORGANISM: Yarrowia lipolytica

<400> SEQUENCE: 46
atgactatcg actcacaata ctacaagtcg cgagacaaaa acgacacggc acccaaaatc      60
gcgggaatcc gatatgcccc gctatcgaca ccattactca accgatgtga gaccttctct     120
ctggtctggc acattttcag cattcccact ttcctcacaa ttttcatgct atgctgcgca     180
attccactgc tctggccatt tgtgattgcg tatgtagtgt acgctgttaa agacgactcc     240
ccgtccaacg gaggagtggt caagcgatac tcgcctattt caagaaactt cttcatctgg     300
aagctctttg gccgctactt ccccataact ctgcacaaga cggtggatct ggagcccacg     360
cacacatact acctctgga cgtccaggag tatcacctga ttgctgagag atactggccg     420
cagaacaagt acctccgagc aatcatctcc accatcgagt actttctgcc cgccttcatg     480
aaacggtctc tttctatcaa cgagcaggag cagcctgccg agcgagatcc tctcctgtct     540
cccgtttctc ccagctctcc gggttctcaa cctgacaagt ggattaacca cgacagcaga     600
tatagccgtg gagaatcatc tggctccaac ggccacgcct cgggctccga acttaacggc     660
aacggcaaca atggcaccac taaccgacga cctttgtcgt ccgcctctgc tggctccact     720
gcatctgatt ccacgcttct taacgggtcc ctcaactcct acgccaacca gatcattggc     780
gaaaacgacc cacagctgtc gcccacaaaa ctcaagccca ctggcagaaa atacatcttc     840
ggctaccacc cccacggcat tatcggcatg ggagcctttg gtggaattgc caccgaggga     900
gctggatggt ccaagctctt tccgggcatc cctgtttctc ttatgactct caccaacaac     960
ttccgagtgc ctctctacag agagtacctc atgagtctgg gagtcgcttc tgtctccaag    1020
aagtcctgca aggcccctcct caagcgaaac cagtctatct gcattgtcgt tggtggagca    1080
caggaaagtc ttctggccag acccggtgtc atggacctgg tgctactcaa gcgaaagggt    1140
tttgttcgac ttggtatgga ggtcggaaat gtcgcccttg ttcccatcat ggcctttggt    1200
gagaacgacc tctatgacca ggttagcaac gacaagtcgt ccaagctgta ccgattccag    1260
cagtttgtca agaacttcct tggattcacc cttcctttga tgcatgcccg aggcgtcttc    1320
```

| | |
|---|---|
| aactacgatg tcggtcttgt cccctacagg cgacccgtca acattgtggt tggttccccc | 1380 |
| attgacttgc cttatctccc acaccccacc gacgaagaag tgtccgaata ccacgaccga | 1440 |
| tacatcgccg agctgcagcg aatctacaac gagcacaagg atgaatattt catcgattgg | 1500 |
| accgaggagg gcaaaggagc cccagagttc cgaatgattg agtaa | 1545 |

<210> SEQ ID NO 47
<211> LENGTH: 1572
<212> TYPE: DNA
<213> ORGANISM: Yarrowia lipolytica

<400> SEQUENCE: 47

| | |
|---|---|
| atgatcatct tatacgtttt ggccgttgcg gtctccttcc tcatcttcaa gagagtcacc | 60 |
| tacacgatgc gaagccgaga gctcgccaag aagtggcact gtgaggagcc tcacaacctg | 120 |
| aatgagttcc ccctgaactt gccgctcttc ttcctcatca tcaatgcctc tcgacgacac | 180 |
| gagctgctcg atacccctact tggccttttc cgatcctttg ctcccaccaa gactgttaag | 240 |
| caggtgcttc tgggctcctt cactatcatc cccaccaacg atcccgagaa catcaaggcc | 300 |
| gttctggcca ctcagttcaa ggacttctgc tgggccagc gacacggcca gcttgccccc | 360 |
| gttctgggag acggaatctt cactctggac ggccagggat ggcagcactc tcgagccatg | 420 |
| ctgcgacccc agtttgctcg agaccaggtg tctgacgtcg agatgatcga gcgacacgtg | 480 |
| cagatgatgt tgctgcgaat tcccaacaac aagaagttcg acatccagga gctcttcttc | 540 |
| aacctgaccc ttgatactgc caccgagttt ctgtttggcc agaccgtcgg ctcccagacc | 600 |
| gtcgagatgc ccaacgagga caagtctacc gtctctgata tgcccaagga tatgcgaaag | 660 |
| tctttccagg aggactttaa tgtggcccag caccacggtg gaatccgaac tagattccag | 720 |
| atgttctact ggctgtggcg acccactgag ctcttctctt cctccaagcg agtccacgcc | 780 |
| tttgtcgacc actacgtcga gaaggctctt gccaactccg acgaagagaa gtccgacgac | 840 |
| aagtacattt tcctgcgaga actggcccga gaagtcaagg acccccgagt tctgcgagac | 900 |
| caggccctca acattctgct tgctggccga gacaccaccg ccggtgttct gtcctggatc | 960 |
| gtctacgagc tggcccgaca ccccgaggtg tggaagaagc tgcgagccga gattcaccag | 1020 |
| gactttggtg acggcagcga tctctcccag atcacctttg agggtcttaa gcgatgcgag | 1080 |
| tacctgcgat ttgtcatcaa cgagactctg cgactctatc cttctgttcc tcttaacgtc | 1140 |
| cgatacgcct ctcgagatac cactcttccc cgaggaggag gacccgacga gtccaagcct | 1200 |
| atccttgtcc gaaagggaga caccattgtc tacaacgtct tctctatgca ccgaactgag | 1260 |
| gagttctggg gcaaggactg cgacgagttc cgacctgagc gatgggctga aagggctct | 1320 |
| cgaggctggg agtacctgcc cttcaacgga ggaccccgaa tttgcctggg ccagcagtac | 1380 |
| gctctcactg agacctcgta cgtcatcact cgaatctgcc agctgttcac caatatcgag | 1440 |
| aacgctgaca cagctgtcga gcctcctcag aagctgcacg ccctcactct gtgccatctt | 1500 |
| aacggtgtgt tcgttaagat gacccgggac gaggctgcct ttgccgagac cgagaagctc | 1560 |
| attaacgcat aa | 1572 |

<210> SEQ ID NO 48
<211> LENGTH: 1632
<212> TYPE: DNA
<213> ORGANISM: Yarrowia lipolytica

<400> SEQUENCE: 48

| | |
|---|---|
| atggccacac tccaccccga agacgccgca ggacggcccg tgcgacgacg acctcgtccc | 60 |

-continued

```
tccagttcgg gcggctccag atcgccgtcc accaaacgac actcgatagt gcgggagcat       120
ctcggagaag agctcaatgt gcccgacggc caggaaatgg acctgggcca ggtcaacaag       180
aacctcaatg ccgcatacgc caaggccgag aaggactcgg acgacgagaa ggaaaagaag       240
gaggagggcg tggtggacga gctgccgagg aagtattcct accctcgatt ctcaaagaac       300
aaccgacgct acagattcac cgacatcaag ttcaagccaa caccgtcgat tctcgacaag       360
ttcgcccaca aggactcgga gttctttggc ttctacaccc tgctgtggat ggtgtttgcc       420
ttctgcgtct tccgaaccgg cctgctcaac tacacaaacg aaggcatcct gttccggggc       480
cagattttcg ccattctcag caaagatctc tggaaagtcg cattggtcga tctgggcatg       540
tacctgacca cctatctgtc tgtgtttctg caattggccg tcaagcacgg tctggtcgac       600
tggaactcgt ttggctggat catccagaac gtgcaccaga ccctgttcct cttcttctac       660
ctttgggtcg ccaagtcgag taacctgcct tggatcggta acatcttcat tgtgcttcat       720
gcctttgtca tgctcatgaa acaacactcg tacgccttct acaatggcta cctatggact       780
gtcgaggacg agctctccca cgcaaagcag cgtctcaccg aagacattcc tgtttcagag       840
aaggaggatc tcaagctgga catcgagttc tgcgagacag agctcaaggt ccaatccaga       900 cacaccccctt tccccaccaa catcaccttt tctaactact tctggtactc catgttccca       960
acgctcgtct acgaaattga gttccctcga accccccgaa tcaagtggac atacgtgctg      1020
gagaaggtcg ccgcagtctt tggcgtcttc ttccttatga tctgggtcgc agagtcgtac      1080
ctgtatcccc ctgtggtggc tgttattcaa atgcgagacg aacccttctg gaacaaggtc      1140
cgaatctatc ccattttcct gtcggacatt ctgctgccct ttgtcattga gtacatgctt      1200
gttttctaca tcatctggga cgccattctc aacggcattg ccgagctcac tcgcttcgcc      1260
gacagagact tttatggccc ctggtggaac tgtaccagct gggagcagtt tagccgagaa      1320
tggaacattc ctgtctacca gttcctcaag cgacacgtct accactcgtc catctctgct      1380
ttcaagttct ccaagggcgc agctaccctc accaccttct tgctgtcttc tcttgtccac      1440
gagctggtca tgtttgccat cttaagaag ttccgaggat acctgctgtt gctgcagatg       1500
acccagctgc ccctggccat gctgcagaaa accaaatgga tccaggacag accgtttttt     1560
ggcaacgctt tcttctggtt ctcgctcatg atcggacctt ctctcatgtg ttccatgtac     1620
ctcctcttct aa                                                         1632
```

<210> SEQ ID NO 49
<211> LENGTH: 897
<212> TYPE: DNA
<213> ORGANISM: Yarrowia lipolytica

<400> SEQUENCE: 49

```
atggttgcca tccgatccac tctctccgtc gccgctctcg ccgctgtcgt ccaggccgct        60
ggaaacccca tcatcgcctc tatcgccaac gacgttgtgc agggtattgc tgccgccaag       120
accgacgact ccctctctga cgctgatgcc acctccgaga tccaggctgt tgttgacatc       180
gtcaccaaca ccccgatgt ggcgctctc ttcaccgccg ctgtccccgt tattgccatc         240
ggccttgacg agaccaactt cccctctctg ctcgacgctg cctccaagac tcttgatgtc       300
tttgagggtt ccgacgacta caagaaggct gttgagggct caacgccgc ctttgagcac        360 tacgatgtcc cccaggctct gtccaacatc atctccaaca tcggtgccgt tctcgccatt      420
gttaccccct ctctcccctc tctgacccc gagttctccg acaagtggga gaccgccact       480
```

| | |
|---|---|
| tctcgagttc tcgagctcgc cacctctctt ggtatcctcg gtggaggaaa gcccaaggtt | 540 |
| gctgaggcca cttctgctgc tgccgaggcc acctccgctg ctgccgaggc cacctccgct | 600 |
| gctgccgagg ccacctccgc cgccgccgct ccctcttctt ctgccgccgc cgctaaggag | 660 |
| tcttctgctg cccccgccaa ggagtcttct gccgcccccg ccaaggagtc tgctgccccc | 720 |
| gccaaggagt ctgctgcccc tgccaaggag tctgctgccc caaggaatc tgctaaggct | 780 |
| tccgctgctc ccgctgccgc ctccaaggct ccccagcagg ccaacggtgc ttctgccttc | 840 |
| aacgtccagc tcgccgctgg tgtcgccatt gttggtgccg ttgccgctct catctaa | 897 |

<210> SEQ ID NO 50
<211> LENGTH: 1062
<212> TYPE: DNA
<213> ORGANISM: Yarrowia lipolytica

<400> SEQUENCE: 50

| | |
|---|---|
| atgtctcttc ttgaacgaga gcttcaaatt gaggagattg atatcaatct ctaccggtct | 60 |
| gccaaggagc tttggcgacc tatcggtcag cgaggtatct ttggcggctc tgtcattgct | 120 |
| caggccctga tggctgctac caaaactgtg cccccagagt tcattatcca ttccatgcac | 180 |
| tgctactttg tgttatctgg aaaccccgac caccccgtgc tctaccacgt tgagcgggtc | 240 |
| cgagatggca gaagcttcgc tacccgaaca gtccaggcca acagcgggg acgtgtgatc | 300 |
| ttcaccacta catgctcttt ccaggttgac aagggcaacg aaacatgca tcatcagagc | 360 |
| cgaatgtacg agcgagaggt caagagcagt ggaaaggctt ttgatggcga acacgaggcc | 420 |
| accaacggaa ttcctgctcc cgagaattgc gtctcctcgc tggaggtgtc caagtacctc | 480 |
| aacaagcagg gcgtgatcag tgacgatatt ctcaagaaga tggtggatcg atcagttgag | 540 |
| gatcccattg aaattagact agtgaccggt cttctgaaca aggacgatgg tctgcttcct | 600 |
| catgaacgaa gaatcaagtt ctgggttcga tgcaaacctg ttattgagcg agacgacgtt | 660 |
| cagtcggtcg gtattgctta cctcagtgac tctttcctgc tgggaacagc tatccgagtc | 720 |
| cagccctca atcccggtgc tgcctctatg gttgtttccc tggaccacac aatctacttt | 780 |
| catggcaagt tccgagctga tgaatggctg ctgcacgtga ttgattccaa ctggagtgga | 840 |
| aacgagcggg cactggtccg aggacgactc tacaaccaac agggagtctt ggtcgccaca | 900 |
| gtgttccagg agggtgtcat tcgattgaag gagaaataca aaggcaaggc tgtagagacc | 960 |
| acagatgact atcttagcag cggaacgaga actgatgctg agaaggagga gtctaagaag | 1020 |
| aagggagcca tggctgctaa gagtattgac agtaagctgt aa | 1062 |

<210> SEQ ID NO 51
<211> LENGTH: 879
<212> TYPE: DNA
<213> ORGANISM: Yarrowia lipolytica

<400> SEQUENCE: 51

| | |
|---|---|
| atgctccgaa caatctccag aacccggacc atggtcccca gccgacattt gatctcatac | 60 |
| agattcttct ccgacgtgtc cacgaccaag ggagagacgt tcactctgac caaacacttt | 120 |
| ttggatgccc caataccgc ccacattgcc gtctactcgc tcaaccggcc cgaggccatg | 180 |
| aactccatct ccaagaagct tctggaggaa tttgagacct acatcaactc gctggcagcc | 240 |
| gaaggacgtc atcagaatgt caccaacact cgtgctctga ttctgagctc ggagctgccc | 300 |
| aaggttttct gtgctggagc agatctcaag gagcgaaaga catttactga tgctgacacc | 360 |
| gctgccttcc ttaacaagct caatggcact ctcgacacca tccagagcct gcacatgccc | 420 |

```
actatcactg ccattcaggg ctttgccctc ggaggaggcg ctgagatctc cctggccaca      480
gacttccgag ttctgtctga tgtgcccaa tttggtctgc ccgagacccg tttggcaatc      540
ttgcctggcg ctggaggaac caagcgactc cccaagctga ttggatactc tcgagctctt      600
gatctggtgc tcactggacg acgagtaaag gccgacgagg ctctccatct tggtattgcc      660
aaccgaaccg gcgagaacgc cctcgagact gcccttgaaa tggctaagct catctgtgag      720
ggaggaccca ttgcgatcaa tgcggcaaag atggctgttc gaggccagtc caaggagtgg      780
gagatcgccg cctacaacaa ggtggtcaat tcggaagaca agttcgaggc tctgtcggca      840
ttcaaggaaa agcgaaagcc cattttcaag ggtcgataa                            879
```

<210> SEQ ID NO 52
<211> LENGTH: 1242
<212> TYPE: DNA
<213> ORGANISM: Yarrowia lipolytica

<400> SEQUENCE: 52

```
atggaaaccc tagcaaattg gcttctaccc gacacccca agcctctgga catcaagcaa       60 ctgactttg gccgacctgg gggaaacaag ggcttcacct tctccaccat ccctctgccc      120
ctcaagacca atgaggtact tattgaggtg aaggcggcct cactcaatcc atgggaccta     180
aaggtgtgga agcagcccca gacttggctc aaggaagagc atggcttggg ccaggatttc     240
tccggtatca tcagcgatct gggccaggga gctgcgtcaa agggctggaa ggttggcgat     300
cgtgtctgtg gtctcaaact tcactacggt agtcagggaa ccattgcgtc ccacattgtt     360
attgacctca acaagaccaa gtactctatg acccacattc ccgacaacat gactttcgag     420
gaggccgcag cgttcccact cgtgtttgga gccgcctggg agggcctgtc acattgccca     480
atgcaggcga ttagagatca gaccctcaac gtctgtattc tgggaggagg aacagccgtg     540
ggccagatgg ccatccagct ggccaagaac cacctgcgag ccaagcacgt ggtgtgcacc     600
acagccggcg gcgagtcgga ggagattgca cgtgatctcg gtgcagacca tgttatcgat     660
tacaaggctg ccggaaacgt cggagacgcc attgagtaca ttgtcggcaa ccaggagcta     720
gacgatacca acgaccagca cagggtgcgg tttgcaaact cgtactccac taatggcgag     780
aaatttgacg tgatcctcga ctgcgccgga ggtgctggag ctggagacgt gctggcgaag     840
gccaagtcgc ttctcaagcc ctacaatgag ggatccgcct ttgtcaccct gtgggagac     900 tacaataccc ccaaggtcaa tgcctcggtt gtccacggct ccaatggtcc ctctcctctc     960
atttccaagt ccatctccac atatgactcc gcttcatatt ggtacggagg ctggactcat    1020
aagctggctt ccagaccgg ctcttcaggt tttagataca tcaccgccaa tgtcaagggc    1080
tctggtgact ggatcaacca agcccacgct ggcttcgcat ccaactctat caaggtcgca    1140
attgacacgg tataccctg gaccaagtac gacgacgcct ttgagcagct cctgagccga    1200
aaggtcaagg gcaaaattgt tctgcgaatc caggactttt aa                        1242
```

<210> SEQ ID NO 53
<211> LENGTH: 4980
<212> TYPE: DNA
<213> ORGANISM: Yarrowia lipolytica

<400> SEQUENCE: 53

```
atggcgcact actacccgtc gggcgtgtcg tcggtcggca acttcgactc gctagatgtc       60
gagatcagat cgctggccga gggaatggta cacaaaccct accatcgaga atcgcgatac     120
```

-continued

| | | | | | |
|---|---|---|---|---|---|
| attttcgacc | acacctttga | cgacgagttt | cgagaagagc | atgaggacga | atacgactat | 180 |
| gatatgctgc | ggaagacgtc | ttttgagaac | cccgacgtca | acccttacgt | ggaggccagt | 240 |
| gcggagccgg | agctggatcc | ctggtcgggc | gagttcaact | cgcgaaagtg | gatcaagacc | 300 |
| gtgctgggtc | tcaaggagcg | atttggaaac | agtaagggaa | tcacgccgg | cgtgtcgttc | 360 |
| aagaacctgg | gtgcctacgg | gtacggcagt | cgcagtgact | accagaagac | gtttctcaac | 420 |
| gtcattgtgg | ccactggaga | tttgctgcga | agtgctattg | cgctaaacg | gacaagcaaa | 480 |
| atccagattc | tgcgcaagtg | cgatggactg | gtgcttccag | gtgaaacctg | tgtagttctg | 540 |
| ggacgtcccg | gatcaggatg | cactacattt | ctcaagagta | ttgcttgcga | gacgtacgga | 600 |
| tttcatgtgg | aggaagagac | acaatggaac | tatcagggcg | taccacgaga | tgtcatgaca | 660 |
| aagcattgcc | gaggagaaat | tgtctacaat | gctgaacacg | atatccattt | ccctcacttg | 720 |
| acggtcggac | agaccctcat | gtttgcggct | ctagcccgaa | ctccccgaaa | ccgagtgctg | 780 |
| ggagtgaccc | gagagcagta | tgctcgtcac | acccgagatg | ttaccatggc | cactctcggt | 840 |
| ctgtctcaca | caatcaacac | caaggttgga | tccgatctag | tgcgtggagt | ctccggtgga | 900 |
| gagagaaaac | gagtctctat | tgccgagtcc | gtcgtctgcg | gagcgcctct | acagtgctgg | 960 |
| gataactcca | ctcgaggtct | ggatgctgcg | aacgccaccg | aattcattcg | atctctgcga | 1020 |
| ctttccgccc | agatgacagg | cgcctccatg | tttgtgtctc | tgtaccaggc | ttcccaggag | 1080 |
| gcctacgaca | tgttcgacaa | ggtgtgtctg | ctgtacgagg | acgacaaat | cttcttcggt | 1140 |
| aaggccggag | aggccacatc | atactttgag | ggtctgggat | tcgagcgagc | ccatcgccag | 1200 |
| accactggtg | attttctgac | ctcccttaca | aaccctgtcg | agcgaagaat | caaggctgga | 1260 |
| tgggagaagc | tcgtgcctcg | aactcccgag | gagtttgagt | ctcgatggag | atcgtcccga | 1320 |
| acacacgctc | tgttagttta | caacatcgac | cgattcaata | ccactcatcc | tcttggtggt | 1380 |
| cagggttatg | tcgagttcat | gaagctccga | aaggagtctc | aggcccgaaa | taccgtctg | 1440 |
| tcgtcgccat | atctgctctc | ctggcccatg | caggttcgtt | tgtgtctctg | gagaggcttc | 1500 |
| ttgttggtga | gaggagactt | gtccatgacg | ctgatgacca | tcattggtaa | cttcatcatg | 1560 |
| gccctcattc | tggcatcaat | gtactataat | ttgcgagagt | cgactgatgc | cttcttctcg | 1620 |
| cgatctgccc | tgcttttctt | ggccatgttg | ctgaacgcta | tggcctccgt | tttggagatt | 1680 |
| ttcgtgctgt | acgacagcg | accactgatt | gagaaacaca | aacgatatgc | attgtaccat | 1740 |
| cccttttgcag | aatcaatcgc | gtcaatgttg | gttgatttac | cgaccaaact | ggcaactctg | 1800 |
| atttcagtca | acctcgctct | ttacttcatg | actaacctga | gacgaacccc | gggtgccttc | 1860 |
| ttcatcttcc | tgctctttttc | gttcacctgt | accatggcaa | tgtccatgat | tttccggttc | 1920 |
| actgcttctg | tcaccaagac | tatggaacag | gctctggccc | ccgcctctgt | gctagttttg | 1980 |
| gcactggtta | tttacactgg | tttcacgctt | cccgtcgatt | acatgcatgg | atgggcccga | 2040 |
| tggatgaatt | acctcaatcc | tgttgcttat | gcgtttgagg | cagtaatggt | gaacgagttc | 2100 |
| cgaaacagaa | ggttcccttg | tggactttac | gttccttccc | ggtctttcta | caactctgtg | 2160 |
| cccgctgagt | ccaagtcttg | tgtggctatc | ggcgccaagc | tcggccagga | ctacgtcgat | 2220 |
| ggctccgtgt | tcatcagcac | ggcctacaag | tacgagactg | gacacctgtg | gcgaaacctg | 2280 |
| ggcattctgt | gggcctttgc | tggctttttc | tgcggcgtct | acctgcttgc | tgccgagtac | 2340 |
| gtgaccatgg | cccagtccaa | gggtgaggtt | ctgctgttca | agcgatccca | gcatcgaaag | 2400 |
| aacctcaagg | ccaagcctga | caagcgattc | caagacgttg | agcttggaga | caacctcggc | 2460 |
| gaccacaact | tggaccaaaa | cctcggcgac | aaccactcga | cgtactctta | ccagcaaccc | 2520 |

```
atccaggctc agattccccc ttctcggtac gcccagcagg ctcccatgac tcccgctcct    2580
atgatgcatg tccccatgac tcctggtggc atgctttctc ccggtcagca aatgttctct    2640
cccggtcagc aaatgatgac gcctggtccc atgtcacccg caggcatgat gactcccggt    2700
tttacatatg tgccccccca tggagacact attcaccaac cgcctaccgt tggagacgac    2760
atcaactaca cgactcccgc gccccaggtg aacttcaccc ctgccactcc agctcagtac    2820
actactcccg ccaccccagc tcagtacaac actcctggca cccctggtat tactggtggg    2880
tacgagcccc ctcatggaga cactgttcac atgccccca cagttggtga tgacacaaac    2940
tacattccca ccaaggttcg caccaacctg tctctcaact cgtccaaatc taacttgcag    3000
cactctggag tgttccaatg gaccgatgtt tgctacgata tcaaggttgc tggtgagaac    3060
aagcgattgc tggaccatat cgacggttac gtgaagcccg gtaccctcac cgctctcatg    3120
ggagcttctg gtgctggaaa gactactctt cttgatgtgc tggctgatcg aaaatccact    3180
ggtattgttc atggagacat gttggtcaat ggccagcagc gaaacgcctc tttccagcga    3240
aagaccggat acgttcaaca gcaggatttg catactgcca ctgccactgt tcgtgagtct    3300
ctcgagttct cagctctgtt gcgacagccc tcttctgtgt ctcgagctga caagctggct    3360
tacgtcgatg aggtcatttc tattcttgag atggattctt acgctgatgc cgttgttggt    3420
gttcctggtg aaggtcttaa cgtggaacag cgaaagcgtc tgactatcgg cgtcgagctt    3480
gctgccaagc ccgagctgct gcttttcctg gatgagccta cctccggtct ggattcccag    3540
actgcttggt ctatcgtctc tctgctcaaa agctggctg ccaacggtca ggctatcctg    3600
tgtaccatcc atcagccctc tgccattctg ttccaagagt ttgatcgact tctgttcctg    3660
gcagccggtg gaaagacagt gtactacgga gacctcggtg ataaggcgtc tctgctcatt    3720
gaatactttg aaagtaacgg tgctgaccct tgtcctgata acggtaaccc tgccgaatgg    3780
atgctggagg taattggtgc tgctcctggt tcccgggcca agaaggactg gccctcagtc    3840
tggcgatact cccagcttcg acgacaacag cgtgaggaac tcgatgatat gcgtcttgca    3900
ttcaacgctg actctcaggc agctcttgca gttggaggag aagacactga tttcgccgtg    3960
tctcagtgga cccagctgta ctacgttacc aagcgactgc tgcagttcca ctggcgaact    4020
ccctcctatc tgtggtccaa gatgactctg tgtattggtt gtgctctgtt cattggtttc    4080
tccttctaca gtcggctcg agacattcag ggtcttcaga accaaatgtt tagtattttc    4140
ctcatgttcc tgattttcac cacagttgcc gagcagatta tgcctctttt catgattcag    4200
cgagacttgt acgaggctcg agagcgtgct tccaagactt actcgtggca ggtgttcctc    4260
ggcggaaata tgctcgcgga gcttccctgg cagattatcg tggcggttgt cgtcttcttc    4320
tgcatgtact accccattgg attctatcga attgcggctg agaaccacca gacacaggag    4380
cgaggagctc tctacttcct cttcctgctg gtcttcttca tttacgactc tacctacgct    4440
cacatgattg gtgtcatgtt caacaaccac gagacggcag ccaactttgc atacctgctc    4500
ttctccttct gtcttatgtt ctgtggtgtg ctggccacga aggagtccat gcctggattc    4560
tggatcttca tgtaccgagc gtcgcctctg acatacttca ttggcggttt catggccact    4620
ggtttggccg gaggaaaggt gacatgttcg caacatgaga ttttgcagtt caagcctctc    4680
aagggcaact cttgtgcaca gtacatgaaa cccttcctgg acaatgctgg catcttcaag    4740
ggctacctgc tcaatgaaac tgccaccgac atgtgtcact attgccccat cgagaacgct    4800
gatgcctacc tcgacaatgc ctccattttc tatggagacc gatggcgaaa ctttggcatt    4860
```

```
gtgtttgcct atcccatctt caacgtttgt gccaccttta tgctctacta cgttcttcga    4920
gttcctggcg tgcgatacaa gattgcgtcc aaggtccgat ggcgacgaaa gaagcagtaa    4980

<210> SEQ ID NO 54
<211> LENGTH: 1191
<212> TYPE: DNA
<213> ORGANISM: Yarrowia lipolytica

<400> SEQUENCE: 54
atgactgaga acgtgcctca aggtcagatc accatgcctc ttcagcaggg cggtgctcgg      60
gagatttctc ctcaagcact tgctgtggca gactacctgc ggagccacaa gctgctcaaa     120
cagcggcccg gaatcctcaa cggtaagcga tccgactttt tccgtgttaa gcgagccatt     180
cgtgcactag aagaccccaa atacaagcag cttcagtcaa agcccaactc caagctgccg     240
cccatcaact cgcgaaacga ggccatctca atcttccgac tcatgcccat caaccagatg     300
gctctcagag tggataagct gcccacacag acagcgctga tgatgaaaca aaagcccgag     360
cagggagtcc ccgtgctgca ggtgaacccc cagcaggagt ttggcgacga tatgtactac     420
acatggttct ataacccccgt cccattgacc acatatctgt acggcgctct cggagtggcc     480
gccatctttg ccggtgtgct gtttcctctg tggcctatct tcctgcgaca gggcgtgtgg     540
tacctgtccg ttggcatgct gggactcatt ggtgtcttct ttggcattgc actggtccga     600
ctggtcatct ttgtgctcac ctggcccacc gtaaagcccg gtatctggat cttccccaat     660
ctctttgctg atgttggctt cgttgactcc ttcatccccc tgtgggcctg gcacggaacc     720
cccgagcgag acctgctgcc ccagaagttc aagaacaaga gaagaagaa gaacgctggc     780 accgtgattg agtccaagga gccccgcga aagctgacca aggaggaaaa gcagaagcag     840
aaggaggcca acgcccagat ggagcagatg caggctgctt ccagacccca gctctccagc     900
ttcgccactc agatgcaaca gatcaaggag atgtccgact ctggcatcga ccccccagatc     960 attgctgccc agtccaggc tcagtaccct cccgataagc aggctgctat caagctggag    1020
aacgagcaag cccaggccaa gcttgatgag cgaatccgag aacttgctgc tcagattcag    1080
gataagacca atgccaataa gactggcgac aagatcgagg aggtcgctga caaagaaaat    1140
aaggaggctc ccaagagaat tgttactctg gaggatgcta acgacgagta a             1191

<210> SEQ ID NO 55
<211> LENGTH: 1416
<212> TYPE: DNA
<213> ORGANISM: Yarrowia lipolytica

<400> SEQUENCE: 55
atggccggtg taagatttct cgacctggtg aaaccgttca cgcccttctt gcccgaggtc      60
caggcgcccg agcgaaaggt gcccttcaac cagaagatca tgtggaccgc cgtgaccctc     120 atgatttttcc tggtcatgag tgagatccct ctgtacggta tcaactcgtc agacaaatcc     180
gacgcgctgt actggctgcg aatgatgctt gcttccaacc gaggctctct gatggagctc     240
ggtatcaccc ccattgtgtc gtccggaatg tgttccagc tgcttggagg aacccagctg     300
atcgaggtca acatggacct caagtccgat cgagagcttt accagaccgc ccagaaactg     360
tttgccatca tcctctcgct tggtcaggcc accgtctacg tcttgactgg catgtacggt     420 cccccccaagg atctcggtgt cggtgtctgt ctgcttctca tcttccagct tgttcttgcc     480
gcccttgttg ttattctgct cgatgagctg ctgcagaagg gttacggtct cggatccggt     540
atctcgctct tcattgccac caacatctgt gagcagatct tctggaaggc ttttgccccc     600
```

```
accactgtca acaagggccg gggctacgag tttgagggcg ccattgtcgc gtttgtgcac    660
ctactcttca cccgaaagga caagaagcga gccatcattg aggctttcac ccgacaggat    720
ctgcctaaca tgtctcagct ggtgactact gtggccattt cgctgccgt catctacctc     780 cagggcttcc gagtcgacat ccccgtcaag tcatccaagc agcgaggccc ctacggcgtc    840
ttccccatca agctcttcta cacctccaac ctgcccatca tgctgcagtc cgccctgacc    900
tccaacatct tcatcatctc ccagatgctg ttcaagaagt cccccacgaa cgtgctcgtc    960
cggctgctcg gtgtgtggga cggccgagag ggcatgcagc agctcttccc cgtctccggt   1020
atcgcctatt acatgcagcc cccttcaac gccaaggagg cactggctga ccccgtcaag   1080
accgtcatct acattgcctt tgttctgggc gtatgtgccg tcttctctgc cacctggatt   1140
gagatttccg gctcttctcc ccgagatgtg gccaagcagt caaggagca gggtctggtg    1200 attgctggcc gacgagagac ttctgcctac aaggagctca agcgaatcat ccccaccgct   1260
gcagcttttg gaggagccac cattggcgct ctgtcagtcg cctccgacct gctcggagcc   1320
ctcagctccg gaaccggtat cctcatggcc gtgaccacaa tctacggcta ctacgagatg   1380
gccgccaagg agggctacgt tgatgctgct atttaa                              1416

<210> SEQ ID NO 56
<211> LENGTH: 1880
<212> TYPE: DNA
<213> ORGANISM: Yarrowia lipolytica

<400> SEQUENCE: 56
atgctcgatc tggtgaaacc attccaggcc attctgcctg agattgttgt tcctgctcga    60
aaggtgagta ttgttgatcg agagacgacg atgacaagtg gaggacattg aggacattga    120
gagagagaaa tgacaggatg cacggacgaa ttcaagagat cttagtctct gatggtactg    180
attgacgatg atcaacccct gcccaacatg tgtaaccct caacatgtcc attttgaatc     240
aacaacatgg caaatgcgac cggaatgata cccgatgtgc tgacgctagc gcactatagg    300
tgatcagcga tggtgttgcc gatccaaacg acctcaatgg ttgtgttagg atctcatcat    360
cagacgttgc cactgcagat caactcagtg ctgtagctcc tctcaaagct acttccaggt    420
aaacgattct attgtatttc tgtgatcaac ttggttcacg tcagtcagat tgtctcgcta    480
agttgcttaa ctgctaccct gctctcggtt tctacatact aacccagctc ccttttacg     540 acaaaatcgc ctacactgtc ggaatcgcca tcactttttt catcatggcc ggcatcccgc    600
tctacggcgc ccacgcctcc acctcagacc cctactcgtt tacccgagcc atctccgcct    660
cttctcacgg cactctgatg gagctcggtg tgggtcccat ggtcacctct ggaatcatct    720
tccagatcct gggaggtttc caggccctta atgtcaattt tgacattcga gccgaccgag    780
agctcttcca gagcggccag aagatctttg ctcttctgct caccttcttc catgccatct    840
tcctcgtctt cttcgctcag acttacggta ccatttcaac cgactctgct gtttcagagc    900
tctctctcgg agctgcggtt ctaattgttg cccagctgac cgccgctggt ctcgtgctca    960
ttctgctcgg cgagattgtc gacaagggct actctttcgg ctctggttct ggtctcttca   1020
ccgctctgtc cgtctcccaa aacttcatgt ggcagaacct tgccctgctc aaggtgcacc   1080
aggagtttgt aggatccatc cctgccctgc tcatgggtct gtggaagaac ggactgttca   1140
actttggcgg ctcttaccga tacgttattg agaactcctt cttccgacag aacctgccca   1200
acctgctgca gctgtacatg tctgtggccg tgttcatgct gaccatctac ctgaacactt   1260
```

```
tccgggtgga catccccatc aagtcgtcgc gagtgcgatc tcttgccacc gcattcccg    1320 tcaagctgct ttacactggc tctatgtgcc tcttcctgct gtctgccttc tcccagaacg    1380
ttctcatcta ctcgcagtct ctttacgtgc agttccctga caacctcatg gtgcaggttc    1440
ttggtagctg gggagctgac ggctctcccg tgggcggcat tgcctattac atcagtccca    1500
acaactttgg atacgatgtc atcaagatgg tgctctactc tgtttacacc attgtgggct    1560
gcactctctt ttccaagtac tgggctgaga tttccggctc cgcccccaag gacgtggcca    1620
agcagttcca ggcccagtcc attgtgattg tcggccagcg agcccagtct gctccccgag    1680
agctggccaa ggtcatcccc gtggctgctg ctgttggtgg agctgttgtg ggcgccattg    1740
tggccttctg cgacattttt ggcggtcttg gagcctctgc cgcacccatg attgtcgccg    1800
tgacttccat gaacaattat tttgagattc ttgcccagga gggtgatatt gctcagatgg    1860
gcaaggcttt tggaatgtag                                                1880

<210> SEQ ID NO 57
<211> LENGTH: 853
<212> TYPE: DNA
<213> ORGANISM: Yarrowia lipolytica

<400> SEQUENCE: 57
atggtaagtg ttcgtttgtg ccccgagccg caaagccata ctaacacagt ccactagcgc      60
ccaagttccc ggaggccccg ctgcccagat gaagtgagta tgacaccgga gggagaaaaa     120
gagaccacga catggatcgt ggcagaaaga ccataagact gatggtcgcg tttggggaat     180
gtaaatgaga tgatccagat gatgggatca tgacagtgga ttggacgcgt agtaggattg     240
gtgggtggga agttgtggtg tgttggggat gtttggggtg gatgttaaca cacacaacac     300
cttaggtgcc aggttttaaa aacagtgcta gggtgtttgt ggtaagagtg ttactctacg     360
actgtgacgc acgacacaag cggcaccacc attaagactt acaatccacc catcttctca     420
ccccacgccc acatccttc acacgtacac gcacacgtac atgtccccac atgcatacac      480
cacgtcatgg atcagaacag gatccaagtt gacgatgact cgatcaagac tcgagggatg     540
gcgctacgca gttcgcggat gaacaggacg tggctaccaa ctcgtgatct ccacacggtc     600
gtatccattt ccatactaac ctaggcgacg aaacaacgct cagcgacagg aggccaaggc     660
ctcgcagcga cccacctcca cacgatctgt cggtgctggc ggatcgtcct ccaccatgct     720
caagctctac actgacgagt cccagggtct caaggtcgac cccgtagtgg tcatggtgct     780
ctctctgggt ttcatcttct ccgttgttgc tctccacatt ctcgccaagg tgtccaccaa     840
gctgcttgga taa                                                        853

<210> SEQ ID NO 58
<211> LENGTH: 544
<212> TYPE: DNA
<213> ORGANISM: Yarrowia lipolytica

<400> SEQUENCE: 58
atgcctgctg aagataaggt ctccaagaac gttcctctcg agttcatcca ggagggaact      60
gcattcctca caagtgcac aaagcccgac cgaaagggtg agtatggata acacgacgaa     120
gcggaggtcc tgacacgaca gagtcgagct gagacacgaa gtcgtgctgt gacgcggagt     180
cgtgatgttt cacgtcgcaa atcgtcatgt gattcagaca caaacagaat catactaact     240
cagaatacac caagatcgtt cgagccgttg gtgttggttt cctcgtcatg ggagccattg     300
gctacattgt caagcttgtg agtatgactg acgcgacaaa cagacagaac gggtaacccg     360
```

```
acacaaacgc cacatagaag gaggatacac atggatgaca aacgcgatat cacgatcatc    420
ttcacacgat gattcttgtc tctgagctat gtgtcaatga cactggtctc aactacccag    480
ccctacctct caactcttgc taactcaggt tcacatcccc atccgacatg tcattgccgc    540
ctag                                                                 544
```

<210> SEQ ID NO 59
<211> LENGTH: 1950
<212> TYPE: DNA
<213> ORGANISM: Artificial Sequence
<220> FEATURE:
<223> OTHER INFORMATION: Synthetic DNA encoding homolog of Sec63 from Y. lipolytica

<400> SEQUENCE: 59

```
atgccttcgt actcttatga tgaagagtcg acgtgtggc catactttgc ggtcacgttg     60
ggctcactgg tgctagtccc ctggactctc agtgccgtct atccggttct gtgtccccc   120 aagacccagg cgactcttcc cgagggcgtg actccattcc gtcccccca tgcggcggac   180 attgactcgt tccagagcaa gcaacggcgc ggaaagctgc tgtccaagcg caacgtggct   240
ctggttgcgg ggtgggcggc tctgattgga gcgctggtgt tcatttcaca acaggaggtc   300
aaggtcaagg ccgacacgtt tgatccgtac gagattctgg gcgtgtcctt ctcggccaca   360
gagaagcaaa tcaagagcca ctacaaaaag ctgtcggtca agctgcatcc cgacaagatc   420
aagctggtgg ctaaccagac catggagcag gtggaggacg cgtgggtcca gatcacaaag   480
gcctacaagg cgctgacaga cgaagtcacc cgaaacaact ttctggagtt tggccatcct   540
gacggccccc agcagaccga ccacggtatt gctctgccca gtggctcgt ggagggccag    600 ggctctcct tgctcattgg tgtctacgcc attgtcgtgg gagtcatcct ccctacacc    660 attggcaagt ggtggaccgg agtcaagtcc tacactcgtc gtggaatcca caacaagacc   720
gcagcccggt tcttctccat catggccaag gagcagccag actacatcac tcacaagcga   780
atcctggagg ccgtgtccga ggccgaggag taccgaatca acttccccga gctcaccagc   840
aagcaggtct acgagcttct agacgactac ctccacagaa aggcttcttc caagcccgcc   900
gctatgctgg gcgtggctgc tttggccccc aagctgctgg atggctttgc cgacattgcc   960
atcgagttca gcctctgga ggtggttcag cgaattattg aggttcagcg agccatggtt    1020
caggccgttt ctctcgacca tcttcctctt ggagagatgc tgcagctccc tcacgtggac   1080
tacgagcagg tgaccaagaa tgccaagggc tacggtaccg ctccatcct gggcttcaag    1140 gatgcccaat tcaaggagat tctgggcgtc gacaaatctg atattacatc ggtcaagaac   1200
accgccaacg ctgtgcccaa gattgatatt gtggatgcct acttcaaggt gcctggtgaa   1260
gacgtggtga ccccccagtc tgctgcccat cttgttctac gaatccgggt gcggccattt   1320
ggaaccaagc gacctctcaa cattgatacc gccaagctca gcatgatct gcatctcgac    1380 gagcctatcg aggtgctcaa ggagcccaca atcaccaaca gcaacgctcc tctgctgcct   1440
cacacctacg caccctactt ccctgctctc catcagggca agtgggttgt gtttatcacc   1500
tctgacaagg acaacaagat tgtcgagggt cccgcgagga tcacccggct cgacgtatcc   1560
aacctgagca atctcaagcc tggcaaggac gtggaggatg gcgttatcgg caccttcaag   1620
atccagctca agaaccccac tcccatgttc cccggcaagt tttcgtacaa ggttaacgtg   1680
ctcaacacgg cttactttgg cgtcgatgct gtagagaagc tgaacgtgga ggtcaagaac   1740
ccggagattc ccgctgatga cgacgacgag gacgacattt ccgagcctga ggaggactcc   1800
```

```
attgctggcg ctctggcttc tgcccggggc cagagcacca agaaggccgc cgtagtggac    1860
gacgatgagg aggactccga ggaggaggag gatctttcgg atatcgacac cgacaccgag    1920
gacgaggctg aggatcccaa gaagaagtaa                                     1950

<210> SEQ ID NO 60
<211> LENGTH: 543
<212> TYPE: DNA
<213> ORGANISM: Yarrowia lipolytica

<400> SEQUENCE: 60
atggaaagca gcagcggcgt ttccatctac acgcccttca tctactttgc cgtgcttgtg      60
acggcgctgg ccgtgtttgg caagatctac cgatcccggc aggcggtcaa cctggcagga    120
gtcgaaccgt ggtaccccga tcacattccc cgagacatct acttcactct gcgggaccat    180
acgtcgcccc gtccatccga aaaggtgctc aaggccgctc ttctacgacg gtcggcggaa    240
aacatcaagc gaatcatcaa aaccaaggag gccaagcccc atctgactgc tcttcacgag    300
gcgggatcca ttggagatga tctgctgcat cagttcacgg cgtgggagaa gatgatcgaa    360
atggagctca cgactgtgc tgctgaggcc aacacatacg ccgaaaactg ggcccaaacc    420
atgtttgcta ctgcgtcgga gatcatccag aacgagggtc tgcgaagacg agtcaacgag    480
ctcaacgaga aggagaaggc ctttgatgcc gacctggtcc aggccaaggt cattgtcgct    540
tag                                                                  543

<210> SEQ ID NO 61
<211> LENGTH: 594
<212> TYPE: DNA
<213> ORGANISM: Yarrowia lipolytica

<400> SEQUENCE: 61
atgaccgtgc ctgctcctat cagctacgac gaatccgccc gaaaggtatc catcgccaag      60
gacgcctcgc tgacccccga gtacaagaag gagctgcaga tcgagctcga caagctcaac    120
tccttcgcca aagagatggt tgcatgccca ggatcgattc ctcctcctcc caacgaggcc    180
aaccgaaacc tggccatcca ggtcgccaag ctgcgggact ccggcgctat gcagttcaag    240
gccggcaagc cccaggaggc tctgacccag atcaacatgg ctctggacat ggctctcaag    300
cgacctctgt acgaggccac tggagctgcc attgccgatg tttctgaggt gctggcttac    360
cgatgcgaca tcaacatggt gctgggtaac tgggccgcgg cctacgccga tgctgaactt    420
ctgtgtctca tcaagcccca gatcccccag aactacctcc gaaagggtaa gtgtctgcag    480
acagccacaa gtacctggaa ggccaaacag gcataccaaa gcggtctcat gtacgccgcc    540
gaggacaaaa ttttgttggg tgccctctct gaggtcgagg caatgctggc ctaa           594

<210> SEQ ID NO 62
<211> LENGTH: 2013
<212> TYPE: DNA
<213> ORGANISM: Yarrowia lipolytica

<400> SEQUENCE: 62
atgaagttct ctatgccttc gtggggcgtc gttttttacg ccctcctggt atgccttctg      60
cctttccttt ccaaggccgg cgttcaggct gatgacgtgg actcttatgg caccgtcatt    120
ggtatcgatc tgggtaccac ctactcctgt gttggtgtca tgaagggtgg ccgagtcgag    180
attctggcca acgaccaggg ttctcgaatc accccctcct acgtggcctt caccgaggac    240
```

```
gagcgactcg ttggagacgc tgccaagaac caggctgcca acaaccctt caacaccatt      300 ttcgacatta agcgactcat tggtcttaag tacaaggacg agtccgtcca gcgagacatc      360
aagcacttcc cctacaaggt caagaacaag gacggcaagc ccgttgttgt tgtcgagacc      420
aagggcgaga agaagaccta cccccccgag agatctccg ccatgattct taccaagatg      480
aaggacattg cccaggacta ccttggcaag aaggtcaccc acgctgtcgt caccgtccct      540
gcctacttca acgatgccca cgacaggcc accaaggatg ccggtatcat tgctggtctc      600
aacgttctgc gaattgttaa cgagcccacc gctgccgcca ttgcctacgg cctggaccac      660
accgatgacg agaagcagat tgttgtctac gatcttggtg gaggaacctt cgatgtttct      720
cttctgtcta tcgagtctgg tgtctttgag gttcttgcca ctgctggtga cacccatctt      780
ggtggtgagg atttcgacta ccgagtcatc aagcactttg tcaagcagta caacaagaag      840
cacgacgtcg acattaccaa gaacgctaag accattggta agctcaaacg agaggttgag      900
aaggccaagc gaactctgtc ttcccagatg tccactcgaa tcgagattga gtccttcttc      960
gatggagagg acttctcgga gaccctgacc cgagccaagt tcgaggagct caacattgat     1020
ctgttcaagc gaaccctcaa gcccgttgag caggttctca aggactctgg cgtcaagaag     1080
gaggatgtcc acgacattgt tcttgttggt ggttccaccc gaatccccaa ggtccaggag     1140
ctgctggaga gttctttga cggcaagaag gcctccaagg gtatcaaccc cgatgaggct     1200
gttgcttacg gagctgctgt ccaggctggt gttctttccg cgcgaggacgg tgttgaggac     1260 attgtcctgc tcgatgttaa ccccctgact cttggtattg agaccactgg tggtgtcatg     1320
accaagctca tcaaccgaaa caccaacatc cccaccaaga agtcccagat tttctccacc     1380
gctgttgaca accagtctac cgtgctgatt caggtctttg agggagagcg aaccatgtcc     1440
aaggacaaca acctgcttgg taagttcgag ctcaagggta ttccccctgc tccccgaggt     1500
gtcccccaga ttgaggtcac cttcgagctt gacgctaacg gaattctgcg agtcaccgcc     1560
cacgataagg gcaccggcaa gtccgagacc attaccatcc caacgacaa gggccgtctc     1620 tccaaggacg agattgagcg aatggttgag gaggctgagc gatttgccga ggaggatgct     1680
ctcatccgag agaccattga ggctaagaac tctctcgaga actacgccca ctctctccga     1740
aaccaggttg ctgacaagtc tggtctcggt ggcaagattt ctgccgacga caaggaggct     1800
ctcaacgacg ctgtcaccga gactctcgag tggctggagg ccaactccgt gtctgccacc     1860
aaggaggact ttgaggagaa gaaggaggct ctgtctgcca ttgcctaccc catcacctcc     1920
aagatctacg agggtggaga aggtggagac gagtccaacg acggtggatt ctacgctgat     1980
gatgatgagg ctccttcca cgatgagctt taa                                  2013

<210> SEQ ID NO 63
<211> LENGTH: 1281
<212> TYPE: DNA
<213> ORGANISM: Yarrowia lipolytica

<400> SEQUENCE: 63
atgaagttca gcaagactct actactggcc ctcgtggctg gtgccctggc caagggcgag       60
gatgaaatct gcagagttga aagaactcc ggcaaggaaa tctgctaccc caaggtgttt      120
gtccctaccg aggagtggca agtggtatgg cccgaccagg tgattcccgc gggcctgcac      180
gtgcgaatgg actatgaaaa cggcgtcaag gaggccaaaa tcaacgaccc taacgaagag      240
gttgagggcg tggctgttgc agttggagaa gaggttcccg agggcgaagt tgtcattgag      300
gacctcaccg aggagaacgg ggatgagggt attagcgcca acgaaaaggt ccagagggcc      360
```

-continued

```
attgagaagg ccatcaagga aaagcgaatc aaggagggcc ataagcccaa ccccaacatt    420
cctgaaagtg accaccagac cttctctgat gccgtcgctg ccctgagaga ctacaaggtc    480
aatggacagg cagccatgct tccaattgct ctttcccaac tcgaggaact gtctcacgag    540
attgatttcg gtattgctct gagcgacgtt gaccccctca atgcgctcct gcagatcctt    600
gaagacgcaa aggtcgatgt ggagtctaag atcatggctg ctcgaaccat tggtgcttct    660
ctaagaaaca acccacatgc tctcgacaag gtgattaact ccaaggttga tctggtcaaa    720
tctcttctgg acgatcttgc ccagtcttcc aaggagaagg cagataagct ctcttcttct    780
cttgtttacg ccctctctgc ggttctgaag actccagaga ctgtcactcg attcgttgat    840
cttcacggag gtgacactct tcgacagctg tacgagactg gctctgacga cgtaaaagga    900
cgagtgtcta ctctaattga ggatgttctc gccaccctg atctgcacaa cgacttctct    960
tcgatcacag gcgctgtcaa gaaacgctct gccaactggt gggaagacga actcaaggag   1020
tggtctggcg tgttccagag atcgctcccc tctaagctgt cctccaaggt gaagtccaag   1080
gtctatactt ctctggcagc tattcgacga aacttccgag agtctgttga tgtcagcgaa   1140
gagttcctcg agtggcttga ccaccccaag aaggctgctg ctgagatcgg agatgatctc   1200
gtcaagctta ttaagcagga ccgaggcgag ttatggggca atgccaaggc tcgaaagtac   1260
gacgctcgtg atgagcttta a                                             1281
```

<210> SEQ ID NO 64
<211> LENGTH: 396
<212> TYPE: PRT
<213> ORGANISM: Yarrowia lipolytica

<400> SEQUENCE: 64

```
Met Thr Glu Asn Val Pro Gln Gly Gln Ile Thr Met Pro Leu Gln Gln
1               5                   10                  15

Gly Gly Ala Arg Glu Ile Ser Pro Gln Ala Leu Ala Val Ala Asp Tyr
            20                  25                  30

Leu Arg Ser His Lys Leu Leu Lys Gln Arg Pro Gly Ile Leu Asn Gly
        35                  40                  45

Lys Arg Ser Asp Phe Phe Arg Val Lys Arg Ala Ile Arg Ala Leu Glu
    50                  55                  60

Asp Pro Lys Tyr Lys Gln Leu Gln Ser Lys Pro Asn Ser Lys Leu Pro
65                  70                  75                  80

Pro Ile Asn Ser Arg Asn Glu Ala Ile Ser Ile Phe Arg Leu Met Pro
                85                  90                  95

Ile Asn Gln Met Ala Leu Arg Val Asp Lys Leu Pro Thr Gln Thr Ala
            100                 105                 110

Leu Met Met Lys Gln Lys Pro Glu Gln Gly Val Pro Val Leu Gln Val
        115                 120                 125

Asn Pro Gln Gln Glu Phe Gly Asp Asp Met Tyr Tyr Thr Trp Phe Tyr
    130                 135                 140

Asn Pro Val Pro Leu Thr Thr Tyr Leu Tyr Gly Ala Leu Gly Val Ala
145                 150                 155                 160

Ala Ile Phe Ala Gly Val Leu Phe Pro Leu Trp Pro Ile Phe Leu Arg
                165                 170                 175

Gln Gly Val Trp Tyr Leu Ser Val Gly Met Leu Gly Leu Ile Gly Val
            180                 185                 190

Phe Phe Gly Ile Ala Leu Val Arg Leu Val Ile Phe Val Leu Thr Trp
        195                 200                 205
```

```
Pro Thr Val Lys Pro Gly Ile Trp Ile Phe Pro Asn Leu Phe Ala Asp
    210                 215                 220

Val Gly Phe Val Asp Ser Phe Ile Pro Leu Trp Ala Trp His Gly Thr
225                 230                 235                 240

Pro Glu Arg Asp Leu Leu Pro Gln Lys Phe Lys Asn Lys Lys Lys Lys
                245                 250                 255

Lys Asn Ala Gly Thr Val Ile Glu Ser Lys Glu Pro Pro Arg Lys Leu
                260                 265                 270

Thr Lys Glu Glu Lys Gln Lys Gln Lys Glu Ala Asn Ala Gln Met Glu
            275                 280                 285

Gln Met Gln Ala Ala Phe Gln Thr Gln Leu Ser Ser Phe Ala Thr Gln
        290                 295                 300

Met Gln Gln Ile Lys Glu Met Ser Asp Ser Gly Ile Asp Pro Gln Ile
305                 310                 315                 320

Ile Ala Ala Gln Leu Gln Ala Gln Tyr Pro Pro Asp Lys Gln Ala Ala
                325                 330                 335

Ile Lys Leu Glu Asn Glu Gln Ala Gln Ala Lys Leu Asp Glu Arg Ile
                340                 345                 350

Arg Glu Leu Ala Ala Gln Ile Gln Asp Lys Thr Asn Ala Asn Lys Thr
            355                 360                 365

Gly Asp Lys Ile Glu Glu Val Ala Asp Lys Glu Asn Lys Glu Ala Pro
        370                 375                 380

Lys Arg Ile Val Thr Leu Glu Asp Ala Asn Asp Glu
385                 390                 395

<210> SEQ ID NO 65
<211> LENGTH: 505
<212> TYPE: PRT
<213> ORGANISM: Hahella chejuensis

<400> SEQUENCE: 65

Met Lys Gln Ser Leu Thr Leu Thr Ala Phe Ala Asn Lys Asn Val Leu
1               5                   10                  15

Ile Thr Gly Thr Thr Gly Phe Val Gly Lys Val Val Leu Glu Lys Leu
                20                  25                  30

Leu Arg Ser Val Pro Thr Ile Gly Lys Ile Tyr Leu Leu Ile Arg Gly
            35                  40                  45

Asn Ser Lys Asn Pro Thr Ala Arg Lys Arg Phe Gln Asn Glu Ile Ala
        50                  55                  60

Thr Ser Ser Ile Phe Asp Thr Leu Lys Ala Ser Gln Gly Ser Arg Phe
65                  70                  75                  80

Glu Glu Leu Cys Glu Thr Arg Ile His Cys Val Thr Gly Glu Val Thr
                85                  90                  95

Glu Pro Leu Phe Gly Leu Ser Glu Lys Asp Phe Thr Asp Leu Ala Ala
                100                 105                 110

Asp Ile Asp Val Ile Ile Asn Ser Ala Ala Ser Val Asn Phe Arg Glu
            115                 120                 125

Ala Leu Asp Gln Ala Leu Thr Ile Asn Thr Leu Cys Leu Lys Asn Ile
        130                 135                 140

Ile Glu Leu Ser Arg Arg Ala Ala Asp Cys Pro Val Val Gln Val Ser
145                 150                 155                 160

Thr Cys Tyr Val Asn Gly Phe Asn Gln Gly Val Met Glu Glu Ile
                165                 170                 175

Val Ser Pro Ala Gly Glu Arg Ile Glu Arg Ser Glu Arg Gly Tyr Tyr
```

```
                    180                 185                 190
Glu Val Glu Pro Leu Ile Ala Arg Leu Leu Gln Asp Val Gln Val
            195                 200                 205

Ser Ala Ala Ala Asp Asp His Ser Arg Glu Lys Asp Leu Ile Asp
        210                 215                 220

Leu Gly Ile Lys Glu Ala Asn Lys Tyr Gly Trp Asn Asp Thr Tyr Thr
225                 230                 235                 240

Phe Thr Lys Trp Met Gly Glu Gln Leu Leu Met Lys Glu Leu Tyr Gly
                245                 250                 255

Lys Thr Leu Thr Ile Leu Arg Pro Ser Ile Val Glu Ser Thr Leu Leu
            260                 265                 270

Gly Pro Ala Pro Gly Trp Ile Glu Gly Val Lys Val Ala Asp Ala Ile
            275                 280                 285

Ile Leu Ala Tyr Ala Arg Glu Lys Val Ser Leu Phe Pro Gly Lys Lys
        290                 295                 300

Asn Ala Val Ile Asp Ile Ile Pro Ala Asp Leu Val Ala Asn Ser Ile
305                 310                 315                 320

Ile Leu Ser Ala Thr Glu Ala Leu Leu Asp Ser Gly Ala His Arg Ile
                325                 330                 335

Tyr Gln Cys Cys Ser Ser Glu Val Asn Pro Ile Arg Ile Arg Glu Val
            340                 345                 350

Ile Gly His Val Gln Gln Glu Ala Glu His Asn Tyr Gln Thr His Asp
            355                 360                 365

Lys Leu Phe Tyr Arg Lys Pro Lys Lys Pro Phe Val Met Ile Pro Gly
        370                 375                 380

Ala Val Phe His Ala Leu Met Ala Ile Ser Phe His Met Leu Lys Trp
385                 390                 395                 400

Ser Ser Arg Leu Gln Ser Leu Phe Gly Arg Lys Ala Ser Gly Arg Lys
                405                 410                 415

Leu Ser Asn Met Glu Thr Thr Met Lys Leu Ser Lys Val Phe Ser Phe
            420                 425                 430

Tyr Thr Ser Pro Ser Tyr Thr Phe Ser Asn Arg Arg Leu Gln Glu Leu
        435                 440                 445

Ser Thr Arg Leu Gly Glu Tyr Asp Gln Ser Glu Phe Pro Val Asn Ala
450                 455                 460

Gly Met Tyr Asp Trp Ala His Tyr Leu Arg Glu Val His Val Ala Gly
465                 470                 475                 480

Leu Asn Lys Tyr Ala Leu Arg Pro Lys Val Val Lys Met Asn Pro Pro
                485                 490                 495

Ala Ala Lys Pro Arg Ser Arg Ala Ala
            500                 505

<210> SEQ ID NO 66
<211> LENGTH: 769
<212> TYPE: PRT
<213> ORGANISM: Marine actinobacterium PHSC20C1

<400> SEQUENCE: 66

Met Thr Thr Ile Arg Ala Leu Thr Thr Glu His Val Phe Leu Thr Gly
1               5                   10                  15

Ala Thr Gly Phe Val Gly Gln Ala Ile Leu Glu Arg Leu Leu Ser Ser
            20                  25                  30

His Pro Glu Thr Arg Ile Ser Ile Leu Val Arg Gly Lys Gly Ala Thr
        35                  40                  45
```

-continued

```
Thr Gly Glu Gly Arg Leu Thr Asn Leu Met Arg Lys Pro Val Phe Ala
 50                  55                  60
Gln Trp Met Glu Ser Leu Gly Lys Glu Gln Ala Leu Ala Glu Val Ala
 65                  70                  75                  80
Arg Arg Val Thr Val Ile Glu Gly Ser Leu Thr Asp Val Gly Thr Leu
                 85                  90                  95
Pro Asp Asp Ile Asp Ile Val Ile His Gly Ala Ser Thr Val Ser Phe
                100                 105                 110
Asp Pro Pro Ile Asp Glu Ala Phe Asp Thr Asn Val Gly Gly Ala Thr
            115                 120                 125
Gly Ile Tyr Thr Ala Leu Leu Ala Ser Lys Ser Arg Pro His Val Val
130                 135                 140
His Ile Ser Thr Ala Tyr Val Gly Gly Ile Arg Lys Gly Ile Val Pro
145                 150                 155                 160
Glu Ala Ser Leu Val His Asn Val Asp Trp Arg Ala Glu Tyr Glu Ala
                165                 170                 175
Ala Arg Thr Ala Arg Thr Arg Val Glu Phe Glu Ser Arg Gln Pro Glu
            180                 185                 190
Ala Leu Arg Ala Gln Leu Thr Ala Ala Lys Ala Arg His Gly Lys Ala
        195                 200                 205
Gly Pro Gln Ala Val Ala Gln Phe Thr Glu Ala Ala Arg Ala Glu Trp
210                 215                 220
Val His Asp Arg Leu Val Asp Tyr Gly Arg Met Arg Ala Glu Ser Leu
225                 230                 235                 240
Gly Trp Thr Asp Val Tyr Thr Leu Thr Lys Ala Phe Ala Glu Arg Val
                245                 250                 255
Ala Glu Glu Met Trp Ala Gln Ala Gly His Arg Leu Ser Val Val Arg
            260                 265                 270
Pro Ser Ile Ile Glu Ser Ala Leu His His Pro Phe Pro Gly Trp Ile
        275                 280                 285
Asp Gly Phe Lys Val Ala Asp Pro Leu Ile Leu Ala Tyr Gly Arg Gly
290                 295                 300
Gln Leu Pro Asp Phe Pro Gly Leu Pro Asp Ser Ile Leu Asp Val Ile
305                 310                 315                 320
Pro Val Asp Phe Val Val Asn Ala Thr Leu Ala Ala Ala Ala Ala Lys
                325                 330                 335
Ala Asp Pro Lys Ala Pro Arg Tyr Tyr His Val Ser Ser Gly Ala Ser
            340                 345                 350
Asn Pro Leu Pro Phe His Arg Met Tyr Glu Asn Val Asn Ala Tyr Phe
        355                 360                 365
Thr Ala Asn Pro Leu Pro Ala Glu Asp Gly Glu Ile Ser Val Pro Leu
370                 375                 380
Trp Arg Phe Pro Gly Gly Gln Arg Val Glu Arg Ala Leu Val Lys Arg
385                 390                 395                 400
Glu Arg Gln Ala Ala Arg Ala Glu Arg Val Ile Thr Arg Met Pro Thr
                405                 410                 415
Thr Pro Arg Thr Arg Arg Trp Leu Asp Glu Val Lys Ser Gly Gln His
            420                 425                 430
Gln Leu Glu Val Leu Arg Ala Phe Thr Asn Leu Tyr Arg Ala Tyr Val
        435                 440                 445
Gln Thr Glu Ile Ile Phe Asp Asp Ala Asn Thr Arg Glu Leu Leu Ala
450                 455                 460
Ser Leu Pro Lys Lys Thr Ala His Ser Ala Arg Phe Asp Val Thr Glu
```

```
            465                 470                 475                 480

Ile Asp Trp Glu Asn Tyr Phe Gln Gln Val His Phe Pro Ala Ile Thr
                            485                 490                 495

Thr Leu Thr Arg Ala Phe Ala Asn Arg Pro Ala Ala Lys Thr Arg Thr
                        500                 505                 510

Ala Lys Lys Leu Pro Glu Arg Thr Asp Val Val Ala Val Phe Asp Leu
                    515                 520                 525

Glu Gly Thr Val Val Asp Ser Asn Leu Val Lys Gln Tyr Leu Leu Leu
                530                 535                 540

Trp Gly Gly Thr Val Pro Arg Ala Lys Val Leu His Asp Leu Ala Asn
        545                 550                 555                 560

Phe Thr Phe Ser Leu Arg Lys Tyr Met Arg Ala Glu Arg Arg Asp Arg
                        565                 570                 575

Gly Glu Phe Ile Arg Thr Phe Met Arg Arg Tyr Glu Gly Phe Lys Ile
                    580                 585                 590

Ala Glu Ile Glu Arg Met Val Arg Gly Ser Phe Gly Arg Ala Met Met
                595                 600                 605

Arg Arg Val Met Pro Asp Ala Leu Arg Arg Val Gln Glu His Arg Asp
        610                 615                 620

Ala Gly His Arg Thr Ile Leu Val Thr Gly Thr Ile Asp Leu Met Val
        625                 630                 635                 640

Thr Pro Phe Leu Pro Tyr Phe Asp Glu Val Val Ala Gly Arg Met His
                        645                 650                 655

Glu Arg Asp Gly Ile Leu Thr Gly Phe Leu Ala Asp Pro Pro Leu Val
                    660                 665                 670

Asp Glu Ala Arg Ala Ala Trp Leu Arg His Tyr Ala Asp Gln Asn Gly
                675                 680                 685

Phe Asn Leu Thr Gln Ser Tyr Gly Tyr Gly Asp Ser His Ala Asp Leu
        690                 695                 700

Met Trp Leu Gln Leu Val Gly Asn Pro Ser Ala Val Asn Pro Asp Val
        705                 710                 715                 720

Asn Leu Tyr Lys His Ala Gln Glu Lys Arg Trp Asn Val Leu Asp Trp
                        725                 730                 735

Lys Arg Arg Ser Pro Asn Ser Arg Ile Pro Arg Pro Arg Asp Ala Ala
                    740                 745                 750

Ala Ala Thr Gln Glu Gly Asp Gly His Ser Ser Thr Pro Ser Ser Gln
                755                 760                 765

Ser

<210> SEQ ID NO 67
<211> LENGTH: 542
<212> TYPE: PRT
<213> ORGANISM: Unknown
<220> FEATURE:
<223> OTHER INFORMATION: Synthetic polypeptide encoded by DNA from
      NCBI locus EP750655 from marine metagenome collection

<400> SEQUENCE: 67

Met Ile Arg Glu Asn Leu Ser Gly Lys Arg Ile Ala Ile Thr Gly Ser
1               5                   10                  15

Thr Gly Phe Leu Gly Thr Ala Leu Val Glu Arg Phe Leu Arg Ser Val
                20                  25                  30

Pro Asp Cys Glu Leu Val Leu Leu Val Arg Pro Gly Arg Arg Gly Ala
            35                  40                  45

Glu His Arg Val Lys Arg Asp Ile Leu Lys Asn Asp Ala Phe Asp Arg
```

```
                50                  55                  60
Leu Arg Asp Ala Phe Lys Glu Asp Pro Ile Ala Ala Gly Gly Leu Asp
 65                  70                  75                  80

Gly Glu Thr Phe Asp Glu Met Cys Asp Arg Arg Val Phe Ala Val Lys
                 85                  90                  95

Gly Asp Val Gly Gln Asp Gly Leu Leu Asp Asp Ala Gly Leu Thr
                100                 105                 110

Leu Phe Ser Thr Val Asp Ile Ala Val His Ser Ala Ala Thr Val Ser
                115                 120                 125

Phe Asp Ser Ala Leu Asp Asp Ala Val Gln Val Asn Leu Leu Gly Pro
                130                 135                 140

Gly Arg Val Ala Ala Ala Leu Arg Val Ala Ala Glu Ala Arg Thr Glu
145                 150                 155                 160

Pro Thr Pro Gly Gly Leu Ala Pro Gly Glu Lys Ala Tyr Leu Val Ala
                165                 170                 175

Val Ser Thr Cys Tyr Val Ala Gly Ser Arg Arg Gly Asn Ala Pro Glu
                180                 185                 190

Gln Met Val Gln Asp Ser Pro Phe Phe Val Asp Val Asp Trp Arg Ala
                195                 200                 205

Glu Ala His Asn Ala Phe Gln Ala Arg Lys Asp Ala Glu Gln Ala Ser
                210                 215                 220

Arg Thr Pro Gln Arg Leu Lys Ala Leu Glu Ala Asp Ala Ile Lys Thr
225                 230                 235                 240

Leu Gly Ala Ala Gly Thr Pro Ala Ile Ala Glu Arg Val Glu Ser Leu
                245                 250                 255

Arg Gln Lys Trp Val Gly Glu Lys Met Thr Glu Thr Gly Arg Val Arg
                260                 265                 270

Ala Ala Ser Leu Gly Phe Pro Asp Ala Tyr Ala Phe Thr Lys Ala Leu
                275                 280                 285

Gly Glu Arg Ser Leu Val Glu Thr Arg Asp Gly Val Pro Val Ala Ile
                290                 295                 300

Val Arg Pro Ser Ile Ile Glu Ser Ala Leu Ala Glu Pro Val Pro Gly
305                 310                 315                 320

Trp Ile Arg Gly Phe Arg Met Ala Glu Pro Val Ile Ala Ala Tyr Ala
                325                 330                 335

Arg Gly Leu Leu Lys Glu Phe Pro Gly Val Pro Glu Gly Val Ile Asp
                340                 345                 350

Val Ile Pro Val Asp Leu Val Val Ala Ser Ile Leu Ala Thr Ala Ala
                355                 360                 365

Arg Gly Pro His Ile Ser Glu Gln Ser Gly Glu His Glu Pro Asp Ile
                370                 375                 380

Ile Gln Ile Ala Ser Gly Ser Ala Asn Pro Phe Lys Tyr Gly Gln Met
385                 390                 395                 400

Val Asp Leu Val Gln Ala Tyr Phe Thr Lys Asn Pro Val Tyr Asp Glu
                405                 410                 415

Lys Asn Gln Pro Ile Ser Val Pro Asp Trp Thr Phe Pro Gly Arg Gly
                420                 425                 430

Arg Val Thr Arg Gln Leu Asn Arg Ala Lys Phe Ala Leu Thr Thr Gly
                435                 440                 445

Glu Arg Ile Leu Asp Ala Leu Pro Leu Arg Gly Lys Gln Ala Glu Ile
                450                 455                 460

Gly Ala Asp Leu Glu Gln Gln Lys Glu Gln Leu Asp Arg Ala Gly Gly
465                 470                 475                 480
```

```
Tyr Val Glu Leu Tyr Gly Ala Tyr Thr Glu Cys Glu Ala Thr Tyr Gln
                485                 490                 495

Leu Asp Arg Met Tyr Ala Leu Trp Asn Ser Leu Asp Glu Ala Asp Gln
            500                 505                 510

Arg Asp Phe Asn Met Asp Pro Leu Ser Ile Asp Trp Pro His Tyr Ala
        515                 520                 525

His Asp Ile Gln Leu Pro Ser Thr Val Lys Met Ala Arg Leu
    530                 535                 540

<210> SEQ ID NO 68
<211> LENGTH: 523
<212> TYPE: PRT
<213> ORGANISM: Unknown
<220> FEATURE:
<223> OTHER INFORMATION: Synthetic polypeptide encoded by DNA from
      marine sample JCVI_SCAF_1101670217388

<400> SEQUENCE: 68

Met Ile Lys Gln Asn Leu Ser Gly Lys Arg Ile Ala Ile Thr Gly Ala
1               5                   10                  15

Thr Gly Phe Leu Gly Thr Ala Leu Val Glu Arg Leu Leu Ser Ser Ile
            20                  25                  30

Pro Asp Cys Glu Leu Leu Leu Val Arg Pro Gly Arg Arg Gly Ala
        35                  40                  45

Glu Lys Arg Ala Glu Arg Glu Ile Leu Arg Asn Asp Ala Phe Asn Asn
    50                  55                  60

Leu Arg Glu Lys Leu Gly Thr Asp Gly Phe Asp Lys Leu Cys Lys Lys
65                  70                  75                  80

Arg Val Lys Ala Ile Ser Gly Asp Val Gly Ile Asp Gly Leu Gly Leu
                85                  90                  95

Asp Glu Asn Gly Leu Thr Glu Leu Ala Lys Cys Asp Leu Phe Ile His
            100                 105                 110

Ser Ala Ala Val Val Ser Phe Asp Ser Pro Leu Asp Gln Ala Val Glu
        115                 120                 125

Val Asn Leu Leu Gly Pro Val Arg Ile Ala Gln Thr Leu Asn Glu Leu
    130                 135                 140

Ala Val Ser Pro His Leu Val Ser Ile Ser Thr Cys Tyr Val Ala Gly
145                 150                 155                 160

Ser Arg Arg Gly Ala Ala Pro Glu Glu Pro Val Asp Ala Ser Pro Phe
                165                 170                 175

Phe Val Asp Val Asp Trp Arg Ile Glu Val Asp Ala Ala Arg Arg Ile
            180                 185                 190

Arg Gln Glu Thr Glu Thr Ala Ser Arg Thr Pro Glu Arg Leu Glu Glu
        195                 200                 205

Phe Arg Lys Glu Ala Arg Glu Glu Ile Gly Ala Ala Gly Ile Pro Ala
    210                 215                 220

Leu Ala Ser Lys Thr Glu Gln Leu Arg Ser Arg Trp Val Asp Asp Arg
225                 230                 235                 240

Met Ala Glu Ala Gly Arg Ser Arg Ala His Ser Leu Gly Phe Pro Asp
                245                 250                 255

Ala Tyr Ala Tyr Thr Lys Ala Leu Gly Glu Ile Ala Leu Arg Glu Thr
            260                 265                 270

Ala His Thr Ile Pro Val Ser Ile Val Arg Pro Ser Ile Ile Glu Ser
        275                 280                 285

Ala Leu Ala Glu Pro Phe Pro Gly Trp Ile Arg Gly Phe Arg Met Ala
```

-continued

```
                290                 295                 300
Glu Pro Val Ile Ile Ser Tyr Ala Arg Gly Leu Leu Lys Asp Phe Pro
305                 310                 315                 320

Gly Ile Pro Glu Gly Thr Ile Asp Val Ile Pro Val Asp Leu Val Ala
                325                 330                 335

Asn Ser Ile Ile Leu Ser Leu Ala Glu Ala Leu Ser Gly Ser Gly Gln
                340                 345                 350

Arg Arg Ile Tyr Gln Cys Cys Ser Gly Gly Ser Asn Pro Ile Ser Leu
                355                 360                 365

Gly Lys Phe Ile Asp Tyr Leu Met Ala Glu Ala Lys Thr Asn Tyr Ala
                370                 375                 380

Ala Tyr Asp Gln Leu Phe Tyr Arg Arg Pro Thr Lys Pro Phe Val Ala
385                 390                 395                 400

Val Asn Arg Lys Leu Phe Asp Val Val Gly Gly Met Arg Val Pro
                405                 410                 415

Leu Ser Ile Ala Gly Lys Ala Met Arg Leu Ala Gly Gln Asn Arg Glu
                420                 425                 430

Leu Lys Val Leu Lys Asn Leu Asp Thr Thr Arg Ser Leu Ala Thr Ile
                435                 440                 445

Phe Gly Phe Tyr Thr Ala Pro Asp Tyr Ile Phe Arg Asn Asp Ser Leu
                450                 455                 460

Met Ala Leu Ala Ser Arg Met Gly Glu Leu Asp Arg Val Leu Phe Pro
465                 470                 475                 480

Val Asp Ala Arg Gln Ile Asp Trp Gln Leu Tyr Leu Cys Lys Ile His
                485                 490                 495

Leu Gly Gly Leu Asn Arg Tyr Ala Leu Lys Glu Arg Lys Leu Tyr Ser
                500                 505                 510

Leu Arg Ala Ala Asp Thr Arg Lys Lys Ala Ala
                515                 520

<210> SEQ ID NO 69
<211> LENGTH: 515
<212> TYPE: PRT
<213> ORGANISM: Unknown
<220> FEATURE:
<223> OTHER INFORMATION: Synthetic polypeptide encoded by DNA from
      marine sample JCVI_SCAF_1097205236585

<400> SEQUENCE: 69

Met Ile Lys Glu Ser Leu Arg Gly Lys Lys Ile Ala Ile Thr Gly Ser
1               5                   10                  15

Thr Gly Phe Leu Gly Thr Ala Leu Val Glu Leu Leu Arg Glu Ile
                20                  25                  30

Asp Asp Val Gln Leu Arg Leu Leu Ile Arg Pro Ser Gly Lys Arg Ser
                35                  40                  45

Ala Ser Lys Arg Leu Glu Arg Asp Ile Leu Arg Asn Asp Ala Phe Asp
                50                  55                  60

Gln Leu Arg Glu Lys Leu Gly Thr Glu Gly Phe Asn Glu Leu Ala Ser
65                  70                  75                  80

Asn Ala Val Glu Ala Leu Ser Ala Asp Ile Ser Leu Asp Asn Leu Gly
                85                  90                  95

Leu Asp Asp Thr Gly Leu Arg Glu Leu Ser Glu Cys Asp Ile Val Ile
                100                 105                 110

His Ser Ala Ala Val Ser Phe Asp Glu Pro Leu Asp Arg Ala Ala
                115                 120                 125
```

```
Glu Val Asn Leu Met Gly Pro Val Arg Leu Val Glu Thr Leu Gln Asn
130                 135                 140

Leu Asp Ala Glu Pro His Leu Val Met Val Ser Thr Cys Tyr Val Ala
145                 150                 155                 160

Gly Asn Arg Lys Gly Thr Ala Pro Glu Lys Pro Leu Ser Gln Ser Pro
                165                 170                 175

Phe Tyr Val Pro Leu Asn Trp Arg Glu Glu Thr Glu Ala Ala Arg Arg
            180                 185                 190

Thr Arg Ser Tyr Thr Glu Asp Asp Ser Arg Arg Ser Glu Asn Leu Glu
        195                 200                 205

Lys Phe Arg Gly Glu Ala Lys Ser Glu Leu Gly Ala Pro Gly Ile Ser
    210                 215                 220

Val Ile Ala Thr Lys Thr Glu Gln Ile Arg Glu Arg Trp Val Lys Glu
225                 230                 235                 240

Lys Met Val Glu Ala Gly Arg Glu Arg Ala Thr Ser Leu Gly Phe Pro
                245                 250                 255

Asp Ala Tyr Ala Phe Thr Lys Ala Met Ala Glu Gln Ala Val Gln Glu
            260                 265                 270

Ile Arg Gly Asn Ile Pro Leu Ser Ile Val Arg Pro Ser Ile Ile Glu
        275                 280                 285

Ser Ser Trp Gly Asn Pro Lys Ser Gly Trp Ile Arg Gly Phe Arg Met
    290                 295                 300

Ala Glu Pro Ile Ile Leu Asn Phe Gly Arg Gly Thr Leu Lys Glu Phe
305                 310                 315                 320

Pro Gly Ile Pro Glu Gly Ile Ile Asp Val Ile Pro Val Asp Leu Val
                325                 330                 335

Ala Ser Ala Ile Val Ala Val Ala Ala Gln Glu Lys Pro Ser Asp Pro
            340                 345                 350

Phe Val Val Gln Val Ala Ser Gly Ala Cys Asn Pro Ile Lys Ile Gly
        355                 360                 365

Ile Leu Ala Asp Tyr Val His Glu Phe Phe Gly Asn Phe Pro Ile Leu
    370                 375                 380

Asp Asp Lys Asn Gln Pro Ile Thr Pro Ser Lys Trp Glu Phe Pro Gly
385                 390                 395                 400

Arg Gly Arg Val Val Thr Gln Leu Thr Arg Ala Lys Arg Ile Leu Gln
                405                 410                 415

Ala Ala Glu Asn Gly Leu His Lys Leu Pro Ile Arg Gly Asn Gln Ala
            420                 425                 430

Met Ile Val Ala Asp Leu Glu Glu Lys Arg Asn Glu Leu Asp Lys Ala
        435                 440                 445

Met Glu Tyr Ile Thr Leu Tyr Gly Lys Tyr Val Glu Cys Glu Ala Ile
    450                 455                 460

Tyr Asp Val Ala Asn Leu Leu His Leu Trp Asp Ser Ile Asp Asp Gly
465                 470                 475                 480

Asp Arg Ser Ser Phe Leu Phe Asp Pro Arg Ile Ile Asp Trp Arg Lys
                485                 490                 495

Tyr Val Tyr Asp Ile His Leu Pro Thr Val Ile Thr Gln Gly Arg Val
            500                 505                 510

Lys Thr Thr
        515

<210> SEQ ID NO 70
<211> LENGTH: 372
<212> TYPE: PRT
```

<213> ORGANISM: Unknown
<220> FEATURE:
<223> OTHER INFORMATION: Synthetic polypeptide encoded by DNA from marine sample JCVI_SCAF_1101670289386

<400> SEQUENCE: 70

Met Ser Asn Thr Thr Val Ile Phe Leu Thr Gly Val Thr Gly Tyr Leu
1               5                   10                  15
Gly Ser Arg Leu Leu Val Gln Leu Ser Asn Leu Pro Val Lys Ile Tyr
            20                  25                  30
Cys Leu Val Arg Pro Ala Arg Ser Glu Asn Gly Ala Gln Gly Arg Leu
        35                  40                  45
Leu Lys Ile Leu Glu Asp Asn Asn Ile Thr Pro Glu Glu Gly Lys Tyr
50                  55                  60
Ile Ala Val Glu Gly Asp Ile Arg Lys Asp Lys Leu Gly Ile Ser Asp
65                  70                  75                  80
Glu Lys Tyr Leu Ser Leu Ser Arg Glu Val Glu Val Phe His Ser
                85                  90                  95
Ala Ala Ser Val Asn Phe Leu Ser Thr Lys Glu Ala Leu Lys Ser Ile
            100                 105                 110
Asn Val Val Gly Ala Ile Asn Val Met Asn Phe Ala Gln Arg Cys Tyr
        115                 120                 125
Ala Asn Asn Gln Ser Phe Asp Lys Phe Cys Leu Val Ser Thr Ala Tyr
130                 135                 140
Val Ala Gly Lys Thr Ser Gly Val Ala Glu Glu Ile Pro Val Thr Lys
145                 150                 155                 160
Ala Arg Val Phe Asn Asn Asn Tyr Glu Glu Ser Lys Trp Leu Ala Glu
                165                 170                 175
Gln Arg Val Val Glu Glu Val Asp Asp Leu Pro Tyr Val Val Ile Arg
            180                 185                 190
Pro Ser Ile Ile Ile Gly Ser Ala Ile Asp Gly Arg Ala Glu Ser Gln
        195                 200                 205
Asn Val Ile Tyr Gly Pro Phe Arg Ile Met Ile Gln Tyr Asp Asn Lys
210                 215                 220
Lys Pro Gln Trp Leu Pro Gly Tyr Lys Ser Thr Arg Leu Asp Phe Val
225                 230                 235                 240
Pro Val Asp Tyr Val Ala Glu Cys Cys Arg His Ile Ile Phe Glu Lys
                245                 250                 255
Asp Pro Lys Pro Ile Tyr His Leu Thr Ser Gly Pro Asp Asn Gln Ala
            260                 265                 270
Gly Met Asn Asn Met Phe Lys Ser Val Ser Asp Val Phe Ser Val Thr
        275                 280                 285
Val Lys Leu Tyr Pro Tyr Trp Leu Phe Asp Met Phe Ile Lys Pro Phe
290                 295                 300
Leu Lys Leu Arg Lys Asn Lys Asp Asp Leu Lys Phe Leu Arg Ile Ala
305                 310                 315                 320
Asp Ala Tyr Gly Asn Tyr Met Lys Tyr Lys Thr Gln Phe Asp Asp Arg
                325                 330                 335
Asn Thr Ala Glu Leu Arg Tyr Lys Asn Gly Ile Val Arg Pro Ser Trp
            340                 345                 350
Asn Asp Val Phe Thr Lys Ser Ile Arg Tyr Ala Lys Asp Thr Asn Phe
        355                 360                 365
Ala Arg Asp Val
370

-continued

```
<210> SEQ ID NO 71
<211> LENGTH: 490
<212> TYPE: PRT
<213> ORGANISM: Vitis vinifera

<400> SEQUENCE: 71
```

| | | | | | | | | | | | | | | | |
|---|---|---|---|---|---|---|---|---|---|---|---|---|---|---|---|
| Met | Glu | Leu | Gly | Ser | Ile | Val | Glu | Phe | Leu | Glu | Asn | Lys | Ser | Ile | Leu |
| 1 | | | | 5 | | | | | 10 | | | | | 15 | |
| Val | Thr | Gly | Ala | Thr | Gly | Phe | Leu | Ala | Lys | Ile | Phe | Val | Glu | Arg | Ile |
| | | | 20 | | | | | 25 | | | | | 30 | | |
| Leu | Arg | Thr | Gln | Pro | Asn | Val | Lys | Lys | Leu | Phe | Leu | Leu | Leu | Arg | Ala |
| | | | 35 | | | | | 40 | | | | | 45 | | |
| Gly | Asp | Thr | Lys | Ser | Ala | Thr | Gln | Arg | Leu | His | Asn | Glu | Val | Ile | Gly |
| | 50 | | | | | 55 | | | | | 60 | | | | |
| Lys | Glu | Leu | Phe | Trp | Val | Leu | Arg | Glu | Lys | Trp | Ala | Ser | Asp | Phe | Asn |
| 65 | | | | | 70 | | | | | 75 | | | | | 80 |
| Ser | Phe | Val | Ser | Lys | Lys | Leu | Thr | Pro | Val | Pro | Gly | Asp | Ile | Ser | Cys |
| | | | | 85 | | | | | 90 | | | | | 95 | |
| Asp | Asp | Leu | Gly | Val | Thr | Asp | Ser | Asn | Leu | Arg | Glu | Glu | Met | Trp | Arg |
| | | | 100 | | | | | 105 | | | | | 110 | | |
| Glu | Val | Asp | Ile | Val | Val | Asn | Leu | Ala | Ala | Thr | Thr | Asn | Phe | Asp | Glu |
| | | | 115 | | | | | 120 | | | | | 125 | | |
| Arg | Tyr | Asp | Val | Ala | Leu | Gly | Ile | Asn | Ala | Leu | Gly | Ala | Arg | His | Val |
| | 130 | | | | | 135 | | | | | 140 | | | | |
| Leu | Asp | Phe | Ala | Lys | Lys | Cys | Val | Lys | Ile | Lys | Met | Leu | Leu | His | Val |
| 145 | | | | | 150 | | | | | 155 | | | | | 160 |
| Ser | Thr | Ala | Tyr | Val | Ala | Gly | Glu | Gln | Ser | Gly | Leu | Ile | Leu | Glu | Gln |
| | | | | 165 | | | | | 170 | | | | | 175 | |
| Pro | Phe | Gln | Met | Gly | Glu | Thr | Leu | Asn | Gly | Thr | Phe | Gly | Leu | Asp | Ile |
| | | | 180 | | | | | 185 | | | | | 190 | | |
| Glu | Glu | Glu | Lys | Lys | Leu | Met | Glu | Glu | Arg | Leu | Asp | Glu | Leu | Gln | Ser |
| | | | 195 | | | | | 200 | | | | | 205 | | |
| Glu | Gly | Ala | Thr | Arg | Glu | Ala | Val | Thr | Leu | Ala | Met | Lys | Asp | Phe | Gly |
| | 210 | | | | | 215 | | | | | 220 | | | | |
| Ile | Gln | Arg | Ala | Lys | Met | His | Gly | Trp | Pro | Asn | Thr | Tyr | Val | Phe | Thr |
| 225 | | | | | 230 | | | | | 235 | | | | | 240 |
| Lys | Ala | Met | Gly | Glu | Met | Leu | Leu | Gly | His | Leu | Lys | Glu | Asn | Leu | Pro |
| | | | | 245 | | | | | 250 | | | | | 255 | |
| Leu | Ala | Ile | Leu | Arg | Pro | Thr | Ile | Val | Ser | Ser | Thr | Tyr | Lys | Glu | Pro |
| | | | 260 | | | | | 265 | | | | | 270 | | |
| Phe | Pro | Gly | Trp | Val | Glu | Gly | Ile | Arg | Thr | Ile | Asp | Ser | Phe | Ala | Val |
| | | | 275 | | | | | 280 | | | | | 285 | | |
| Gly | Tyr | Gly | Lys | Gly | Arg | Leu | Thr | Phe | Phe | Leu | Gly | Asp | Ile | Glu | Ala |
| | 290 | | | | | 295 | | | | | 300 | | | | |
| Ile | Val | Asp | Val | Ile | Pro | Ala | Asp | Met | Val | Val | Asn | Ser | Met | Ile | Val |
| 305 | | | | | 310 | | | | | 315 | | | | | 320 |
| Ala | Met | Ala | Ala | His | Ala | Asn | Gln | Pro | Cys | Glu | Val | Ile | Tyr | Gln | Val |
| | | | | 325 | | | | | 330 | | | | | 335 | |
| Gly | Ser | Ser | Val | Lys | Asn | Pro | Val | Arg | Tyr | Ser | Asn | Leu | Gln | Asp | Phe |
| | | | 340 | | | | | 345 | | | | | 350 | | |
| Gly | Leu | Arg | Tyr | Phe | Thr | Lys | Asn | Pro | Trp | Ile | Asn | Lys | Asp | Gly | Lys |
| | | | 355 | | | | | 360 | | | | | 365 | | |
| Ala | Val | Lys | Val | Gly | Lys | Val | Thr | Val | Leu | Ser | Thr | Met | Asp | Ser | Phe |
| | 370 | | | | | 375 | | | | | 380 | | | | |

```
His Arg Tyr Met Ala Leu Arg Tyr Leu Leu Leu Lys Gly Leu Gln
385                 390                 395                 400

Phe Val Asn Thr Ala Phe Cys Gln Tyr Phe Arg Gly Thr Tyr Thr Asp
            405                 410                 415

Leu Asn Arg Arg Ile Lys Phe Leu Leu Arg Leu Ile Glu Leu Tyr Lys
        420                 425                 430

Pro Tyr Leu Phe Phe Lys Gly Val Phe Asp Asp Met Asn Thr Glu Lys
            435                 440                 445

Leu Arg Met Ala Val Thr Ala Ser Gly Ala Glu Ala Asp Leu Phe Tyr
    450                 455                 460

Phe Asp Pro Lys Cys Ile Asp Trp Glu Asp Tyr Phe Met Asn Ile His
465                 470                 475                 480

Ile Pro Gly Ala Val Lys Tyr Val Phe Lys
                485                 490

<210> SEQ ID NO 72
<211> LENGTH: 991
<212> TYPE: PRT
<213> ORGANISM: Vitis vinifera

<400> SEQUENCE: 72

Met Ala Val Ser Thr Thr Thr Thr Pro Asn Thr Ser Ile Thr Asn Gly
1               5                   10                  15

Leu Gly Ile Leu Gln Phe Leu Ala Gly Lys Thr Tyr Phe Ile Thr Gly
            20                  25                  30

Ala Thr Gly Leu Leu Ala Lys Ala Val Glu Lys Ile Leu Arg Arg
        35                  40                  45

Ala Pro Asp Val Gly Lys Ile Phe Ile Leu Ile Lys Ala Lys Asn Lys
    50                  55                  60

Glu Ala Ala Val Asp Arg Leu Lys Thr Glu Ile Ile Asn Ser Glu Leu
65                  70                  75                  80

Phe Glu Cys Leu Lys Gln Arg His Gly Lys Tyr Tyr Gln Asp Phe Met
                85                  90                  95

Leu Ser Lys Leu Ala Pro Val Val Gly Asn Leu Cys Glu Ser Asp Leu
            100                 105                 110

Gly Ile Asp Ala Asn Leu Ile Ser Glu Ile Ala Glu Glu Val Asp Val
        115                 120                 125

Ile Ile Asn Ser Ala Ala Asn Thr Asn Phe Glu Glu Arg Tyr Asp Val
    130                 135                 140

Ser Leu His Ala Asn Thr Ile Gly Pro Cys Arg Leu Met Asp Phe Ala
145                 150                 155                 160

Lys Lys Tyr Cys Lys Asn Leu Arg Val Phe Leu His Val Ser Thr Ala
                165                 170                 175

Tyr Val Asn Gly Glu Arg Glu Gly Met Ile Thr Glu Lys Pro Phe Tyr
            180                 185                 190

Met Gly Glu Ser Ile Ala Arg Glu Lys Val Ala Ser Glu Phe Leu Pro
        195                 200                 205

Leu Ser Tyr Pro Ala Leu Asp Val Asp Asp Glu Ile Lys Ile Ala Leu
    210                 215                 220

Asp Ser Lys Val Ala Phe Glu Gly Asn Leu Glu Asp Gln Lys Met Lys
225                 230                 235                 240

Glu Leu Gly Leu Glu Arg Ala Arg Ile His Gly Trp His Asn Pro Tyr
                245                 250                 255

Glu Phe Thr Lys Ala Met Gly Glu Met Met Ile Asn Ser Met Arg Gly
```

-continued

```
            260                 265                 270
Asp Ile Pro Leu Val Ile Ile Arg Pro Thr Ala Ile Glu Ser Thr Leu
            275                 280                 285
Glu Asp Pro Phe Pro Gly Trp Ile Gln Gly Asn Arg Tyr Leu Ile Ser
            290                 295                 300
Leu Pro Phe Ser Cys Pro Cys Thr Lys Ser His Ile Phe Ser Tyr Asn
305                 310                 315                 320
Gln Met Leu Asp Pro Met Ile Leu Ser Tyr Gly Lys Gly Asn Leu Pro
                    325                 330                 335
Ser Phe Leu Val Asn Pro Glu Val Val Ile Asp Met Ile Pro Val Asp
                    340                 345                 350
Met Val Val Asn Ala Ile Ile Ala Ala Met Ala Lys His Gly Ile Ala
                    355                 360                 365
Gly Lys Pro Gly Ile Lys Val Tyr His Val Gly Ser Ser Ala Val Asn
            370                 375                 380
Leu Leu Pro Leu Gly Asp Leu Phe Lys Tyr Ser Tyr Glu His Phe Ile
385                 390                 395                 400
Cys Ser Pro Ile Asn Met Asp Thr Glu Gly Lys Thr Thr Asp Met Lys
                    405                 410                 415
Glu Met Lys Phe Phe Ser Ser Met Asp Asp Phe Ser Ser His Met Gln
                    420                 425                 430
Thr Glu Ile Val Gln Gln Arg Arg Leu Ala Ile Ser Gly Asn Asn Ala
            435                 440                 445
Ser Gln Arg Leu Glu Arg Lys Cys Lys Met Ile Val Glu His Ala Ile
            450                 455                 460
Asn Leu Ala Arg Val Tyr Gln Pro His Met Phe Phe Arg Gly Ser Ser
465                 470                 475                 480
Phe Gln Glu Lys Thr Tyr Phe Ile Thr Gly Gly Thr Gly Phe Leu Ala
                    485                 490                 495
Lys Ala Val Val Glu Lys Ile Leu Arg Thr Ala Pro Asp Val Gly Lys
                    500                 505                 510
Ile Phe Val Leu Ile Lys Ala Lys Asn Lys Glu Ala Ala Met Asp Arg
                    515                 520                 525
Leu Lys Thr Glu Ile Ile Asp Ser Glu Leu Phe Glu Cys Leu Lys Gln
            530                 535                 540
Arg His Gly Lys Tyr Tyr Gln Asp Phe Ile Leu Ser Lys Leu Ala Pro
545                 550                 555                 560
Val Val Gly Asn Leu Cys Glu Ser Asp Leu Gly Ile Asp Ala Asn Ser
                    565                 570                 575
Ile Ser Glu Ile Ala Glu Glu Val Asp Val Ile Ile Asn Ser Ala Ala
                    580                 585                 590
Asn Thr Asn Phe Glu Glu Arg Tyr Asp Val Ser Leu Ser Thr Asn Val
                    595                 600                 605
Leu Gly Pro Arg Arg Leu Met Asp Phe Thr Asn Lys Tyr Cys Lys Asn
            610                 615                 620
Leu Arg Val Phe Leu His Val Ser Thr Ala Tyr Val Ser Gly Glu Arg
625                 630                 635                 640
Glu Gly Met Ile Met Glu Lys Pro Phe His Met Gly Glu Arg Ile Ala
                    645                 650                 655
Arg Glu Lys Ala Ala Ser Glu Phe Pro Pro Leu Ala Tyr Pro Val Leu
                    660                 665                 670
Asp Val Asp Gly Glu Ile Glu Ile Ala Leu Asp Ser Lys Val Ala Phe
                    675                 680                 685
```

Glu Gly Asn Leu Glu Asp Glu Lys Met Lys Ala Leu Gly Leu Glu Arg
            690                 695                 700

Ala Arg Ile His Gly Trp His Asn Pro Tyr Glu Phe Thr Lys Ala Met
705                 710                 715                 720

Gly Glu Met Leu Ile Asn Ser Met Arg Gly Asp Ile Pro Leu Val Ile
                725                 730                 735

Ile Arg Pro Thr Ala Ile Gly Ser Thr Leu Asp Asp Pro Phe Pro Gly
            740                 745                 750

Trp Ile Gln Gly Asn Arg Tyr Leu Ile Ser Leu Pro Phe Ser Cys Pro
            755                 760                 765

Cys Thr Lys Ser His Phe Phe Ser Asn Asn Gln Met Ala Asp Pro Leu
            770                 775                 780

Ile Leu Ser Tyr Gly Arg Val Asn Leu Pro Ser Phe Leu Val Asn Pro
785                 790                 795                 800

Glu Ala Val Ile Asp Met Ile Pro Val Val Met Val Asn Ala Ile
            805                 810                 815

Ile Ala Ala Met Ala Lys His Gly Ile Ala Gly Lys Pro Gly Ile Lys
            820                 825                 830

Val Tyr His Val Gly Ser Ser Ala Val Asn Pro Leu Pro Leu Gly Asp
            835                 840                 845

Leu Phe Lys His Ser Tyr Glu His Phe Ile Cys Ser Pro Ile Asn Met
850                 855                 860

Asp Thr Glu Gly Lys Thr Val Asp Met Lys Glu Met Lys Ile Phe Ser
865                 870                 875                 880

Pro Met Asp Asp Phe Ser Ser His Met Gln Thr Glu Ile Val Gln Gln
            885                 890                 895

Arg Arg Leu Thr Ile Ser Gly Asn Lys Ala Ser Gln Arg Leu Glu Arg
            900                 905                 910

Lys Cys Lys Met Ile Val Glu His Ala Ile Asn Leu Ala Arg Val Tyr
            915                 920                 925

Gln Pro Tyr Met Phe Phe Arg Gly Arg Phe Asp Asn Ser Asn Thr His
            930                 935                 940

Asn Leu Met Glu Gly Met Ser Glu Glu Met Lys Arg Phe Arg Leu
945                 950                 955                 960

Asp Val Glu Asn Val Asp Trp Glu Asp Tyr Ile Thr Asn Ile His Ile
            965                 970                 975

Ser Gly Leu Lys Lys His Val Met Lys Gly Arg Gly Met Pro Lys
            980                 985                 990

<210> SEQ ID NO 73
<211> LENGTH: 548
<212> TYPE: PRT
<213> ORGANISM: Stigmatella aurantiaca

<400> SEQUENCE: 73

Met Ser Gln Leu Pro Glu Leu Asn Val Ser Gln Ala Phe Thr Gly Lys
1               5                   10                  15

Arg Leu Leu Phe Ala Gly Ser Thr Gly Phe Val Gly Lys Val Thr Leu
            20                  25                  30

Ser Met Leu Leu Thr His Tyr Gly Gln Ala Leu Asp Lys Val Tyr Val
            35                  40                  45

Leu Val Arg Lys Gly Ser Ala Ala Ser Ala Glu Arg Arg Phe Phe Asp
        50                  55                  60

Lys Val Ala Ile Ser Glu Pro Phe Gln Pro Leu Arg Asp Ala Leu Gly

```
            65                  70                  75                  80
Glu Glu Ala Ala Leu Glu Phe Ile Arg Gln Lys Cys His Val Leu Asp
                85                  90                  95
Gly Asp Ile Thr Asp Pro Leu Met Gly Leu Thr Glu Ala Gln Ala Asp
            100                 105                 110
Glu Leu Thr Gly Lys Val Ala Ala Ile Val Asn Cys Ala Gly Leu Val
        115                 120                 125
Ser Phe Asn Pro Ser Leu Glu Val Gly Leu Asn Val Asn Thr His Gly
    130                 135                 140
Val Lys Tyr Ser Val Asp Leu Ala Leu Lys Trp Ser Ala Pro Leu Ile
145                 150                 155                 160
His Met Ser Thr Ala Phe Val Ala Gly Asn Arg Ser Gly Leu Val Phe
                165                 170                 175
Glu Asp Glu Glu Val Ala Gly Tyr Phe Pro Lys Lys Asp Glu Leu Asp
            180                 185                 190
Gly Arg Asp Phe Ser Leu Glu Gln Glu Leu Lys Asp Ala Glu Arg Ile
        195                 200                 205
Val Ala Arg Leu Arg Glu Gln Ala Asp Asp Lys Ala Leu Thr Ser Leu
    210                 215                 220
Phe Arg Lys Lys Ala Leu Asp Arg Leu Ala Glu Gly Arg Asp Ser
225                 230                 235                 240
Arg Asp Glu Lys Thr Leu Arg Leu Ala Val Gly Arg Glu Arg Lys Leu
                245                 250                 255
Trp Leu Thr Thr Glu Leu Val Arg Ala Gly Met Glu Arg Ala Gln His
            260                 265                 270
Trp Gly Trp Pro Asn Thr Tyr Thr Tyr Thr Lys Ser Leu Gly Glu Gln
        275                 280                 285
Val Met Ala Ala Thr Pro Gly Leu Arg Tyr Ser Ile Val Arg Pro Ser
    290                 295                 300
Ile Val Glu Thr Ser Arg His Phe Pro Phe Pro Gly Trp Asn Glu Gly
305                 310                 315                 320
Phe Thr Thr Ser Ala Pro Leu Ala Phe Ala Gly Ile Lys Gly Gln Arg
                325                 330                 335
Gly Ile Pro Ala Gly Phe Lys Thr Ile Leu Asp Ile Pro Val Asp
            340                 345                 350
Gln Val Ala Gly Ala Thr Leu Gly Ile Thr Ala His Ser Leu Thr Val
        355                 360                 365
His Glu Arg Arg Val Tyr His Leu Ala Ser Gly Asp Glu Asn Pro Phe
    370                 375                 380
Tyr Ala Ser Arg Ser Val Glu Leu Val Gly Leu Tyr Arg Arg Arg Tyr
385                 390                 395                 400
Tyr Arg Asn Lys Glu Gly Gly Asn Ala Leu Leu Asn Glu Val Arg Ala
                405                 410                 415
Arg Ile Glu Pro Gln Pro Ile Thr Arg Gln Arg Phe Glu Ser Leu Ser
            420                 425                 430
Ala Pro Ala Phe Met Lys Gly Ala Arg Leu Leu Lys Gln Val Ile Glu
        435                 440                 445
Glu Val Arg Pro Ala Trp Gly Ala Pro Thr Val Gln Ala Leu Leu Asp
    450                 455                 460
Arg Ala Lys Val Lys Leu Asp Asp Val Glu Glu Gln Ala Ser Ser Leu
465                 470                 475                 480
Ser Gln Leu Ile Glu Leu Phe Leu Pro Phe Leu Trp Glu Asn Arg Tyr
                485                 490                 495
```

```
Val Phe Arg Cys Asp Asn Thr Arg Ser Val Tyr Ala Arg Met Leu Pro
            500                 505                 510

Ser Asp Arg Ala Lys Ile Pro Trp Asp Pro Glu Asn Ile Asn Trp Arg
        515                 520                 525

Glu Tyr Trp Met Glu Thr His Leu Pro Gly Leu Glu Lys Phe Val Phe
    530                 535                 540

Pro Gly Leu Glu
545

<210> SEQ ID NO 74
<211> LENGTH: 250
<212> TYPE: DNA
<213> ORGANISM: Yarrowia lipolytica

<400> SEQUENCE: 74
cagcgaatgg cgtcctccaa tcagggccgt cagcgaagtc ggcgtgtgat agtgcgtggg      60
gagcgaatag agtttctggg gggggcggc ccaaaacgtg aaatccgagt acgcatgtag     120
agtgtaaatt gggtgtatag tgacattgtt tgactctgac cctgagagta atatataatg     180
tgtacgtgtc cccctccgtt ggtcttcttt ttttctcctt tctcctaacc aacacccaaa     240
ctaatcaatc                                                            250

<210> SEQ ID NO 75
<211> LENGTH: 250
<212> TYPE: DNA
<213> ORGANISM: Yarrowia lipolytica

<400> SEQUENCE: 75
taaaccagtt gcacacgttt ccgtggttta tgaccatctc attacgtcac cagttatggg      60
gaaccttatt gcctctcttt ctgaactcta aacccagcca atcacagctc gaacatatgt     120
aagcttggtg tcccaacagc agccccgggg cggacccgaa gttatttaac ctccacacat     180
tttgatttat aagagcaaag gttccctcca acgctactaa gtcaacacaa caacactaca     240
cacacaacat                                                            250

<210> SEQ ID NO 76
<211> LENGTH: 250
<212> TYPE: DNA
<213> ORGANISM: Yarrowia lipolytica

<400> SEQUENCE: 76
cgctccgcgg aggggaattc tacctttgga ttgtttcata agcacgtata atcgtcccct      60
cattggtaaa taatctgact aggtttcggc taggtttggc ttgcctgcat cccaggtgca     120
gctgctgact attcgagtac ctctagtgcc ttgctgtgag acaaggatta gtaaaagtgg     180
agatgatata taaggaggga acaggaccct tcgtccctgg ctcaattgaa cagtaacatc     240
tacaaacaac                                                            250

<210> SEQ ID NO 77
<211> LENGTH: 283
<212> TYPE: PRT
<213> ORGANISM: Saccharomyces cerevisiae

<400> SEQUENCE: 77

Met Val Ala Glu Gln Thr Gln Glu Asn Met Ser Ala Val Gly Pro Gly
1               5                   10                  15

Ser Asn Ala Gly Ala Ser Val Asn Gly Gly Ser Ala Thr Ala Ile Ala
```

```
                    20                  25                  30
Thr Leu Leu Arg Asn His Lys Glu Leu Lys Gln Arg Gln Gly Leu Phe
            35                  40                  45
Gln Ala Lys Gln Thr Asp Phe Phe Arg Tyr Lys Arg Phe Val Arg Ala
        50                  55                  60
Leu His Ser Glu Glu Tyr Ala Asn Lys Ser Ala Arg Gln Pro Glu Ile
65                  70                  75                  80
Tyr Pro Thr Ile Pro Ser Asn Lys Ile Glu Asp Gln Leu Lys Ser Arg
                85                  90                  95
Glu Ile Phe Ile Gln Leu Ile Lys Ala Gln Met Val Ile Pro Val Lys
            100                 105                 110
Lys Leu His Ser Gln Glu Cys Lys Glu His Gly Leu Lys Pro Ser Lys
            115                 120                 125
Asp Phe Pro His Leu Ile Val Ser Asn Lys Ala Gln Leu Glu Ala Asp
        130                 135                 140
Glu Tyr Phe Val Trp Asn Tyr Asn Pro Arg Thr Tyr Met Asp Tyr Leu
145                 150                 155                 160
Ile Val Ile Gly Val Val Ser Ile Ile Leu Ala Leu Val Cys Tyr Pro
                165                 170                 175
Leu Trp Pro Arg Ser Met Arg Arg Gly Ser Tyr Tyr Val Ser Leu Gly
            180                 185                 190
Ala Phe Gly Ile Leu Ala Gly Phe Phe Ala Val Ala Ile Leu Arg Leu
        195                 200                 205
Ile Leu Tyr Val Leu Ser Leu Ile Val Tyr Lys Asp Val Gly Gly Phe
        210                 215                 220
Trp Ile Phe Pro Asn Leu Phe Glu Asp Cys Gly Val Leu Glu Ser Phe
225                 230                 235                 240
Lys Pro Leu Tyr Gly Phe Gly Glu Lys Asp Thr Tyr Ser Tyr Lys Lys
                245                 250                 255
Lys Leu Lys Arg Met Lys Lys Lys Gln Ala Lys Arg Glu Ser Asn Lys
            260                 265                 270
Lys Lys Ala Ile Asn Glu Lys Ala Glu Gln Asn
        275                 280

<210> SEQ ID NO 78
<211> LENGTH: 246
<212> TYPE: PRT
<213> ORGANISM: Kluyveromyces lactis

<400> SEQUENCE: 78

Met Ser Glu Pro Ser Pro Gln Ser Thr Ile Ala Ile Ala Asn Leu Leu
1               5                   10                  15
Arg Thr His Ser Asp Leu Lys Gln Arg Gln Gly Leu Phe Gln Ser Arg
            20                  25                  30
Leu Val Asp Phe Phe Arg Tyr Lys Arg Phe Val Arg Ala Leu Lys Ser
        35                  40                  45
Asp Lys Tyr Lys Ala Lys Ser Lys Lys Gln Pro Glu Leu Tyr Pro Ala
        50                  55                  60
Val Thr Ser Asp Glu Asp Ala Arg Asn Ile Phe Val Ser Leu Ile Lys
65                  70                  75                  80
Ala Gln Phe Val Val Pro Ala Val Lys Leu His Ser Ala Glu Cys Lys
                85                  90                  95
Glu His Gly Leu Lys Pro Asn Lys Ser Tyr Pro Asn Leu Leu Leu Ser
            100                 105                 110
```

```
Asn Lys Ala Thr Leu Gln Pro Asp Glu Tyr Tyr Val Trp Ser Tyr Asn
            115                 120                 125

Pro Lys Ser Ile Tyr Asp Tyr Leu Thr Val Ile Gly Ile Val Gly
        130                 135                 140

Val Leu Ala Phe Val Cys Tyr Pro Leu Trp Pro Pro Tyr Met Lys Arg
145                 150                 155                 160

Gly Thr Tyr Tyr Leu Ser Ile Ala Ala Leu Ala Leu Ile Gly Val Phe
                165                 170                 175

Phe Gly Ile Ala Ile Val Arg Leu Ile Val Tyr Leu Leu Ser Leu Ala
            180                 185                 190

Ala Val Ser Glu Lys Gly Gly Phe Trp Leu Phe Pro Asn Leu Phe Glu
        195                 200                 205

Asp Cys Gly Val Ile Glu Ser Phe Lys Pro Leu Tyr Gly Phe Gly Glu
        210                 215                 220

Lys Glu Cys Tyr Ser Phe Leu Lys Lys Glu Lys Arg Lys His Arg Ser
225                 230                 235                 240

Val Ala Lys Lys Gln Lys
                245

<210> SEQ ID NO 79
<211> LENGTH: 273
<212> TYPE: PRT
<213> ORGANISM: Schizosaccharomyces pombe

<400> SEQUENCE: 79

Met Asp Ser Ser Asn Val Pro Val Leu Lys Asp Glu Asp Lys Cys Lys
1               5                   10                  15

Phe Ser Met Arg Phe Thr Asn Phe Leu Lys Ser Arg Pro Glu Leu Lys
            20                  25                  30

Thr Lys Pro Ala Ile Leu Asn Gly Lys Arg Val Tyr Tyr Phe Arg Val
        35                  40                  45

Lys Arg Val Leu Arg Phe Leu Thr Ser Glu Ala Tyr Thr Pro Lys Lys
    50                  55                  60

Tyr Lys Gly Phe Pro Glu Ile Ser Ser Arg Glu Glu Ala Ile Glu Val
65                  70                  75                  80

Leu Lys Leu Leu Ile Met Asn Ser Met Leu Val Arg Val Asp Lys Leu
                85                  90                  95

Pro Pro Lys Gln Arg Lys Gln Lys Leu Val Glu Leu Gln Ile Asn Arg
            100                 105                 110

Asn Gln Asp Phe Gln Asp Met His Tyr Val Trp Leu Tyr Glu Pro
            115                 120                 125

Leu Pro Lys Arg Val Met Ala Leu Ala Val Leu Phe Ala Leu Val Val
        130                 135                 140

Leu Ala Leu Val Leu Phe Pro Leu Trp Pro Met Phe Met Arg Lys Gly
145                 150                 155                 160

Ala Trp Tyr Leu Ser Met Gly Gly Leu Gly Val Ile Gly Leu Phe Phe
                165                 170                 175

Val Leu Val Ile Leu Arg Phe Phe Leu Phe Cys Ile Thr Ala Val Ile
            180                 185                 190

Val Arg Pro Gly Ile Trp Leu Phe Pro Asn Leu Leu Ala Asp Val Gly
        195                 200                 205

Phe Cys Asp Ser Phe Lys Pro Leu Trp Ser Trp His Asn Ser Lys Ser
        210                 215                 220

Glu Val Lys Lys Thr Arg Lys Ser Lys Lys Leu Ser Lys Lys Ala Thr
225                 230                 235                 240
```

```
Ser Pro Ala Ala Ser Ala Thr Pro Glu Lys Ser Ser Thr Ser Thr Thr
            245                 250                 255

Ser Leu Lys Asn Leu Arg His Arg Asn Pro Thr Val Glu Glu Val Ser
            260                 265                 270

Glu
```

GENE DISRUPTANTS PRODUCING FATTY ACYL-COA DERIVATIVES

CROSS-REFERENCES TO RELATED APPLICATIONS

The present application is a divisional application of U.S. Non-provisional application Ser. No. 13/330,650, filed Dec. 19, 2011, granted Oct. 13, 2015 as U.S. Pat. No. 9,157,103, which claims the benefit of U.S. Provisional Application Nos. 61/502,697, filed Jun. 29, 2011 and 61/427,032 filed Dec. 23, 2010, the entire content of each of which are incorporated herein by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 90834-820567_ST25.TXT, created on Dec. 11, 2011, 188,336 bytes, machine format IBM-PC, MS-Windows operating system, is hereby incorporated by reference in its entirety for all purposes.

FIELD OF THE INVENTION

This invention relates to modified microbial organisms exhibiting improved properties, especially improved production of fatty acyl-CoA derivatives.

BACKGROUND OF THE INVENTION

Microbial organisms produce fatty acyl-CoA and fatty acyl-CoA derivatives, such as fatty alcohols, fatty acids, fatty aldehydes, fatty esters, fatty acetates, wax esters, alkanes, and alkenes. Such fatty acyl-CoA derivatives may be used to produce a wide variety of products, including jet and diesel fuels (e.g., biodiesel), chemical surfactants, polymers, nutritional supplements, pharmaceuticals, food additives, cosmetics, and personal care products.

Fatty acids are a principal component of cell membranes and are used by organisms for energy storage. Fatty acids are metabolized by β-oxidation of fatty acyl-CoA, or conversely, fatty acids are synthesized from acetyl-CoA by fatty acid synthase multi-enzyme complexes. Fatty alcohols are the reduction products of fatty acyl-thioester substrates (e.g., fatty acyl-CoA or fatty acyl-ACP), and like fatty acids, can be produced enzymatically by cultured cells. Enzymes that convert fatty acyl-thioester substrates (e.g., fatty acyl-CoA or fatty acyl-ACP) to fatty alcohols are commonly referred to as "fatty alcohol forming acyl-CoA reductases" or "fatty acyl reductases" ("FARs").

The commercial production and recovery of fatty alcohols from microbial organisms is challenging, in part because fatty alcohols are not very stable in many microorganisms. The fatty alcohols (e.g., hexadecanol) can be used as a carbon source for the microorganism, and may thus be metabolized by the microorganism before recovery for commercial purposes. The fatty alcohols are likely degraded by enzymes that catalyze the oxidation of alkanes to fatty acids (via fatty alcohols). Fatty acids can then be further degraded to acetyl-CoA by enzymes in the β-oxidation pathway or converted to storage lipids by a set of acetyltransferases.

Accordingly, there is a need for microbial organisms for the efficient production of fatty acyl-CoA derivatives.

BRIEF SUMMARY OF THE INVENTION

This invention provides modified microbial organisms exhibiting improved properties, including improved production of fatty acyl-CoA derivatives. In some aspects, the modified microbial organisms have a disrupted gene that confers improved production of fatty acyl-CoA derivatives compared to a control organism of the same type in which the gene is not disrupted. In one embodiment the organism is *Yarrowia lipolytica*.

In one aspect, the invention relates to a microbial organism in which one or more endogenous genes is disrupted, wherein the endogenous gene is YALI0C17545 or a homolog thereof and/or YALI0E28336 or a homolog thereof, and comprising an exogenous gene encoding a functional fatty acyl reductase (FAR) protein operably linked to a promoter. In another aspect, both the endogenous YALI0C17545 gene, or homolog thereof, and the endogenous gene YALI0E28336, or homolog thereof, are disrupted. In another aspect, the microbial organism further comprises a disruption of one or more of endogenous gene YALI0E11099, or a homolog thereof, and endogenous gene YALI0E28534, or a homolog thereof. In another aspect, both the endogenous gene YALI0E11099, or homolog thereof, and the endogenous gene YALI0E28534, or homolog thereof, are disrupted. In another aspect, the microbial organism further comprises a disruption of one or more endogenous genes selected from YALI0B10406, YALI0A19536, YALI0E32769, YALI0E30283, YALI0E12463, YALI0E17787, YALI0B14014, YALI0A10769, YALI0A15147, YALI0A16379, YALI0A20944, YALI0B07755, YALI0B10175, YALI0B13838, YALI0C02387, YALI0C05511, YALI0D01738, YALI0D02167, YALI0D04246, YALI0D05291, YALI0D07986, YALI0D10417, YALI0D14366, YALI0D25630, YALI0E03212, ALI0E07810, YALI0E12859, YALI0E14322, YALI0E15378, YALI0E15400, YALI0E18502, YALI0E18568, YALI0E22781, YALI0E25982, YALI0E28314, YALI0E32417, YALI0F01320, YALI0F06578, YALI0F07535, YALI0F14729, YALI0F22121, YALI0F25003, YALI0E14729, YALI0B17512, and homologs thereof. In another aspect, the endogenous gene YALI0B17512 is disrupted.

In another aspect, two or more of the endogenous genes are disrupted. In another aspect, three or more of the endogenous genes are disrupted. In another aspect, four or more of the endogenous genes are disrupted.

In another aspect, the microbial organism comprises: a deletion of all or a portion of the coding sequence of the endogenous gene, a mutation in the endogenous gene such that the gene encodes a polypeptide having reduced activity, antisense RNA or small interfering RNA that inhibits expression of the endogenous gene, or a modified regulatory sequence that reduces expression of the endogenous gene. In one embodiment, the microbial organism comprises a deletion of all or a portion of the coding sequence of the endogenous gene.

In one aspect, the exogenous gene encodes a functional FAR protein comprising a polypeptide sequence having at least 80%, at least 85%, at least 90%, at least 91%, at least 92%, at least 93%, at least 94%, at least 95%, at least 96%, at least 97%, at least 98%, or at least 99% sequence identity to a *Marinobacter algicola* FAR protein comprising SEQ ID NO:2. In another aspect, the exogenous gene encodes a functional FAR protein comprising a polypeptide sequence having at least 80%, at least 85%, at least 90%, at least 91%, at least 92%, at least 93%, at least 94%, at least 95%, at least 96%, at least 97%, at least 98%, or at least 99% sequence identity to a *Marinobacter aquaeolei* FAR protein comprising SEQ ID NO:4. In another aspect, the exogenous gene encodes a functional FAR protein comprising a polypeptide sequence having at least 80%, at least 85%, at least 90%, at least 91%, at least 92%, at least 93%, at least 94%, at least 95%, at least 96%, at least 97%, at least 98%, or at least 99% sequence identity to a *Oceanobacter* sp. RED65 FAR protein comprising SEQ ID NO:6. In one aspect, the exogenous gene includes a nucleic acid sequence having at least 80% sequence identity, often at least 85%, at least 90%, at least 91%, at least 92%, at least 93%, at least 94%, at least 95%, at least 96%, at least 97%, at least 98%, or at least 99% sequence identity to the nucleic acid sequence of FAR_Maa (SEQ ID NO:1), FAR_Maq (SEQ ID NO:3), or FAR_Ocs (SEQ ID NO:5). In one embodiment, the fatty acyl reductase is a gene having at least 80% sequence identity, often at least 85%, at least 90%, at least 91%, at least 92%, at least 93%, at least 94%, at least 95%, at least 96%, at least 97%, at least 98%, or at least 99% sequence identity to the nucleic acid sequence of FAR_Maa (SEQ ID NO:1).

In one aspect, the functional FAR protein is a FAR variant comprising one or more amino acid substitutions relative to SEQ ID NO:2, 4, or 6, respectively, wherein a cell in which the FAR variant is expressed produces at least 1.5-fold more fatty acyl-CoA derivatives than a corresponding cell of the same type in which a wild-type FAR protein from which the FAR variant is derived is expressed. In another aspect, the exogenous FAR gene encodes a FAR variant that comprises from 1 to about 50, e.g., 1, 2, 3, 4, 5, 6, 7, 8, 9, 10, 11, 12, 13, 14, 15, 16, 17, 18, 19, 20, 25, 30, or 40 amino acid substitutions relative to FAR_Maa (SEQ ID NO:2), FAR_Maq (SEQ ID NO:4), or FAR_Ocs (SEQ ID NO:6). In one embodiment, the exogenous FAR gene encodes a FAR variant that comprises from 1 to about 50, e.g., 1, 2, 3, 4, 5, 6, 7, 8, 9, 10, 11, 12, 13, 14, 15, 16, 17, 18, 19, 20, 25, 30, or 40 amino acid substitutions relative to FAR_Maa (SEQ ID NO:2).

In another aspect, the microbial organism has multiple copies of the endogenous gene (e.g., a diploid number) and more than one copy of the endogenous gene is disrupted. In another aspect, the microbial organism expresses multiple copies of the exogenous gene. In another aspect, the exogenous gene is integrated into the genome of the microbial organism.

In another aspect, the microbial organism further comprises a second exogenous gene that encodes a fatty acid synthase (FAS), an ester synthase, an acyl-ACP thioesterase (TE), a fatty acyl-CoA synthase (FACS), an acetyl-CoA carboxylase (ACC), a xylose isomerase, or an invertase.

In one aspect, the microbial organism is algae, bacteria, mold, filamentous fungus, or yeast, such as an oleaginous yeast. In one aspect, the microbial organism is a yeast. In one aspect, the yeast is *Yarrowia, Brettanomyces, Candida, Cryptococcus, Endomycopsis, Hansenula, Kluyveromyces, Lipomyces, Pachysolen, Pichia, Rhodosporidium, Rhodotorula, Saccharomyces, Schizosaccharomyces, Trichosporon,* or *Trigonopsis*. In one aspect, the yeast is an oleaginous yeast, such as *Yarrowia lipolytica, Yarrowia paralipolytica, Candida revkauji, Candida pulcherrima, Candida tropicalis, Candida utilis, Candida curvata D, Candida curvata R, Candida diddensiae, Candida boldinii, Rhodotorula glutinous, Rhodotorula graminis, Rhodotorula mucilaginosa, Rhodotorula minuta, Rhodotorula bacarum, Rhodosporidium toruloides, Cryptococcus (terricolus) albidus* var. *albidus, Cryptococcus laurentii, Trichosporon pullans, Trichosporon cutaneum, Trichosporon cutancum, Trichosporon pullulans, Lipomyces starkeyii, Lipomyces lipoferus, Lipomyces tetrasporus, Endomycopsis vernalis, Hansenula ciferri, Hansenula saturnus,* or *Trigonopsis variabilis*. In one aspect, the yeast is *Yarrowia lipolytica*.

In another aspect, the microbial organism exhibits at least a 1-fold, at least a 1.2-fold, at least a 1.5-fold, at least a 4-fold, or at least a 20-fold increase in the production of a fatty acyl-CoA derivative compared to a control organism of the same type (e.g., an otherwise identical control microbial organism in which the one or more genes are not disrupted).

In another aspect, the invention relates to a microbial organism comprising one or more disrupted endogenous genes, wherein at least one of the disrupted genes is YALI0C17545, YALI0E28336, YALI0E11099, YALI0B10406, YALI0A19536, YALI0E28534, YALI0E32769, YALI0E30283, YALI0E12463, YALI0E17787, YALI0B14014, YALI0A10769, YALI0A15147, YALI0A16379, YALI0A20944, YALI0B07755, YALI0B10175, YALI0B13838, YALI0C02387, YALI0C05511, YALI0D01738, YALI0D02167, YALI0D04246, YALI0D05291, YALI0D07986, YALI0D10417, YALI0D14366, YALI0D25630, YALI0E03212, ALI0E07810, YALI0E12859, YALI0E14322, YALI0E15378, YALI0E15400, YALI0E18502, YALI0E18568, YALI0E22781, YALI0E25982, YALI0E28314, YALI0E32417, YALI0F01320, YALI0F06578, YALI0F07535, YALI0F14729, YALI0F22121, YALI0F25003, YALI0E14729, YALI0B17512, or a homolog of any of these, and an exogenous gene encoding a functional fatty acyl reductase operably linked to a promoter, wherein the microbial organism exhibits at least a 1-fold, at least a 1.2-fold, at least a 1.5-fold, at least a 4-fold, or at least a 20-fold increase in the production of a fatty acyl-CoA derivative compared to a control organism of the same type (e.g., an otherwise identical control microbial organism in which the one or more genes are not disrupted).

In yet another aspect, at least one of the disrupted endogenous genes is YALI0C17545, YALI0E28336, YALI0E11099, YALI0B10406, YALI0A19536, YALI0E28534, YALI0E32769, YALI0E30283, YALI0E12463, YALI0E14729, YALI0B17512, or a homolog of any of these.

In one aspect, YALI0C17545 or a homolog thereof is disrupted. In another aspect, YALI0E28336 or a homolog thereof is disrupted. In yet another aspect, both YALI0C17545 or a homolog thereof and YALI0E28336 or a homolog thereof are disrupted.

In yet another aspect, the microbial organism further comprises a second disrupted gene that is YALI0C17545, YALI0E28336, YALI0E11099, YALI0B10406, YALI0A19536, YALI0E28534, YALI0E32769, YALI0E30283, YALI0E12463, YALI0E17787, YALI0B14014, YALI0A10769, YALI0A15147, YALI0A16379, YALI0A20944, YALI0B07755, YALI0B10175, YALI0B13838, YALI0C02387, YALI0C05511, YALI0D01738, YALI0D02167, YALI0D04246, YALI0D05291, YALI0D07986, YALI0D10417, YALI0D14366, YALI0D25630, YALI0E03212, ALI0E07810, YALI0E12859, YALI0E14322, YALI0E15378, YALI0E15400, YALI0E18502, YALI0E18568, YALI0E22781, YALI0E25982, YALI0E28314, YALI0E32417, YALI0F01320, YALI0F06578, YALI0F07535, YALI0F14729, YALI0F22121, YALI0F25003, YALI0E14729, YALI0B17512 or a homolog of any of these.

In one aspect, the microbial organism comprises two disrupted endogenous genes. When two genes are disrupted, YALI0C17545 or a homolog thereof and/or YALI0E30283 or a homolog thereof can be disrupted. In another aspect, the microbial organism comprises three disrupted endogenous genes. In yet another aspect, the microbial organism comprises four or more disrupted endogenous genes.

In another aspect, the microbial organism comprises a combination of disrupted endogenous genes, or homologs thereof. The combination can be:
  a. YALI0C17545 and YALI0E28336;
  b. YALI0C17545 and YALI0B10406;
  c. YALI0C17545 and YALI0E28534;
  d. YALI0C17545 and YALI0E30283;
  e. YALI0E28336 and YALI0E30283;
  f. YALI0E11099 and YALI0E30283;
  g. YALI0A19536 and YALI0E30283;
  h. YALI0A19536 and YALI0E28534;
  i. YALI0E30283 and YALI0E12463;
  j. YALI0B10406 and YALI0E14729;
  k. YALI0C17545 and YALI0E14729;
  l. YALI0E11099 and YALI0E14729;
  m. YALI0C17545, YALI0E28336, and YALI0E11099;
  n. YALI0C17545, YALI0E28336, and YALI0B10406;
  o. YALI0C17545, YALI0E28336, and YALI0A19536;
  p. YALI0C17545, YALI0E28336, and YALI0E28534;
  q. YALI0C17545, YALI0E28336, and YALI0E32769;
  r. YALI0C17545, YALI0E28336, and YALI0E12463;
  s. YALI0C17545, YALI0E11099, and YALI0B10406;
  t. YALI0C17545, YALI0B10406, and YALI0A19536;
  u. YALI0E28336, YALI0E11099, and YALI0B10406;
  v. YALI0E11099, YALI0B10406, and YALI0A19536;
  w. YALI0C17545, YALI0E28534, and YALI0B17512;
  x. YALI0E11099, YALI0A19536, YALI0B10406, and YALI0B17512;
  y. YALI0C17545, YALI0E28336, YALI0E11099, and YALI0B10406;
  z. YALI0C17545, YALI0E28336, YALI0E11099, and YALI0A19536;
  aa. YALI0C17545, YALI0E28336, YALI0E11099, and YALI0E28534;
  bb. YALI0C17545, YALI0E28336, YALI0E11099, and YALI0E32769;
  cc. YALI0C17545, YALI0E28336, YALI0B10406, and YALI0A19536;
  dd. YALI0C17545, YALI0E28336, YALI0B10406, and YALI0E32769;
  ee. YALI0C17545, YALI0E28336, YALI0A19536, and YALI0E28534;
  ff. YALI0C17545, YALI0E28336, YALI0E28534, and YALI0E32769;
  gg. YALI0C17545, YALI0E28336, YALI0E28534, and YALI0E12463;
  hh. YALI0E28336, YALI0E11099, YALI0B10406, and YALI0E32769; or
  ii. YALI0E11099, YALI0E28336, YALI0C17545, and YALI0E14729.

In one aspect, a *Yarrowia lipolytica* cell comprises one or more disrupted endogenous genes, wherein at least one disrupted gene is YALI0C17545, YALI0E28336, YALI0E11099, YALI0B10406, YALI0A19536, YALI0E28534, YALI0E32769, YALI0E30283, YALI0E12463, YALI0E14720, YALI0B17512, or a homolog of any of these, and an exogenous gene encoding a functional fatty acyl reductase operably linked to a promoter, wherein the *Yarrowia lipolytica* cell exhibits at least a 1-fold, at least a 1.2-fold, at least a 1.5-fold, at least a 4-fold, or at least a 20-fold increase in the production of a fatty acyl-CoA derivative compared to a control organism of the same type (e.g., an otherwise identical control microbial organism in which the one or more genes are not disrupted). In one aspect, the exogenous gene includes a nucleic acid sequence having at least 80% sequence identity, often at least 85%, at least 90%, at least 95%, at least 96%, at least 97%, at least 98%, or at least 99% sequence identity to a nucleic acid sequence of FAR_Maa (SEQ ID NO:1), FAR_Maq (SEQ ID NO:3), or FAR_Ocs (SEQ ID NO:5), or it encodes a polypeptide that includes an amino acid sequence having at least 80% sequence identity, often at least 85%, at least 90%, at least 95%, at least 96%, at least 97%, at least 98%, or at least 99% sequence identity to a polypeptide of FAR_Maa (SEQ ID NO:2), FAR_Maq (SEQ ID NO:4), or FAR_Ocs (SEQ ID NO:6); or encodes a FAR variant polypeptide that comprises from 1 to about 50, e.g., 1, 2, 3, 4, 5, 6, 7, 8, 9, 10, 11, 12, 13, 14, 15, 16, 17, 18, 19, 20, 25, 30, or 40 amino acid substitutions relative to FAR_Maa (SEQ ID NO:2), FAR_Maq (SEQ ID NO:4), or FAR_Ocs (SEQ ID NO:6). In one embodiment, the exogenous FAR gene encodes a FAR variant that comprises from 1 to about 50, e.g., 1, 2, 3, 4, 5, 6, 7, 8, 9, 10, 11, 12, 13, 14, 15, 16, 17, 18, 19, 20, 25, 30, or 40 amino acid substitutions relative to FAR_Maa (SEQ ID NO:2).

In another aspect, the invention provides a microbial organism in which one or more endogenous genes is disrupted, wherein the endogenous gene is selected from YALI0C17545, YALI0E28336, YALI0E11099, YALI0B10406, YALI0A19536, YALI0E28534, YALI0E32769, YALI0E30283, YALI0E12463, YALI0E17787, YALI0B14014, YALI0A10769, YALI0A15147, YALI0A16379, YALI0A20944, YALI0B07755, YALI0B10175, YALI0B13838, YALI0C02387, YALI0C05511, YALI0D01738, YALI0D02167, YALI0D04246, YALI0D05291, YALI0D07986, YALI0D10417, YALI0D14366, YALI0D25630, YALI0E03212, ALI0E07810, YALI0E12859, YALI0E14322, YALI0E15378, YALI0E15400, YALI0E18502, YALI0E18568, YALI0E22781, YALI0E25982, YALI0E28314, YALI0E32417, YALI0F01320, YALI0F06578, YALI0F07535, YALI0F14729, YALI0F22121, YALI0F25003, YALI0E14729, YALI0B17512, and homologs thereof. In another aspect, the endogenous gene YALI0B17512, or homolog thereof, is disrupted. In another aspect, YALI0B17512 encodes a polypeptide comprising a cytoplasmic domain and the disruption comprises a deletion of at least a portion of the cytoplasmic domain. In another aspect, one or more of the endogenous gene YALI0C17545, or homolog thereof, and the endogenous gene YALI0E28336, or homolog thereof, is disrupted.

In another aspect, the invention provides a method for producing a fatty acyl-CoA derivative comprising providing a microbial organism as described herein; and culturing the microbial organism under conditions in which fatty acyl-CoA derivatives are produced. The method can further include recovering (e.g., isolating) the fatty acyl-CoA derivative. In one aspect, at least 5 g/L or at least 15 g/L of fatty acyl-CoA derivatives per liter of culture medium is produced.

In another aspect, a method for producing a fatty acyl-CoA derivative can include contacting a cellulose-containing biomass with one or more cellulases to yield fermentable sugars; and contacting the fermentable sugars with the microbial organism. In another aspect, the method for producing a fatty acyl-CoA derivative can include contacting fermentable sugars comprising sucrose with the microorganism as described herein.

In one aspect, the fatty acyl-CoA derivative is a fatty alcohol, fatty acid, fatty aldehyde, fatty ester, fatty acetate, wax ester, alkane, or alkene. In another aspect, the fatty acyl-CoA derivative is a fatty alcohol. In one aspect, the fatty acyl-CoA derivative has a carbon chain length of 8 to 24 carbon atoms, such as a fatty alcohol with 8 to 24 carbon atoms.

In another aspect, the invention provides a composition comprising the fatty acyl-CoA derivative(s) produced by a method as described herein.

DETAILED DESCRIPTION OF THE INVENTION

I. Definitions

Figure 1:
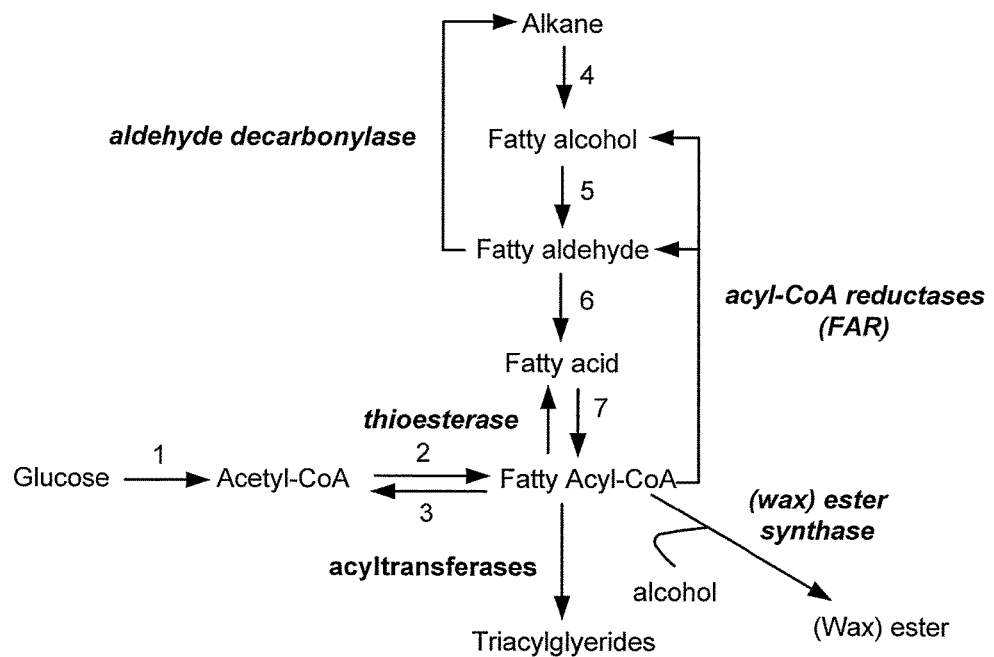
FIG. 1 illustrates routes to biosynthesis of fatty acyl-CoA derivatives in *Y. lipolytica*. Native pathways for biosynthesis of fatty acyl-CoA from glucose (reactions 1-3) and for degradation of alkanes and products of alkane oxidation to fatty acyl-CoA are shown (reactions 4-7). Native and exogenous pathways for production of fatty acyl-CoA derived products are also shown, and include: acyltransferases (triacylglycerides), thioesterases (fatty acids), ester synthases (esters), acyl-CoA reductases ("FARs") (fatty aldehydes and fatty alcohols), and aldehyde decarbonylases (alkanes).

Unless defined otherwise, all technical and scientific terms used herein generally have the same meaning as commonly understood by one of ordinary skill in the art to which this invention belongs. Generally, the nomenclature used herein and the laboratory procedures in analytical chemistry, cell culture, molecular genetics, organic chemistry, and nucleic acid chemistry and hybridization described below are those well known and commonly employed in the art. It is noted that as used herein, "a," "an," and "the" include plural references unless the context clearly dictates otherwise. The term "comprising" and its cognates are used in their inclusive sense; that is, equivalent to the term "including" and its corresponding cognates.

The techniques and procedures are generally performed according to conventional methods in the art and various general references. See, e.g., Sambrook et al., 2001, *Molecular Cloning: A Laboratory Manual*, 3rd ed.; Ausubel, ed., 1990-2008, *Current Protocols in Molecular Biology*. Standard techniques, or modifications thereof, are used for nucleic acid and polypeptide synthesis and for chemical syntheses and chemical analyses. Generally, enzymatic reactions and purification steps are performed according to the manufacturer's specifications. For techniques regarding yeast recombinant techniques, nutrition, and growth, see, e.g., Walker, 1998, *Yeast Physiology and Biotechnology*.

The term "disrupted," as applied to a gene, refers to any genetic modification that decreases or eliminates the expression of the gene and/or the functional activity of the corresponding gene product (mRNA and/or protein). Genetic modifications include complete or partial inactivation, suppression, deletion, interruption, blockage, or down-regulation of a gene. This can be accomplished, for example, by gene "knockout," inactivation, mutation (e.g., insertion, deletion, point, or frameshift mutations that disrupt the expression or activity of the gene product), or by use of inhibitory RNAs (e.g., sense, antisense, or RNAi technology). A disruption may encompass all or part of a gene's coding sequence.

The term "knockout" has its conventional meaning in the art, and refers to an organism or cell in which a specific gene has been inactivated by genetic manipulation, generally by a recombination event in which all or a portion of gene is deleted or a heterologous DNA is inserted, so that the cell or organism does not produce a functional product encoded by the gene. Knockout also refers to the process of making an organism or cell with an inactivated gene, usually by replacing at least a portion of a coding sequence of a gene with an artificial piece of DNA (e.g., encoding a selection marker) and/or deleting at least a portion of the coding sequence of the gene, so that a functional gene product is not expressed in the cell or organism. In some embodiments the entire coding sequence of the gene is excised.

"Coding sequence" refers to that portion of a nucleic acid that encodes for an amino acid sequence of a protein.

The term "expression" includes any step involved in the production of a polypeptide including, but not limited to, transcription, post-transcriptional modification, translation, post-translational modification, and secretion.

The term "fatty acyl-CoA derivative" is a compound that can be metabolically derived from fatty acyl-CoA, fatty acyl-ACP, or other similar fatty acyl thioester in a microorganism. Derivatives include, but are not limited to, fatty alcohols, fatty acids, fatty aldehydes, fatty esters, fatty acetates, wax esters, alkanes, and alkenes. Saturated or unsaturated fatty acyl-CoA derivatives can be described using the notation "Ca:b," where "a" is an integer that represents the total number of carbon atoms, and "b" is an integer that refers to the number of double bonds in carbon chain. Unsaturated fatty acyl Co-A derivatives can be referred to as "cis$\Delta^x$" or "trans$\Delta^x$" wherein "cis" and "trans" refer to the carbon chain configuration around the double bond. The "x" indicates the number of the first carbon of the double bond, where carbon 1 is, e.g., the carboxylic acid carbon of the fatty acid or the carbon bound to the —OH group of the fatty alcohol. For the derivatives described below, "R" is a $C_8$ to $C_{24}$ saturated, unsaturated, linear, branched, or cyclic hydrocarbon (or "$C_7$ to $C_{23}$" in derivative formulas expressly articulating the terminal carbon).

The term "fatty alcohol" as used herein refers to an aliphatic alcohol of the formula R—OH, where "R" is as defined above. In some embodiments, a fatty alcohol produced according to the methods disclosed herein is a C8-C24 saturated or unsaturated fatty alcohol (i.e., a C8, C9, C10, C11, C12, C13, C14, C15, C16, C17, C18, C19, C20, C21, C22, or C24 fatty alcohol). In some embodiments, one or more of the following fatty alcohols is produced: 1-octanol (C8:0), 1-decanol (C10:0), 1-dodecanol (C12:0), 1-tetradecanol (C14:0), 1-hexadecanol (C16:0), 1-octadecanol (C18:0), 1-icosanol (C20:0), 1-docosanol (C22:0), 1-tetracosanol (C24:0), cis $\Delta^9$-1-hexadecenol (C16:1), and cis $\Delta^{11}$-1-octadecenol (C18:1). It is understood that, unless otherwise specified, a reference to a "Cx fatty alcohol" includes both saturated and unsaturated fatty alcohols having "x" carbon atoms.

The term "fatty acid" as used herein refers to a compound of the formula

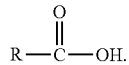

The term "fatty aldehyde" as used herein refers to a compound of the formula

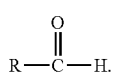

The term "fatty esters" includes compounds of the formula

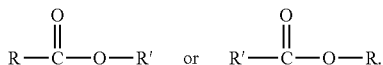

where R' is a short chain, e.g., $C_1$ to $C_6$, preferably $C_1$ to $C_4$ hydrocarbon. For example, fatty acyl-CoA can be reacted with a short chain alcohol (e.g., methanol or ethanol) to form conventional fatty esters. Conversely, fatty alcohols can be reacted with short chain thioesters (e.g., acetyl CoA) to form esters. Both ester types are encompassed by the term "fatty esters."

The term "fatty acetates" as used herein refers to a compound of the formula

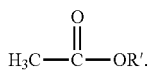

The term "wax esters" as used herein refers to an ester derived from a long chain fatty acid and a long chain alcohol.

Reference herein to particular endogenous genes by name is for illustration and not limitation. It is understood that gene names vary from organism to organism and reference to a gene name is not intended to be limiting, but is intended to encompass homologs (i.e., which may be endogenous to a related microbial organism) and polymorphic variants. Homologs and variants can be identified based on sequence identity and/or similar biological (e.g., enzymatic) activity. In certain embodiments, the invention includes a polynucleotide or polypeptide sequence with at least 50%, 60%, 70%, 85%, 90%, 91%, 92%, 93%, 94%, 95%, 96%, 97%, 98%, or 99% identity with the named gene or gene product.

"Identity" or "percent identity," in the context of two or more polynucleotide or polypeptide sequences, refers to two or more sequences or sub-sequences that are the same or have a specified percentage of nucleotides or amino acid residues, respectively, that are the same. Percent identity may be determined by comparing two optimally aligned sequences over a comparison window, wherein the portion of the polynucleotide or polypeptide sequence in the comparison window may comprise additions or deletions (i.e., gaps) as compared to the reference sequence (which may also contain gaps to optimize the alignment) for alignment of the two sequences. For example, the sequence can have a percent identity of at least 50%, 60%, 70%, 85%, 90%, 91%, 92%, 93%, 94%, 95%, 96%, 97%, 98%, or 99% over a specified region to a reference sequence when compared and aligned for maximum correspondence over a comparison window, or designated region as measured using a sequence comparison algorithms or by manual alignment and visual inspection.

Alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, John Wiley & Sons, Inc. (1995 Supplement) (Ausubel)).

Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, "polynucleotide" refers to a polymer of deoxyribonucleotides or ribonucleotides in either single- or double-stranded form, and complements thereof.

The terms "polypeptide" and "protein" are used interchangeably herein to refer to a polymer of amino acid residues.

"Improved production" refers to an increase in the amount of measurable fatty acyl-CoA derivatives produced by a modified microbial organism (i.e., a microbial organism in which one or more endogenous genes is disrupted) as compared to the amount produced by a control microbial organism of the same type in which the genes are not disrupted, when cultured under the same conditions. "Control organism of the same type" means an organism of the same species having a genome that is essentially identical to the genome of the modified microbial organism, except for a disrupted gene or combination of genes described here. For example, a *Y. lipolytica* strain (e.g., DSMZ 1345) in which a fatty acid synthase is overexpressed would be a "control organism of the same type" for the same *Y. lipolytica* strain (e.g., DSMZ 1345) in which a fatty acid synthase is overexpressed and in which the specified gene or combination of genes is disrupted. The term "otherwise identical organism" is used interchangeably with "control organism of the same type." The improved production may occur by any mechanism, e.g., increased production and/or decreased degradation or utilization.

The term "functional," as used in reference to a polypeptide, means that the polypeptide exhibits catalytic activity in vivo. The term "functional" can be used interchangeably with the term "biologically active."

The terms "wild-type" or "native" used in reference to a polypeptide or protein mean a polypeptide or protein expressed by a microorganism found in nature. When used in reference to a microorganism, the term means a naturally occurring (not genetically modified) microorganism.

A "FAR" (also known as "fatty alcohol forming acyl-CoA reductase" or "fatty acyl reductase") as used herein refers to an enzyme that converts fatty acyl-thioester substrates (e.g., fatty acyl-CoA or fatty acyl-ACP) to fatty alcohols. "CoA" is a non-protein acyl carrier group factor (or moiety) involved in the synthesis and oxidation of fatty acids. "ACP" is a polypeptide or protein subunit of fatty acid synthase used in the synthesis of fatty acids.

The term "wild-type FAR," as used herein, refers to a FAR polypeptide that is produced in nature. In some embodiments, a wild-type FAR is produced by a gammaproteobacteria, including but not limited to strains of *Marinobacter*, *Oceanobacter*, and *Hahella*. Naturally occurring FAR polypeptides are described, for example, in US patent publication 2011/0000125, incorporated by reference herein. In some embodiments, a wild-type FAR is a naturally-occurring FAR polypeptide that is produced by the *Marinobacter algicola* strain DG893 (SEQ ID NO:2). In some embodiments, a wild-type FAR is a naturally-occurring FAR polypeptide that is produced by the *Marinobacter aquaeolei* strain VT8 (SEQ ID NO:4) In some embodiments, a wild-type FAR is a naturally-occurring FAR polypeptide that is produced by *Oceanobacter* sp. RED65 (SEQ ID NO:6).

The term "FAR variant," as used herein, refers to full-length FAR polypeptides having substitutions at one or more amino acid positions relative to a wild-type FAR polypeptide, and functional fragments thereof, wherein a cell (e.g., a microbe) in which the variant is expressed is capable of catalyzing increased production of fatty alcohols as compared to a cell in which the wild-type FAR polypeptide is expressed. In some embodiments, a FAR variant comprises at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a FAR polypeptide of SEQ ID NO:2, SEQ ID NO:4, or SEQ ID NO:6 and also comprises one or more amino acid substitutions that give rise to increased fatty acyl-CoA derivative (e.g., fatty alcohol) production as compared to the fatty acyl-CoA derivative production that can be achieved with the wild-type FAR polypeptide from which it is derived. FAR variants are described, for example, in U.S. application Ser. No. 13/171, 138, incorporated by reference herein. As used herein, except where otherwise clear from context, reference to a "FAR," "FAR protein," "FAR variant," or "FAR fragment" is intended to refer to a functional FAR protein, functional FAR variant, or functional FAR fragment, even if not explicitly indicated.

The term "endogenous" refers to a gene or protein that is originally contained within an organism (i.e., encodes a sequence found in the wild-type organism). Conversely, the terms "exogenous" or "heterologous," as used in reference to a gene, refer interchangeably to a gene that originates outside the microorganism, such as a gene from another species, or a modified or recombinant gene. An exogenous or heterologous gene may be introduced into the microorganism by methods known in the art.

Nucleic acid sequences may be "introduced" into a cell by transfection, transduction, transformation, or any other method. A nucleic acid sequence introduced into a eukaryotic or prokaryotic cell may be integrated into a chromosome or may be maintained in an episome.

The terms "transform" or "transformation," as used in reference to a cell, means a cell has a non-native nucleic acid sequence integrated into its genome or as an episome (e.g., plasmid) that is maintained through multiple generations.

"Vector" refers to a DNA construct comprising a DNA protein coding sequence. A vector may be an expression vector comprising a protein coding sequence operably linked to a suitable control sequence (i.e., promoter) capable of effecting the expression of the DNA in a suitable host.

"Operably linked" means that DNA sequence segments are arranged so that they function in concert for their intended purposes, e.g., a promoter controls transcription of a gene sequence to which it is operably linked.

"Promoter sequence" is a nucleic acid sequence that is recognized by a cell for expression of the coding region. The control sequence may comprise an appropriate promoter sequence. The promoter sequence contains transcriptional control sequences, which mediate the expression of the polypeptide. The promoter may be any nucleic acid sequence which shows transcriptional activity in the cell of choice including mutant, truncated, and hybrid promoters, and may be obtained from genes encoding extracellular or intracellular polypeptides either endogenous or exogenous (heterologous) to the host cell.

The term "culturing" refers to growing a population of microbial cells under suitable conditions in a liquid or solid medium. Most often a liquid medium is used. In some embodiments, culturing refers to the fermentative bioconversion of a substrate to an end product.

The term "contacting" refers to combining an enzyme and a substrate under conditions in which the enzyme can act on the substrate. Those skilled in the art will recognize that mixing a solution containing an enzyme (e.g., a cellulase) with a substrate (e.g., a cellulose-containing biomass) will effect "contacting." Similarly, in the context of culturing microorganisms, culturing microorganisms in a medium containing a substrate (e.g., a fermentable sugar) will effect "contacting" the microorganism with the substrate.

The term "cellulase" refers to a category of enzymes capable of disrupting the crystalline structure of cellulose and hydrolyzing cellulose (β-1,4-glucan or β-D-glucosidic linkages) to shorter oligosaccharides, disaccharides (e.g., cellobiose), and/or monosaccharides (e.g., glucose). Cellulases include endoglucanases, cellobiohydrolases, and beta-glucosidases.

The terms "cellulose-containing biomass," "cellulosic biomass," and "cellulosic substrate" refer to materials that include cellulose. Biomass can be derived from plants, animals, or microorganisms, and may include agricultural, industrial, and forestry residues, municipal solid wastes, industrial wastes, and terrestrial and aquatic crops grown for energy purposes. Examples of biomass include, but are not limited to, wood, wood pulp, paper pulp, corn fiber, corn grain, corn cobs, crop residues such as corn husks, corn stover, grasses, wheat, wheat straw, barley, barley straw, hay, rice straw, switchgrass, waste paper, paper and pulp processing waste, woody or herbaceous plants, fruit or vegetable pulp, distillers grain, rice hulls, cotton, hemp, flax, sisal, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

"Fermentable sugar" means simple sugars (monosaccharides, disaccharides, and short oligosaccharides) including but not limited to glucose, fructose, xylose, galactose, arabinose, mannose, and sucrose.

The term "recoverable fatty acyl-CoA derivative" refers to the amount of fatty acyl-CoA derivatives that can be isolated from a reaction mixture yielding the fatty acyl-CoA derivatives according to methods known in the art.

II. Introduction

We have discovered that, surprisingly, disruption of certain endogenous genes and combinations of genes in a microbial organism, e.g., *Yarrowia lipolytica*, expressing a fatty acyl reductase (FAR) results in increased production of fatty acyl-CoA derivatives. A FAR (also known as "fatty alcohol forming acyl-CoA reductase" or "fatty acyl reductase") refers to an enzyme that catalyzes the reduction of a fatty acyl-CoA, a fatty acyl-ACP, or other fatty acyl thioester complex to a fatty alcohol, in a reaction linked to the oxidation of NAD(P)H to NAD(P)+, as shown in the following Scheme 1:

Scheme I

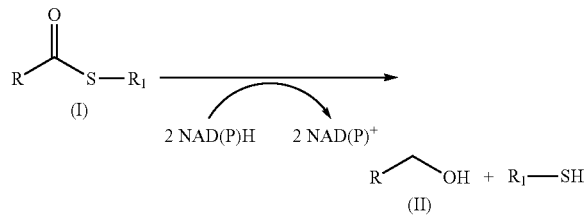

wherein "R" represents a C7 to C23 saturated, unsaturated, linear, branched or cyclic hydrocarbon chain, and "R₁" represents CoA, ACP or other fatty acyl thioester substrates. CoA is a non-protein acyl carrier group factor (or moiety) involved in the synthesis and oxidation of fatty acids. "ACP" is a polypeptide or protein subunit of fatty acid synthase used in the synthesis of fatty acids. In some embodiments, a fatty aldehyde intermediate may be produced in the reaction depicted in Scheme 1.

Wild-type FAR proteins have been described in WO 2011/008535 (published 20 Jan. 2011), incorporated by reference herein for all purposes. Certain FAR enzymes isolated from genera of the class of marine bacteria such as gammaproteobacteria found in seawater (and particularly FARs obtained from strains of *Marinobacter* and *Oceanobacter* or taxonomic equivalents thereof) are capable of generating high yields of fatty alcohols when genes encoding these enzymes are expressed in heterologous cells. As described in the Examples section below, it has now been discovered that microbial organisms in which certain genes or combinations of genes are disrupted and which express a gene encoding a FAR protein have increased production of fatty acyl-CoA derivatives, as compared to otherwise identical microbial organisms expressing the exogenous gene encoding the FAR protein in which genes have not been disrupted. Thus, in one aspect the present invention relates to a microbial organism exhibiting increased production of fatty acyl-CoA derivatives, wherein the microbial organism comprises one or more disrupted endogenous genes and an exogenous gene encoding a FAR protein. These modified microbial organisms may be used in commercial production of fatty acyl-CoA derivatives.

Various aspects of the invention are described in the following sections.

III. Disruption of Endogenous Genes

Endogenous Genes for Disruption

In one aspect, the present invention relates to recombinant microbial organisms, such as yeasts, in which one or more endogenous genes are disrupted, and which exhibit improved production of fatty acyl-CoA derivatives, and methods of using such microbial organisms.

The endogenous genes described herein are named with reference to the *Yarrowia lipolytica* genome. Dujon, et al., 2004, "Genome evolution in yeasts" *Nature* 430:35-44. The abbreviated gene name (e.g., "C17545") and the full gene name (e.g., "YALI0C17545") are used interchangeably, and both encompass polymorphic variants of the gene. In some embodiments, the host cell is other than *Y. lipolytica*, and the endogenous gene is a homolog of the *Y. lipolytica* gene. As noted above, gene names vary from organism to organism and any gene name used herein is not intended to be limiting, but is intended to encompass homologs as well. Table 1 provides a listing of nucleotide sequences for exemplary disrupted genes from *Y. lipolytica* as well as activities of the encoded proteins. Biological activities are assigned based on reference to the scientific literature and/or based on functional and sequence characterization. While the known or predicted biological activities may be useful for identifying homologs, a nucleotide sequence and/or protein for use in the present invention is not limited to those nucleotide sequences and/or proteins that have previously been identified as being involved in fatty acyl-CoA derivative production.

In some embodiments, a microbial organism of the present invention (e.g., algae, bacteria, mold, filamentous fungus, or yeast, e.g., *Yarrowia lipolytica*) has one or more disrupted endogenous genes selected from the genes listed in Table 1 and homologs thereof.

TABLE 1

Nucleotide sequences for disrupted genes in *Yarrowia lipolytica*

| Y. lipolytica gene name | SEQ ID NO. (DNA) | Known or Predicted Biological Activity |
|---|---|---|
| YALI0C17545 | 7 | Phosphatidylinositol transfer protein |
| YALI0E28336 | 8 | |
| YALI0E11099 | 9 | Beta-oxidation enzyme PAT1 |
| YALI0B10406 | 10 | Enoyl-CoA hydratase |
| YALI0A19536 | 11 | Alcohol dehydrogenase |
| YALI0E28534 | 12 | |
| YALI0E32769 | 13 | Acyltransferase DGAT2 |
| YALI0E30283 | 14 | GUP1 |
| YALI0E12463 | 15 | SOR1 |
| YALI0E17787 | 16 | Fatty alcohol dehydrogenase ADH2 |
| YALI0B14014 | 17 | GMC oxidoreductase |
| YALI0A10769 | 18 | Alcohol dehydrogenase |
| YALI0A15147 | 19 | Fatty alcohol dehydrogenase ADH4 |
| YALI0A16379 | 20 | Fatty alcohol dehydrogenase ADH3 |
| YALI0A20944 | 21 | Peroxisomal membrane protein |
| YALI0B07755 | 22 | CoA ligase |
| YALI0B10175 | 23 | Alcohol dehydrogenase |
| YALI0B13838 | 24 | Alkane monooxygenase ALK5 |
| YALI0C02387 | 25 | Transcription factor YAS1 |
| YALI0C05511 | 26 | Phosphatidylinositol transfer protein |
| YALI0D01738 | 27 | Alcohol dehydrogenase |
| YALI0D02167 | 28 | Alcohol dehydrogenase |
| YALI0D04246 | 29 | Peroxisomal membrane protein PXA2 |
| YALI0D05291 | 30 | Transcription factor SCS2 |
| YALI0D07986 | 31 | Acyltransferase DGAT1 |
| YALI0D10417 | 32 | |
| YALI0D14366 | 33 | |
| YALI0D25630 | 34 | Fatty alcohol dehydrogenase ADH1 |
| YALI0E03212 | 35 | FAD binding oxidoreductase |
| YALI0E07810 | 36 | Alcohol dehydrogenase |
| YALI0E12859 | 37 | Acyl-CoA ligase |
| YALI0E14322 | 38 | 2,4-dienoyl-CoA reductase |
| YALI0E15378 | 39 | Beta-oxidation enzyme MFE2 |
| YALI0E15400 | 40 | Fatty aldehyde dehydrogenase ALDH2 |
| YALI0E18502 | 41 | Flavoprotein oxygenase |
| YALI0E18568 | 42 | Beta-oxidation enzyme POT1 |
| YALI0E22781 | 43 | Oxysterol binding protein |
| YALI0E25982 | 44 | Alkane monooxygenase ALK1 |
| YALI0E28314 | 45 | |
| YALI0E32417 | 46 | Transcription factor YAS2 |
| YALI0F01320 | 47 | Alkane monooxygenase ALK2 |
| YALI0F06578 | 48 | Acyltransferase ARE2 |
| YALI0F07535 | 49 | |
| YALI0F14729 | 50 | Thioesterase |
| YALI0F22121 | 51 | Enoyl-CoA hydratase |
| YALI0F25003 | 52 | Alcohol dehydrogenase |
| YALI0E14729g | 53 | ABC1 alkane transporter |
| YALI0B17512g | 54 | Sec62 ER protein translocase |

In some embodiments, the microbial organism, e.g. *Yarrowia lipolytica*, has one or more endogenous genes disrupted, wherein at least one of the disrupted genes is YALI0C17545, YALI0E28336, YALI0E11099, YALI0B10406, YALI0A19536, YALI0E28534, YALI0E32769, YALI0E30283, YALI0E12463, YALI0E17787, YALI0B14014, YALI0A10769, YALI0A15147, YALI0A16379, YALI0A20944, YALI0B07755, YALI0B10175, YALI0B13838, YALI0C02387, YALI0C05511, YALI0D01738, YALI0D02167, YALI0D04246, YALI0D05291, YALI0D07986, YALI0D10417, YALI0D14366, YALI0D25630, YALI0E03212, ALI0E07810, YALI0E12859, YALI0E14322, YALI0E15378, YALI0E15400, YALI0E18502, YALI0E18568, YALI0E22781, YALI0E25982, YALI0E28314, YALI0E32417, YALI0F01320, YALI0F06578, YALI0F07535, YALI0F14729, YALI0F22121, YALI0F25003, YALI0E14729, YALI0B17512, or a homolog of any of these.

In some embodiments, the disrupted endogenous gene is C17545 (SEQ ID NO:7) or a homolog thereof. In some embodiments, the disrupted endogenous gene is E28336 (SEQ ID NO:8) or a homolog thereof. In some embodiments, the disrupted endogenous gene is E11099 (SEQ ID NO:9) or a homolog thereof. In some embodiments, the disrupted endogenous gene is E28534 (SEQ ID NO:12) or a homolog thereof. In some embodiments, the disrupted endogenous gene is B17512 (SEQ ID NO:54) or a homolog thereof.

In some embodiments, the microbial organism, e.g. *Yarrowia lipolytica*, is in which one, two, three, four, or five endogenous genes in the microbial organism are disrupted. In some embodiments, one or more, two or more, three or more, four or more, or five or more endogenous genes are disrupted. Microbial organisms with multiple disrupted endogenous genes may advantageously exhibit synergistic effects, as has been observed in yeast (see Examples, below). The present invention includes but is not limited to exemplary embodiments shown in the Examples section. In some embodiments, the microbial organism has two, three, or four disrupted endogenous genes.

In another embodiment, the microbial organism has at least two disrupted endogenous genes. In some embodiments, both the first disrupted gene and the second disrupted gene are selected from the following: YALI0C17545, YALI0E28336, YALI0E11099, YALI0B10406, YALI0A19536, YALI0E28534, YALI0E32769, YALI0E30283, YALI0E12463, YALI0E17787, YALI0B14014, YALI0A10769, YALI0A15147, YALI0A16379, YALI0A20944, YALI0B07755, YALI0B10175, YALI0B13838, YALI0C02387, YALI0C05511, YALI0D01738, YALI0D02167, YALI0D04246, YALI0D05291, YALI0D07986, YALI0D10417, YALI0D14366, YALI0D25630, YALI0E03212, ALI0E07810, YALI0E12859, YALI0E14322, YALI0E15378, YALI0E15400, YALI0E18502, YALI0E18568, YALI0E22781, YALI0E25982, YALI0E28314, YALI0E32417, YALI0F01320, YALI0F06578, YALI0F07535, YALI0F14729, YALI0F22121, YALI0F25003, YALI0E14729, YALI0B17512, or a homolog of any of these. In some embodiments three, four, five, or more than five genes from this list are disrupted.

In embodiments having two disrupted genes, particularly useful genes for disruption include, but are not limited to, the C17545 gene (or homolog thereof) and/or the E30283 gene (or homolog thereof) and/or the E28336 gene (or homolog thereof) and/or the E11099 gene (or homolog thereof) and/or the E28534 gene (or homolog thereof) and/or the B17512 gene (or homolog thereof). In some embodiments, both the C17545 gene (or homolog thereof) and the E28336 gene (or homolog thereof) are disrupted. In some embodiments, both the C17545 gene (or homolog thereof) and the E11099 gene (or homolog thereof) are disrupted. In some embodiments, both the C17545 gene (or homolog thereof) and the E28534 gene (or homolog thereof) are disrupted. In some embodiments, both the C17545 gene (or homolog thereof) and the B17512 gene (or homolog thereof) are disrupted. In some embodiments, both the E28336 gene (or homolog thereof) and the E11099 gene are disrupted. In some embodiments, both the E28336 gene (or homolog thereof) and the E28534 gene (or homolog thereof) are disrupted. In some embodiments, both the E28336 gene (or homolog thereof) and the B17512 gene (or homolog thereof) are disrupted. In some embodiments, both the E11099 gene (or homolog thereof) and the E28534 gene (or homolog thereof) are disrupted. In some embodiments, both the E11099 gene (or homolog thereof) and the B17512 gene (or homolog thereof) are disrupted. In some embodiments, both the E38534 gene (or homolog thereof) and the B17512 gene (or homolog thereof) are disrupted.

In one embodiment, the microbial organism, e.g. *Yarrowia lipolytica*, has at least one disrupted endogenous gene that is YALI0C17545, YALI0E28336, YALI0E11099, YALI0B10406, YALI0A19536, YALI0E28534, YALI0E32769, YALI0E30283, YALI0E12463, YALI0E14729, YALI0B17512 or a homolog of any of these. In another embodiment, the microbial organism has a first disrupted gene and a second disrupted gene, both selected from this group of genes. In this embodiment, the microbial organism may have additional disrupted genes (e.g., a third, fourth, or fifth disrupted gene also selected from this group), or it may have only two disrupted genes.

In some embodiments, the microbial organism, e.g. *Yarrowia lipolytica*, has two disrupted genes, or homologs thereof. In some embodiments, microbial organisms which exhibit improved production of fatty acyl-CoA derivatives comprise any of the following combinations of two disrupted endogenous genes:
 a. YALI0C17545 and YALI0E28336;
 b. YALI0C17545 and YALI0B10406;
 c. YALI0C17545 and YALI0E28534;
 d. YALI0C17545 and YALI0E30283;
 e. YALI0E28336 and YALI0E30283;
 f. YALI0E11099 and YALI0E30283;
 g. YALI0A19536 and YALI0E30283;
 h. YALI0A19536 and YALI0E28534;
 i. YALI0E30283 and YALI0E12463;
 j. YALI0E14729 and YALI0B10406;
 k. YALI0E14729 and YALI0C17545; and
 l. YALI0E14729 and YALI0E11099; and homologs of (a)-(l).

In another embodiment, the microbial organism, e.g. *Yarrowia lipolytica*, has three or more (e.g., 3) disrupted genes, or homologs thereof. In some embodiments, microbial organisms which exhibit improved production of fatty acyl-CoA derivatives comprise any of the following combinations of three disrupted endogenous genes:
 m. YALI0C17545, YALI0E28336, and YALI0E11099;
 n. YALI0C17545, YALI0E28336, and YALI0B10406;
 o. YALI0C17545, YALI0E28336, and YALI0A19536;
 p. YALI0C17545, YALI0E28336, and YALI0E28534;
 q. YALI0C17545, YALI0E28336, and YALI0E32769;
 r. YALI0C17545, YALI0E28336, and YALI0E12463;
 s. YALI0C17545, YALI0E11099, and YALI0B10406;
 t. YALI0C17545, YALI0B10406, and YALI0A19536;
 u. YALI0E28336, YALI0E11099, and YALI0B10406;
 v. YALI0E11099, YALI0B10406, and YALI0A19536; and
 w. YALI0C17545, YALI0E28534, and YALI0B17512; and homologs of (m)-(w).

In some embodiments, wherein the microbial organism, e.g. *Yarrowia lipolytica*, has three or more (e.g., 3) disrupted genes, two or more of the disrupted genes are selected from the C17545 gene, the E28336 gene, the E11099 gene, the E28534 gene, the B17512 gene, and homologs thereof. In some embodiments, the C17545 gene (or homolog thereof) and the E28336 gene (or homolog thereof) are disrupted. In some embodiments, the C17545 gene (or homolog thereof) and the E11099 gene (or homolog thereof) are disrupted. In some embodiments, the C17545 gene (or homolog thereof) and the E28534 gene (or homolog thereof) are disrupted. In some embodiments, the C17545 gene (or homolog thereof) and the B17512 gene (or homolog thereof) are disrupted. In some embodiments, the E28336 gene (or homolog thereof) and the E11099 gene are disrupted. In some embodiments, the E28336 gene (or homolog thereof) and the E28534 gene (or homolog thereof) are disrupted. In some embodiments, the E28336 gene (or homolog thereof) and the B17512 gene (or homolog thereof) are disrupted. In some embodiments, the E11099 gene (or homolog thereof) and the E28534 gene (or homolog thereof) are disrupted. In some embodiments, the E11099 gene (or homolog thereof) and the B17512 gene (or homolog thereof) are disrupted. In some embodiments, the E38534 gene (or homolog thereof) and the B17512 gene (or homolog thereof) are disrupted. In some embodiments, all three of the disrupted genes are selected from the C17545 gene, the E28336 gene, the E11099 gene, the E28534 gene, the B17512 gene, and homologs thereof. In some embodiments, the C17545 gene (or homolog thereof), the E28336 gene (or homolog thereof), and the E11099 gene (or homolog thereof) are disrupted. In some embodiments, the C17545 gene (or homolog thereof), the E28336 gene (or homolog thereof), and the E28534 gene (or homolog thereof) are disrupted. In some embodiments, the C17545 gene (or homolog thereof), the E28336 gene (or homolog thereof), and the B17512 gene (or homolog thereof) are disrupted. In some embodiments, the C17545 gene (or homolog thereof), the E11099 gene (or homolog thereof), and the B17512 gene (or homolog thereof) are disrupted. In some embodiments, the C17545 gene (or homolog thereof), the E28534 gene (or homolog thereof), and the B17512 gene (or homolog thereof) are disrupted. In some embodiments, the E28336 gene (or homolog thereof), the E11099 gene (or homolog thereof), and the E28534 gene (or homolog thereof) are disrupted. In some embodiments, the E28336 gene (or homolog thereof), the E11099 gene (or homolog thereof), and the B17512 gene (or homolog thereof) are disrupted. In some embodiments, the E28336 gene (or homolog thereof), the E28534 gene (or homolog thereof), and the B17512 gene (or homolog thereof) are disrupted. In some embodiments, the E11099 gene (or homolog thereof), the E28534 gene (or homolog thereof), and the B17512 gene (or homolog thereof) are disrupted.

In yet another embodiment, the microbial organism has four or more (e.g., 4) disrupted genes, or homologs thereof. In some embodiments, microbial organisms which exhibit improved production of fatty acyl-CoA derivatives comprise any of the following combinations of four disrupted endogenous genes:
 x. YALI0C17545, YALI0E28336, YALI0E11099, and YALI0B10406;
 y. YALI0C17545, YALI0E28336, YALI0E11099, and YALI0A19536;
 z. YALI0C17545, YALI0E28336, YALI0E11099, and YALI0E28534;
 aa. YALI0C17545, YALI0E28336, YALI0E11099, and YALI0E32769;
 bb. YALI0C17545, YALI0E28336, YALI0B10406, and YALI0A19536;
 cc. YALI0C17545, YALI0E28336, YALI0B10406, and YALI0E32769;
 dd. YALI0C17545, YALI0E28336, YALI0A19536, and YALI0E28534;
 ee. YALI0C17545, YALI0E28336, YALI0E28534, and YALI0E32769;
 ff. YALI0C17545, YALI0E28336, YALI0E28534, and YALI0E12463;
 gg. YALI0E28336, YALI0E11099, YALI0B10406, and YALI0E32769;
 hh. YALI0E11099, YALI0EA19536, YALI0B10406, and YALI0B17512; and ii YALI0E11099, YALI0E28336, YALI0C17545, and YALI0E14729; and homologs of (x)-(ii).

In some embodiments, wherein the microbial organism, e.g. *Yarrowia lipolytica*, has four or more (e.g., 4) disrupted genes, two or more of the disrupted genes are selected from the C17545 gene, the E28336 gene, the E11099 gene, the E28534 gene, the B17512 gene, and homologs thereof. In some embodiments, three or more of the disrupted genes are selected from the C17545 gene, the E28336 gene, the E11099 gene, the E28534 gene, the B17512 gene, and homologs thereof. In some embodiments, all four of the disrupted genes are selected from the C17545 gene, the E28336 gene, the E11099 gene, the E28534 gene, the B17512 gene, and homologs thereof. In some embodiments, the C17545 gene (or homolog thereof), the E28336 gene (or homolog thereof), the E11099 gene (or homolog thereof), and the E28534 gene (or homolog thereof) are disrupted. In some embodiments, the C17545 gene (or homolog thereof), the E28336 gene (or homolog thereof), the E11099 gene (or homolog thereof), and the B17512 gene (or homolog thereof) are disrupted. In some embodiments, the E28336 gene (or homolog thereof), the E11099 gene (or homolog thereof), the E28534 gene (or homolog thereof), and the 817512 gene (or homolog thereof) are disrupted.

In some embodiments, any one of the endogenous genes or specific combinations of endogenous genes listed in Table 3 or Table 4 are disrupted in the organism. In some embodiments, the organism comprises additional disrupted genes. The genes recited in Table 3 and Table 4 are named with reference to the *Yarrowia lipolytica* genome; however, one of skill in the art will recognize that equivalent disruptions can be made in a microbial organism other than *Y. lipolytica* (e.g., in algae, bacteria, mold, filamentous fungus, or yeast) by disrupting a homolog(s) of a gene listed in Table 3 or Table 4 in that microbial organism.

In addition to any of the endogenous gene disruptions described herein, one or more additional genes can optionally be disrupted (e.g., by "knockout," inactivation, mutation, or inhibition as described herein), introduced, and/or modified in a microbial organism of the present invention. These additional genes can be, but do not need to be, genes that have previously been identified as being involved in fatty acyl-CoA derivative production.

Methods of Disruption

As described in the definitions, the term "disrupted," as applied to a gene, refers to a genetic modification that decreases or eliminates the expression of the gene and/or the biological activity of the corresponding gene product (mRNA and/or protein) (e.g., for the genes listed in Table 1, the known or predicted biological activity listed in Table 1). In some embodiments, the disruption eliminates or substantially reduces expression of the gene product as determined by, for example, immunoassays. "Substantially reduces," in this context, means the amount of expressed protein is reduced by at least 50%, often at least 75%, sometimes at least 80%, at least 90% or at least 95% compared to expression from the undisrupted gene. In some embodiments, a gene product (e.g., protein) is expressed from the disrupted gene but the protein is mutated (e.g, a deletion of one or more amino acids, or an insertion of one or more amino acid substitutions) such that the biological activity (e.g., enzymatic activity) of the protein is completely eliminated or substantially reduced. As used herein, "completely eliminated" means the gene product has no measurable activity. "Substantially reduced," in this context, means the biological activity of the protein is reduced by at least 50%, often at least 75%, sometimes at least 80%, at least 90% or at least 95% compared to the unmutated protein. The biological activity of a gene product (e.g., protein) can be measured by a functional assay such as an enzyme assay. For example, in some embodiments, the microbial organism has a deletion of all or a portion of the protein-encoding sequence of the endogenous gene, a mutation in the endogenous gene such that the gene encodes a polypeptide having no activity or reduced activity (e.g., insertion, deletion, point, or frameshift mutation), reduced expression due to antisense RNA or small interfering RNA that inhibits expression of the endogenous gene, or a modified or deleted regulatory sequence (e.g., promoter) that reduces expression of the endogenous gene, any of which may bring about a disrupted gene. In some embodiments, all of the genes disrupted in the microorganism are disrupted by deletion.

It will be understood that methods for gene disruption in yeast and other microorganisms are well known, and the particular method used to reduce or abolish the expression of the endogenous gene is not critical to the invention. In one embodiment, disruption can be accomplished by homologous recombination, whereby the gene to be disrupted is interrupted (e.g., by the insertion of a selectable marker gene) or made inoperative (e.g., "gene knockout"). Methods for gene knockout and multiple gene knockout are well known. See, e.g., Example 5, infra; Rothstein, 2004, "Targeting, Disruption, Replacement, and Allele Rescue: Integrative DNA Transformation in Yeast" In: Guthrie et al., Eds. *Guide to Yeast Genetics and Molecular and Cell Biology*, Part A, p. 281-301; Wach et al., 1994, "New heterologous modules for classical or PCR-based gene disruptions in *Saccharomyces cerevisiae*" Yeast 10:1793-1808. Methods for insertional mutagenesis are also well known. See, e.g., Amberg et al., eds., 2005, *Methods in Yeast Genetics*, p. 95-100; Fickers et al., 2003, "New disruption cassettes for rapid gene disruption and marker rescue in the yeast *Yarrowia lipolytica*" Journal of Microbiological Methods 55:727-737; Akada et al., 2006, "PCR-mediated seamless gene deletion and marker recycling in *Saccharomyces cerevisiae*" Yeast 23:399-405; Fonzi et al., 1993, "Isogenic strain construction and gene mapping in *Candida albicans*" Genetics 134:717-728.

Antisense inhibition is well known in the art. Endogenous genes can be disrupted by inhibiting transcription, stability, and/or translation using antisense methods. For antisense technology, a nucleic acid strand (DNA, RNA, or analog) complementary to the gene's mRNA. is introduced into the cell. This complementary strand will bind to the gene's mRNA and thus effectively disrupt the gene.

The method of disruption can be applied independently for each disrupted gene. Thus, when multiple genes are disrupted, the genes need not be disrupted in the same way. For example, a microbial organism can have one gene that is disrupted or replaced by an artificial piece of DNA ("knockout"), one gene that is disrupted by an insertion mutation, and another gene whose promoter is altered to decrease expression. In some embodiments, two or more genes are disrupted in the same manner. In some embodiments, two or more genes are disrupted by the same disruption event (e.g., recombination event). In one embodiment, all of the disrupted genes are disrupted in the same manner or by the same disruption event. In one embodiment, all of the disrupted genes are "knockout" genes, that is, genes that are inactivated by disrupting or replacing at least a portion of the coding sequence. In another embodiment, all of the disrupted genes are knockout genes that are disrupted by the same disruption event.

In one embodiment, multiple gene copies are disrupted. A "gene copy," as used herein, refers to the same target gene (e.g., an endogenous gene as described herein) on a homologous chromosome in a diploid or polyploid organism. For example, a microbial organism may have multiple sets of chromosomes and thus possess multiple copies of each target gene. In some embodiments, a microbial organism is diploid (i.e., having two sets of chromosomes and thus two copies of each target gene). In some embodiments, a microbial organism is polyploid (i.e., having more than two sets of chromosomes). In some embodiments, a microbial organism is triploid (i.e., having three sets of chromosomes and thus three copies of each target gene). In some embodiments, a microbial organism is tetraploid (i.e., having four sets of chromosomes and thus four copies of each target gene). In some embodiments, a microbial organism has 2, 3, 4, 5, 6, 7, 8, 9, 10, or more copies of a target gene. In some embodiments, the microbial organism possesses 2, 3, 4, 5, 6, 7, 8, 9, 10, or more disrupted copies of a target endogenous gene. In one embodiment, all copies of the target endogenous gene are disrupted in the microbial organism.

The term "one or more gene copies" refers to the number of copies of the same target gene, while "one or more disrupted genes" refers to one or more individual genes. For example, a microbial organism can have two disrupted gene copies while having only one disrupted gene.

Where two or more endogenous genes are disrupted, the number of copies to be disrupted can be selected independently for each disrupted gene. Multiple copies of a gene can be disrupted by, e.g., performing multiple rounds of recombination with a recoverable marker.

IV. Expression of Truncated Sec62

In another aspect, the invention relates to recombinant microbial organisms, such as yeast, in which an endogenous gene encoding a Sec62 protein, or a homolog or allelic variant thereof, has been modified. Sec62 is a protein that is involved in the translocation of proteins into the endoplasmic reticulum in yeast. Yarrowia Sec62 is encoded by YALI0B17512, has the amino acid sequence set forth as SEQ ID NO:64, and contains a cytoplasmic domain (amino acids 207 to 396 of SEQ ID NO:64). See also GenBank Accession No. CAA67878.1 and Swennen et al., 1997, "Cloning the *Yarrowia lipolytica* homologue of the *Saccharomyces cerevisiae* SEC62 gene," *Curr Genet* 31(2):128-132. As described in the example below, we have discovered that yeast cells expressing a truncated Sec62 protein which lacks a complete cytoplasmic domain have increased production of fatty acyl-CoA derivatives as compared to a control yeast cell in which the Sec62 protein is not truncated.

Thus, the invention provides a microbial organism expressing a truncated Sec62 protein or homolog. The organism can be used for any of the methods or processes described herein, and may be combined with disrupted genes described herein and in combinations described herein.

Thus, in some embodiments, the organism, e.g. an algae, a bacteria, a mold, a filamentous fungus, or a yeast (e.g., *Yarrowia lipolytica*), is one in which the endogenous gene encoding Sec62 (YALI0B17512 or a homolog thereof) comprises a partial deletion of the sequence encoding at least a portion of the cytoplasmic domain of the encoded Sec62 protein. In some embodiments, the partial deletion of the coding sequence comprises a deletion of the entire cytoplasmic domain of the encoded Sec62 protein.

In some embodiments, the Sec62 protein is SEQ ID NO:64 or is a homolog or allelic variant substantially identical to SEQ ID NO:64 (e.g, has a sequence identity of at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% to SEQ ID NO:64). In some embodiments, the Sec62 protein is isolated or derived from an organism selected from the group consisting of *Saccharomyces cerevisiae* (Genbank Accession No. CAB56541.1; SEQ ID NO:77), *Kluyveromyces lactis* (Genbank Accession No. CAH00127.1; SEQ ID NO:78), and *Schizosaccharomyces pombe* (Genbank Accession No. CAB16220.1; SEQ ID NO:79).

In some embodiments, the microbial organism (e.g., *Y. lipolytica*) expresses a truncated Sec62 protein or homolog in which the entire cytoplasmic domain (corresponding to amino acids 207-396 of SEQ ID NO:64) has been deleted. In some embodiments, the microbial organism expresses a truncated Sec62 protein or homolog in which a portion of the cytoplasmic domain is deleted, e.g., from about position 210 to about position 396; from about position 250 to about position 396; from about position 300 to about position 396; from about position 330 to about position 396; from about position 210 to about position 350; from about position 210 to about position 300; from about position 250 to about position 350; or from about position 300 to about position 350, wherein the amino acids are numbered with reference to SEQ ID NO:64. In some embodiments, the microbial organism expresses a truncated Sec62 protein or homolog in which a portion of the cytoplasmic domain from about position 267 to about position 396 is deleted. In some embodiments, the microbial organism expresses a truncated Sec62 protein or homolog in which a portion of the cytoplasmic domain from about position 302 to about position 396 is deleted. In some embodiments, the microbial organism expresses a truncated Sec62 protein or homolog in which a portion of the cytoplasmic domain from about position 337 to about position 396 is deleted.

In some embodiments, a microbial organism is diploid (i.e., having two sets of chromosomes and thus two copies of the gene encoding Sec62). In some embodiments, a microbial organism is polyploid (i.e., having more than two sets of chromosomes and thus more than two copies of the gene encoding Sec62). In some embodiments, more than one copy of the Sec62 gene is modified to express a truncated Sec62 protein. In some embodiments, all of the copies of the Sec62 gene are modified to express a truncated Sec62 protein.

It will be understood that the particular method used to delete all or a portion of the cytoplasmic domain of Sec62 is not critical to the invention. In some embodiments, deletion of the cytoplasmic domain or portion thereof can be accomplished by replacing the portion of the sequence that encodes the cytoplasmic domain or portion thereof with an artificial piece of DNA (e.g., a selectable marker). In some embodiments, deletion of the cytoplasmic domain or portion thereof can be accomplished by removing the portion of the coding sequence that encodes the cytoplasmic domain or portion thereof.

V. Exogenous Far Expression

FAR Protein

In one aspect, the modified microbial organism exhibiting improved production of fatty acyl-CoA derivatives (e.g., a microbial organism, such as *Yarrowia lipolytica*, in which one, two, three, four, or more endogenous genes is disrupted as described herein) expresses or overexpresses a FAR. As described in the Examples section, microbial organisms in which certain endogenous genes or combinations of genes are disrupted and which express an exogenous gene encoding a FAR protein have increased production of fatty acyl-CoA derivatives, as compared to control microbial organisms (e.g., otherwise identical microbial organisms) expressing the exogenous gene encoding the FAR protein in which the corresponding endogenous genes have not been disrupted.

In some embodiments, the organism, e.g. an algae, a bacteria, a mold, a filamentous fungus, or a yeast (e.g., *Yarrowia lipolytica*), expresses an exogenous FAR protein (i.e., a FAR not normally expressed in the organism, such as a protein derived from a different species). In some embodiments, the exogenous FAR protein is a wild-type FAR protein. In some embodiments, the exogenous FAR protein is selected or engineered for increased activity or yield of fatty acyl-CoA derivatives, e.g., fatty alcohols (i.e., a FAR variant as described herein). In some embodiments, the FAR protein is a FAR protein or variant as described in US patent publication 2011/0000125 or in U.S. patent application Ser. No. 13/171,138, filed Jun. 28, 2011, the entire contents of each of which are incorporated herein by reference.

In one embodiment, the exogenous FAR protein is from a genus of marine bacteria such as gammaproteobacteria (e.g., *Marinobacter* and *Oceanobacter*). In one embodiment, the exogenous FAR protein is from a species of the genus *Marinobacter* including, but not limited to, *M. aquaeolei, M. arcticus, M. actinobacterium*, and *M. lipolyticus*. In one embodiment, the exogenous FAR protein is from *M. algicola* (also referred to herein as "FAR_Maa"). In one embodiment, the exogenous FAR protein is from *M. aquaeolei* (also referred to herein as "FAR_Maq"). In another embodiment, the exogenous FAR protein is from a species of the genus *Oceanobacter* including, but not limited to, *Oceanobacter* sp. Red65 (renamed *Bermanella marisrubi*) (also referred to herein as "FAR_Ocs"), *Oceanobacter* strain WH099, and *O. kriegii*. In another embodiment, the exogenous FAR protein is from *Hahella* including, but not limited to, *H. chejuensis* and equivalent species thereof.

In one embodiment, the exogenous FAR gene is FAR_Maa (wild-type FAR from *Marinobacter algicola* strain DG893, SEQ ID NO:1), FAR_Maq (wild-type FAR from *Marinobacter aquaeolei*, SEQ ID NO:3), FAR_Ocs (wild-type FAR from *Oceanobacter* sp. RED65, SEQ ID NO:5), or a fragment that encodes a functional FAR enzyme. In one embodiment, the FAR gene has a DNA sequence identity of at least 80%, at least 85%, at least 90%, at least 91%, at least 92%, at least 93%, at least 94%, at least 95%, at least 96%, at least 97%, at least 98%, or at least 99% to any of SEQ ID NOs:1, 3, or 5. In one embodiment, the FAR gene has a DNA sequence identity of at least 80%, at least 85%, at least 90%, at least 91%, at least 92%, at least 93%, at least 94%, at least 95%, at least 96%, at least 97%, at least 98%, or at least 99% to SEQ ID NO:1.

In another embodiment, the exogenous FAR protein has a sequence identity of at least 80%, at least 85%, at least 90%, at least 91%, at least 92%, at least 93%, at least 94%, at least 95%, at least 96%, at least 97%, at least 98%, or at least 99% to any of SEQ ID NOs:2, 4, or 6, which correspond to the polypeptide sequences of wild-type FAR_Maa, wild-type FAR_Maq, and wild-type FAR_Ocs, respectively. In one embodiment, the FAR protein has a sequence identity of at least 80%, at least 85%, at least 90%, at least 91%, at least 92%, at least 93%, at least 94%, at least 95%, at least 96%, at least 97%, at least 98%, or at least 99% to SEQ ID NO:2.

In other embodiments, the FAR enzyme is FAR_Hch (*Hahella chejuensis* KCTC 2396, GenBank No. YP_436183.1, SEQ ID NO:65), FAR_Mac (from marine actinobacterium strain PHSC20C1, SEQ ID NO:66), FAR_JVC (JCVI_ORF_1096697648832, GenBank No. EDD40059.1, SEQ ID NO:67), FAR_Fer (JCVI_SCAF_1101670217388, SEQ ID NO:68), FAR_Key (JCVI_SCAF_1097205236585, SEQ ID NO:69), FAR_Gal (JCVI_SCAF_1101670289386, SEQ ID NO:70), or a variant or functional fragment thereof. Table 2 provides the approximate amino acid sequence identity of these bacterial FAR proteins to FAR_Maa (SEQ ID NO:2) and FAR_Ocs (SEQ ID NO:6).

TABLE 2

Amino acid sequence identity of homologs relative to FAR_Maa and FAR_Ocs

| FAR Gene | % Sequence Identity to FAR_Maa (SEQ ID NO: 2) | % Sequence Identity to FAR_Ocs (SEQ ID NO: 6) |
|---|---|---|
| FAR_Maa | 100 | 46 |
| FAR_Mac | 32 | 31 |
| FAR_Fer | 61 | 36 |
| FAR_Gal | 25 | 25 |
| FAR_JVC | 34 | 30 |
| FAR_Key | 32 | 30 |
| FAR_Maq | 78 | 45 |
| FAR_Hch | 54 | 47 |

In other embodiments, the FAR enzyme or functional fragment is isolated or derived from an organism selected from the group consisting of *Vitis vinifera* (GenBank Accession No. CAO22305.1, SEQ ID NO:71; or CAO67776.1, SEQ ID NO:72), *Desulfatibacillum alkenivorans* (GenBank Accession No. NZ_ABI101000018.1), *Stigmatella aurantiaca* (NZ_AAMD01000005.1, SEQ ID NO:73), and *Phytophthora ramorum* (GenBank Accession No.: AAQX01001105.1).

FAR Variants

In some embodiments, variants of FAR enzymes are used, such as functional fragments and variants selected using molecular evolution technology. A "functional fragment," as used herein, refers to a polypeptide having an amino-terminal and/or carboxy-terminal deletion and/or internal deletion, but in which the remaining amino acid sequence is identical or substantially identical to the corresponding positions in the sequence to which it is being compared (e.g., a full-length wild-type FAR protein or full-length FAR variant protein) and which retains substantially all (e.g., retains at least 50%, at least 55%, at least 60%, at least 65%, at least 70%, at least 75%, at least 80%, at least 85%, at least 90%, at least 95%, or more) of the activity of the full-length polypeptide (e.g., the full-length wild-type FAR protein or full-length FAR variant protein). Functional fragments can comprise up to 60%, 65%, 70%, 75%, 80%, 85%, 90%, 95%, 96%, 97%, 98%, and 99% of the full-length FAR protein. Thus, a functional fragment, in this context, is a fragment of a naturally occurring FAR polypeptide, or variant thereof, that has catalytic activity. In some embodiments, the functional fragment has at least 50% of the activity of the corresponding full-length wild-type FAR from which it is derived (e.g., FAR_Maa, FAR_Maq, or FAR_Ocs).

In some embodiments, a FAR variant comprises one or more mutations (e.g., substitutions) as compared to a wild-type FAR, such that the resulting FAR variant polypeptide has improved characteristics and/or properties as compared to the wild-type FAR, such as, for example, increased fatty alcohol production when the FAR variant is expressed in a host cell. In some embodiments, a variant FAR protein may have from 1 to 50, e.g., 1, 2, 3, 4, 5, 6, 7, 8, 9, 10, 11, 12, 13, 14, 15, 16, 17, 18, 19, 20, 25, 30, 35, 40, 45, or more amino acid substitutions relative to a native (wild-type) FAR protein such as FAR_Maa (SEQ ID NO:2), FAR_Maq (SEQ ID NO:4), or FAR_Ocs (SEQ ID NO:6). In some embodiments, a variant FAR protein may have from 1 to 50, e.g., 1, 2, 3, 4, 5, 6, 7, 8, 9, 10, 11, 12, 13, 14, 15, 16, 17, 18, 19, 20, 25, 30, 35, 40, 45, or more amino acid substitutions relative to the native FAR protein of SEQ ID NO:2. In some embodiments, a variant FAR protein may have from 1 to 50, e.g., 1, 2, 3, 4, 5, 6, 7, 8, 9, 10, 11, 12, 13, 14, 15, 16, 17, 18, 19, 20, 25, 30, 35, 40, 45, or more amino acid substitutions relative to the native FAR protein of SEQ ID NO:4. In some embodiments, a variant FAR protein may have from 1 to 50, e.g., 1, 2, 3, 4, 5, 6, 7, 8, 9, 10, 11, 12, 13, 14, 15, 16, 17, 18, 19, 20, 25, 30, 35, 40, 45, or more amino acid substitutions relative to the native FAR protein of SEQ ID NO:6.

In some embodiments, a FAR variant comprises at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to a wild-type FAR (e.g., a FAR polypeptide of SEQ ID NO:2, SEQ ID NO:4, or SEQ ID NO:6) and further comprises one or more amino acid substitutions (e.g., e.g., 1, 2, 3, 4, 5, 6, 7, 8, 9, 10, 11, 12, 13, 14, 15, 16, 17, 18, 19, 20, 25, 30, 35, 40, 45, or more amino acid substitutions) relative to the wild-type FAR, and is capable of producing at least about 1.5-fold, at least about 2-fold, at least about 3-fold, at least about 4-fold, at least about 5-fold, at least about 6-fold, at least about 7-fold, at least about 8-fold, at least about 9-fold, or at least about 10-fold more fatty alcohol than the wild-type FAR from which it is derived when assayed under the same conditions.

In certain embodiments, the microbial organism does not express an endogenous FAR (i.e., the genome of the wild-type organism does not encode a FAR). In some embodiments, the microbial organism is an organism that expresses an endogenous FAR protein. In certain embodiments, the microbial organism is an organism that does not express an exogenous FAR protein. In some embodiments, the microbial organism is an organism that expresses neither an endogenous FAR protein nor an exogenous FAR protein. In some embodiments, the microbial organism expresses both endogenous FAR(s) and exogenous FAR(s).

Methods for introducing exogenous genes (e.g., FAR encoding genes) into a host organism and expressing an exogenous protein are known in the art. See Section VII below.

VI. Microbial Organisms

Host Cells

The microbial organism in which one or more endogenous genes are disrupted, and which exhibits improved production of fatty acyl-CoA derivatives, can be any "host cell" that produces fatty acyl-CoA derivatives. Suitable host cells include, but are not limited to, algae, bacteria, mold, filamentous fungus, and yeast, including oleaginous yeast (e.g., *Yarrowia lipolytica*). In some embodiments, the microbial organism is an oleaginous organism, e.g., an organism that tends to store its energy source in the form of oil. The host cell can be eukaryotic or prokaryotic.

In one embodiment, the microbial organism is a fungus. Suitable fungal host cells include, but are not limited to, *Ascomycota, Basidiomycota, Deuteromycota, Zygomycota, Fungi imperfecti*. Particularly preferred fungal host cells are yeast cells and filamentous fungal cells.

In one embodiment, the microbial organism is a yeast. In one embodiment, the yeast is from one of the genera: *Yarrowia, Brettanomyces, Candida, Cryptococcus, Endomycopsis, Hansenula, Kluyveromyces, Lipomyces, Pachysolen, Pichia, Rhodosporidium, Rhodotorula, Saccharomyces, Schizosaccharomyces, Trichosporon*, or *Trigonopsis*. In one embodiment, the yeast is from the genus *Yarrowia*. In some embodiments of the invention, the yeast cell is *Hansenula polymorpha, Saccharomyces cerevisiae, Saccaromyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, and *Yarrowia lipolytica*.

In one embodiment, the microbial organism is an oleaginous yeast. Oleaginous yeasts accumulate lipids such as tri-acyl glycerols. Examples of oleaginous yeast include, but are not limited to, *Yarrowia lipolytica, Yarrowia paralipolytica, Candida revkauji, Candida pulcherrima, Candida tropicalis, Candida utilis, Candida curvata D, Candida curvata R, Candida diddensiae, Candida boldinii, Rhodotorula glutinous, Rhodotorula graminis, Rhodotorula mucilaginosa, Rhodotorula minuta, Rhodotorula bacarum, Rhodosporidium toruloides, Cryptococcus (terricolus) albidus var. albidus, Cryptococcus laurentii, Trichosporon pullans, Trichosporon cutaneum, Trichosporon cutancum, Trichosporon pullulans, Lipomyces starkeyii, Lipomyces lipoferus, Lipomyces tetrasporus, Endomycopsis vernalis, Hansenula ciferri, Hansenula saturnus*, and *Trigonopsis variabilis*.

In one embodiment, the yeast is *Yarrowia lipolytica*. Exemplary *Yarrowia lipolytica* strains include, but are not limited to, DSMZ 1345, DSMZ 3286, DSMZ 8218, DSMZ 70561, DSMZ 70562, DSMZ 21175 available from the Deutsche Sammlung von Mikroorganismen and Zellkulturen GmbH, and also strains available from the Agricultural Research Service (NRRL) such as but not limited to NRRL YB-421, NRRL YB-423, NRRL YB-423-12 and NRRL YB-423-3.

In one embodiment, the host cell is a filamentous fungus. The filamentous fungal host cells of the present invention include all filamentous forms of the subdivision Eumycotina and Oomycota (Hawksworth et al., 1995, in *Ainsworth and Bisby's Dictionary of The Fungi*, 8th ed.). Filamentous fungi are characterized by a vegetative mycelium with a cell wall composed of chitin, cellulose, and other complex polysaccharides. As used herein, the filamentous fungal host cells of the present invention are morphologically distinct from yeast. Exemplary filamentous fungal cells include, but are not limited to, species of *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotri-*

*chum, Talaromyces, Thermoascus, Thielavia, Trametes, Tolypocladium, Trichoderma, Verticillium, Volvariella,* including teleomorphs, anamorphs, synonyms, basionyms, and taxonomic equivalents thereof.

In some embodiments, the host cell is an algal cell such as *Chlamydomonas* (e.g., *C. Reinhardtii*) and *Phormidium* (*P.* sp. ATCC29409).

Suitable prokaryotic cells include gram positive, gram negative and gram-variable bacterial cells. Exemplary prokaryotic host cells include, but are not limited to, species of *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, The rmosynechococcus, Thermococcus, Ureaplasma, Xanthomonas, Xylella, Yersinia,* and *Zymomonas*. In some embodiments, the host cell is a species of *Agrobacterium, Acinetobacter, Azobacter, Bacillus, Bifidobacterium, Buchnera, Geobacillus, Campylobacter, Clostridium, Corynebacterium, Escherichia, Enterococcus, Erwinia, Flavobacterium, Lactobacillus, Lactococcus, Pantoea, Pseudomonas, Staphylococcus, Salmonella, Streptococcus, Streptomyces,* or *Zymomonas*.

Transformation and Cell Culture

In another embodiment, the invention provides a method comprising providing a microbial organism as described herein, and culturing the microbial organism under conditions in which fatty acyl-CoA derivatives are produced. In some embodiments, the microbial organism having one or more disrupted endogenous genes is capable of improved production as described above, e.g., at least a 1-fold increase in the production of fatty acyl-CoA derivatives compared to a control organism of the same type (e.g., an otherwise identical control microbial organism in which the one or more genes are not disrupted).

In some embodiments, a polynucleotide encoding a FAR polypeptide (e.g., a wild-type FAR polypeptide or a FAR variant polypeptide) is introduced into the microbial organism for expression of the wild-type FAR polypeptide or FAR variant polypeptide. The polynucleotide may be introduced into the cell as a self-replicating episome (e.g., expression vector) or may be stably integrated into the host cell DNA.

Methods, reagents, and tools for transforming microbial organisms described herein, such as bacteria, yeast (including oleaginous yeast) and filamentous fungi are known in the art. General methods, reagents and tools for transforming, e.g., bacteria can be found, for example, in Sambrook et al (2001) *Molecular Cloning: A Laboratory Manual,* 3$^{rd}$ ed., Cold Spring Harbor Laboratory Press, New York. Methods, reagents and tools for transforming yeast are described in "Guide to Yeast Genetics and Molecular Biology," C. Guthrie and G. Fink, Eds., *Methods in Enzymology* 350 (Academic Press, San Diego, 2002). Methods, reagents and tools for transforming, culturing, and manipulating *Y. lipolytica* are found in "*Yarrowia lipolytica,*" C. Madzak, J. M. Nicaud and C. Gaillardin in "Production of Recombinant Proteins. Novel Microbial and Eucaryotic Expression Systems," G. Gellissen, Ed. 2005, which is incorporated herein by reference for all purposes. In some embodiments, introduction of the DNA construct or vector of the present invention into a host cell can be effected by calcium phosphate transfection, DEAE-Dextran mediated transfection, PEG-mediated transformation, electroporation, or other common techniques (See Davis et al., 1986, *Basic Methods in Molecular Biology,* which is incorporated herein by reference).

The microbial organisms can be cultured in conventional nutrient media modified as appropriate for activating promoters, selecting transformants, or amplifying the FAR polynucleotide. Culture conditions, such as temperature, pH and the like, will be apparent to those skilled in the art. As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique,* third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques,* fourth edition W.H. Freeman and Company; and Ricciardelli, et al., (1989) *In Vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); Jones, ed. (1984) *Plant Gene Transfer and Expression Protocols,* Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue* and supplement (1997) also from Sigma-Aldrich, Inc (St Louis, Mo.) ("Sigma-PCCS"), all of which are incorporated herein by reference.

VII. Additional Metabolic Engineering

In one embodiment, the modified microbial organism exhibiting improved production of fatty acyl-CoA derivatives contains an exogenous gene operably linked to a promoter that is functional in the microbial organism. The incorporation of an exogenous gene (e.g., a FAR gene as described above) can be accomplished by techniques well known in the art.

In some embodiments, the microbial organism can be modified to express or over-express one or more genes encoding enzymes, other than FAR, that are involved in fatty acyl-CoA derivative biosynthesis. See FIG. 1. In particular embodiments, the gene encodes a fatty acid synthase (FAS), an ester synthase, an acyl-ACP thioesterase (TE), a fatty acyl-CoA synthase (FACS), or an acetyl-CoA carboxylase (ACC). For example, in one embodiment, the microbial organism can be modified to express an ester synthase to produce fatty esters. Similarly, in another embodiments, the microbial organism can be modified to express thioestersase to produce fatty acids. Any of these exemplary genes can be used instead of, or in addition to, FAR. When multiple exogenous genes are expressed, in some embodiments, the expression vector encoding a first enzyme (e.g., FAR) and the expression vector encoding a second enzyme (e.g., an FAS, ester synthase, TE, FACS, or ACC) are separate nucleic acids. In other embodiments, the first enzyme and the second enzyme are encoded on the same expression vector, and expression of each enzyme is independently regulated by a different promoter.

As shown in FIG. 1, the various fatty acyl-CoA derivatives may be produced by the microbial organism. When recovery of a particular derivative is desired, the expression or activity of one or more of the polypeptides involved in this metabolic pathway can be altered to preferentially yield the desired derivative. For example, one can modify the expression or activity of one or more of acetyl-CoA carboxylase, pyruvate decarboxylase, isocitrate dehydrogenase, ATP-citrate lyase, malic enzyme, AMP-deaminase, glucose-6-phosphate dehydrogenase, 6-phosphogluconate dehydrogenase, fructose 1,6 bisphosphatase, NADH kinase, transhydrogenase, acyl-CoA:diacylglycerol acyltransferase, phospholipid:diacylglycerol acyltransferase, acyl-CoA:cholesterol acyltransferase, triglyceride lipase, and acyl-coenzyme A oxidase.

As another example, the microbial organism can be modified to utilize particular desired substrates. For example, although wild-type *Y. lipolytica* does not preferentially utilize xylose as a substrate, it can be genetically engineered to do so. See, e.g., Brat et al., 2009, "Functional expression of a bacterial xylose isomerase in *Saccharomyces cerevisiae*" *Applied and Environmental Microbiology* 75:2304-11; Ho et al., 1998, "Genetically engineered *Saccharomyces* yeast capable of effective cofermentation of glucose and xylose" *Applied and Environmental Microbiology* 64:1852-59. Similarly, *Y. lipolytica* may also be engineered to utilize sucrose. See, e.g., Nicaud et al., 1989, "Expression of invertase activity in *Yarrowia lipolytica* and its use as a selectable marker" *Current Genetics* 16:253-260. It may be advantageous to engineer the microbial organisms to be tailored to particular environmental conditions, for example, to utilize feedstock obtained from a cellulosic or lignocellulosic biomass wherein the feedstock may be contacted with cellulase enzymes to provide fermentable sugars including but not limited to glucose, fructose, xylose, and sucrose.

In some embodiments, a microbial organism as described herein (e.g., a microbial organism comprising one or more disrupted endogenous genes selected from YALI0C17545, YALI0E28336, YALI0E11099, YALI0B10406, YALI0A19536, YALI0E28534, YALI0E32769, YALI0E30283, YALI0E12463, YALI0E17787, YALI0B14014, YALI0A10769, YALI0A15147, YALI0A16379, YALI0A20944, YALI0B07755, YALI0B10175, YALI0B13838, YALI0C02387, YALI0C05511, YALI0D01738, YALI0D02167, YALI0D04246, YALI0D05291, YALI0D07986, YALI0D10417, YALI0D14366, YALI0D25630, YALI0E03212, ALI0E07810, YALI0E12859, YALI0E14322, YALI0E15378, YALI0E15400, YALI0E18502, YALI0E18568, YALI0E22781, YALI0E25982, YALI0E28314, YALI0E32417, YALI0F01320, YALI0F06578, YALI0F07535, YALI0F14729, YALI0F22121, YALI0F25003, YALI0E14729, YALI0B17512, and homologs thereof, and an exogenous gene encoding an exogenous FAR operably linked to a promoter) further comprises an exogenous gene encoding an enzyme that catalyzes the hydrolysis of a fermentable sugar (e.g., sucrose, arabinose, or mannose). Examples of enzymes that catalyze the hydrolysis of a fermentable sugar include, but are not limited to, sucrases and invertases. Thus, in some embodiments, the exogenous gene encodes a sucrase or an invertase. In some embodiments, the exogenous gene is a SUC2 gene, which encodes invertase. Invertases (EC 3.2.1.26) catalyze the hydrolysis of sucrose resulting in a mixture of glucose and fructose. Sucrases are related to invertases but catalyze the hydrolysis of sucrose by a different mechanism.

The exogenous gene encoding the enzyme that catalyzes the hydrolysis of a fermentable sugar may be derived from any suitable microbial organism, e.g., from algae, bacteria, mold, filamentous fungus, or yeast. In some embodiments, the microbial organism comprising one or more disrupted endogenous genes is *Y. lipolytica*, and the exogenous gene encoding an enzyme that catalyzes the hydrolysis of sucrose is from *Saccharomyces cerevisiae*. In some embodiments, the exogenous gene is *Saccharomyces cerevisiae* SUC2 invertase.

Targeted Integration of an Exogenous Gene

In some embodiments, expression of an exogenous gene in the microbial organism is accomplished by introducing the exogenous gene into the organism on an episomal plasmid. In some embodiments, expression of the exogenous gene is accomplished by integrating the gene into the genome of the microbial organism. Integration of the exogenous gene into the genome of the microbial organism has various advantages over the use of plasmids, including but not limited to less variation in protein expression, greater flexibility in the choice of fermentation media, and the potential for high levels of expression by introducing multiple copies of a single gene.

Thus, in some embodiments, a microbial organism having one or more disrupted endogenous genes as described herein further comprises an exogenous gene encoding an enzyme that is involved in fatty acyl-CoA derivative biosynthesis (e.g., a FAR enzyme), wherein the exogenous gene is integrated into the genome of the microbial organism. In some embodiments, the microbial organism comprises an exogenous gene encoding a FAR protein (e.g., a wild-type FAR protein that is identical or substantially identical to the FAR polypeptide of any of SEQ ID NOs:2, 4, or 6, or a FAR variant protein as described herein) that is integrated into the genome of the microbial organism.

In some embodiments, the microbial organism comprises one copy of the exogenous gene. In some embodiments, the microbial organism comprises two, three, four, five, or more copies of the exogenous gene. In some embodiments, multiples copies of the exogenous gene (e.g., two, three, four, five, or more copies) are integrated into the genome of the microbial organism in a direct repeat structure or an inverted repeat structure.

In some embodiments, integration of the exogenous gene into the genome of the microbial organism may be targeted to one or more particular regions of the microbial genome. The genome of the microbial organism can be mapped to identify regions wherein integration of an exogenous gene results in improved expression of the gene, or an improved property (e.g., improved fatty alcohol production) relative to the expression of the exogenous gene in a control organism of the same type (e.g., an otherwise identical organism) by a plasmid (also called "hotspots" of expression). As shown below in the Examples, following integration of an exogenous gene encoding the FAR protein into a *Y. lipolytica* strain, strains were identified that showed particularly good improvement in fatty alcohol production relative to a *Y. lipolytica* strain that expressed FAR via plasmid. These integration hotspots of expression, once mapped, can then be targeted for subsequent integration of an exogenous gene via homologous recombination.

Thus, in some embodiments, the exogenous gene is integrated into a chromosomal site in the genome of the microbial organism that is a hotspot of expression. In some embodiments, wherein the microbial organism is *Y. lipolytica*, the exogenous gene is integrated into the genome of the microbial organism at one or more of the chromosomal sites described herein, for example in Example 1.

Targeted integration of an exogenous gene into the genome of a microbial organism of the present invention can also be accomplished via "seamless" marker recycling. As described in the Examples section below, in seamless marker recycling a bifunctional selectable marker is introduced into a specific genomic location, either to disrupt a native gene or to introduce an exogenous gene. Integrants are identified using the selectable marker (positive selection, e.g., using a marker that confers antibiotic resistance). The marker is then excised, or "recycled," via homologous recombination between two flanking repeats, and organisms that have successfully recycled the marker are identified by counterselection (negative selection, e.g., using a marker that induces toxicity). The selectable marker can then be used again to introduce additional modifications into the genome of the organism. This method is advantageous because it permits a theoretically unlimited number of targeted modifications (e.g., targeted deletions of genes or targeted integrations of exogenous genes) to be made to the genome of an organism, thus facilitating strain development.

Thus, in some embodiments, an exogenous gene (e.g., a gene encoding an enzyme that is involved in fatty acyl-CoA derivative biosynthesis, e.g., a FAR enzyme) is integrated into the genome of a microbial organism of the present invention (e.g., a microbial organism having one or more disrupted endogenous genes as described herein) using a recyclable bifunctional selectable marker having a positive selectable marker and a negative selectable marker, wherein integration of the exogenous gene into the genome is identified using the positive selectable marker and wherein subsequent recycling of the bifunctional marker is identified using the negative selectable marker. In some embodiments, the bifunctional selectable marker has a hygromycin positive selectable marker and a thymidine kinase negative selectable marker.

Vectors

Expression vectors may be used to transform a microbial organism of the present invention (e.g., a microbial organism having one or more disrupted endogenous genes as described herein) with a gene encoding a FAR enzyme, and/or a gene encoding an enzyme other than FAR that is involved in fatty acyl-CoA derivative biosynthesis, and/or a gene encoding an enzyme that catalyzes the hydrolysis of a fermentable sugar. A recombinant expression vector can be any vector, e.g., a plasmid or a virus, which can be manipulated by recombinant DNA techniques to facilitate expression of the exogenous gene in the microbial organism. In some embodiments, the expression vector is stably integrated into the chromosome of the microbial organism. In other embodiments, the expression vector is an extrachromosomal replicative DNA molecule, e.g., a linear or closed circular plasmid, that is found either in low copy number (e.g., from about 1 to about 10 copies per genome equivalent) or in high copy number (e.g., more than about 10 copies per genome equivalent).

Expression vectors for expressing the one or more exogenous genes are commercially available, e.g., from Sigma-Aldrich Chemicals, St. Louis, Mo. and Stratagene, LaJolla, Calif. In some embodiments, examples of suitable expression vectors are plasmids which are derived from pBR322 (Gibco BRL), pUC (Gibco BRL), pREP4, pCEP4 (Invitrogen) or pPoly (Lathe et al., 1987, *Gene* 57:193-201).

In some embodiments, an expression vector optionally contains a ribosome binding site (RBS) for translation initiation, and a transcription terminator, such as PinII. The vector also optionally includes appropriate sequences for amplifying expression, e.g., an enhancer.

Figure 2:
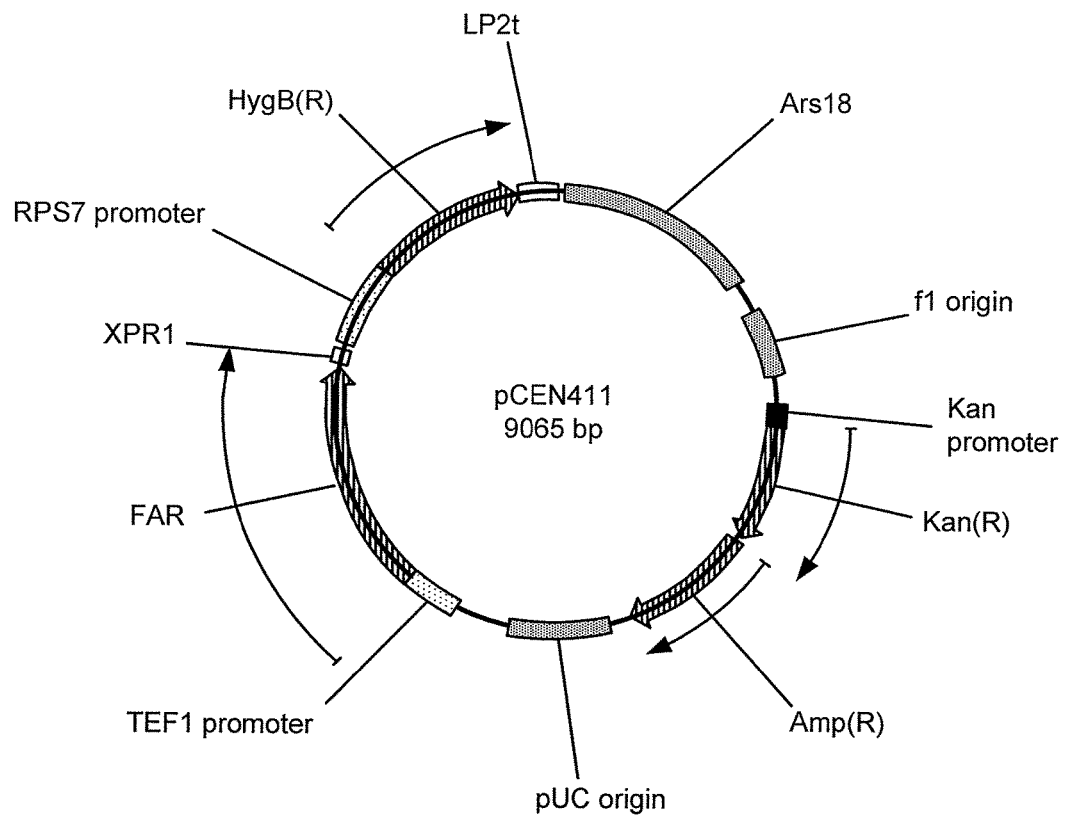
FIG. 2 illustrates plasmid pCEN411 for expression of FAR genes in *Y. lipolytica*.

In particular embodiments, the present disclosure provides an autonomous replicating plasmid for expression of exogenous genes in *Yarrowia*, and particularly in *Y. lipolytica*. An exemplary plasmid is shown in FIG. 2 and described in the Examples. Such a plasmid can be further modified for expression of exogenous genes useful for fatty acyl-CoA derivative production in yeast, inter alia, *Y. lipolytica*.

In some embodiments, wherein more than one exogenous gene is to be expressed in the microbial organism (e.g., a first exogenous gene encoding a wild-type FAR polypeptide or a FAR variant polypeptide, and a second exogenous gene encoding an enzyme other than FAR that is involved in fatty acyl-CoA derivative biosynthesis or an enzyme that catalyzes the hydrolysis of a fermentable sugar), the expression vector encoding the FAR polypeptide and the expression vector encoding the second enzyme are separate nucleic acids. In other embodiments, the FAR polypeptide and the second enzyme are encoded on the same expression vector, and expression of each enzyme is independently regulated by a different promoter.

Promoters

The promoter sequence is a nucleic acid sequence that is recognized by a host cell for expression of a polynucleotide, such as a polynucleotide containing the coding region. Generally, the promoter sequence contains transcriptional control sequences, which mediate expression of the polynucleotide. The promoter may be any nucleic acid sequence that shows transcriptional activity in the host cell of choice including mutant, truncated, and hybrid promoters, and may be obtained from genes encoding extracellular or intracellular polypeptides either homologous or heterologous to the host cell. Methods for the isolation, identification and manipulation of promoters of varying strengths are available in or readily adapted from the art. See, e.g., Nevoigt et al. (2006) *Appl. Environ. Microbiol.* 72:5266-5273, the disclosure of which is herein incorporated by reference in its entirety.

In a yeast host, useful promoters include, but are not limited to those from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Exemplary *Y. lipolytica* promoters include, but are not limited to, TEF1, RPS7 (Müller et al., 1998, "Comparison of expression systems in the yeasts *Saccharomyces cerevisiae, Hansenula polymorpha, Klyveromyces lactis, Schizosaccharomyces pombe* and *Yarrowia lipolytica*." Yeast 14:1267-1283), GPD, GPM (U.S. Pat. No. 7,259,255), GPAT (U.S. Pat. No. 7,264,949), FBA1 (U.S. Pat. No.

7,202,356), the Leu2 promoter and variants thereof (U.S. Pat. No. 5,786,212), the EF1alpha protein promoter (WO 97/44470), Xpr2 (U.S. Pat. No. 4,937,189), TefI, CamI (YALI0C24420g), YALI0DI6467g, Tef4 (YALI0BI2562g), Yef3 (YALI0E13277g), Pox2, Yat1 (US 2005/0130280), promoters disclosed in US 2004/0146975 and U.S. Pat. No. 5,952,195, CYP52A2A (US 2002/0034788); sequences from fungal (e.g., *C. tropicalis*) catalase, citrate synthase, 3-ketoacyl-CoA thiolase A, citrate synthase, O-acetylhornserine sulphydrylase, protease, camitine O-acetyltransferase, hydratasedehydrogenase, epimerase genes; Pox4 genes (US 2004/0265980); and Met2, Met3, Met6, Met25, and YALI0DI2903g genes. See also WO 2008/042338. Other useful promoters for yeast host cells are described by Romanos et al., 1992, "Foreign gene expression in yeast: a review" *Yeast* 8:423-488.

For bacterial host cells, suitable promoters include, but are not limited to, promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus megaterium* promoters, and prokaryotic beta-lactamase gene (Villa-Kamaroff et al., *Proc. Natl Acad. Sci. USA* 75: 3727-3731 (1978)), as well as the tac promoter (DeBoer et al., *Proc. Natl Acad. Sci. USA* 80: 21-25 (1993)). Further promoters include trp promoter, phage lambda $P_L$, T7 promoter and the like. Promoters suitable for use in the invention are described in Gilbert et al., 1980, "Useful proteins from recombinant bacteria" *Sci Am* 242:74-94, and Sambrook et al., supra.

For filamentous fungal host cells, suitable promoters include, but are not limited to, promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase).

The promoter can be any of the promoters listed in U.S. patent application Ser. No. 13/330,324. In particular, the promoter can be a promoter region from a portion of the *Y. lipolytica* gene YALI0E12683, a promoter region from a portion of the *Y. lipolytica* gene YALI0E19206, or a promoter region from a portion of the *Y. lipolytica* gene YALI0E34749. In some embodiments, the promoter comprises the nucleotide sequence of SEQ ID NO:74 (a 0.25 kb sequence of YALI0E12683), SEQ ID NO:75 (a 0.25 kb sequence of YALI0E19206), or SEQ ID NO:76 (a 0.25 kb sequence of YALI0E34749). In some embodiments, the promoter has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, and at least 99% sequence identity to the nucleotide sequence of SEQ ID NO:74, SEQ ID NO:75, or SEQ ID NO:76.

Other Regulatory Elements

Expression of the exogenous gene may be enhanced by also incorporating transcription terminators, leader sequences, polyadenylation sequences, secretory signals, propeptide coding regions, regulatory sequences, and/or selectable markers as would be apparent to one of skill in the art. The choice of appropriate control sequences for use in the polynucleotide constructs of the present disclosure is within the skill in the art and in various embodiments is dependent on the recombinant host cell used and the desired method of recovering the fatty alcohol compositions produced.

Useful regulatory sequences for *Yarrowia* include, but are not limited to, Xpr2 promoter fragments (U.S. Pat. No. 6,083,717). Useful terminator sequences include, but are not limited to, *Y. lipolytica* Xpr2 (U.S. Pat. No. 4,937,189) and Pox2 (YALIOFI 0857g) terminator sequences.

In various embodiments, the expression vector includes one or more selectable markers, which permit easy selection of transformed cells. Selectable markers for use in a host organism as described herein include, but are not limited to, genes that confers antibiotic resistance (e.g., ampicillin, kanamycin, chloramphenicol, hygromycin, or tetracycline resistance) to the recombinant host organism that comprises the vector.

VIII. Improved Production of Fatty Acyl-CoA Derivatives

The modified microbial organisms described herein exhibit improved production of fatty acyl-CoA derivatives. The yield of fatty acyl-CoA derivatives of the modified microbial organism of the invention can be compared to a control organism of the same type (e.g., an otherwise identical control microbial organism in which the endogenous gene has not been disrupted). In one embodiment, the modified microbial organism has at least one disrupted endogenous gene that is YALI0C17545, YALI0E28336, YALI0E11099, YALI0B10406, YALI0A19536, YALI0E28534, YALI0E32769, YALI0E30283, YALI0E12463, YALI0E17787, YALI0B14014, YALI0A10769, YALI0A15147, YALI0A16379, YALI0A20944, YALI0B07755, YALI0B10175, YALI0B13838, YALI0C02387, YALI0C05511, YALI0D01738, YALI0D02167, YALI0D04246, YALI0D05291, YALI0D07986, YALI0D10417, YALI0D14366, YALI0D25630, YALI0E03212, ALI0E07810, YALI0E12859, YALI0E14322, YALI0E15378, YALI0E15400, YALI0E18502, YALI0E18568, YALI0E22781, YALI0E25982, YALI0E28314, YALI0E32417, YALI0F01320, YALI0F06578, YALI0F07535, YALI0F14729, YALI0F22121, YALI0F25003, YALI0E14792, YALI0B17512, or a homolog of any of these, and an exogenous gene encoding a functional fatty acyl reductase operably linked to a promoter. In some embodiments, the organism exhibits at least a 1.2-fold increase in the production of fatty acyl-CoA derivatives as compared to a control organism of the same type (e.g., an otherwise identical control microbial organism in which the one or more endogenous genes are not disrupted). In other embodiments, the improved production is at least 1-fold, at least 1.2-fold, at least 1.5-fold, at least 2.5-fold, at least 4-fold, at least 10-fold, at least 15-fold, at least 20-fold, at least 30-fold, at least 40-fold, at least 50-fold, or at least 60-fold compared to the control microbial organism. In some embodiments, the exogenous gene encoding a fatty acyl reductase is a gene having at least 80% sequence identity to the nucleotide sequence of FAR_Maa (SEQ ID NO:1), FAR_Maq (SEQ ID NO:3), or FAR_Ocs (SEQ ID NO:5). In some embodiments, the exogenous gene encodes a FAR polypeptide having at least 80% sequence identity to wild-type FAR_Maa (SEQ ID NO:2), wild-type FAR_Maq (SEQ ID NO:4), or wild-type FAR_Ocs (SEQ ID NO:6). In some embodiments, the exogenous gene encodes a FAR variant derived from FAR_Maa (SEQ ID NO:2), FAR_Maq (SEQ ID NO:4), or FAR_Ocs (SEQ ID NO:6).

In some embodiments, the invention provides a microbial organism (e.g., an algae, a bacteria, a mold, a filamentous fungus, a yeast, or an oleaginous yeast) comprising one, two, three, four, or more disrupted endogenous genes wherein at least one of the disrupted endogenous genes is selected from C17545 gene, the E28336 gene, the E11099 gene, the E28534 gene, and homologs thereof, and an exogenous gene encoding a functional fatty acyl reductase gene operably linked to a promoter, wherein the microbial organism exhibits at least a 1-fold, at least a 1.2-fold, at least a 1.5-fold, at least a 2.5-fold, at least a 4-fold, at least a 10-fold, at least a 15-fold, or at least a 20-fold increase in the production of fatty acyl-CoA derivatives as compared to a control microbial organism (e.g., an otherwise identical control microbial organism in which the one or more genes are not disrupted).

In one embodiment, the invention provides a *Yarrowia lipolytica* cell comprising at least one disrupted endogenous gene that is YALI0C17545, YALI0E28336, YALI0E11099, YALI0B10406, YALI0A19536, YALI0E28534, YALI0E32769, YALI0E30283, YALI0E12463, YALI0E14729, or YALI0B17512 or a homolog of any of these, and an exogenous gene encoding a functional fatty acyl reductase gene operably linked to a promoter, wherein the *Yarrowia lipolytica* cell exhibits at least a 1-fold increase in the production of fatty acyl-CoA derivatives as compared to a control microbial organism (e.g., an otherwise identical control microbial organism in which the one or more genes are not disrupted). In certain embodiments, the invention provides a *Yarrowia lipolytica* cell comprising a disrupted gene or combination of disrupted genes set forth in Table 3 or in Table 4. In certain embodiments, the invention provides a yeast cell comprising a disrupted gene that is a homolog of, or combination of disrupted genes that are homologs of, the genes set forth in Table 3 or in Table 4.

The control microbial organism can be, e.g., *Y. lipolytica* DSMZ 1345 (wild-type) or *Y. lipolytica* strain CY-201 (a *Y. lipolytica* DSMZ 1345 variant that grows poorly in growth on media with hexadecane as the sole carbon source). In some embodiments, the control microbial organism is a recombinant organism having the identically incorporated exogenous genes as the microbial organism with the disrupted gene(s). For example, both the microbial organism having one or more disrupted endogenous genes and the control microbial organism may contain an exogenous FAR gene.

When comparing the microbial organism having one or more disrupted endogenous genes to the control microbial organism, the organisms should be cultured under essentially identical conditions, and the fatty acyl-CoA derivatives should be measured or recovered using essentially identical procedures.

Fatty Alcohol Production

In some embodiments, the fatty acyl-CoA derivative that is produced is a fatty alcohol. Thus, in some embodiments, the invention provides a modified microbial organism that exhibits at least a 1-fold, at least a 1.2-fold, at least a 1.5-fold, at least a 2.5-fold, at least a 4-fold, at least a 10-fold, at least a 15-fold, or at least a 20-fold increase in the production of fatty alcohols as compared to a control microbial organism in which the one or more genes are not disrupted.

Fatty alcohol production can be measured by methods described in the Examples section (e.g., Examples 3 and 6) and/or using any other methods known in the art. Fatty alcohol production by an organism of the present invention (e.g., a microbial organism having a disrupted endogenous gene) can be described as an absolute quantity (e.g., moles/liter of culture) or as a fold-improvement over production by a control organism (e.g., a microbial organism in which the endogenous gene was not disrupted). Fatty alcohol production by a microbial organism of the present invention can be measured, for example, using gas chromatography. In general, the microbes are cultured, total or secreted fatty alcohols are isolated, and fatty alcohol amount and/or content is measured.

Any number of assays can be used to determine whether a microbial organism comprising at least one disrupted endogenous gene as described herein produces an increased amount of fatty alcohols (e.g., at least 1 times more fatty alcohols) as compared to a control microbial organism in which the one or more genes are not disrupted, including exemplary assays described herein. In one exemplary assay, fatty alcohols produced by productive *Y. lipolytica* strains are collected by extraction of cell cultures using 1 mL of isopropanol:hexane (4:6 ratio). The extraction mixture is centrifuged and the upper organic phase is transferred into a 96-well plate and analyzed by gas chromatography (GC) equipped with flame ionization detector (FID) and HP-5 column (length 30 m, I.D. 0.32 mm, film 0.25 um), starting at 100° C., and increasing the temperature at a rate of 25° C./min to 246° C., then holding for 1.96 min.

IX. Methods of Producing Fatty Acyl-CoA Derivatives

The present disclosure also provides methods of producing fatty acyl-CoA derivatives using the microbial organisms as described herein, as well as the resultant fatty acyl-CoA derivative compositions produced by said methods.

Fermentation

Fermentation of the host cell is carried out under suitable conditions and for a time sufficient to produce fatty acyl-CoA derivatives. Conditions for the culture and production of cells, including filamentous fungi, bacterial, and yeast cells, are readily available. Cell culture media in general are set forth in Atlas and Parks, eds., 1993, *The Handbook of Microbiological Media*. The individual components of such media are available from commercial sources, e.g., under the DIFCO™ and BBL™ trademarks. In some embodiments, the aqueous nutrient medium is a "rich medium" comprising complex sources of nitrogen, salts, and carbon, such as YP medium, comprising 10 g/L of peptone and 10 g/L yeast extract of such a medium. In other embodiments, the aqueous nutrient medium is Yeast Nitrogen Base (DIFCO™) supplemented with an appropriate mixture of amino acids, e.g., SC medium. In particular embodiments, the amino acid mixture lacks one or more amino acids, thereby imposing selective pressure for maintenance of an expression vector within the recombinant host cell.

The culture medium can contain an assimilable carbon source. Assimilable carbon sources are available in many forms and include renewable carbon sources and the cellulosic and starch feedstock substrates obtained therefrom. Exemplary assimilable carbon sources include, but are not limited to, monosaccharides, disaccharides, oligosaccharides, saturated and unsaturated fatty acids, succinate, acetate and mixtures thereof. Further carbon sources include, without limitation, glucose, galactose, sucrose, xylose, fructose, glycerol, arabinose, mannose, raffinose, lactose, maltose, and mixtures thereof. The culture media can include, e.g., feedstock from a cellulose-containing biomass, a lignocellulosic biomass, or a sucrose-containing biomass.

In some embodiments, "fermentable sugars" are used as the assimilable carbon source. "Fermentable sugar" means simple sugars (monosaccharides, disaccharides, and short oligosaccharides) including, but not limited to, glucose, fructose, xylose, galactose, arabinose, mannose, and sucrose. In one embodiment, fermentation is carried out with a mixture of glucose and galactose as the assimilable carbon source. In another embodiment, fermentation is carried out with glucose alone to accumulate biomass, after which the glucose is substantially removed and replaced with an inducer, e.g., galactose for induction of expression of one or more exogenous genes involved in fatty acyl-CoA derivative production. In still another embodiment, fermentation is carried out with an assimilable carbon source that does not mediate glucose repression, e.g., raffinose, to accumulate biomass, after which the inducer, e.g., galactose, is added to induce expression of one or more exogenous genes involved in fatty acyl-CoA derivative production. In some embodiments, the assimilable carbon source is from cellulosic and starch feedstock derived from but not limited to, wood, wood pulp, paper pulp, grain, corn stover, corn fiber, rice, paper and pulp processing waste, woody or herbaceous plants, fruit or vegetable pulp, distillers grain, grasses, rice hulls, wheat straw, cotton, hemp, flax, sisal, corn cobs, sugar cane bagasse, switch grass, and mixtures thereof.

In one embodiment, the method of making fatty acyl-CoA derivatives further includes the steps of contacting a cellulose-containing biomass with one or more cellulases to yield a feedstock of fermentable sugars, and contacting the fermentable sugars with a microbial organism as described herein. In one embodiment, the microbial organism is *Y. lipolytica*, and the fermentable sugars are glucose, sucrose, and/or fructose.

The microorganisms can be grown under batch, fed-batch, or continuous fermentations conditions, which are all known in the art. Classical batch fermentation is a closed system, wherein the compositions of the medium is set at the beginning of the fermentation and is not subject to artificial alternations during the fermentation. A variation of the batch system is a fed-batch fermentation, where the substrate is added in increments as the fermentation progresses. Fed-batch systems are useful when catabolite repression is likely to inhibit the metabolism of the cells and where it is desirable to have limited amounts of substrate in the medium. Continuous fermentation is an open system where a defined fermentation medium is added continuously to a bioreactor, and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out a temperature of about 10° C. to about 60° C., about 15° C. to about 50° C., about 20° C. to about 45° C., about 20° C. to about 40° C., about 20° C. to about 35° C., or about 25° C. to about 45° C. In one embodiment, the fermentation is carried out at a temperature of about 28° C. and/or about 30° C. It will be understood that, in certain embodiments where thermostable host cells are used, fermentations may be carried out at higher temperatures.

In some embodiments, the fermentation is carried out for a time period of about 8 hours to 240 hours, about 8 hours to about 168 hours, about 8 hours to 144 hours, about 16 hours to about 120 hours, or about 24 hours to about 72 hours.

In some embodiments, the fermentation will be carried out at a pH of about 3 to about 8, about 4.5 to about 7.5, about 5 to about 7, or about 5.5 to about 6.5.

In one embodiment, the method of producing fatty acyl-CoA derivatives comprises:
a) providing a microbial organism (e.g., a *Yarrowia lipolytica* cell) having one or more disrupted endogenous genes, wherein at least one disrupted gene is YALI0C17545, YALI0E28336, YALI0E11099, YALI0B10406, YALI0A19536, YALI0E28534, YALI0E32769, YALI0E30283, YALI0E12463, YALI0E17787, YALI0B14014, YALI0A10769, YALI0A15147, YALI0A16379, YALI0A20944, YALI0B07755, YALI0B10175, YALI0B13838, YALI0C02387, YALI0C05511, YALI0D01738, YALI0D02167, YALI0D04246, YALI0D05291, YALI0D07986, YALI0D10417, YALI0D14366, YALI0D25630, YALI0E03212, ALI0E07810, YALI0E12859, YALI0E14322, YALI0E15378, YALI0E15400, YALI0E18502, YALI0E18568, YALI0E22781, YALI0E25982, YALI0E28314, YALI0E32417, YALI0F01320, YALI0F06578, YALI0F07535, YALI0F14729, YALI0F22121, YALI0F25003, YALI0E14720, YALI0B17512, or a homolog of any of these, and an exogenous gene encoding a functional fatty acyl reductase operably linked to a promoter; and
b) culturing the microbial organism (e.g., the *Yarrowia* cell) to allow production of a fatty acyl-CoA derivative, wherein the culturing conditions include a temperature of about 20° C. to about 40° C., a time period of about 16 to about 120 hours, and a culture medium containing fermentable sugars obtained from a cellulosic feedstock.

In another embodiment, the above method is modified to include a culture medium containing sucrose. In some embodiments, wherein the culture medium contains sucrose, the microbial organism (e.g., the *Yarrowia* cell) further comprises an exogenous gene encoding an invertase (e.g., *Saccharomyces cerevisiae* SUC2 invertase).

In some embodiments, the method of producing fatty acyl-CoA derivatives yields at least 0.5 g/L fatty acyl-CoA derivatives as described below.

Production Levels

The methods described herein produce fatty acyl-CoA derivatives in high yield.

Routine culture conditions, e.g., culture of yeast, for such as *Yarrowia lipolytica*, may yield about 0.5 g to about 35 g fatty acyl-CoA derivatives, e.g., fatty alcohols, per liter of culture medium (e.g., nutrient medium), depending upon the gene(s) disrupted. In some embodiments, the amount of fatty acyl-CoA derivatives, e.g., fatty alcohols, produced by the methods described herein is at least 0.5 g/L, at least 1 g/L, at least 1.5 g/L, at least 2 g/L, at least 2.5 g/L, at least 3 g/L, at least 3.5 g/L, at least 4 g/L, at least 4.5 g/L, at least about 5 g/L, or at least 10 g/L, at least 20 g/L, at least 30 g/L, at least 40 g/L, or at least 50 g/L of culture medium.

In some embodiments, the amount of fatty acyl-CoA derivatives, e.g., fatty alcohols, produced by the methods described herein is about 40 mg/g to about 1 g/g, about 40 mg/g to about 5 g/g, about 100 mg/g to about 1 g/g, about 100 mg/g to about 5 g/g, about 500 mg/g to about 2 g/g, about 1 g/g to about 4 g/g, or about 2 g/g to about 3 g/g of dry cell weight by routine modification of culturing conditions.

In certain embodiments, the amount of fatty acyl-CoA derivatives, e.g., fatty alcohols, produced by the methods described herein is about 4% to about 20%, about 10% to about 20%, about 20% to about 30%, about 30% to about 40%, about 40% to about 50%, about 50% to about 60%, about 60% to about 70%, or about 70% to about 80% of dry cell weight by routine modification of culturing conditions.

Recovery of Fatty Acyl-CoA Derivatives

The methods can further include a step of recovering, e.g., isolating, the fatty acyl-CoA derivatives to yield fatty acyl-CoA derivative compositions. Recovering or isolating the produced fatty acyl-CoA derivatives refers to separating at least a portion of the fatty acyl-CoA derivatives from other components of the culture medium or fermentation process. Suitable protocols for recovering or isolating fatty acyl-CoA derivatives from recombinant host cells and/or culture medium (e.g., distillation, chromatography) are known to the skilled artisan. In certain embodiments, the derivatives are purified (e.g., substantially free of organic compounds other than the derivative(s)). The derivatives can be purified using purification methods well known in the art.

In some embodiments, recombinant microorganism hosts secrete the fatty acyl-CoA derivatives into the nutrient medium. In this case, the fatty acyl-CoA derivatives can be isolated by solvent extraction of the aqueous nutrient medium with a suitable water immiscible solvent. Phase separation followed by solvent removal provides the fatty acyl-CoA derivative, which may then be further purified and fractionated using methods and equipment known in the art. In other embodiments, the secreted fatty acyl-CoA derivatives coalesce to form a water immiscible phase that can be directly separated from the aqueous nutrient medium either during the fermentation or after its completion.

In some embodiments, fatty acyl-CoA derivatives, e.g., fatty alcohols, are isolated by separating the cells from the aqueous nutrient medium, for example by centrifugation, resuspension, and extraction of the fatty acyl-CoA derivatives from the recombinant host cells using an organic solvent or solvent mixture.

For microorganism hosts that do not secrete the fatty acyl-CoA derivatives into the nutrient media, the fatty acyl-CoA derviatives can be recovered by first lysing the cells to release the fatty acyl-CoA derivatives and extracting the fatty acyl-CoA derivatives from the lysate using conventional means. See Clontech Laboratories, Inc., 2009, *Yeast Protocols Handbook*, 100:9156-9161.

X. Fatty Acyl-CoA Derivatives

As described above, the fatty acyl-CoA derivatives include various compounds produced enzymatically by cellular metabolic pathways as shown in FIG. 1. Genetic modification of the enzymes involved in these pathways can preferentially yield particular derivatives, e.g., fatty alcohols. See Section VII above. Additionally or alternatively, particular fatty acyl-CoA derivatives can be chemically modified (in culture or post-recovery) to yield a different derivative.

The fatty acyl-CoA derivative compositions can include saturated (e.g., monounsaturated), unsaturated, and branched fatty acyl-CoA derivatives, e.g., fatty alcohols. In some embodiments, the amount of unsaturated fatty acyl-CoA derivatives (e.g., fatty alcohols) can be less than 50%, less than 40%, less than 30%, less than 20%, less than 10%, less than 5%, or less than 1% of the total fatty acyl-CoA derivative composition. In some embodiments, the amount of saturated fatty acyl-CoA derivatives can be less than 50%, less than 40%, less than 30%, less than 20%, less than 10%, less than 5%, or less than 1% of the total fatty acyl-CoA derivative composition. In some embodiments, the amount of branched fatty acyl-CoA derivatives can be less than 50%, less than 40%, less than 30%, less than 20%, less than 10%, less than 5%, or less than 1% of the total fatty acyl-CoA derivative composition.

In some embodiments, fatty acyl-CoA derivatives (e.g., fatty alcohols, fatty esters, alkanes, alkenes, etc.) having a carbon chain length of C8 to C20, C10 to C18, C14 to C18, or C16 to C18 comprise at least 80%, at least 85%, at least 90%, at least 92%, at least 95%, at least 97%, or at least 99% by weight of the total fatty acyl-CoA derivative composition. In some embodiments, fatty alcohols having a carbon chain length of C8 to C20, C10 to C18, C14 to C18, or C16 to C18 comprise at least 80%, at least 85%, at least 90%, at least 92%, at least 95%, at least 97%, or at least 99% by weight of a total fatty alcohol composition. In some embodiments, the fatty acyl-CoA derivatives (e.g., fatty alcohols) have a carbon chain length of C16 to C18. Such C16 to C18 fatty acyl-CoA derivatives, e.g., fatty alcohols, can be saturated, unsaturated, or a mixture of saturated and unsaturated derivatives. When the derivative is an alkane or alkene, it is noted that alkanes and/or alkenes having particular carbon chain lengths can be isolated from longer and/or shorter alkanes and/or alkenes, for example by HPLC.

In some embodiments, the fatty acyl-CoA derivative is a fatty alcohol. The fatty alcohol can be one or more of 1-octanol (C8:0), 1-decanol (C10:0), 1-dodecanol (C12:0), 1-tetradecanol (C14:0), 1-hexadecanol (C16:0), 1-octadecanol (C18:0), 1-icosanol (C20:0), 1-docosanol, 1-tetracosanol, hexadecenol (C16:1), and octadecenol (C18:1).

Alkane and/or Alkene Compositions

In some embodiments, the fatty acyl-CoA derivative is an alkane and/or alkene. The alkanes and/or alkenes can be isolated from the reaction mixture (which may contain unreduced fatty alcohols) to yield a composition comprising substantially all alkanes and/or alkenes. Alternatively, the alkanes/alkenes and un-reduced fatty alcohols can be isolated from the reaction mixture to yield a composition comprising alkanes and/or alkenes and fatty alcohols. In some embodiments, the fatty acyl-CoA derivative compositions comprise at least 10%, at least 20%, at least 30%, at least 40%, at least 50%, at least 60%, at least 70%, at least 80%, at least 85%, at least 90%, at least 92%, at least 95%, at least 96%, at least 97%, at least 98%, or at least 99% alkanes and/or alkenes by weight of the composition after reduction.

In some embodiments, the alkane is octane, decane, dodecane, tetradecane, hexadecane, octadecane, icosane, docosane, tetracosane, or mixtures thereof. In some embodiments, the alkene is octene, decene, dodecene, tetradecene, hexadecene, octadecene, icosene, docosene, tetracosene, or mixtures thereof.

In some embodiments, fatty alcohols produced according to the methods described herein can be reduced to yield alkanes and/or alkenes having the same carbon chain length as the fatty alcohol starting materials. Without being bound by any particular theory, the hydroxyl group of an alcohol is a poor leaving group, and therefore, in principle a chemical moiety that binds to the oxygen atom of the hydroxyl group to make it a better leaving group can be used to reduce the fatty alcohols described herein.

Any method known in the art can be used to reduce the fatty alcohols. In some embodiments, reduction of fatty alcohols can be carried out chemically, for example, by a Barton deoxygenation (or Barton-McCombie deoxygenation), a two-step reaction in which the alcohol is first converted to a methyl xanthate or thioimidazoyl carbamate, and the xanthate or thioimidazoyl carbamate is reduced with a tin hydride or trialkylsilane reagent under radical conditions to produce the alkane and/or alkene. See Li et al., 2007, *Modern Organic Synthesis in the Laboratory, p.* 81-83.

In another embodiment, alkanes can be produced by hydrogenation of fatty alcohols or fatty acids.

Ester Compositions

In other embodiments, fatty alcohols are reacted with a carboxylic acid to form acid esters. Esterification reactions of fatty alcohols are well-known in the art. In certain embodiments, the transesterification reaction is carried out in the presence of a strong catalyst, e.g., a strong alkaline such as sodium hydroxide. In other embodiments, an esterification reaction is carried out enzymatically using an enzyme that catalyzes the conversion of fatty alcohols to acid esters, such as lipoprotein lipase. See, e.g., Tsujita et al., 1999, "Fatty Acid Alcohol Ester-Synthesizing Activity of Lipoprotein Lipase" *J. Biochem.* 126:1074-1079.

XI. Exemplary Compositions Comprising Fatty Acyl-CoA Derivatives

In yet another aspect, the present invention relates to the use of the microbial organisms as described herein for the production of various compositions, including but not limited to, fuel compositions (e.g., biodiesels and petrodiesels), detergent compositions (e.g., laundry detergents in liquid and powder form, hard surface cleaners, dishwashing liquids, and the like); industrial compositions (e.g., lubricants, solvents; and industrial cleaners); and personal care compositions (e.g., soaps, cosmetics, shampoos, and gels).

Fuel Compositions

In certain embodiments, the fatty acyl-CoA derivative compositions described herein can be used as components of fuel compositions. In certain embodiments, the fatty acyl-CoA derivatives produced by the methods described above can be used directly in fuel compositions. Fuel compositions containing fatty acyl-CoA derivatives produced by the methods of the present invention include any compositions used in powering combustion engines, including but not limited to biodiesel fuels and petrodiesel fuels (e.g., jet fuels and rocket fuels).

In some embodiments, the fuel composition is diesel fuel. Diesel fuel is any fuel used in diesel engines and includes both petrodiesel and biodiesel. Petrodiesel is a specific fractional distillate of fossil fuel oil. It is comprised of about 75% saturated hydrocarbons and 25% aromatic hydrocarbons. Biodiesel is not derived from petroleum but from vegetable oil or animal fats and contains long chain alkyl esters. Biodiesel is made by the transesterification of lipids (e.g., spent vegetable oil from fryers or seed oils) with an alcohol and burns cleaner than petrodiesel. Biodiesel can be used alone or mixed with petrodiesel in any amount for use in modern engines.

In some embodiments, the fuel composition is kerosene. Kerosene is a combustible hydrocarbon that is also a specific fractional distillate of fossil fuel and contains hydrocarbons having 6 to 16 carbon atoms. Kerosene has a heat of combustion comparable to that of petrodiesel and is widely used in jet fuel to power jet engines and for heating in certain countries. Kerosene-based fuels can also be burned with liquid oxygen and used as rocket fuel (e.g., RP-1).

In particular embodiments, fatty esters are used as components of biodiesel fuel compositions. In various embodiments, fatty acid esters are used as biodiesel fuel without being mixed with other components. In certain embodiments, the fatty acid esters are mixed with other components, such as petrodiesel fuel. In other embodiments, alkanes and/or alkenes (e.g., C10 to C14) are used as components of jet fuel compositions. In other embodiments, alkanes and/or alkenes are used as components of rocket fuel. In still other embodiments, alkanes and/or alkenes (e.g., C16 to C24) are used as components in petrodiesel-like fuel compositions.

In some embodiments, the fuel compositions comprise an alkane and/or alkene. In certain embodiments, the alkanes and/or alkenes have from 6 to 16 carbons, and the fuel composition is a kerosene-like fuel composition. In various embodiments, the kerosene-like fuel compositions are included in jet fuel compositions. In particular embodiments, the kerosene-like fuel compositions are included in various grades of jet fuel including, but not limited to, grades Avtur, Jet A, Jet A-1, Jet B, JP-4, JP-5, JP-7 and JP-8. In other embodiments, the kerosene-like fuel compositions are included in fuel compositions for heating. In still other embodiments, the kerosene-like fuel compositions are burned with liquid oxygen to provide rocket fuel. In particular embodiments, the kerosene-like fuel compositions are used in RP-1 rocket fuel.

In some embodiments, the alkanes and/or alkenes are used in fuel compositions that are similar to petrodiesel fuel compositions, e.g., fuels that contain saturated and aromatic hydrocarbons. In certain embodiments, the fuel compositions comprise only alkanes and/or alkenes. In other embodiments, the fuel compositions comprise alkanes and/or alkenes mixed with other components, such as petrodiesel fuel.

In certain embodiments, fatty alcohols, fatty esters, alkanes, and/or alkenes are combined with other fuels or fuel additives to produce compositions having desired properties for their intended use. Exemplary fuels and fuel additives for particular applications are well-known in the art. Exemplary fuels that can be combined with the compositions described herein include, but are not limited to, traditional fuels such as ethanol and petroleum-based fuels. Exemplary fuel additives that can be combined with the compositions described herein include, but are not limited to, cloud point lowering additives, surfactants, antioxidants, metal deactivators, corrosion inhibitors, anti-icing additives, anti-wear additives, deposit-modifying additives, and octane enhancers.

Detergent Compositions

In some embodiments, the fatty acyl-CoA derivative compositions described herein, and compounds derived therefrom, can be used as components of detergent compositions. Detergent compositions containing fatty acyl-CoA derivatives produced by the methods of the present invention include compositions used in cleaning applications, including, but not limited to, laundry detergents, handwashing agents, dishwashing detergents, rinse-aid detergents, household detergents, and household cleaners, in liquid, gel, granular, powder, or tablet form. In some embodiments, the fatty acyl-CoA derivatives (e.g., fatty alcohols) produced by the methods described above can be used directly in detergent compositions. In some embodiments, the fatty acyl-CoA derivatives (e.g., fatty alcohols) can be reacted with a sulfonic acid group to produce sulfate derivatives that can be used as components of detergent compositions. Detergent compositions that can be generated using the fatty acyl-CoA derivatives produced by the methods of the present invention include, but are not limited to, hair shampoos and conditioners, carpet shampoos, light-duty household cleaners, light-duty household detergents, heavy-duty household cleaners, and heavy-duty household detergents. Detergent compositions generally include, in addition to fatty acyl-CoA derivatives, one or more or of builders (e.g., sodium carbonate, complexation agents, soap, and zeolites), enzymes (e.g., a protease, a lipase and an amylases); carboxymethyl cellulose, optical brighteners, fabric softeners, colourants and perfumes (e.g., cyclohexyl salicylate).

In some embodiments, sulfate derivatives (e.g., C12-15) derived from fatty acyl-CoA derivatives are used in products such as hair shampoos, carpet shampoos, light-duty household cleaners, and light-duty household detergents. In some embodiments, sulfate derivatives (e.g., C16-C18) derived from fatty acyl-CoA derivatives are used in products such as hair shampoos and conditioners. In some embodiments, sulfate derivatives (e.g., C16-18) derived from fatty acyl-CoA derivatives are used in products such as heavy-duty household cleaners and heavy-duty household detergents.

Personal Care Compositions

In some embodiments, fatty acyl-CoA derivative compositions as described herein, and compounds derived therefrom, can be used as components of personal care compositions. In some embodiments, the fatty acyl-CoA derivatives produced by the methods described above can be used directly in personal care compositions. Personal care compositions containing fatty acyl-CoA derivatives produced by the methods of the present invention include compositions used for application to the body (e.g., for application to the skin, hair, nails, or oral cavity) for the purposes of grooming, cleaning, beautifying, or caring for the body, including but not limited to lotions, balms, creams, gels, serums, cleansers, toners, masks, sunscreens, soaps, shampoos, conditioners, body washes, styling aids, and cosmetic compositions (e.g., makeup in liquid, cream, solid, anhydrous, or pencil form). In some embodiments, the fatty acyl-CoA derivatives (e.g., fatty alcohols) can be reacted with a sulfonic acid group to produce sulfate derivatives that can be used as components of said compositions.

In some embodiments, fatty acyl-CoA derivative compositions (e.g., C12) produced by the methods described herein are used in products such as lubricating oils, pharmaceuticals, and as an emollient in cosmetics. In some embodiments, fatty acyl-CoA derivative compositions (e.g., C14) produced by the methods described herein are used in products such as cosmetics (e.g., cold creams) for its emollient properties. In some embodiments, fatty acyl-CoA derivative compositions (e.g., C16) produced by the methods described herein are used in products such as cosmetics (e.g., skin creams and lotions) as an emollient, emulsifier, or thickening agent. In some embodiments, fatty acyl-CoA derivative compositions (e.g., C18) produced by the methods described herein are used in products such as lubricants, resins, perfumes, and cosmetics, e.g., as an emollient, emulsifier, or thickening agent. In some embodiments, sulfate derivatives (e.g., C12-14) derived from the fatty acyl-CoA derivative compositions produced by the methods described herein are used in products such as toothpastes.

Other Compositions

In some embodiments, fatty acyl-CoA derivatives (e.g., fatty alcohols, especially cetyl alcohol, stearyl alcohol and myristyl alcohol) may be used as food additives (e.g., adjuvants and production aids).

XII. Examples

The following examples are offered to illustrate, but not to limit the claimed invention.

Example 1: Expression of Wild-Type *M. Algicola* DG893 FAR in *Y. lipolytica* Strains Wild-type FAR from *M. algicola* (FAR_Maa) was expressed in *Y. lipolytica* strains. The sequence of the codon optimized *M. algicola* DG893 FAR gene corresponds to SEQ ID NO:1, and the corresponding polypeptide sequence is designated SEQ ID NO:2. An autonomous replicating plasmid, pCEN354, was constructed for expression of the *M. algicola* DG893 FAR gene in *Y. lipolytica* strains. The replicating plasmid was engineered with two antibiotic selection marker cassettes for resistance to hygromycin and phleomycin (HygB(R) or Ble(R), respectively). Expression of each cassette is independently regulated by a strong, constitutive promoter isolated from *Y. lipolytica*: pTEF1 for Ble(R) expression and pRPS7 for HygB(R) expression. Plasmid pCEN354 was used to assemble *Y. lipolytica* expression plasmids. Using "restriction free cloning" methodology, the Ble(R) gene was replaced with the *M. algicola* DG893 FAR gene to provide the plasmid pCEN411 (FIG. 2). In pCEN411, FAR gene expression is under control of the constitutive TEF1 promoter, and the HygB(R) gene allows for selection in media containing hygromycin. Ars18 is an autonomous replicating sequence isolated from *Y. lipolytica* genomic DNA. The resulting plasmid was transformed into *Y. lipolytica* strains using routine transformation methods. See, e.g., Chen et al., 1997, "One-step transformation of the dimorphic yeast *Yarrowia lipolytica*" Appl Microbiol Biotechnol 48:232-235.

FAR was also expressed by integrating an expression cassette to a specific location on the *Y. lipolytica* genome. In this case, the DNA to be integrated contained a *M. algicola* FAR expression cassette and a second expression cassette that encoded hygromycin resistance. The DNA encoding these expression cassettes was flanked on either side by ~1 kb of *Y. lipolytica* DNA that acted to target this DNA to a specific intergenic site on chromosome E. This site was identified as an expression "hot-spot" by random integration of a FAR expression cassette followed by mapping of the integration sites of the most active transformants. Integration constructs were amplified by PCR and transformed into *Y. lipolytica* using routine transformation methods.

Through random integration of a *M. algicola* FAR expression cassette into the *Y. lipolytica* genome, a number of strains were identified with improved fatty alcohol titers relative to strains with plasmid-based FAR expression. The integration locations in five of the best random integrant strains were determined using the "vectorette" PCR method. In each of these strains, there were two copies of the FAR gene in either a direct or inverted repeat structure.

One copy of a *M. algicola* FAR expression cassette was introduced by targeted integration to either the plus or minus strand of one of five hot spots identified in the genome of the *Y. lipolytica* CY-201 strain. Integration site tFARi-1 was located on chromosome E between bp 1433493 and bp 1433495 on the minus strand. Integration site tFARi-2 was located on chromosome C between bp 2526105 and bp 2526114 on the plus strand. Integration site tFARi-3 was located on chromosome B between bp 2431420 and bp 2431425 on the plus strand. Integration site tFARi-4 was located on chromosome D between bp 1669582 and bp 1669588 on the plus strand. Integration site tFARi-5 was located on chromosome D between bp 518746 and bp 518789 on the plus strand. Integration site tFARi-6 was located on chromosome B between bp 2431420 and bp 231425 on the minus strand. Integration site tFARi-7 was located on chromosome D between bp 1669582 and bp 1669588 on the minus strand. Integration site tFARi-8 was located on chromosome D between bp 518746 and bp 518789 on the minus strand.

Example 2: In Vivo Activity of Exogenous *M. algicola* FAR in Recombinant *Y. lipolytica* Strains Two *Y. lipolytica* strains were used for constructing gene knockouts: 1) *Y. lipolytica* DSMZ 1345 obtained from the German Resource Centre for Biological Material (DSMZ), and 2) *Y. lipolytica* CY-201, an improved production host obtained by UV-mutagenesis of *Y. lipolytica* DSMZ 1345 and defective in growth on media with hexadecane as the sole carbon source. When transformed with pCEN411, *Y. lipolytica* CY-201 produced 7- to 10-fold more fatty alcohols compared to *Y. lipolytica* DSMZ 1345 and also significantly reduced the rate of degradation of exogenous 1-hexadecanol in YPD media containing 8% glucose and 500 µg/mL hygromycin. The expression of alternative FAR genes and variants in modified *Y. lipolytica* strains can be assessed using similar methodology.

Example 3: Analysis of Fatty Alcohol Production in *Y. lipolytica* Strains Containing Exogenous FAR

*Y. lipolytica* strains comprising a plasmid containing an exogenous gene encoding *M. algicola* DG893 FAR were grown in 96-well Axygen plates containing 250 µL YPD supplemented with 2% glucose and 500 µg/mL hygromycin. Plates were incubated in a Kuhner shaker-incubator for approximately 40-48 hours at 30° C., 200 rpm and 85% relative humidity. The cell cultures were diluted by transferring 50 µL of overnight grown cultures into the Axygen 96-well plates containing 250 µL YPD supplemented with 2% glucose and 500 µg/mL hygromycin. The plates were incubated for approximately 24-28 hours in a Kuhner shaker-incubator under the same conditions. 20 µL of the cell cultures were transferred into deep 96-well plates containing 380 µL YPD supplemented with 8% glucose and 500 µg/mL hygromycin. The plates were incubated for approximately 22-26 hours under the same conditions. Cells were collected by centrifugation for 10 minutes at 3500 rpm. Cell pellets were resuspended in 400 µL of nitrogen limitation media (1.7 g/L yeast nitrogen base, 1.4 g/L $(NH_4)_2SO_4$, 30 g/L glucose) containing 500 µg/mL hygromycin and incubated for 22-26 hours in a Kuhner shaker-incubator at 30° C., 200 rpm and 85% relative humidity. The cell cultures were extracted with 1 mL of isopropanol:hexane (4:6 ratio) for 2 hrs. The extracts were centrifuged, and the upper organic phase was transferred into polypropylene 96-well plates. Samples were analyzed using the following GC-FID method.

A 1 µL sample was analyzed by GC-FID with a split ratio 1:10 using the following conditions: GC-6890N from Agilent Technologies equipped with FID detection and HP-5 column (length 30 m, I.D. 0.32 mm, film 0.25 um). GC method: start at 100° C., increase the temperature with a rate of 25° C./min to 246° C. and hold for 1.96 min. Total run time, 7.8 min. Under the above GC conditions, the approximate retention times (min) of produced fatty alcohols and acids are as follows: 5.74, C16:1-OH; 5.93, C16:0-OH; 6.11, C16:0-OOMe (internal standard); 6.16, C16:1-OOH; 6.29, C16:0-OOH; 6.80, C18:1-OH; 6.90, C18:0-OH; 7.3, C18:0- and C18:1-OOH. Identification of individual fatty alcohols was done by comparison to commercial standards (Sigma Chemical Company). Under the conditions tested, expression of the *M. algicola* DG893 FAR in the parent *Y. lipolytica* DSMZ 1345 and CY-201 strains resulted in 5-20 mg/L and 100-200 mg/L production of fatty alcohols, respectively. The fatty alcohols were produced were: 70-80% C16:0 (1-hexadecanol), 10-15% 18:0 (1-octadecanol) and 10-15% C18:1 (cis $\Delta^9$-1-octadecenol).

Example 4: Identification of *Y. lipolytica* Gene Targets for Disruption

Genes selected for disruption were identified in several ways. Some genes were selected based on their roles in pathways for hydrocarbon assimilation in alkane-utilizing yeast. Because fatty acyl-CoA is an intermediate in these pathways resulting from oxidation of alkanes, the stability of fatty acyl-CoA derivatives may be improved by disrupting genes responsible for alkane utilization. Other genes for disruption were selected based on their homology to such genes. These included genes whose sequence predicted that they may function as alcohol dehydrogenases or acyltransferases involved in lipid biosynthesis.

Additional genes for disruption include those that encode for proteins involved in import of newly synthesized proteins into the endoplasmic reticulum. These include the subunits of the trimeric protein conducting channel (Sec61, Ssh1, Sbh1, and Sss1), the tetrameric Sec62/Sec63 complex (Sec62, Sec63, Sec66, and Sec72), and other resident endoplasmic reticulum proteins (Kar2 and Sls1) (Boisrame A. et al., "Interaction of Kar2p and Sls1p Is Required for Efficient Co-translational Translocation of Secreted Proteins in the Yeast *Yarrowia lipolytica*," *J. Biol. Chem.* (1998) 273: 30903).

Other genes for disruption were identified by comparison of global gene expression in glucose and glycerol-based media. In particular, genes whose expression is repressed by glycerol were selected, since alkane utilization is repressed in glycerol containing media. Glycerol-repressed genes were identified by microarray analysis using RNA prepared from *Y. lipolytica* DSMZ 1345 cultured in both rich media and lipid accumulation media.

Example 5: Construction and Analysis of Strains Having Disrupted Genes

Knockout strains can be constructed by transforming *Y. lipolytica* with a DNA construct designed to replace most or all of the open reading frame of interest with a selectable marker by homologous recombination. As such, the DNA constructs may comprise a selectable marker flanked by ~1 kb sequences immediately upstream and downstream of the gene of interest that are necessary for homologous recombination to occur. These DNA constructs are contained in plasmids assembled using standard methods for plasmid construction. For transformation, the DNA construct of interest is amplified from the corresponding plasmid using PCR to generate ~1 µg of linear DNA. This DNA is transformed into *Y. lipolytica* using the method described in Madzak et al., 2003, "*Yarrowia lipolytica*." In Gellissen, ed. *Production of Recombinant Proteins Novel Microbial and Eukaryotic Expression Systems*, p. 163-189. Strains in which the gene of interest is replaced with the selectable marker are identified by ability to grow on selective media and by PCR genotyping. Typical selective markers are familiar to those skilled in the art (see, e.g., Fickers et al., 2003, "New disruption cassettes for rapid gene disruption and marker rescue in the yeast *Yarrowia lipolytica*" *Journal of Microbiological Methods* 55:727-737).

In a second step, the selectable marker is excised from the chromosome using methods that are familiar to those skilled in the art. See, e.g., Fickers et al., supra; Akada et al., 2006, "PCR-mediated seamless gene deletion and marker recycling in *Saccharomyces cerevisiae*" *Yeast* 23:399-405; Fonzi et al., 1993, "Isogenic strain construction and gene mapping in *Candida albicans*" *Genetics* 134:717-728. Strains with excised markers can be easily identified by growth on counter-selection media if the selectable marker used is bifunctional, i.e., it encodes an enzyme whose product(s) are essential for growth on positive selection media and toxic on another selection media. Such bifunctional markers are familiar to those skilled in the art.

For construction of strains with multiple gene disruptions, *Y. lipolytica* can be transformed sequentially with a series of DNA constructs designed to knockout the genes of interest. Each transformation can be carried out by the method described above, such that the selectable marker is excised after each disruption step. Thus, any combination of knockouts can be created in a given strain using the collection of plasmids harboring the DNA constructs described above.

Example 6: Analysis of Fatty Alcohol Production in Modified *Y. lipolytica* Strains A collection of ~233 strains comprising strains with single gene disruptions and strains with 2 or more gene disruptions were created in both the DSMZ1345 and CY-201 strain backgrounds. These strains were transformed with plasmid pCEN411 for expression of wild-type *M. algicola* DG893 FAR (see FIG. 2) and screened for fatty alcohol production as described above. Tables 3 and 4 below provide the relative fatty alcohol production for targeted gene disruption *Y. lipolytica* DSMZ 1345 and CY-201 strains expressing wild-type *M. algicola* DG893 FAR gene relative to the corresponding *Y. lipolytica* strain with no targeted gene deletion and expressing wild-type *M. algicola* DG893 FAR gene. The fatty alcohols produced were: 70-80% C16:0 (1-hexadecanol), 10-15% 18:0 (1-octadecanol), and 10-15% C18:1 (cis Δ9-1-octadecenol).

TABLE 3

Targeted gene disruptions in *Y. lipolytica* DSMZ 1345

| Gene(s) Disrupted | Fatty alcohol production relative to DSMZ 1345 |
| --- | --- |
| C17545 E28336 E11099 E28534 | +++++ |
| C17545 E28336 E12463 E28534 | +++++ |
| C17545 E28336 A19536 E28534 | +++++ |
| E28336 E32769 C17545 E28534 | +++++ |
| C17545 E28534 | +++++ |
| C17545 E28336 E12463 | +++++ |
| C17545 E28336 E28534 | +++++ |
| C17545 E28336 A19536 B10406 | +++++ |
| E28336 E32769 C17545 B10406 | +++++ |
| C17545 E28336 E11099 B10406 | +++++ |
| C17545 B10406 E11099 | +++++ |

TABLE 3-continued

Targeted gene disruptions in *Y. lipolytica* DSMZ 1345

| Gene(s) Disrupted | Fatty alcohol production relative to DSMZ 1345 |
| --- | --- |
| C17545 E28336 B10406 | +++++ |
| E28336 E32769 C17545 E11099 | +++++ |
| C17545 E28336 E12463 | +++++ |
| C17545 E28336 E11099 | +++++ |
| C17545 E28336 A19536 E11099 | +++++ |
| C17545 E28534 B17512 | +++++ |
| E11099 A19536 B10406 B17512 | +++++ |
| E28336 C17545 | ++++ |
| E28336 C17545 | ++++ |
| C17545 E28336 E11099 | ++++ |
| C17545 E28336 A19536 | ++++ |
| E11099 A19536 B10406 | ++++ |
| E28336 E32769 C17545 | ++++ |
| C17545 E28336 A19536 | ++++ |
| E28336 E32769 C17545 | ++++ |
| C17545 E28336 | ++++ |
| E28336 B10406 E11099 | ++++ |
| E11099 E30283 | ++++ |
| E28336 E32769 E11099 B10406 | ++++ |
| C17545 B10406 E11099 | ++++ |
| E28336 E30283 | ++++ |
| E30283 | ++++ |
| C17545 E30283 | ++++ |
| A19536 E30283 | ++++ |
| C17545 B10406 A19536 | ++++ |
| E12463 E30283 | ++++ |
| C17545 B10406 | ++++ |
| A19536 E28534 | ++++ |
| B17512 | ++++ |
| E14729 | +++ |
| C17545 E28336 E17787 | +++ |
| E28336 E32769 E28534 | +++ |
| E28336 B10406 | +++ |
| E28336 E28534 | +++ |
| E28336 E15378 E12463 | +++ |
| C17545 B10406 | +++ |
| D25630 A16379 E17787 A15147 C17545 | +++ |
| C17545 E11099 | +++ |
| E28336 E15378 | +++ |
| C17545 A19536 | +++ |
| E28336 E15378 E11099 | +++ |
| B10406 E28534 | +++ |
| E28336 E15378 A19536 | +++ |
| E28336 E32769 A19536 B10406 | +++ |
| E11099 A19536 C17545 | +++ |
| E17787 E28534 | +++ |
| C17545 A12859 | +++ |
| A15147 E17787 A16379 D25630 | +++ |
| D25630 A16379 E17787 A15147 E11099 | +++ |
| C17545 D01738 | +++ |
| E28336 E32769 A19536 E11099 | +++ |
| D25630 A16379 E17787 A15147 A19536 | +++ |
| D25630 A16379 E17787 A15147 E12463 | +++ |
| D25630 A16379 E17787 A15147 E28336 | +++ |
| C17545 E12463 | +++ |
| E28336 E32769 A19536 | +++ |
| E28534 | +++ |
| A19536 E28336 | +++ |
| E28336 D01738 | +++ |
| E28336 E11099 | +++ |
| E28336 A19536 A16379 | +++ |
| C17545 | +++ |
| E17787 C17545 | +++ |
| E28336 E32769 | +++ |
| E28336 A12859 | +++ |
| E28336 B14014 E15378 | +++ |
| E28336 E32769 E11099 | +++ |
| E28336 E32769 A19536 | +++ |
| E28336 | +++ |
| E28336 E32769 | +++ |
| E28336 E32769 E11099 | +++ |
| E12463 | +++ |
| E28336 C02387 | +++ |
| A19536 | +++ |
| E28336 B10406 | +++ |

TABLE 3-continued

Targeted gene disruptions in *Y. lipolytica* DSMZ 1345

| Gene(s) Disrupted | Fatty alcohol production relative to DSMZ 1345 |
|---|---|
| E17787 E28336 | +++ |
| E28336 E32769 E12463 | +++ |
| E28336 A16379 | +++ |
| E28336 E32769 E17787 | +++ |
| E28336 E15378 E17787 | +++ |
| B10406 E11099 | +++ |
| E28336 B10175 A16379 | +++ |
| E12463 E28336 | +++ |
| E11099 A19536 E28336 | +++ |
| E28336 | +++ |
| B10406 E17787 | +++ |
| E28336 C02387 B10175 | +++ |
| B14014 C17545 | +++ |
| B10175 B10406 | +++ |
| E17787 | +++ |
| E11099 | +++ |
| B10406 | +++ |
| E28336 A16379 E15400 | +++ |
| E28336 E06831 | +++ |
| E15400 | +++ |
| A19536 E11099 | +++ |
| B14014 B10406 | +++ |
| E28336 E32769 B10175 | +++ |
| B14014 | +++ |
| B10175 | +++ |
| E11099 B14014 | +++ |
| D01738 | +++ |
| E12859 | +++ |
| B13838 | +++ |
| D02167 | +++ |
| F01320 | +++ |
| E28336 E32769 B14014 | +++ |
| A19536 E15400 | +++ |
| B10406 A19536 | ++ |
| B07755 | ++ |
| B10175 A19536 | ++ |
| D05291 | ++ |
| A15147 E17787 A16379 D25630 | ++ |
| E15378 | ++ |
| F25003 | ++ |
| F22121 | ++ |
| B14014 A12859 | ++ |
| E18502 | ++ |
| C02387 | ++ |
| C08415 | ++ |
| A10769 | ++ |
| F06578 | ++ |
| F07535 | ++ |
| D14366 | ++ |
| F14729 | ++ |
| D07986 | ++ |
| E32769 | ++ |
| A16379 D25630 | ++ |
| E03212 | ++ |
| D10417 | ++ |
| B14014 A16379 | ++ |
| E07810 | ++ |
| B14014 D25630 | ++ |
| E25982 | ++ |
| A20944 | ++ |
| E18568 | ++ |
| E32417 | ++ |
| E28314 | ++ |
| E22781 | ++ |
| A15147 | ++ |
| D04246 | ++ |
| C05511 | ++ |
| E14322 | ++ |
| A17875 E15400 B01298 | ++ |
| D25322 | ++ |
| B04906 | ++ |
| F29623 | ++ |
| A06655 | ++ |
| E17787 A16379 D25630 | ++ |
| F19514 | ++ |
| B13816 | ++ |
| B00462 | ++ |
| E12463 A19536 | ++ |
| E06567 | ++ |
| D17314 | ++ |
| B14014 A15147 E17787 A16379 D25630 | ++ |
| E12463 E11099 | ++ |
| C23859 | ++ |
| E12463 B10406 | ++ |
| B08404 | ++ |
| D25960 | ++ |
| A17875 | ++ |
| E01210 | ++ |
| E27654 | ++ |
| A17875 E15400 B01298 F23793 | ++ |
| E21560 | ++ |
| D12628 | ++ |
| E06831 | ++ |
| D25630 | ++ |
| B10175 E17787 | + |
| E15818 | + |
| E14509 | + |
| C19580 | + |
| B12386 | + |
| A10769 | + |
| A16379 B14014 D25630 | + |
| B10175 E12463 | + |
| B14014 E17787 | + |
| F19580 | + |
| A17875 B01298 | + |
| E01298 | + |
| E32835 | + |
| D04884 | + |
| E17787 E30283 | + |
| E28336 C02387 B14014 | + |
| F10857 | + |
| A07733 | + |
| E15400 B10175 | + |
| C19096 | + |
| D07942 | + |
| E15400 B01298 F23793 | + |
| E11099 B10175 | + |
| E19921 | + |
| E12463 E17787 | + |
| D00176 | + |
| E17787 A19536 | + |
| E04961 | + |
| A19536 E11099 | + |
| C10054 | + |
| E15400 B01298 | + |
| E07766 | + |
| C14784 | + |
| E18700 | + |
| B01298 | + |
| E17787 E11099 | + |
| F23793 | + |
| F23793 B01298 | + |
| E12463 A12859 | + |
| B21692 | + |
| C09284 | + |
| D17864 | + |
| A00374 | + |
| B14014 D01738 | + |
| B14014 E12463 | + |
| E28336 E15378 B10406 | + |
| A16379 | + |
| E12419 | + |
| E16016 | + |
| E12463 D01738 | + |
| D27302 | + |
| C04092 | + |
| E29161 | + |
| B05456 | + |
| F00748 | + |

TABLE 3-continued

Targeted gene disruptions in *Y. lipolytica* DSMZ 1345

| Gene(s) Disrupted | Fatty alcohol production relative to DSMZ 1345 |
|---|---|
| D00891 | + |
| F22539 | + |

+++++ = >30.0 fold improvement
++++ = 10.0 to 30.0 fold improvement
+++ = 1.5 to 9.99 fold improvement
++ = 1.0 to 1.49 fold improvement
+ = 0.0 to 0.99 fold improvement

TABLE 4

Targeted gene disruptions in *Y. lipolytica* CY-201

| Gene(s) Disrupted | Relative fatty alcohol production to CY-201 |
|---|---|
| E14729 | +++++ |
| E11099 E28336 C17545 E14729 | +++++ |
| C17545 B10406 E28336 | ++++ |
| E11099 E28336 C17545 A00374 | ++++ |
| E11099 A19536 C17545 A00374 | ++++ |
| E11099 A19536 C17545 | ++++ |
| C17545 B10406 A19536 | ++++ |
| B10406 E14729 | ++++ |
| C17545 E14729 | ++++ |
| E11099 E14729 | ++++ |
| E28336 E14729 | +++ |
| E11099 E28336 C17545 | +++ |
| E11099 A19536 C17545 B10406 | +++ |
| E11099 E28336 E18502 | +++ |
| C17545 B10406 | +++ |
| E28336 A19536 B10406 | +++ |
| E28336 A19536 B10406 | +++ |
| E28336 A19536 B10406 C17545 | +++ |
| C17545 B10406 | +++ |
| E28336 E11099 | +++ |
| E11099 A19536 C17545 | +++ |
| C17545 B10406 | +++ |
| E28336 A19536 B10406 E11099 | +++ |
| E28336 A19536 | +++ |
| E28336 C17545 | +++ |
| E28534 | +++ |
| E11099 E28336 E18502 | +++ |
| E11099 E28336 F09603 | +++ |
| C17545 A19536 | +++ |
| E28336 | +++ |
| E11099 | +++ |
| E11099 A19536 B10406 | +++ |
| C17545 | +++ |
| E29336 C08415 | +++ |
| E11099 A19536 A00374 | +++ |
| A19536 E11099 | +++ |
| B10406 | +++ |
| E11099 A19536 C08415 | +++ |
| E28336 A19536 | +++ |
| E28336 | +++ |
| C17545 F09603 | ++ |
| C17545 E11099 | ++ |
| E12463 E11099 | ++ |
| A19536 F09603 | ++ |
| E12859 | ++ |
| E11099 E28336 C17545 A19536 | ++ |
| E11099 A19536 | ++ |
| A19536 | ++ |
| E17787 E11099 | ++ |
| E11099 A19536 F09603 | ++ |
| D02167 | ++ |
| E28336 F09603 | ++ |
| E28336 E32769 | ++ |
| B13838 | ++ |
| A00374 | ++ |
| E18502 | ++ |
| E11099 A19536 E18502 | ++ |

TABLE 4-continued

Targeted gene disruptions in *Y. lipolytica* CY-201

| Gene(s) Disrupted | Relative fatty alcohol production to CY-201 |
|---|---|
| F09603 | ++ |
| C08415 | ++ |
| A20944 | ++ |
| F01320 | ++ |
| D04246 | ++ |
| F14729 | ++ |
| C04092 | ++ |
| E11099 F09603 | ++ |
| F19514 | ++ |
| D07942 | ++ |
| E11099 E18502 | ++ |
| F07535 | ++ |
| B07755 | ++ |
| B21692 | ++ |
| B05456 | ++ |
| C19580 | ++ |
| F22121 | ++ |
| E11099 C08415 | ++ |
| D05291 | ++ |
| D01738 | ++ |
| F25003 | ++ |
| E11099 E28336 B10406 | ++ |
| E03212 | + |
| D10417 | + |
| B10175 | + |
| E25982 | + |
| A16379 D25630 | + |
| A19536 C08415 | + |
| B10406 F09603 | + |
| D25630 | + |
| A17875 | + |
| E28336 D07986 E32769 | + |
| B04906 | + |
| D14366 | + |
| E32769 | + |
| E17787 | + |
| B10406 E28336 | + |
| F10857 | + |
| F19514 E32769 | + |
| C02387 | + |
| D07986 E32769 | + |
| B14014 D25630 | + |
| D25630 A16379 E17787 | + |
| F06578 E32769 | + |
| E28336 C02387 | + |
| F06578 | + |
| B14014 D25630 E17787 | + |
| F19514 F06578 D07986 E32769 | + |
| E17787 A16379 D25630 B14014 | + |
| B14014 | + |
| A15147 E17787 B14014 A16379 D25630 | + |
| F19514 F06578 E32769 | + |
| A16379 B14014 D25630 | + |
| B10406 E11099 | + |
| F06578 D07986 E32769 | + |
| E32417 | + |
| E01298 | + |
| E06831 | + |
| E16016 | + |
| E28336 E15378 | + |
| E30283 | + |
| B10406 E18502 | + |
| F19514 D07986 E32769 | + |
| E15378 | + |
| E28336 A00374 | + |
| E15400 F23793 | + |
| D00891 | + |
| E15400g | + |
| B01298 F23793 | + |
| A16379 D25630 A15147 | + |
| E12463 | + |
| A17875 F23793 | + |
| B10406 A19536 | + |
| F22539 | + |
| F23793 | + |

TABLE 4-continued

Targeted gene disruptions in *Y. lipolytica* CY-201

| Gene(s) Disrupted | Relative fatty alcohol production to CY-201 |
|---|---|
| E28336 A19536 A00374 | + |
| E28336 A19536 C17545 | + |

++++ = >4.0 fold improvement
+++ = 1.5 to 4.0 fold improvement
++ = 1.0 to 1.49 fold improvement
+ = 0.0 to 0.99 fold improvement

Example 7: Production of Fatty Alcohol in Fermentation with a Modified *Y. lipolytica* Strain A derivative of the CY-201 strain comprising deletions of YALI0E11099g, YALI0E28336g, YALI0C17545, and YALI0E14729 and harboring two integrated copies of *M. algicola* FAR ("the CY-202 strain") was used to produce fatty alcohol in a stirred tank fermentor. The fermentation followed a two-stage protocol in which cells are propagated in a nutrient-rich medium then transferred into a nutrient limited medium for fatty alcohol production. For the first stage, an inoculation culture was prepared by growing the CY-202 strain in YPD medium (10 g/L yeast extract, 20 g/L peptone, 20 g/L dextrose) in a baffled shake flask at 30° C. for 24 hours. This culture was used to inoculate a fermentor containing 10 L propagation medium (6.7 g/L Yeast Nitrogen base without amino acids, 20.9 g/L Bis Tris buffer, 80 g/L glucose, 10 g/L corn steep liquor, and 0.22 mL/L antifoam (a 1:1 mixture of poly(propylene glycol) and Antifoam B), adjusted to pH 6.5 with KOH. This propagation culture was grown at 30° C. in a batch process with controlled oxygen transfer rate (15-20 mM $O_2$/hr) to a final $OD_{600}$ of 12-18. For the second stage, cells in propagation medium were harvested by centrifugation, then resuspended in 1.1 L fatty alcohol production medium (200 g/L glucose, 1 g/L $KH_2PO_4$, 5 g/L $(NH_4)_2SO_4$, 2.5 mg/L $MgSO_4*7H_2O$ 1 mg/L $FeSO_4*7H_2O$, 0.5 mg/L $H_3BO_3$, 0.5 mg/L $MnSO_4$—$H_2O$, 0.5 mg/L $Na_2MoO_4$-$2H_2O$, 0.5 mg/L $ZnSO_4*7H_2O$, 0.5 mg/L $CoCl_2*H_2O$, 0.1 mg/L KI, 0.1 mg/L $CuCl_2*2H_2O$, 50 mg/L Thiamine HCl, and 50 mg/L inositol, and 0.8 mL/L antifoam). The volume of the cell resuspension was adjusted to give an initial cell density for the second stage of 20 g/L (dry cell weight), then the resuspension was loaded into a stirred tank fermentor. Fermentation was carried out in a batch process at 30° C. with dissolved oxygen control (30% $dO_2$). pH was controlled at 3.5 by addition of KOH. Glucose was added as necessary to prevent glucose exhaustion (35 g/L over the course of the fermentation).

Samples were collected at 24 hrs, 48 hrs, and 72 hrs after inoculation of the production stage culture. Fatty alcohol titer was analyzed by GC-FID essentially as described in Example 3. After 24 hrs, a fatty alcohol titer of 9 g/L was observed. After 48 hrs, a fatty alcohol titer of 16 g/L was observed. After 72 hrs, a fatty alcohol titer of 21 g/L was observed.

Example 8: Partial Deletion of Sec62 Gene

Strains with a partial deletion of the Sec62 gene (YALI0B17512g; SEQ ID NO:54) were constructed by transforming *Y. lipolytica* with a DNA construct designed to (1) mutate codon Trp235 to a stop codon and (2) replace codons 236-396 with a selectable marker by homologous recombination. Thirty nucleotides of the 3' untranslated region immediately following the Sec62 coding sequence were also deleted. This partial deletion corresponds to a deletion of the cytoplasmic domain of Sec62, which begins immediately after the predicted transmembrane domain at Leu206 and continues to the end of the protein at Glu396. As shown in Table 3, this strain (identified in the table as "B17512") gave ~10-fold greater fatty alcohol production relative to the corresponding DSMZ 1345 strain without a partial deletion of the Sec62 gene.

Three other partial deletions of the Sec62 gene (YALI0B17512g) were made by transforming *Y. lipolytica* with a DNA construct that (1) mutated either the codon encoding Glu267, the codon encoding Ala302, or the codon encoding Ile337 to a stop codon and (2) replaced the subsequent codons with a selectable marker using homologous recombination. These strains gave ~1.5- to 2-fold greater fatty alcohol production relative to the corresponding DSMZ 1345 strain without a partial deletion of the Sec62 gene.

The methods used for DNA construction and transformation are described in Example 4 and are familiar to those skilled in the art. Briefly, the transforming DNA construct comprised a bifunctional selectable marker flanked by ~1 kb of genomic sequences immediately upstream and downstream of the nucleotides to be deleted. Following transformation, strains with the desired modification were selected by growth on positive selective media. The selectable marker was then excised from the genome, and strains that had lost the marker were identified by growth on counterselection media. PCR genotyping was used to confirm that strains have the desired modification.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A recombinant fungal cell comprising:
   (a) at least one genetic modification in an endogenous gene with at least 80% nucleotide sequence identity to the polynucleotide of SEQ ID NO: 7, wherein the endogenous gene encodes a phosphatidylinositol transfer protein, and
   wherein the at least one genetic modification comprises (i) a deletion of at least a portion of the coding region of the endogenous gene, (ii) a mutation in the endogenous gene such that the gene encodes a polypeptide having reduced activity; (iii) a modified regulatory sequence that reduces expression of the endogenous gene; or (iv) any combination of (i)-(iii); and
   (b) an exogenous gene encoding a fatty acyl reductase (FAR) protein, wherein the exogenous gene is operably linked to a promoter, wherein the FAR protein has at least 80% amino acid sequence identity to a polypeptide selected from the group consisting of the polypeptides of SEQ ID NO: 2, 4, 6, and 65-73.

2. The recombinant fungal cell of claim 1, wherein said recombinant fungal cell is a recombinant yeast cell.

3. The recombinant fungal cell of claim 2, wherein said recombinant fungal cell is a *Y. lipolytica* cell.

4. The recombinant fungal cell of claim 1 further comprising at least one genetic modification in a second endogenous gene with at least 80% nucleotide sequence identity to the polynucleotide of SEQ ID NO: 9, wherein the second endogenous gene encodes a beta-oxidation enzyme PAT1, and wherein the at least one genetic modification comprises (i) a deletion of at least a portion of the coding region of the endogenous gene, (ii) a mutation in the endogenous gene such that the gene encodes a polypeptide having reduced activity, (iii) a modified regulatory sequence that reduces expression of the endogenous gene, or (iv) any combination of (i)-(iii).

5. The recombinant fungal cell of claim 1 further comprising at least one genetic modification in at least one endogenous gene selected from the group consisting of:
   (a) an endogenous gene with at least 80% nucleotide sequence identity to the polynucleotide of SEQ ID NO: 9, wherein said endogenous gene encodes a beta-oxidation enzyme PAT1,
   (b) an endogenous gene with at least 80% nucleotide sequence identity to the polynucleotide of SEQ ID NO: 10, wherein said endogenous gene encodes an enoyl-CoA hydratase,
   (c) an endogenous gene with at least 80% nucleotide sequence identity to the polynucleotide of SEQ ID NO: 11, wherein said endogenous gene encodes an alcohol dehydrogenase,
   (d) an endogenous gene with at least 80% nucleotide sequence identity to the polynucleotide of SEQ ID NO: 13, wherein said endogenous gene encodes an acyltransferase DGAT2,
   (e) an endogenous gene with at least 80% nucleotide sequence identity to the polynucleotide of SEQ ID NO: 14, wherein said endogenous gene encodes a glycerol uptake protein 1 (GUP1),
   (f) an endogenous gene with at least 80% nucleotide sequence identity to the polynucleotide of SEQ ID NO: 15, wherein said endogenous gene encodes a sorbitol dehydrogenase 1 (SOR1),
   (g) an endogenous gene with at least 80% nucleotide sequence identity to the polynucleotide of SEQ ID NO: 16, wherein said endogenous gene encodes a fatty alcohol dehydrogenase ADH2,
   (h) an endogenous gene with at least 80% nucleotide sequence identity to the polynucleotide of SEQ ID NO: 17, wherein said endogenous gene encodes a GMC oxidoreductase,
   (i) an endogenous gene with at least 80% nucleotide sequence identity to the polynucleotide of SEQ ID NO: 18, wherein said endogenous gene encodes an alcohol dehydrogenase,
   (j) an endogenous gene with at least 80% nucleotide sequence identity to the polynucleotide of SEQ ID NO: 19, wherein said endogenous gene encodes a fatty alcohol dehydrogenase ADH4,
   (k) an endogenous gene with at least 80% nucleotide sequence identity to the polynucleotide of SEQ ID NO: 20, wherein said endogenous gene encodes a fatty alcohol dehydrogenase ADH3,
   (l) an endogenous gene with at least 80% nucleotide sequence identity to the polynucleotide of SEQ ID NO: 21, wherein said endogenous gene encodes a peroxisomal membrane protein,
   (m) an endogenous gene with at least 80% nucleotide sequence identity to the polynucleotide of SEQ ID NO: 22, wherein said endogenous gene encodes a CoA ligase,
   (n) an endogenous gene with at least 80% nucleotide sequence identity to the polynucleotide of SEQ ID NO: 23, wherein said endogenous gene encodes an alcohol dehydrogenase,
   (o) an endogenous gene with at least 80% nucleotide sequence identity to the polynucleotide of SEQ ID NO: 24, wherein said endogenous gene encodes an alkane monooxygenase ALK5,
   (p) an endogenous gene with at least 80% nucleotide sequence identity to the polynucleotide of SEQ ID NO: 25, wherein said endogenous gene encodes a transcription factor YAS1,
   (q) an endogenous gene with at least 80% nucleotide sequence identity to the polynucleotide of SEQ ID NO: 26, wherein said endogenous gene encodes a phosphatidylinositol transfer protein,
   (r) an endogenous gene with at least 80% nucleotide sequence identity to the polynucleotide of SEQ ID NO: 27, wherein said endogenous gene encodes an alcohol dehydrogenase, (s) an endogenous gene with at least 80% nucleotide sequence identity to the polynucleotide of SEQ ID NO: 28, wherein said endogenous gene encodes an alcohol dehydrogenase, (t) an endogenous gene with at least 80% nucleotide sequence identity to the polynucleotide of SEQ ID NO: 29, wherein said endogenous gene encodes a peroxisomal membrane protein PXA2, (u) an endogenous gene with at least 80% nucleotide sequence identity to the polynucleotide of SEQ ID NO: 30, wherein said endogenous gene encodes a transcription factor SCS2, (v) an endogenous gene with at least 80% nucleotide sequence identity to the polynucleotide of SEQ ID NO: 31, wherein said endogenous gene encodes an acyltransferase DGAT1, (w) an endogenous gene with at least 80% nucleotide sequence identity to the polynucleotide of SEQ ID NO: 34, wherein said endogenous gene encodes a fatty alcohol dehydrogenase ADH1, (x) an endogenous gene with at least 80% nucleotide sequence identity to the polynucleotide of SEQ ID NO: 35, wherein said endogenous gene encodes a FAD binding oxidoreductase, (y) an endogenous gene with at least 80% nucleotide sequence identity to the polynucleotide of SEQ ID NO: 36, wherein said endogenous gene encodes an alcohol dehydrogenase, (z) an endogenous gene with at least 80% nucleotide sequence identity to the polynucleotide of SEQ ID NO: 37, wherein said endogenous gene encodes an acyl-CoA ligase, (aa) an endogenous gene with at least 80% nucleotide sequence identity to the polynucleotide of SEQ ID NO: 38, wherein said endogenous gene encodes a 2,4-dienoyl-CoA reductase, (bb) an endogenous gene with at least 80% nucleotide sequence identity to the polynucleotide of SEQ ID NO: 39, wherein said endogenous gene encodes a beta-oxidation enzyme MFE2, (cc) an endogenous gene with at least 80% nucleotide sequence identity to the polynucleotide of SEQ ID NO: 40, wherein said endogenous gene encodes a fatty aldehyde dehydrogenase ALDH2, (dd) an endogenous gene with at least 80% nucleotide sequence identity to the polynucleotide of SEQ ID NO: 41, wherein said endogenous gene encodes a flavoprotein oxygenase, (ee) an endogenous gene with at least 80% nucleotide sequence identity to the polynucleotide of SEQ ID NO: 42, wherein said endogenous gene encodes a beta-oxidation enzyme POT1, (ff) an endogenous gene with at least 80% nucleotide sequence identity to the polynucleotide of SEQ ID NO: 43, wherein said endogenous gene encodes an oxysterol binding protein, (gg) an endogenous gene with at least 80% nucleotide sequence identity to the polynucleotide of SEQ ID NO: 44, wherein said endogenous gene encodes an alkane monooxygenase ALK1, (hh) an endogenous gene with at least 80% nucleotide sequence identity to the polynucleotide of SEQ ID NO: 46, wherein said endogenous gene encodes a transcription factor YAS2, (ii) an endogenous gene with at least 80% nucleotide sequence identity to the polynucleotide of SEQ ID NO: 47, wherein said endogenous gene encodes an alkane monooxygenase ALK2, (jj) an endogenous gene with at least 80% nucleotide sequence identity to the polynucleotide of SEQ ID NO: 48, wherein said endogenous gene encodes an acyltransferase ARE2, (kk) an endogenous gene with at least 80% nucleotide sequence identity to the polynucleotide of SEQ ID NO: 50, wherein said endogenous gene encodes a thioesterase, (ll) an endogenous gene with at least 80% nucleotide sequence identity to the polynucleotide of SEQ ID NO: 51, wherein said endogenous gene encodes an enoyl-CoA hydratase, (mm) an endogenous gene with at least 80% nucleotide sequence identity to the polynucleotide of SEQ ID NO: 52, wherein said endogenous gene encodes an alcohol dehydrogenase, (nn) an endogenous gene with at least 80% nucleotide sequence identity to the polynucleotide of SEQ ID NO: 53, wherein said endogenous gene encodes an ABC1 alkane transporter, and (oo) an endogenous gene with at least 80% nucleotide sequence identity to the polynucleotide of SEQ ID NO: 54, wherein said endogenous gene encodes a Sec62 ER protein translocase, wherein the at least one genetic modification comprises (i) a deletion of at least a portion of the coding region of the endogenous gene, (ii) a mutation in the endogenous gene such that the gene encodes a polypeptide having reduced activity, (iii) a modified regulatory sequence that reduces expression of the endogenous gene, or (iv) any combination of (i)-(iii).

6. The recombinant fungal cell of claim 1, wherein multiple copies of the exogenous gene are expressed.

7. The recombinant fungal cell of claim 1, further comprising a second exogenous gene that encodes a fatty acid synthase (FAS), an ester synthase, an acyl-ACP thioesterase (TE), a fatty acyl-CoA synthase (FACS), an acetyl-CoA carboxylase (ACC), a xylose isomerase, or an invertase.

8. A *Y. lipolytica* recombinant yeast cell comprising:
(a) at least one genetic modification in the YALI0C17545 endogenous gene,
wherein the at least one genetic modification comprises (i) a deletion of at least a portion of the coding region of the endogenous gene, (ii) a mutation in the endogenous gene such that the gene encodes a polypeptide having reduced activity; (iii) a modified regulatory sequence that reduces expression of the endogenous gene; or (iv) any combination of (i)-(iii); and
(b) an exogenous gene encoding a fatty acyl reductase (FAR) protein, wherein the exogenous gene is operably linked to a promoter, wherein the FAR protein has at least 80% amino acid sequence identity to a polypeptide selected from the group consisting of the polypeptides of SEQ ID NO: 2, 4, 6, and 65-73.

9. The *Y. lipolytica* recombinant yeast cell of claim 8 further comprising at least one genetic modification in the YALI0E11099 endogenous gene, wherein the at least one genetic modification comprises (i) a deletion of at least a portion of the coding region of the endogenous gene, (ii) a mutation in the endogenous gene such that the gene encodes a polypeptide having reduced activity; (iii) a modified regulatory sequence that reduces expression of the endogenous gene; or (iv) any combination of (i)-(iii).

10. The *Y. lipolytica* recombinant yeast cell of claim 8 further comprising at least one genetic modification in at least one endogenous gene selected from the group consisting of YALI0B10406, YALI0A19536, YALI0E32769, YALI0E30283, YALI0E12463, YALI0E17787, YALI0B14014, YALI0A10769, YALI0A15147, YALI0A16379, YALI0A20944, YALI0B07755, YALI0B10175, YALI0B13838, YALI0OC2387, YALI0OC5511, YALI0D01738, YALI0D02167, YALI0D04246, YALI0D05291, YALI0D07986, YALI0D10417, YALI0D14366, YALI0D25630, YALI0E03212, YALI0E07810, YALI0E12859, YALI0E14322, YALI0E15378, YALI0E15400, YALI0E18502, YALI0E18568, YALI0E22781, YALI0E25982, YALI0E28314, YALI0E32417, YALI0F01320, YALI0F06578, YALI0F07535, YALI0F14729, YALI0F22121, YALI0F25003, YALI0E14729, and YALI0B17512,
  wherein the at least one genetic modification comprises (i) a deletion of at least a portion of the coding region of the endogenous gene, (ii) a mutation in the endogenous gene such that the gene encodes a polypeptide having reduced activity; (iii) a modified regulatory sequence that reduces expression of the endogenous gene; or (iv) any combination of (i)-(iii).

11. The *Y. lipolytica* recombinant yeast cell of claim 8, wherein multiple copies of the exogenous gene are expressed.

12. The *Y. lipolytica* recombinant yeast cell of claim 8, further comprising a second exogenous gene that encodes a fatty acid synthase (FAS), an ester synthase, an acyl-ACP thioesterase (TE), a fatty acyl-CoA synthase (FACS), an acetyl-CoA carboxylase (ACC), a xylose isomerase, or an invertase.

13. A method of producing a fatty acyl-CoA derivative comprising:
  culturing the recombinant fungal cell of claim 1 under conditions in which the fatty acyl-CoA derivative is produced.

14. The method of claim 13 wherein the fatty acyl-CoA derivative is a fatty alcohol, fatty acid, fatty aldehyde, fatty ester, fatty acetate, wax ester, alkane, or alkene.

15. The method of claim 13 further comprising:
  contacting a cellulose-containing biomass with one or more cellulases to yield fermentable sugars; and
  contacting said recombinant fungal cell with the fermentable sugars under which conditions in which the fatty acyl-coA derivative is produced.

16. The method of claim 13, wherein at least 5 g/L of fatty acyl-CoA derivatives per liter of culture medium is produced.

17. A method for producing a fatty acyl-CoA derivative comprising culturing the *Y. lipolytica* recombinant yeast cell of claim 8 under conditions in which the fatty acyl-CoA derivative is produced.

18. The method claim 17, wherein the fatty acyl-CoA derivative is a fatty alcohol, fatty acid, fatty aldehyde, fatty ester, fatty acetate, wax ester, alkane or alkene.

19. The method of claim 17 further comprising: contacting a cellulose-containing biomass with one or more cellulases to yield fermentable sugars; and contacting said *Y. lipolytica* recombinant yeast cell.

20. The method of claim 17, wherein at least 5 g/L of fatty acyl-CoA derivatives per liter of culture medium is produced.

\* \* \* \* \*